(12) United States Patent
Cai et al.

(10) Patent No.: US 11,306,102 B2
(45) Date of Patent: Apr. 19, 2022

(54) 1,3-DI-SUBSTITUTED KETENE COMPOUND AND APPLICATION THEREOF

(71) Applicant: BEBETTER MED INC., Guangdong (CN)

(72) Inventors: Xiong Cai, Guangzhou (CN); Changgeng Qian, Guangzhou (CN); Chunqiang Ye, Guangzhou (CN); Qijie He, Guangzhou (CN)

(73) Assignee: BEBETTER MED INC., Guangdong (CN)

( * ) Notice: Subject to any disclaimer, the term of this patent is extended or adjusted under 35 U.S.C. 154(b) by 0 days.

(21) Appl. No.: 16/634,827

(22) PCT Filed: Jun. 29, 2018

(86) PCT No.: PCT/CN2018/093760
§ 371 (c)(1),
(2) Date: Jan. 28, 2020

(87) PCT Pub. No.: WO2019/024635
PCT Pub. Date: Feb. 7, 2019

(65) Prior Publication Data
US 2021/0122761 A1    Apr. 29, 2021

(30) Foreign Application Priority Data

Jul. 31, 2017 (CN) .......................... 201710643304.3
Jun. 19, 2018 (CN) .......................... 201810629882.6

(51) Int. Cl.
| | |
|---|---|
| *C07D 495/04* | (2006.01) |
| *C07D 307/80* | (2006.01) |
| *C07D 263/56* | (2006.01) |
| *C07D 307/83* | (2006.01) |
| *C07D 327/06* | (2006.01) |
| *C07D 327/04* | (2006.01) |
| *C07D 307/85* | (2006.01) |
| *C07D 317/54* | (2006.01) |
| *C07D 491/048* | (2006.01) |
| *C07D 277/64* | (2006.01) |
| *C07D 333/54* | (2006.01) |

(52) U.S. Cl.
CPC ......... *C07D 495/04* (2013.01); *C07D 263/56* (2013.01); *C07D 277/64* (2013.01); *C07D 307/80* (2013.01); *C07D 307/83* (2013.01); *C07D 307/85* (2013.01); *C07D 317/54* (2013.01); *C07D 327/04* (2013.01); *C07D 327/06* (2013.01); *C07D 333/54* (2013.01); *C07D 491/048* (2013.01)

(58) Field of Classification Search
CPC .. C07D 495/04; C07D 307/80; C07D 263/56; C07D 307/83; C07D 327/06; C07D 327/04; C07D 307/85; C07D 317/54; C07D 491/048; C07D 277/64; C07D 333/54
See application file for complete search history.

(56) References Cited

U.S. PATENT DOCUMENTS

| | | | |
|---|---|---|---|
| 6,608,101 | B1 | 8/2003 | Ni et al. |
| 6,635,655 | B1 | 10/2003 | Jayyosi et al. |
| 7,547,729 | B2 | 6/2009 | Caumont-Bertrand et al. |
| 7,943,661 | B2 | 5/2011 | Najib et al. |
| 8,461,212 | B2 | 6/2013 | Najib et al. |
| 2020/0239429 | A1* | 7/2020 | Zhu .................... C07D 215/227 |

FOREIGN PATENT DOCUMENTS

| | | |
|---|---|---|
| CA | 904291 | 7/1972 |
| CN | 1447804 | 10/2003 |
| CN | 1668565 | 9/2005 |

(Continued)

OTHER PUBLICATIONS

CAS Registry No. 1088216-43-6, which entered STN on Dec. 22, 2008 (Year: 2008).*
Cariou et al. Expert Opinion on Investigational Drugs, 2014, 23, 1441-1448 (Year: 2014).*
CAS Registry No. 1088216-43-6, Registry, Dec. 22, 2008, 3 pages.
International Search Report issued for International Patent Application No. PCT/CN2018/093760, dated Sep. 21, 2018, 6 pages including English translation.
Liang, X. et al., "Progress in drug treatment of nonalcoholic fatty liver disease," Chin J Clinicians (Electronic Edition), Oct. 15, 2015, vol. 9, No. 20, pp. 1-4 (with English abstract).

(Continued)

*Primary Examiner* — Matthew P Coughlin
(74) *Attorney, Agent, or Firm* — Hamre, Schumann, Mueller & Larson, P.C.

(57) ABSTRACT

Provided are a 1,3-di-substituted ketene compound having a structure as represented by formula (I) and an application thereof. Such a type of compound primarily activates peroxisome proliferator-activated receptor (PPAR) α, and also activates PPPAδ and PPPAγ. The compound may be used to treat various diseases associated with PPAR regulation and control abnormality, such as non-alcoholic fatty liver disease, and especially in treating non-alcoholic hepatitis, and may potentially be used in the treatment of diseases comprising diabetes, obesity, fibrotic diseases, cardiovascular diseases (comprising heart failure, atherosclerosis, and so on), kidney diseases (comprising chronic kidney disease, renal failure, and so on), and brain degenerative diseases (comprising Alzheimer's disease and so on), having great application value.

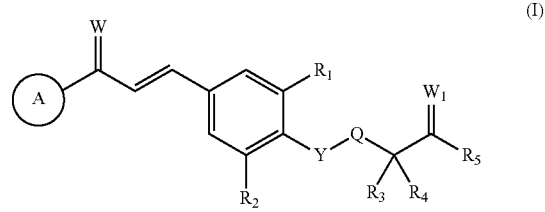

19 Claims, 1 Drawing Sheet

(56) References Cited

FOREIGN PATENT DOCUMENTS

| | | | | |
|---|---|---|---|---|
| CN | 1688532 | 10/2005 | | |
| CN | 1861560 | 11/2006 | | |
| CN | 1930122 | 3/2007 | | |
| CN | 101070316 | 11/2007 | | |
| JP | 2005532386 | 10/2005 | | |
| JP | 2007517841 | 7/2007 | | |
| WO | 2008087365 | 7/2008 | | |
| WO | 2008087367 | 7/2008 | | |
| WO | 2009153496 | 12/2009 | | |
| WO | 2019024635 | 2/2019 | | |
| WO | WO-2019105234 A1 | * | 6/2019 | C07D 215/18 |

OTHER PUBLICATIONS

Doshi, L. et al., "Discovery and development of selective PPARγ modulators as safe and effective antidiabetic agents," Expert Opin. Investig. Drugs (2010) 19(4), pp. 489-512.

Second Office Action issued for Chinese Patent Application No. 201810629882.6, dated Mar. 1, 2019, 10 pages including English translation.

Shukla, P. et al., "Synthesis and antidyslipidemic activity of chalcone fibrates," Bioorganic & Medicinal Chemistry Letters 21 (2011) pp. 3475-3478.

Office Action and Search Report issued for Taiwanese Patent Application No. 107126472, dated Jun. 14, 2019, 10 pages including brief English translation of the objections.

First Office Action issued for Australian Patent Application No. 2018311725, dated May 4, 2020, 5 pages.

Extended European Search Report issued for European Application No. 18841821.4, dated Jul. 14, 2020, 10 pages.

Kamal, A. et al., "Synthesis and anticancer activity of 4beta-alkylamidochalcone and 4beta-cinnamido linked podophyllotoxins as apoptotic inducing agents," European Journal of Medicinal Chemistry, vol. 47, Jan. 1, 2012, pp. 530-545.

Babu, V. H. et al., "Synthesis and Biological Evaluation of some Novel Pyrazolines," Indian Journal of Pharmaceutical Sciences, vol. 69, No. 3, May 1, 2007, pp. 470-473.

Konieczny, M. T. et al., "Structural factors affecting affinity of cytotoxic oxathiole-fused chaicones toward tubulin," European Journal of Medicinal Chemistry, vol. 89, Jan. 1, 2015, pp. 733-742.

World Gastroenterology Organisation Global Guidelines, "Nonalcoholic Fatty Liver Disease and Nonalcoholic Steatohepatitis," Jun. 2012, 29 pages.

Fan, JG et al., "Guidelines for the diagnosis and management of nonalcoholic fatty liver disease: Update 2010," Journal of Digestive Diseases, 12, 2011, pp. 38-44.

Francis, G. A. et al., "Nuclear Receptors and the Control of Metabolism," Annu. Rev. Physiol., 65, 2003, pp. 261-311.

Pawlak, M. et al., "Molecular mechanism of PPARα action and its impact on lipid metabolism, inflammation and fibrosis in non-alcoholic fatty liver disease," J Hepatol, vol. 62, 2015, pp. 720-733.

Han, L. et al., "PPARs: regulators of metabolism and as therapeutic targets in cardiovascular disease. Part I: PPARα," Future Cardiol., Jun. 5, 2017, doi: 10.2217/fca-2016-0059, 20 pages.

Adedapo, AA et al., "Effects of fenofibrate, a PPARα ligand, on the haemodynamics of glycerol-induced renal failure in rats," Hum Exp Toxicol., 32:323-331, 2012, 10 pages.

D'Orio, B. et al., "Targeting PPARalpha in Alzheimer's Disease," Curr Alzheimer Research, vol. 15, 2018, pp. 1-10.

Olefsky, J. M. et al., "PPARγ and the Treatment of Insulin Resistance," Trend Endocrin Met, vol. 11, No. 9, 2000, pp. 362-368.

Koo, JB et al., "Anti-fibrogenic effect of PPAR-γ agonists in human intestinal myofibroblasts," BMC Gastroenterology, 17:73, 2017, 12 pages.

Bays, H. E. et al., "MBX-8025, A Novel Peroxisome Proliferator Receptor-δ Agonist: Lipid and Other Metabolic Effects in Dyslipidemic Overweight Patients Treated with and without Atorvastatin," J Clin Endocrinol Metab, 96(9), 2011, pp. 2889-2897.

Sahebkar, A. et al.,"New peroxisome proliferator-activated receptor agonists: potential treatments for atherogenic dyslipidemia and non-alcoholic fatty liver disease," Expert Opin. Pharmacother., 15(4), 2014, pp. 493-503.

Ratziu, V. et al., "Elafibranor, an Agonist of the Peroxisome Proliferator-Activated Receptor-α and -δ, Induces Resolution of Nonalcoholic Steatohepatitis Without Fibrosis Worsening," Gastroenterology, vol. 150, No. 5, 2016, pp. 1147-1159.

Rosenson, R. S. et al., "Modulating peroxisome proliferator-activated receptors for therapeutic benefit? Biology, clinical experience, and future prospects," Am Heart J, vol. 164, No. 5, 2012, pp. 672-680.

Conlon, D., "Goodbye glitazars?" Br J Diabetes Vasc Dis, vol. 6, Issue 3, 2006, pp. 135-137.

Bénardeau, A. et al., "Aleglitazar, a new, potent, and balanced dual PPARα/γ agonist for the treatment of type II diabetes," Bioorganic Medicinal Chemistry Letters, 19, 2009, pp. 2468-2473.

Schott, J. T. et al., "Effects of Structural and Electronic Characteristics of Chalcones on the Activation of Peroxisome Proliferator-Activated Receptor Gamma," Chemical & Pharmaceutical Bulletin, vol. 61, No. 2, 2013, pp. 229-236. (Cited in Office Action).

Office Action issued for Japanese Patent Application No. 2020-506217, dated Dec. 7, 2021, 4 pages including English translation.

* cited by examiner

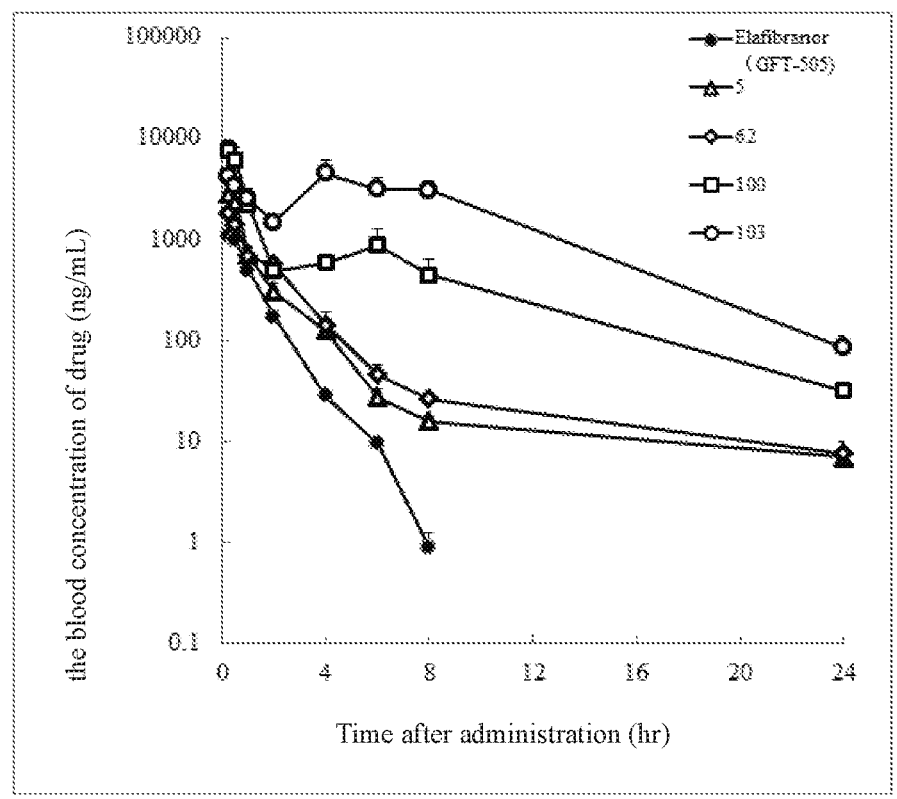

1,3-DI-SUBSTITUTED KETENE COMPOUND AND APPLICATION THEREOF

TECHNICAL FIELD

The present disclosure relates to the field of medicinal chemistry, and in particular to a 1,3-disubstituted ketene compound and use thereof.

BACKGROUND

Non-alcoholic fatty liver disease (NAFLD) refers to a liver disease caused by factors other than alcohol and other causes of definite damage, manifested as excessive fat accumulation in the form of triglycerides (>5% of hepatocyte tissue) in the liver. Non-alcoholic steatohepatitis (NASH) is a steatosis non-alcoholic fatty liver disease associated with inflammation and hepatocyte damage. Typical pathological features of early non-alcoholic steatohepatitis are fat accumulation, inflammation, and mild fibrosis. Progression of non-alcoholic steatohepatitis to advanced stages can lead to advanced liver fibrosis, cirrhosis, liver failure, and liver tumors.

Over the past 20 years, NAFLD has increased dramatically and is now the most common liver disease in western countries. In the United States, the incidence of NAFLD is about 27-34% of the total population, and as high as 75-92% especially in obese people. About 10-20% of NAFLD patients develop into NASH, and 37% of NAFLD patients with high-risk severe obesity develop into NASH. About 6 million people in the United States have progressed to NASH, and of which 600,000 have NASH-related cirrhosis. The main risk factors for NASH include obesity, type 2 diabetes (T2DM), dyslipidemia and metabolic syndrome. Currently, NASH-related cirrhosis is the third most common cause of liver transplantation in the United States and is expected to become the main cause in 2020 (World Gastroenterology Organisation Global Guidelines: NFLD and NASH. June 2012). In the past 20 years, NAFLD in Asian countries has grown rapidly and shows a trend of younger age. The prevalence of NAFLD in adults in the developed regions such as Shanghai, Guangzhou and Hong Kong is about 15% (Fan J G et al: J Dig Dis 12: 38-44, 2011).

Peroxisome proliferators-activated receptors (PPARs) are ligand-activating receptors in the nuclear hormone receptor family, regulate transcription of target genes, and are involved in lipid regulation, lipogenesis, and glycemic control. Therefore, it plays an important regulatory role in energy balance and metabolic function.

The PPARs family contains three subtypes: α, γ, and δ (or β). All three subtypes are involved in the regulation of lipid metabolism.

PPARα is highly expressed in the liver, skeletal muscle, kidney, heart and blood vessel walls, stimulating fatty acid oxidation and uptake and regulating lipoprotein synthesis. Activation of PPARα in liver increases high-density lipoprotein (HDL) and apolipoprotein Apo AI and Apo AII, increases hydrolysis of triglyceride and increases uptake and oxidation of free fatty acid. Furthermore, PPARα has an anti-inflammatory effect by inhibiting cyclooxygenase-2, interleukin-6 and C-reactive protein (Francis G et al, Ann Rev Physiol. 65: 261-311, 2003; Pawlak M et al. J Hepatol 62: 720-733, 2015). Fibric acid derivatives such as clofibrate, fenofibrate and ciprofibrate acted as PPARα agonists can reduce low-density lipoprotein (LDL) and treat hypertriglyceridemia while reducing triglycerides. PPARα agonists can be used in the treatment of cholesteric liver disease, non-alcoholic fatty liver disease and/or type 2 diabetes.

Recent studies have also shown that PPARα regulates many physiological processes such as energy metabolism, redox balance, autophagy and cell cycle, and inflammatory response. PPARα agonists may have broad therapeutic prospects in cardiovascular diseases (Han L at al. Future Cardiol. 2017 Jun. 5. doi: 10.2217/fca-2016-0059), kidney diseases (Adedapo A A et al. Hum Exp Toxicol. 32: 323-331, 2013) and degenerative brain diseases (D Orio B at al. CurAlzheimer Res. 2017 doi: 10.2174/1567205014666170505094549).

PPARγ is expressed in adipose tissue of mammals, and sensitive to insulin, and is involved in transcription of genes for lipid acid uptake and fat storage. Activation of PPARγ leads to insulin sensitization and promotes glucose metabolism (Olefsky J M et al. Trend Endocrin Met 11: 362-368, 2000) and has anti-fibrotic effects (Koo J B et al. BMC Gastroenterol. 17: 73, 2017). PPARγ dysfunction may be associated with many diseases such as obesity, diabetes, atherosclerosis and cancer. PPARγ agonists have been used in the treatment of hyperlipidemia and hyperglycemia. PPARγ can reduce the inflammatory response of many cardiovascular cells, especially endothelial cells. PPARγ activates the PON1 gene, increases the synthesis and release of paraoxonase 1 in the liver, and reduces atherosclerosis. Many insulin sensitizing drugs (such as thiazolidinediones) used to treat diabetes activate PPARγ as a means to lower blood sugar without increasing insulin secretion by the pancreas.

PPARδ is widely expressed in tissues and is expressed at relatively high levels in the brain, stomach, and colon. Activation of PPARδ increases fatty acid metabolism and increases ApoA1/HDL levels, therefore inhibiting inflammation. The PPAR S agonist MBX-8025 significantly reduces human low-density lipoprotein, triglyceride and high sensitivity C-reactive protein, and increases high-density lipoprotein and reduces liver damage. (Bays H E el al. J Clin Endocrinol Metab 2889-97, 2012).

PPAR nuclear receptor polysubtype agonists may be more effective than single subtype agonists for the treatment of diseases associated with lipid and glucose metabolism, inflammation and fibrosis. Elafibranor (GFT-505) is a PPARα and PPARδ receptor agonist that may improve insulin sensitivity, regulate blood glucose balance, lipid metabolism, and reduce inflammation (Sahebkar A et al. Expert Opin Pharmacother 15: 493-503m 2014; Ratziu et al. Gastroenterology 150: 1147-1159, 2016).

SUMMARY

Based on this, the present disclosure provides a novel 1,3-disubstituted ketene compound which has an activity of activating PPAR.

The specific technical solutions are as follows:

A 1,3-disubstituted ketene compound having a structure represented by formula (I) or a pharmaceutically acceptable salt thereof or a stereoisomer thereof or a prodrug molecule thereof:

(I)

wherein

R₁, R₂ are each independently selected from the group consisting of: H, halogen, C1-C6 alkyl, C2-C6 alkenyl, C2-C6 alkynyl, C3-C8 cycloalkyl, C3-C8 cycloalkylmethyl, C1-C6 alkoxy, and hydroxyl:

R₃, R₄ are each independently selected from the group consisting of: H, halogen, C1-C6 alkyl, C2-C6 alkenyl, C2-C6 alkynyl, C3-C8 cycloalkyl, C3-C8 cycloalkylmethyl, C1-C6 alkoxy, hydroxyl, and R₃, R₄ are not H at the same time; or R₃, R₄ are bonded to form a 3-8 membered carbocyclic ring or a 3-8 membered heterocyclic ring:

R₅ is selected from the group consisting of: OR₆, and NR₇R₈:

Q is a single bond or CR₇R₈:

R₆, R₇ and R₈ are each independently selected from the group consisting of: H, C1-C6 alkyl, C3-C8 cycloalkyl, and C3-C8 cycloalkylmethyl;

W, W₁ and Y are each independently selected from the group consisting of: O and S:

ring A is a 8-12 membered substituted or unsubstituted bicyclic fused ring, which is a saturated bicyclic fused ring, a partially unsaturated bicyclic fused ring or an aromatic bicyclic fused ring, and the ring carbon atoms of the bicyclic fused ring are substituted by 0 to 5 hetero atoms which refer to O, N or S.

In some of the embodiments, W, W₁ are selected from O.

In some of the embodiments, the compound has a structure represented by formula (II):

(II)

In some of the embodiments, ring A is selected from the group consisting of:

-continued

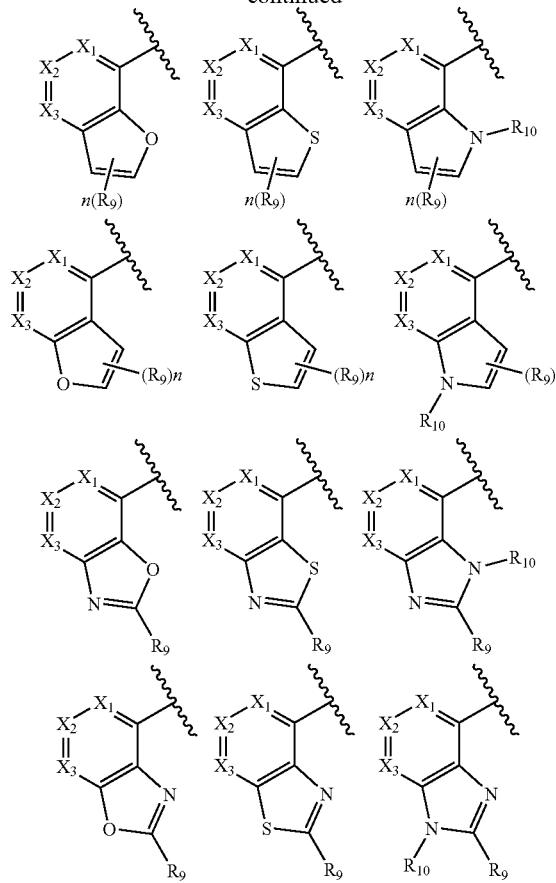

wherein, $X_1$, $X_2$, $X_3$, $X_4$, $X_5$, $X_6$, $X_7$ are each independently selected from the group consisting of: $CR_9$, $CR_{12}$ or N, and at least one of $X_1$, $X_2$, $X_3$, and $X_4$ is $CR_{12}$;

$R_9$ is selected from the group consisting of: H, halogen, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, aryl, heteroaryl, nitro, cyano, —OR, —N(R)$_2$, —SR, —C(O)OR, —C(O)N(R)$_2$, —C(O)R, —S(O)R, —S(O)$_2$R, —S(O)$_2$N(R)$_2$, —N(R)C(O)R;

$R_{10}$ is selected from the group consisting of: H, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, and C1-C4 alkylamino-substituted C1-C6 alkyl;

$R_{11}$ is selected from the group consisting of: H, —SR, —OR, —N(R)$_2$, C1-C6 alkyl, C3-C8 cycloalkyl, and C3-C8 cycloalkylmethyl;

$R_{12}$ is selected from the group consisting of: H, —SR, —OR, —N(R)$_2$, C1-C6 alkyl, C3-C8 cycloalkyl, and C3-C8 cycloalkylmethyl;

m is selected from the group consisting of: 0, 1, and 2;

each of R is selected from the group consisting of: H, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, and C1-C14 alkylamino-substituted C1-C6 alkyl.

In some of the embodiments, ring A is selected from the group consisting of:

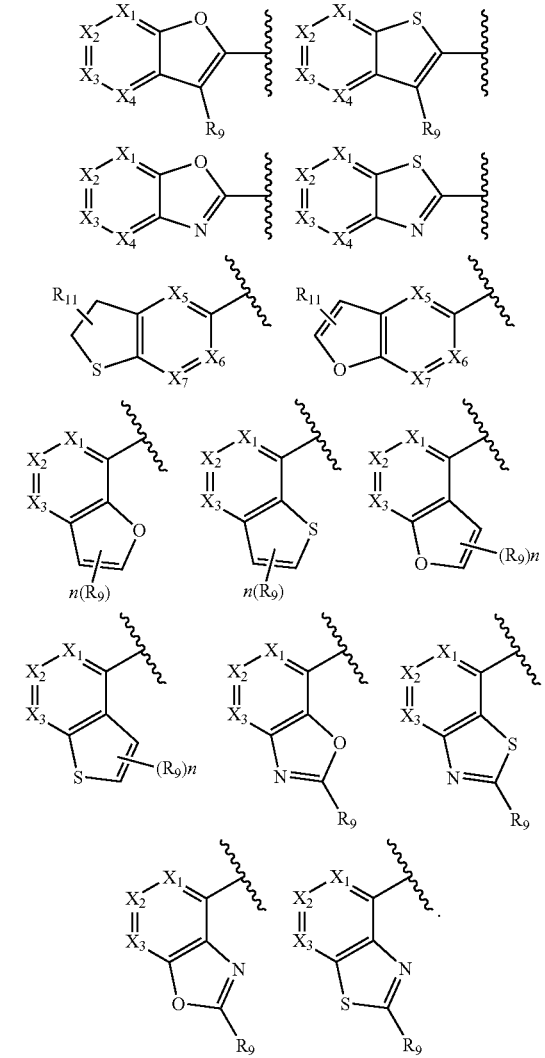

In some of the embodiments, ring A is selected from the group consisting of:

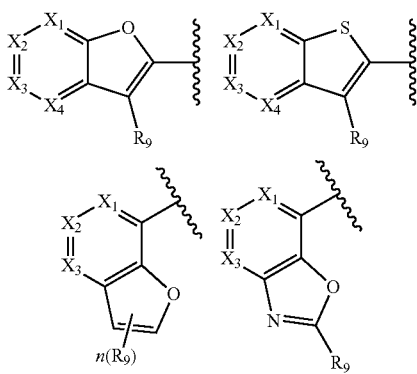

-continued

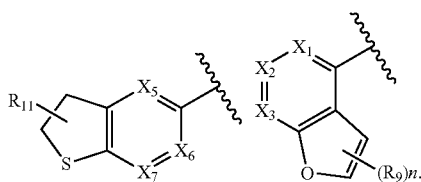 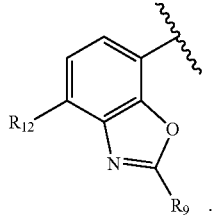

In some of the embodiments, ring A is selected from the group consisting of:

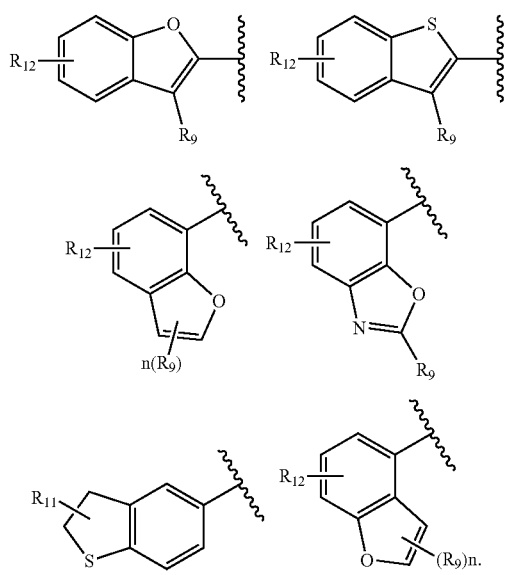

In some of the embodiments, ring A is selected from:

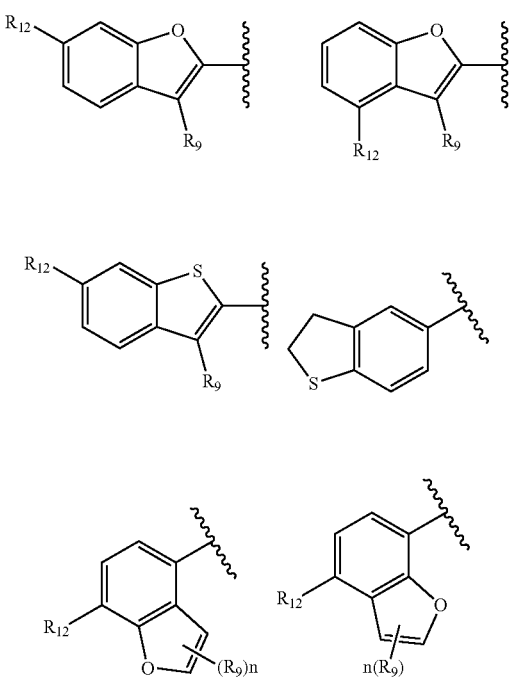

-continued

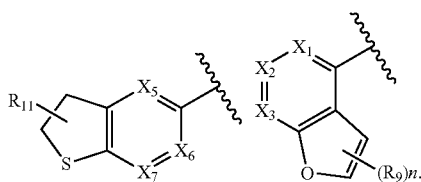

In some of the embodiments, $R_9$ is selected from the group consisting of: H, halogen, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, nitro, cyano, —OR, —N(R)$_2$, —SR, —C(O)OR, —C(O)N(R)$_2$, —C(O)R, —S(O)R, —S(O)$_2$R, —S(O)$_2$N(R)$_2$, and —N(R)C(O)R;

each of R is selected from the group consisting of: H, C1-C6 alkyl. C3-C8 cycloalkyl, C3-C8 cycloalkylmethyl, and halogen-substituted C1-C6 alkyl.

In some of the embodiments, $R_9$ is selected from the group consisting of: H, halogen, C1-C6 alkyl, halogen-substituted C1-C6 alkyl, hydroxy-substituted C1-C6 alkyl, alkoxy-substituted C1-C6 alkyl, —OR, —N(R)$_2$, —SR, —C(O)OR, —C(O)N(R)$_2$, —C(O)R, —S(O)R, —S(O)$_2$R, —S(O)$_2$N(R)$_2$, —N(R)C(O)R; each of R is selected from the group consisting of: H, C1-C6 alkyl, C3-C8 cycloalkyl, C3-C8 cycloalkylmethyl, and halogen-substituted C1-C6 alkyl.

In some of the embodiments, $R_9$ is selected from the group consisting of: H, halogen, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, —OR, —N(R)$_2$, —SR, —C(O)R, and —S(O)R;

wherein, R is selected from the group consisting of: H, C1-C6 alkyl, C3-C8 cycloalkyl, and C3-C8 cycloalkylmethyl.

In some of the embodiments. $R_9$ is selected from the group consisting of: H, C1-C6 alkyl, and halogen-substituted C1-C6 alkyl.

In some of the embodiments, $R_9$ is selected from the group consisting of: H, methyl, ethyl, isopropyl, and trifluoromethyl.

In some of the embodiments, $R_{10}$ is selected from the group consisting of: H, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl.

In some of the embodiments, $R_{10}$ is selected from the group consisting of: H, C1-C6 alkyl, and halogen-substituted C1-C6 alkyl.

In some of the embodiments, $R_{10}$ is selected from: H.

In some of the embodiments, $R_{11}$ is selected from the group consisting of: H, —SR, —OR, —N(R)$_2$, and C1-C6 alkyl; in which R is selected from the group consisting of: H, and C1-C6 alkyl.

In some of the embodiments, $R_{11}$ is selected from: H.

In some of the embodiments, $R_{12}$ is selected from the group consisting of: H, —SR, —OR, —N(R)$_2$, and C1-C6 alkyl; in which R is selected from the group consisting of: H, and C1-C6 alkyl.

In some of the embodiments, $R_{12}$ is selected from the group consisting of: —SR, and —OR; in which R is selected from: C1-C6 alkyl.

In some of the embodiments, $R_1$, $R_2$ are each independently selected from the group consisting of: H, C1-C6 alkyl, C1-C6 alkoxy, and halogen.

In some of the embodiments, $R_1$, $R_2$ are each independently selected from the group consisting of: C1-C3 alkyl, halogen and C1-C3 alkoxy.

In some of the embodiments, $R_1$, $R_2$ are both methyl or $R_1$, $R_2$ are both chlorine.

In some of the embodiments, $R_3$, $R_4$ are each independently selected from the group consisting of: H, C1-C6 alkyl, C1-C6 alkoxy, and halogen; or $R_3$, $R_4$ are bonded to form a 3-8 membered carbocyclic ring.

In some of the embodiments, $R_3$, $R_4$ are each independently selected from: C1-C6 alkyl.

In some of the embodiments, $R_5$ is selected from: $OR_6$; in which $R_6$ is selected from the group consisting of: H and C1-C6 alkyl.

In some of the embodiments, $R_5$ is selected from: $OR_6$; in which $R_6$ is selected from: H.

In some of the embodiments, Y is selected from: O.

In some of the embodiments, $R_1$, $R_2$ are each independently selected from the group consisting of: H, C1-C6 alkyl, C1-C6 alkoxy, and halogen;

$R_3$, $R_4$ are each independently selected from the group consisting of: H, C1-C6 alkyl, C1-C6 alkoxy, and halogen; or $R_3$, $R_4$ are bonded to form a 3-8 membered carbocyclic ring;

$R_5$ is selected from: $OR_6$: in which $R_6$ is selected from the group consisting of: H and C1-C6 alky;

Y is selected from the group consisting of: O and S;

ring A is selected from the group consisting of:

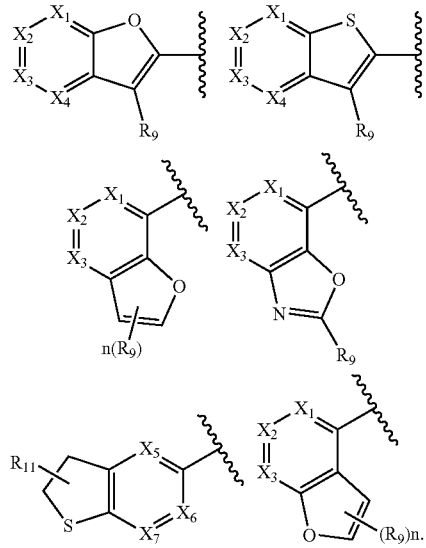

$X_1$, $X_2$, $X_3$, $X_4$, $X_5$, $X_6$, $X_7$ are each independently selected from the group consisting of: $CR_9$, $CR_{12}$ and N, and at least one of $X_1$, $X_2$, $X_3$, and $X_4$ is $CR_{12}$:

$R_9$ is selected from the group consisting of: H, halogen, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, nitro, cyano, —OR, —N(R)$_2$, —SR, —C(O)OR, —C(O)N(R)$_2$, —C(O)R, —S(O)R, —S(O)$_2$R, —S(O)$_2$N(R)$_2$, and —N(R)C(O)R;

$R_{10}$ is selected from the group consisting of: H, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, and C1-C4 alkylamino-substituted C1-C6 alkyl;

$R_{11}$ is selected from the group consisting of: H, —SR, —OR, —N(R)$_2$, and C1-C6 alkyl;

$R_{12}$ is selected from the group consisting of: H, —SR, —OR, —N(R)$_2$, and C1-C6 alkyl;

n is selected from the group consisting of: 0, 1, and 2;

each of R is selected from the group consisting of: H, C1-C6 alkyl, C3-C8 cycloalkyl C3-C8 cycloalkylmethyl and halogen-substituted C1-C6 alkoxy;

In some of the embodiments, $R_1$, $R_2$ are each independently selected from the group consisting of: C1-C3 alkyl, halogen and C1-C3 alkoxy;

$R_3$, $R_4$ are each independently selected from: C1-C6 alkyl;

$R_5$ is selected from: $OR_6$; in which $R_6$ is selected from: H;

Y is selected from: O;

ring A is selected from the group consisting of:

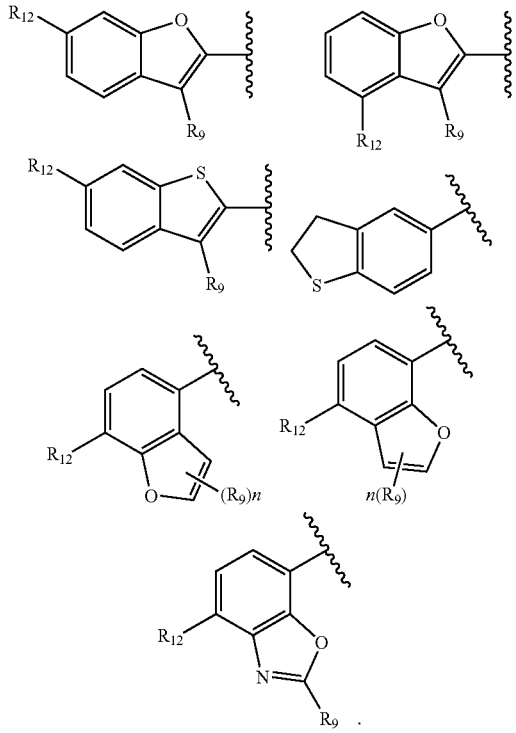

$R_9$ is selected from the group consisting of: H, halogen, C1-C6 alkyl, halogen-substituted C1-C6 alkyl hydroxy-substituted C1-C6 alkyl, alkoxy-substituted C1-C6 alkyl, —OR, —N(R), —SR, —C(O)OR, —C(O)N(R)$_2$, —C(O)R, —S(O)R, —S(O)$_2$R, —S(O)$_2$N(R)$_2$, and —N(R)C(O)R;

$R_{12}$ is selected from the group consisting of: H, —SR, —OR, and C1-C6 alkyl;

n is selected from the group consisting of: 0, and 1;

each of R is selected from the group consisting of: H, C1-C6 alkyl C3-C8 cycloalkyl, C3-C8 cycloalkylmethyl, and halogen-substituted C1-C6 alkyl.

In some of the embodiments, the 1,3-disubstituted ketene compound is selected from the group consisting of:
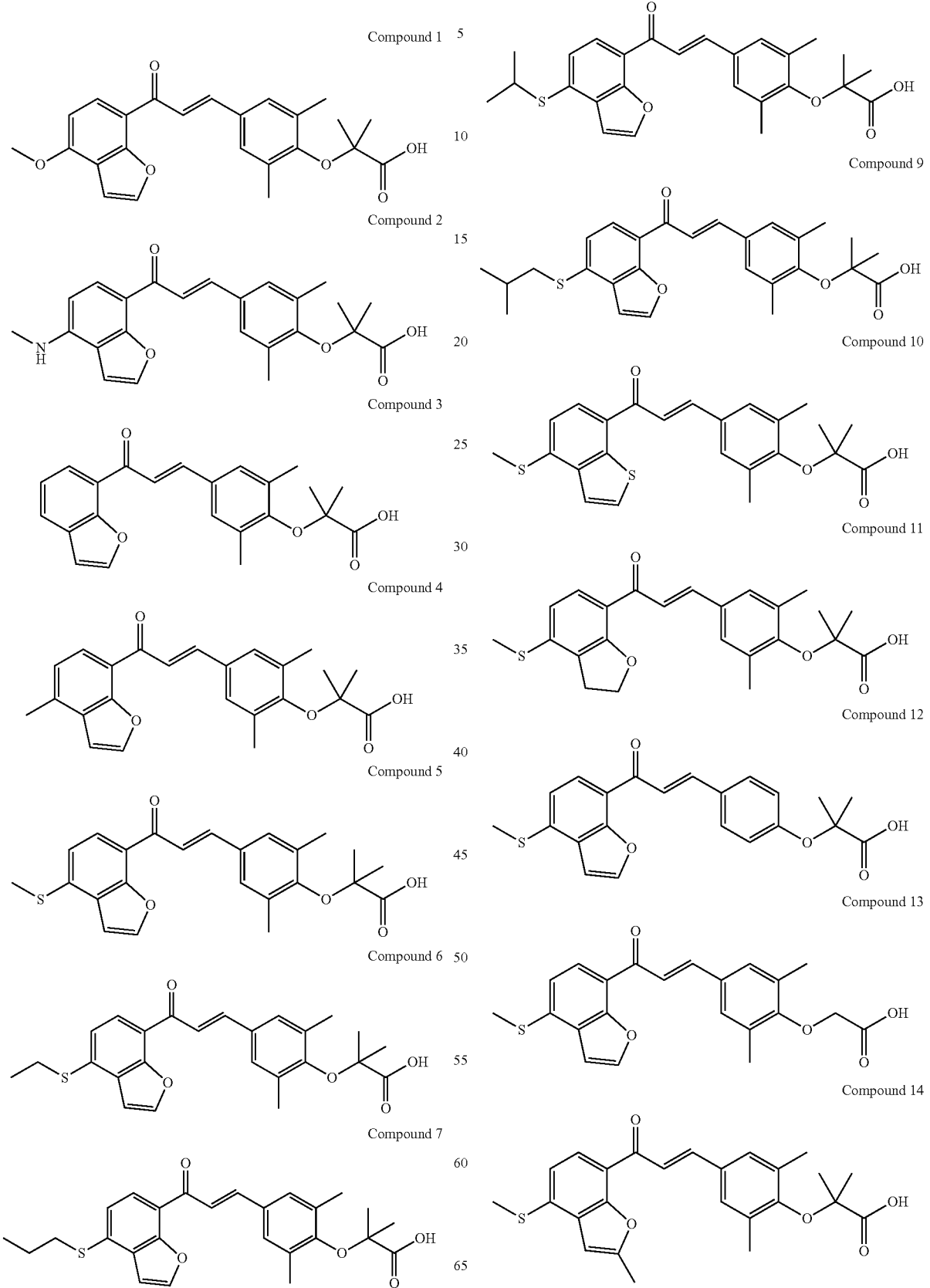

Compound 15
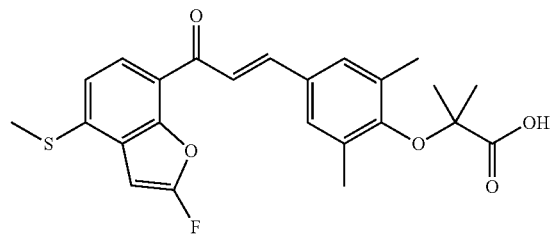
Compound 21
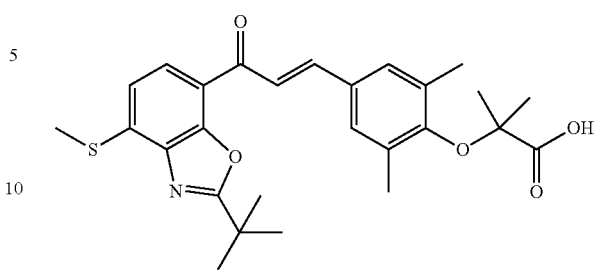
Compound 16
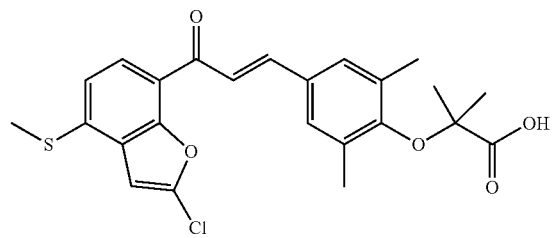
Compound 22
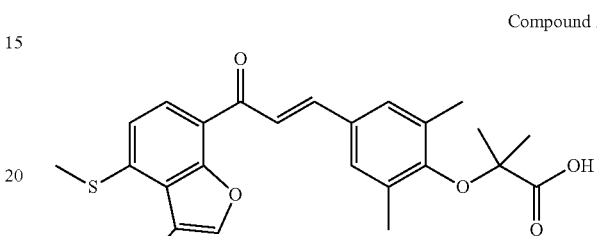
Compound 17
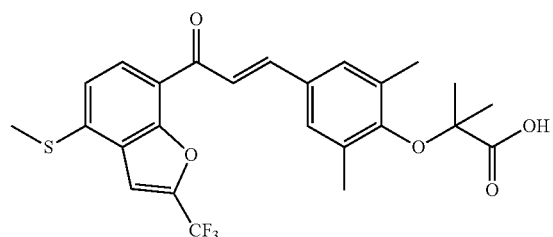
Compound 23
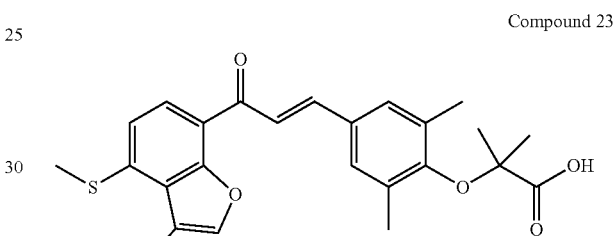
Compound 18
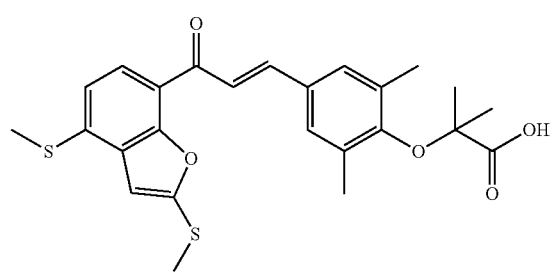
Compound 24
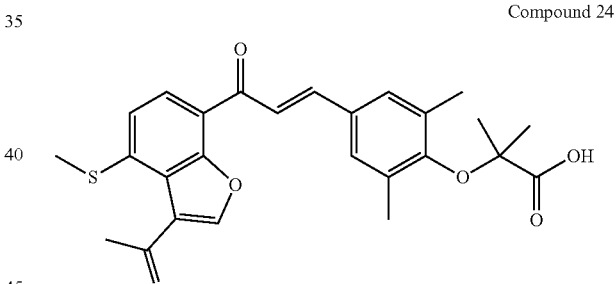
Compound 19
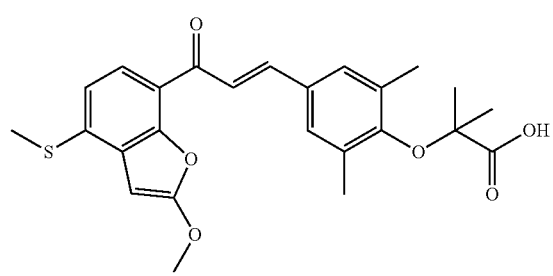
Compound 25
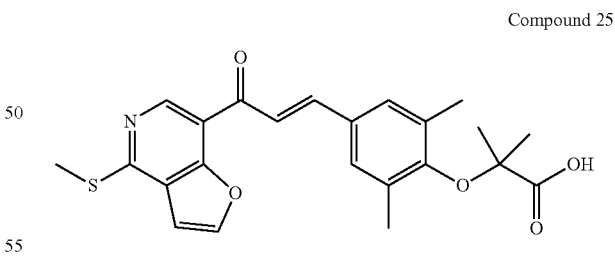
Compound 20
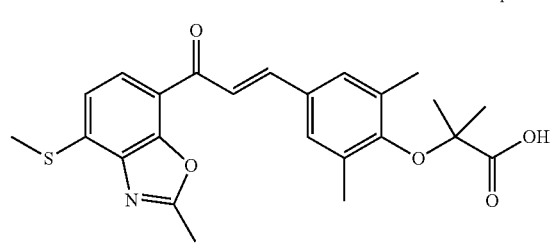
Compound 26
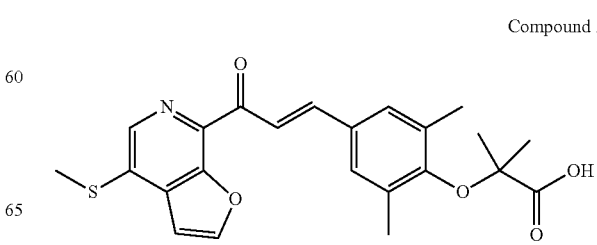

Compound 27
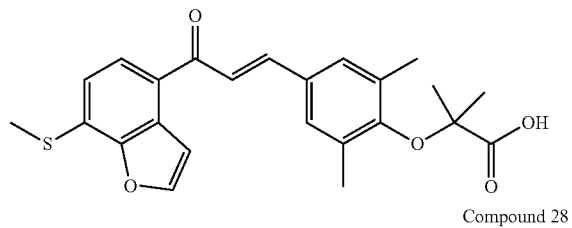
Compound 28
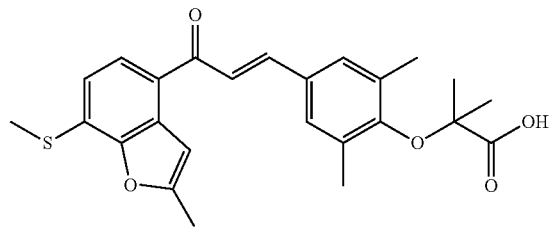
Compound 29
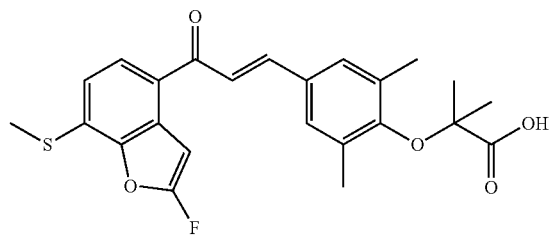
Compound 30
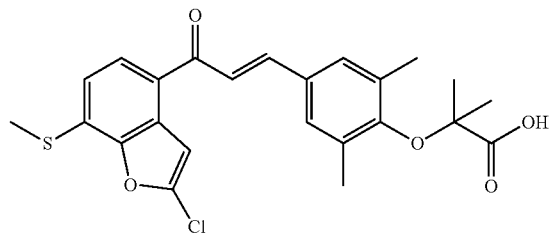
Compound 31
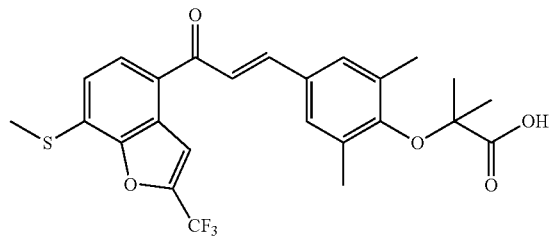
Compound 32
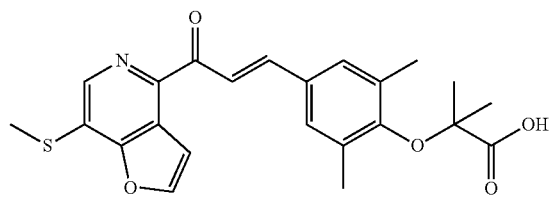
Compound 33
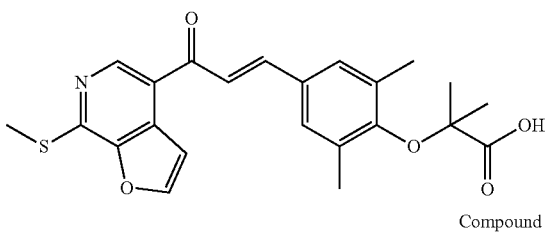
Compound 34
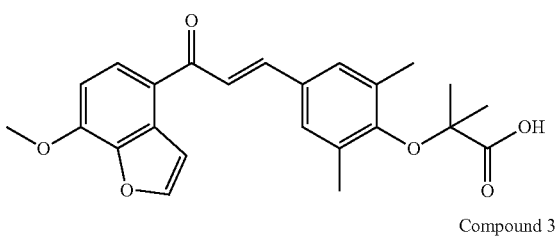
Compound 35
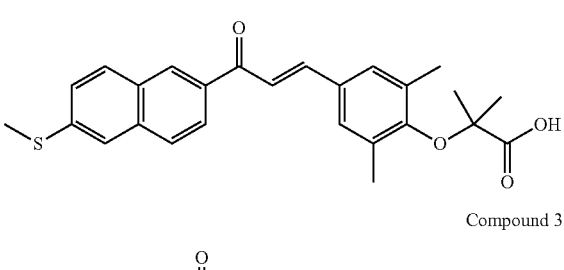
Compound 36
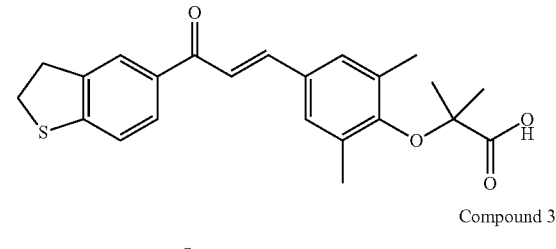
Compound 37
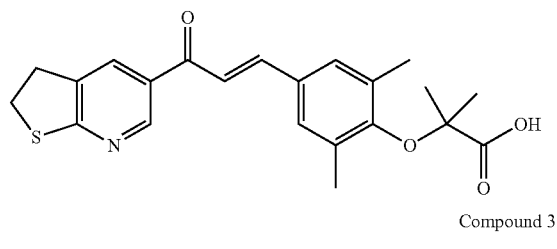
Compound 38
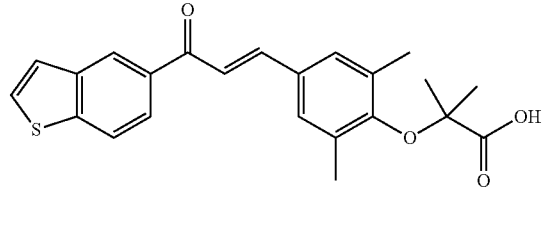
Compound 39

Compound 40
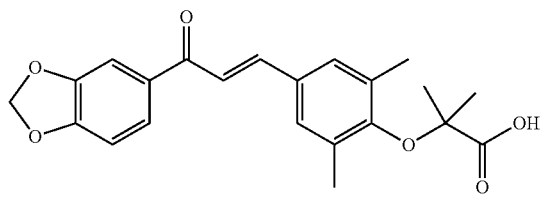
Compound 41
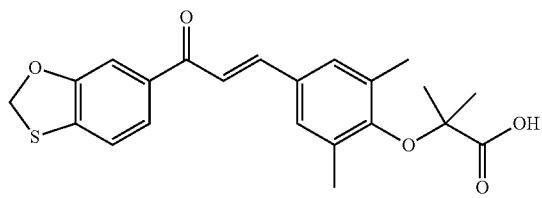
Compound 42
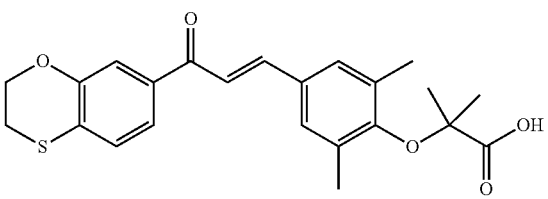
Compound 43
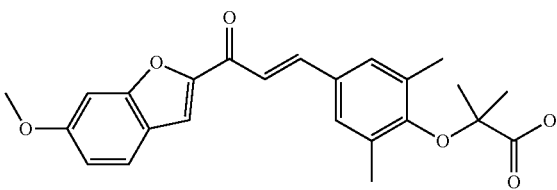
Compound 44
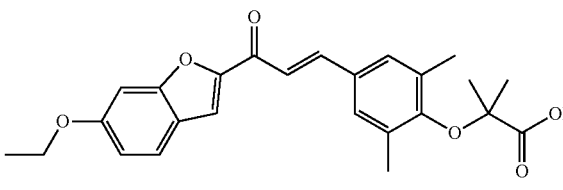
Compound 45
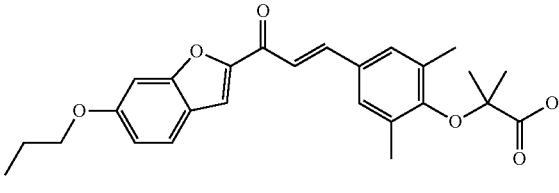
Compound 46
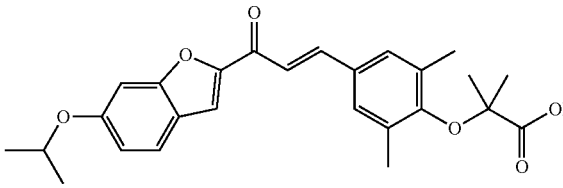
Compound 47
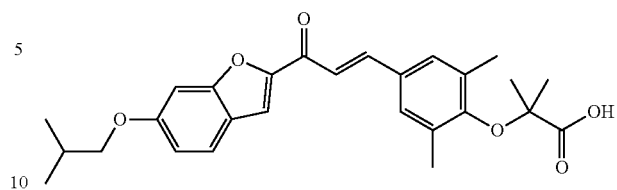
Compound 48
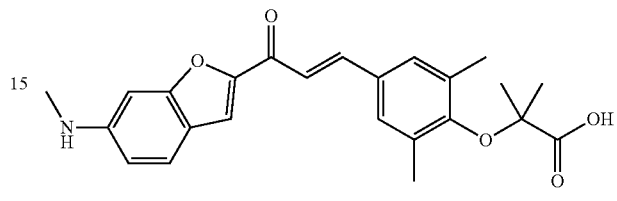
Compound 49
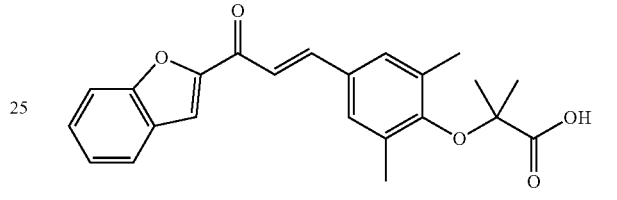
Compound 50
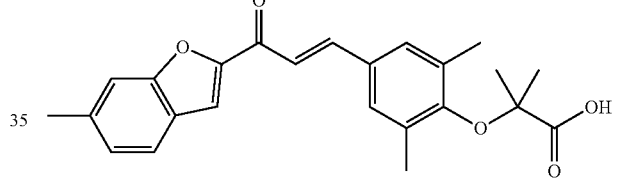
Compound 51
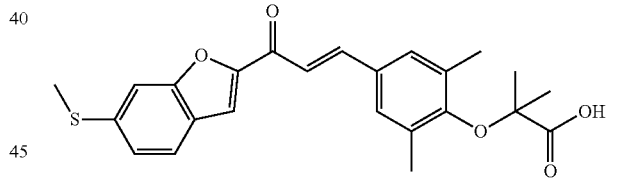
Compound 52
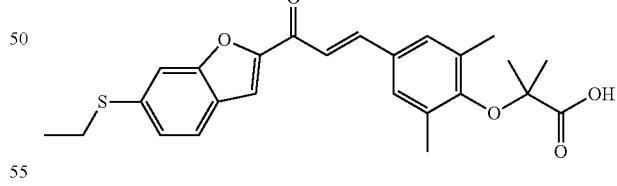
Compound 53
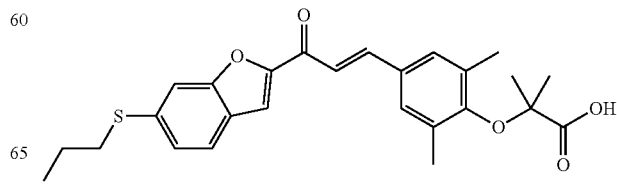

Compound 54
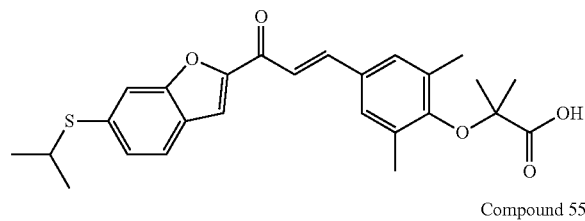
Compound 55
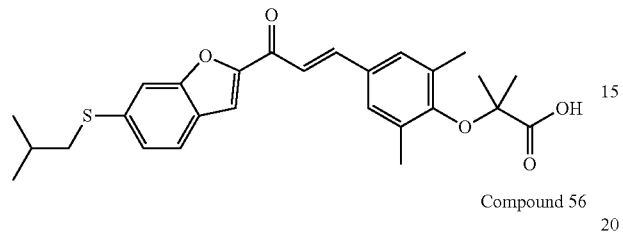
Compound 56
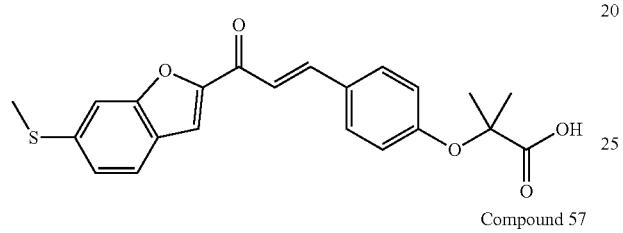
Compound 57
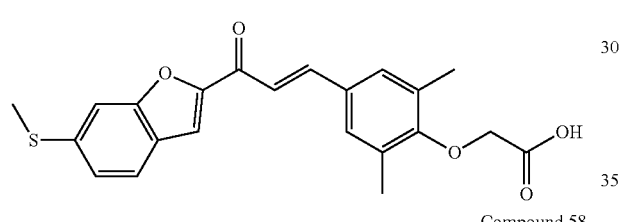
Compound 58
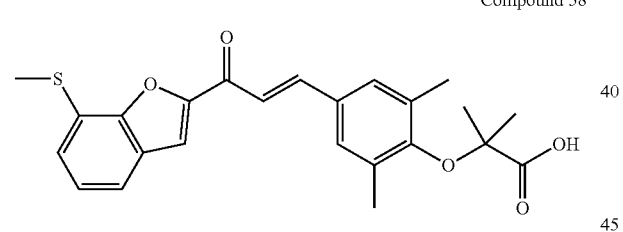
Compound 59
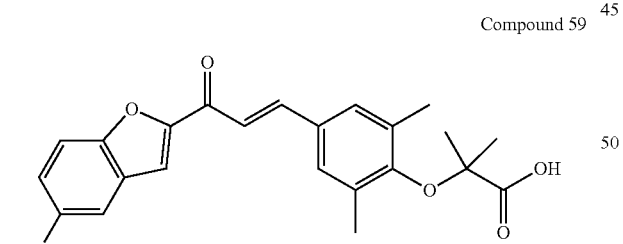
Compound 60
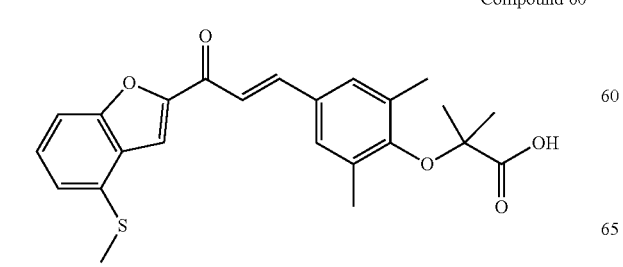
Compound 61
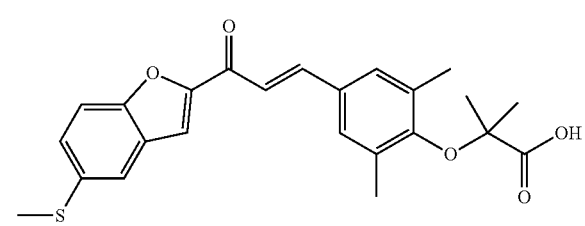
Compound 62
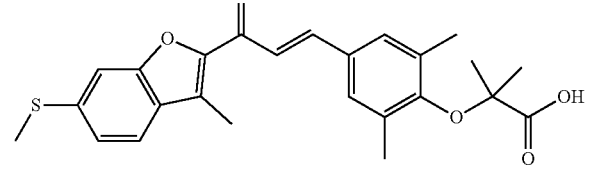
Compound 63
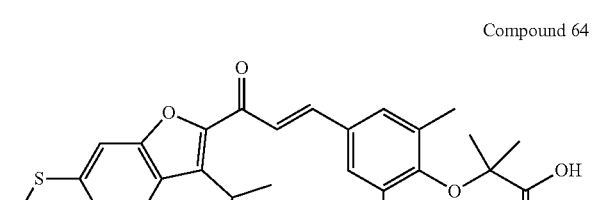
Compound 64
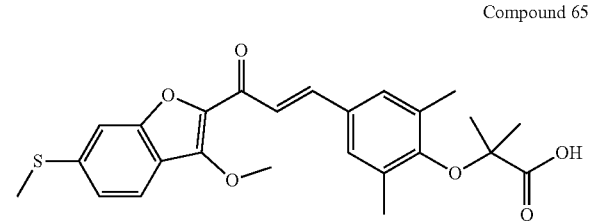
Compound 65
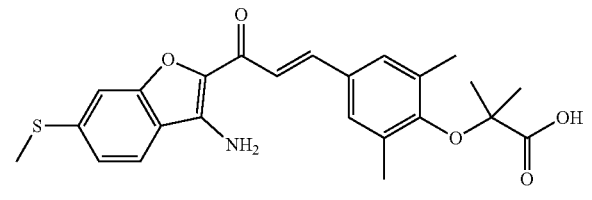
Compound 66
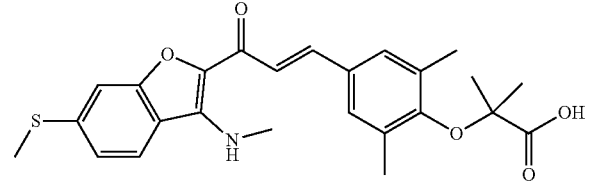
Compound 67

Compound 68
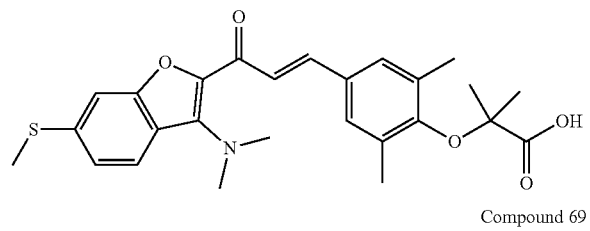
Compound 69
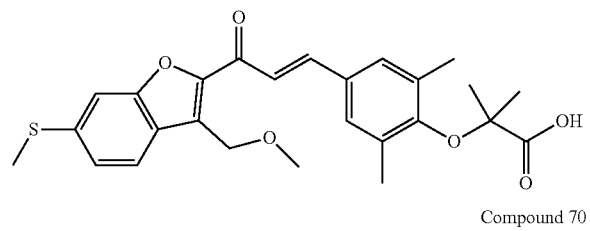
Compound 70
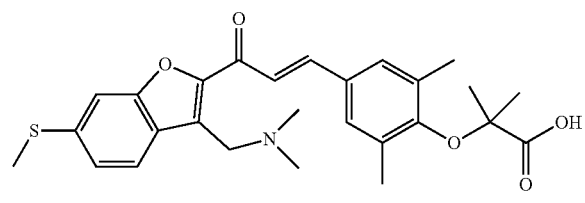
Compound 71
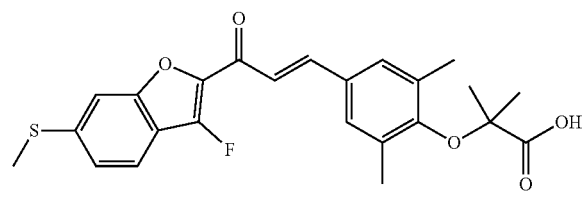
Compound 72
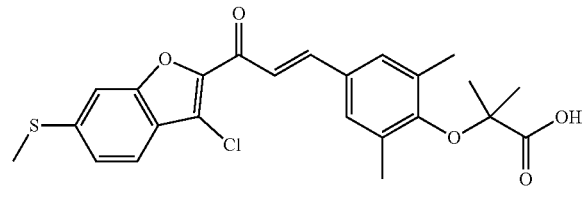
Compound 73
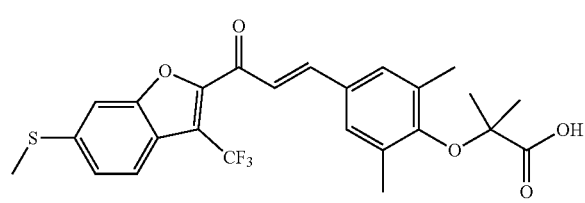
Compound 74
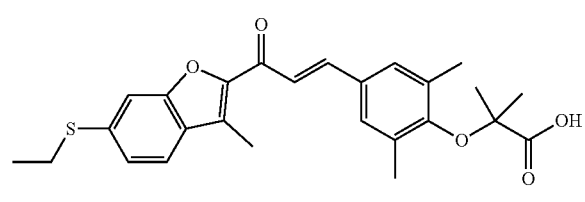
Compound 75
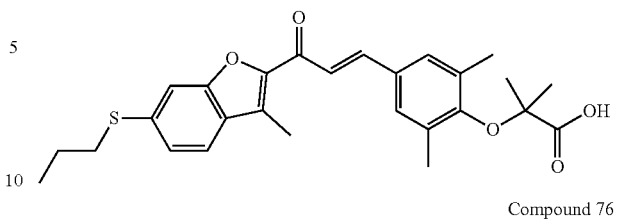
Compound 76
Compound 77
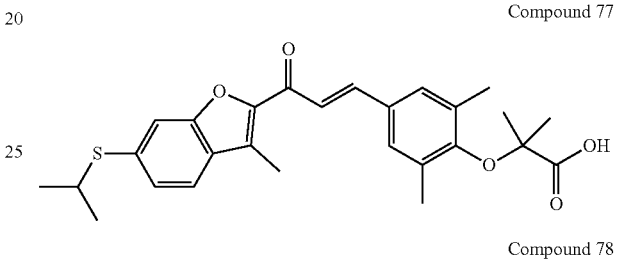
Compound 78
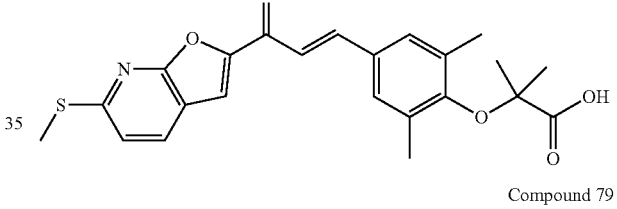
Compound 79
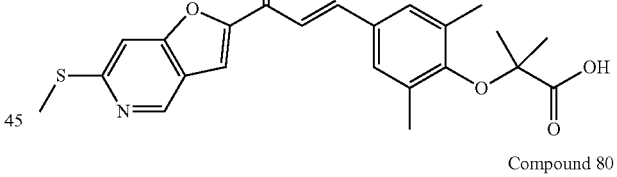
Compound 80
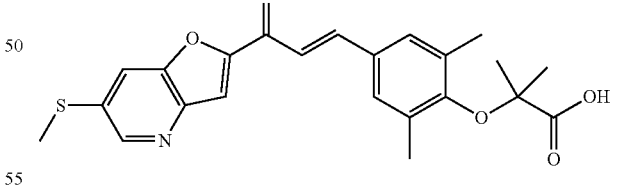
Compound 81
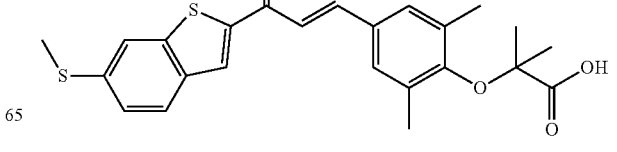

Compound 82
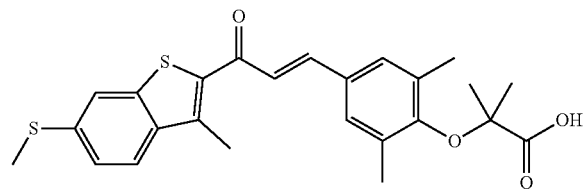
Compound 83
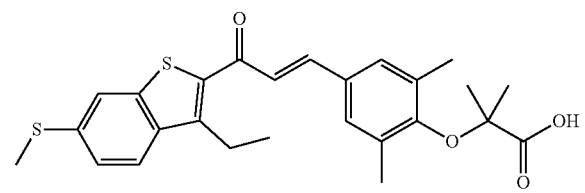
Compound 84
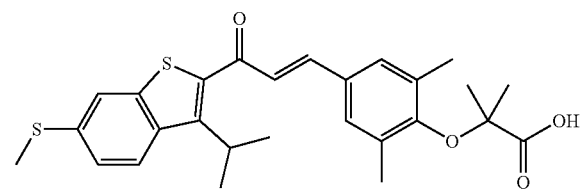
Compound 85
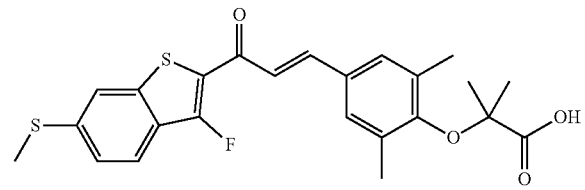
Compound 86
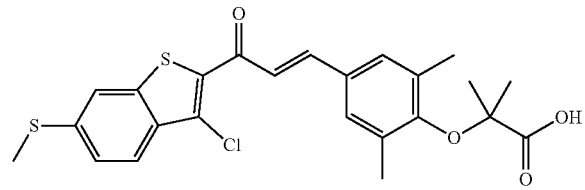
Compound 87
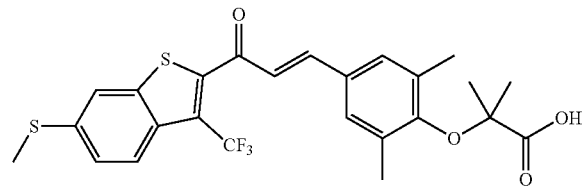
Compound 88
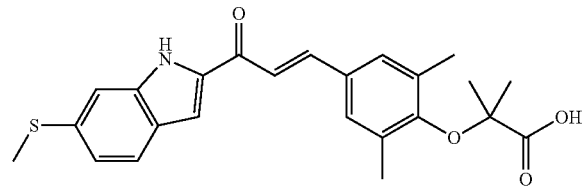
Compound 89
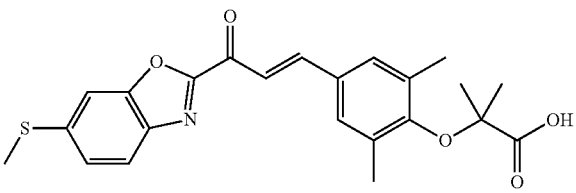
Compound 90
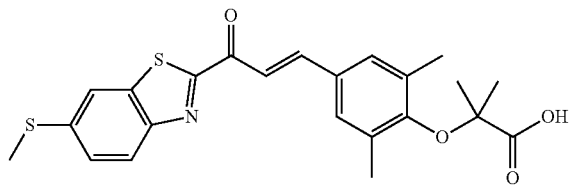
Compound 91
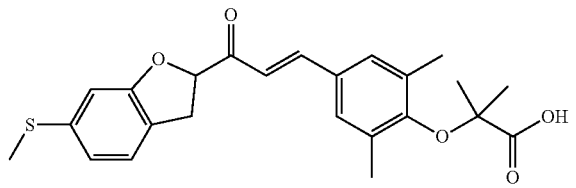
Compound 92
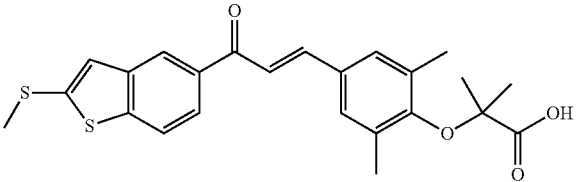
Compound 93
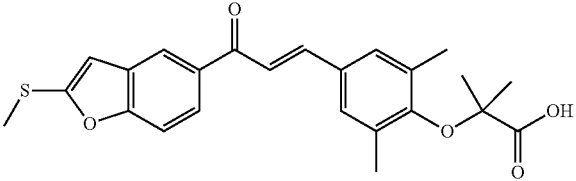
Compound 94
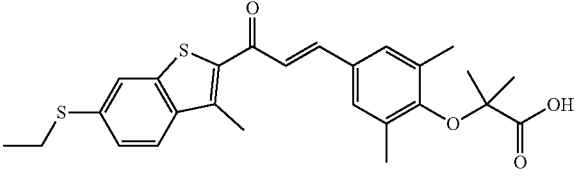
Compound 95
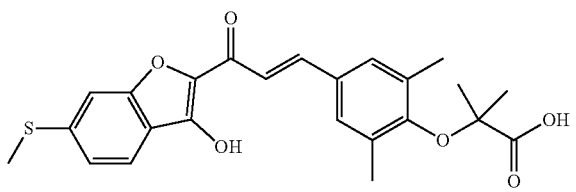

Compound 96
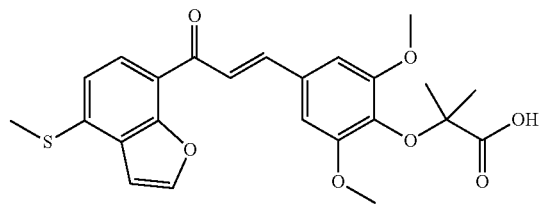
Compound 97
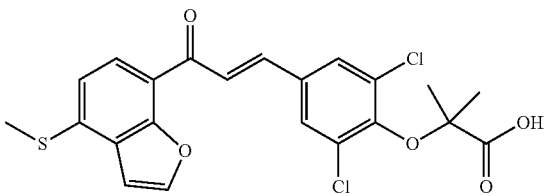
Compound 98
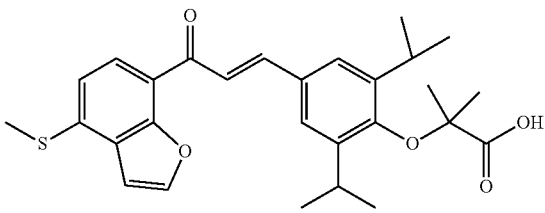
Compound 99
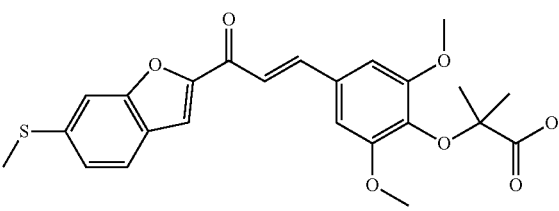
Compound 100
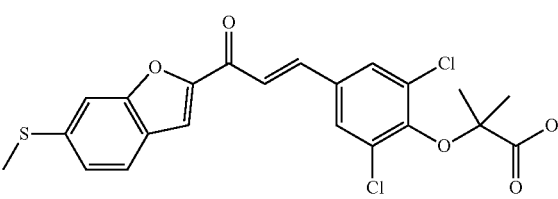
Compound 101
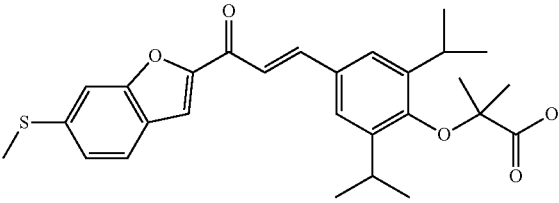
Compound 102
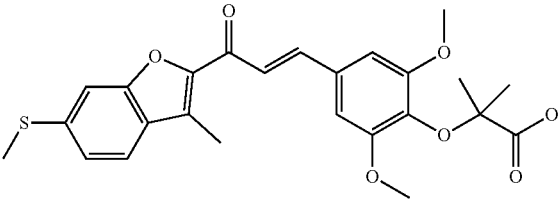
Compound 103
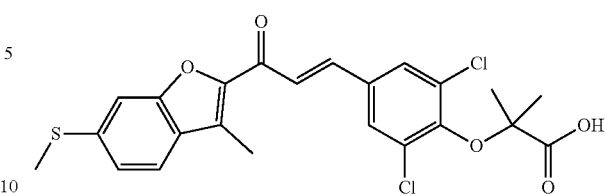
Compound 104
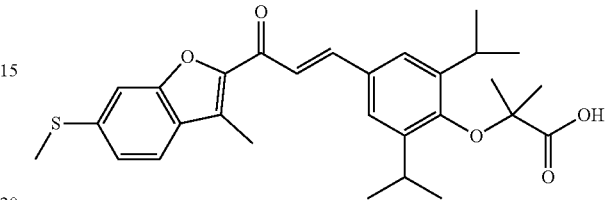
Compound 105
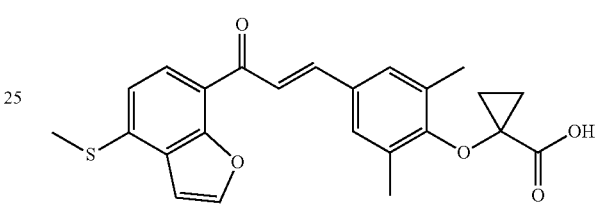
Compound 106
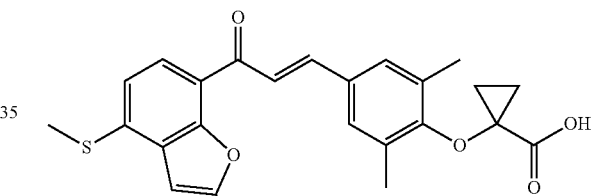
Compound 107
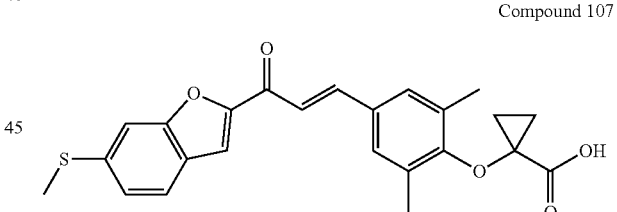
Compound 108
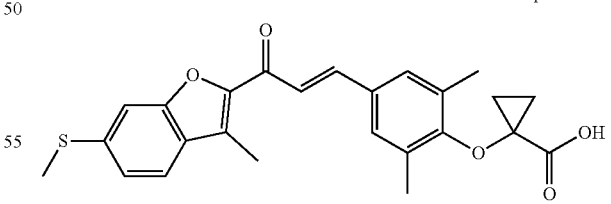
Compound 109
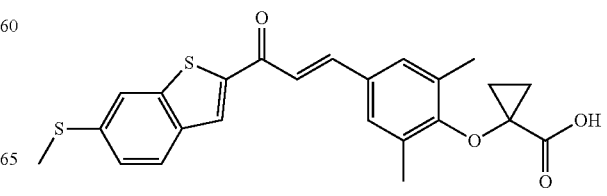

Compound 110

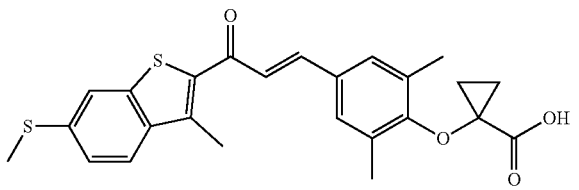

Compound 111

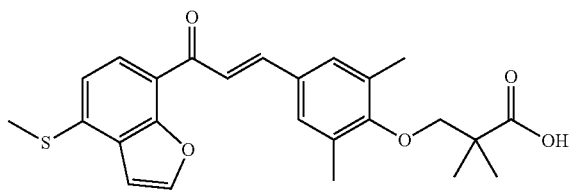

Compound 112

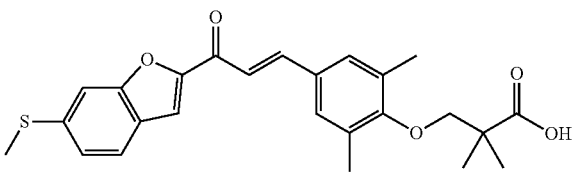

Compound 113

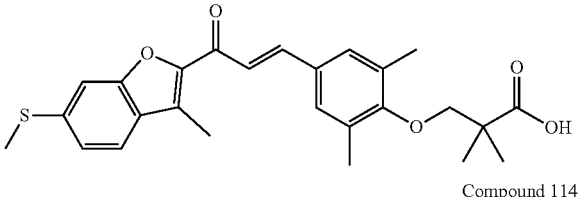

Compound 114

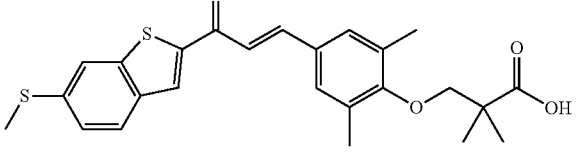

Compound 115

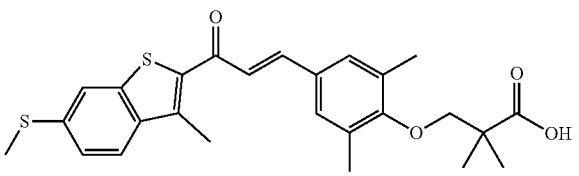

Compound 116

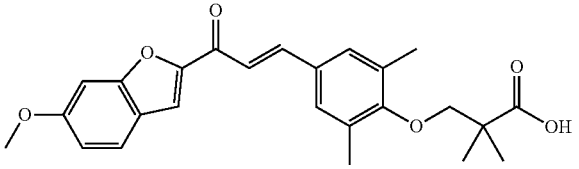

Compound 117

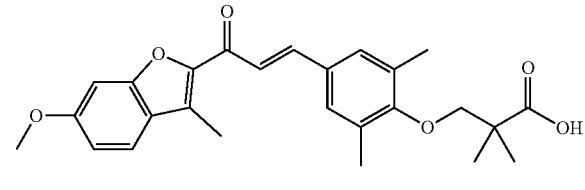

The present disclosure also provides the use of the above 1,3-disubstituted ketene compound or a pharmaceutically acceptable salt thereof or a stereoisomer thereof or a prodrug molecule thereof.

The specific technical solutions are as follows:

The use of the above 1,3-disubstituted ketene compound or a pharmaceutically acceptable salt thereof or a stereoisomer thereof or a prodrug molecule thereof for the preparation of a PPAR agonist.

The use of the above 1,3-disubstituted ketene compound or a pharmaceutically acceptable salt thereof or a stereoisomer thereof or a prodrug molecule thereof for preventing or treating a disease associated with abnormal regulation of PPAR; and the disease associated with abnormal regulation of PPAR includes a disease associated with abnormal metabolism of lipid and glucose, a disease associated with inflammation and abnormal fibrosis, a cardiovascular disease, a kidney disease, and a degenerative brain disease.

In some of the embodiments, the disease associated with abnormal regulation of PPAR includes: non-alcoholic fatty liver disease, nonalcoholic hepatitis, cholestatic liver disease, diabetes, obesity, heart failure, atherosclerosis, chronic kidney disease, renal failure, and Alzheimers disease.

The present disclosure also provides a pharmaceutical composition for preventing or treating a disease associated with abnormal regulation of PPAR.

The specific technical solutions are as follows:

A pharmaceutical composition for preventing or treating a disease associated with abnormal regulation of PPAR, in which an active ingredient comprising the above-mentioned 1,3-disubstituted ketene compound or a pharmaceutically acceptable salt thereof or a stereoisomer thereof or a prodrug molecule thereof.

The above 1,3-disubstituted ketene compound or a pharmaceutically acceptable salt thereof or a stereoisomer thereof or a prodrug molecule thereof can be prepared into a pharmaceutical composition in various corresponding dosage forms together with a pharmaceutically acceptable adjuvant or carrier. It can also be used in combination with other drugs with PPAR agonistic activity to enhance the agonistic activity of PPAR.

The 1,3-disubstituted ketene compounds provided by the present disclosure have an activity of modulating a PPAR agonist, and such compounds mainly activate PPARα and also have agonistic activity against PPPAδ and PPPAγ. It can be used to treat various diseases associated with abnormal regulation of PPAR, such as non-alcoholic fatty liver disease (NAFLD), especially non-alcoholic steatohepatitis (NASH), and also has a potential to treat diabetes, obesity, fibrotic diseases, cardiovascular diseases (including heart failure and atherosclerosis, etc.), kidney diseases (including chronic kidney disease and renal failure, etc.), degenerative brain diseases (including Alzheimers disease, etc.), thereby having greater application value.

BRIEF DESCRIPTION OF THE DRAWINGS

FIG. 1 is a graph showing the measurement results of the blood concentration of compounds 5, 62, 100, 103 and Elafibranor after intragastric administration (20 mg/kg) in rats.

DETAILED DESCRIPTION OF THE EMBODIMENTS

The present disclosure is further explained in the following with reference to the specific embodiments and the accompanying drawings, but without limiting the present disclosure.

In the compounds of the present disclosure, when any variable (e.g., $R_1$, R, etc.) occurs more than once in any of the components, the definition at each occurrence is independent of the definition at other occurrences. Also, combinations of substituents and variables are allowed as long as such combinations stabilize the compound. A line drawn from a substituent into the ring system means that the indicated bond can be attached to any ring atom that can be substituted. It will be appreciated that one of ordinary skill in the art can select substituents and substitution patterns for the compounds of the present disclosure to provide compounds which are chemically stable and which are readily synthesized from the readily available starting materials by techniques in the art and from the methods set forth below. If the substituent itself is substituted by more than one group, it is understood that these groups may be on the same carbon atom or on different carbon atoms as long as the structure is stabilized.

The term "alkyl" as used herein is meant to include branched and straight saturated aliphatic hydrocarbon groups having a specified number of carbon atoms. For example, the definition of "$C_1$-$C_6$" in "$C_1$-$C_6$ alkyl" includes a group having 1, 2, 3, 4, 5 or 6 carbon atoms arranged in a straight chain or a branched chain. The term "cycloalkyl" refers to a monocyclic saturated aliphatic hydrocarbon group having a specified number of carbon atoms. For example, "cycloalkyl" includes cyclopropyl, methyl-cyclopropyl, 2,2-dimethyl-cyclobutyl, 2-ethylcyclopentyl, cyclohexyl and the like.

The term "alkoxy" refers to a group in which an alkyl group is directly attached to oxygen, such as methoxy, ethoxy, and the like.

The term "alkylthio" refers to a group in which an alkyl group is directly attached to sulfur.

The term "C1-C4 alkylamino-substituted C1-C6 alkyl" means that a group in which an alkyl group having 1, 2, 3 or 4 carbon atoms is bonded to a nitrogen atom and the nitrogen atom is bonded to an alkyl group having 1, 2, 3, 4, 5 or 6 carbon atoms, for example, a methylaminomethyl, a methylaminoethyl, a dimethylaminomethyl and the like.

The term "heterocycle" includes saturated heteroatom-containing cycloalkyl and heteroaryl, wherein the hetero atom may be selected from the group consisting of nitrogen, sulfur and oxygen and any oxidized form of nitrogen, sulfur, or phosphorus, preferably a saturated heterocyclic ring containing N, such as piperidine and the like.

The term "substituted" refers to the replacement of hydrogen radical in a particular structure with a group of the specified substituent.

The term "heterocycle" or "heterocyclyl" refers to an aromatic or non-aromatic heterocyclic ring containing 1 to 4 heteroatoms selected from the group consisting of O, N and S, and includes bicyclic groups. "Heterocyclyl" thus includes heteroaryl, as well as dihydrogenated and tetrahydrogenated analogs thereof. The attachment of a heterocyclic substituent can be achieved by a carbon atom or by a hetero atom.

As it is understood by those skilled in the art, "halogen" as used herein is meant to include chloro, fluoro, bromo and iodo.

The present disclosure includes the free forms of the compounds of formula I to formula II, as well as the pharmaceutically acceptable salts and stereoisomers thereof. The pharmaceutically acceptable salts of the present disclosure can be synthesized from the compounds of the present disclosure containing a basic moiety or an acidic moiety by conventional chemical methods. Typically, the salt of the basic compound is prepared by ion exchange chromatography or by reaction of a free base with a stoichiometric amount or excess amount of the inorganic or organic acid in the desired salt in a suitable solvent or combination of solvents. Similarly, a salt of an acidic compound is formed by reaction with a suitable inorganic or organic base.

Thus, the pharmaceutically acceptable salts of the compounds of the present disclosure include conventional non-toxic salts of the compounds of the present disclosure which are formed by the reaction of a basic compound of the present disclosure with an inorganic or organic acid. For example, the conventional non-toxic salts include those prepared from inorganic acids such as hydrochloric acid, hydrobromic acid, sulfuric acid, sulfamic acid, phosphoric acid, nitric acid, and the like, and also include those prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, p-aminobenzenesulfonic acid, 2-acetoxy-benzoic acid, fumaric acid, toluenesulfonic acid, methanesulfonic acid, ethanedisulfonic acid, oxalic acid, isethionic acid, trifluoroacetic acid and the like.

If the compound of the present disclosure is acidic, a suitable "pharmaceutically acceptable salt" refers to a salt prepared by pharmaceutically acceptable non-toxic bases including inorganic bases and organic bases. Salts derived from inorganic bases include aluminum salts, ammonium salts, calcium salts, copper salts, iron salts, ferrous salts, lithium salts, magnesium salts, manganese salts, manganous salts, potassium salts, sodium salts, zinc salts and the like. Ammonium salts, calcium salts, magnesium salts, potassium salts and sodium salts are particularly preferred. Salts derived from pharmaceutically acceptable organic non-toxic bases, include salts of primary, secondary or tertiary amines. Substituted amines include those naturally occurring substituted amines, cyclic amines and basic ion exchange resins, such as arginine, betaine, caffeine, choline. N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, glucosamine, histidine, hydroxycobalamin, isopropylamine, lysine, methylglucamine, morpholine, piperazine, piperidine, pyridine, polyamine resin, procaine, purine, theobromine, triethylamine, trimethylamine, tripropylamine, tromethamine and the like.

In addition to the standard methods known in the literature or exemplified in the experimental procedures, the compounds of the present disclosure can be prepared by the methods of the following synthetic schemes (Schemes 1-6). A better understanding of the compounds and synthetic methods described in the present disclosure can be obtained in conjunction with the synthetic schemes described below. The described synthetic schemes describe the methods that can be used to prepare the compounds of the present disclosure, which are merely illustrative to describe the illustrative schemes but not intended to limit the scope of the present disclosure.

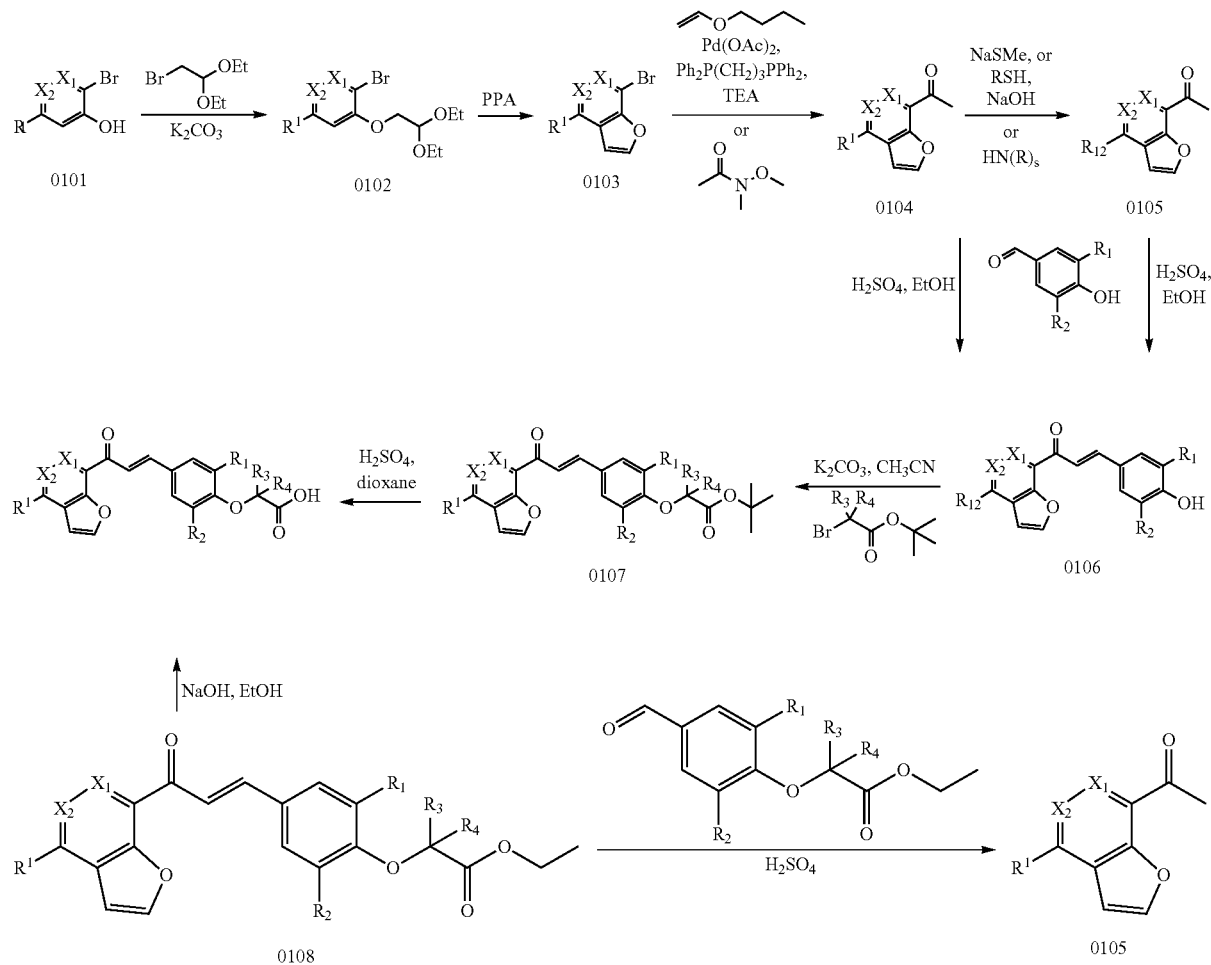
Scheme 1
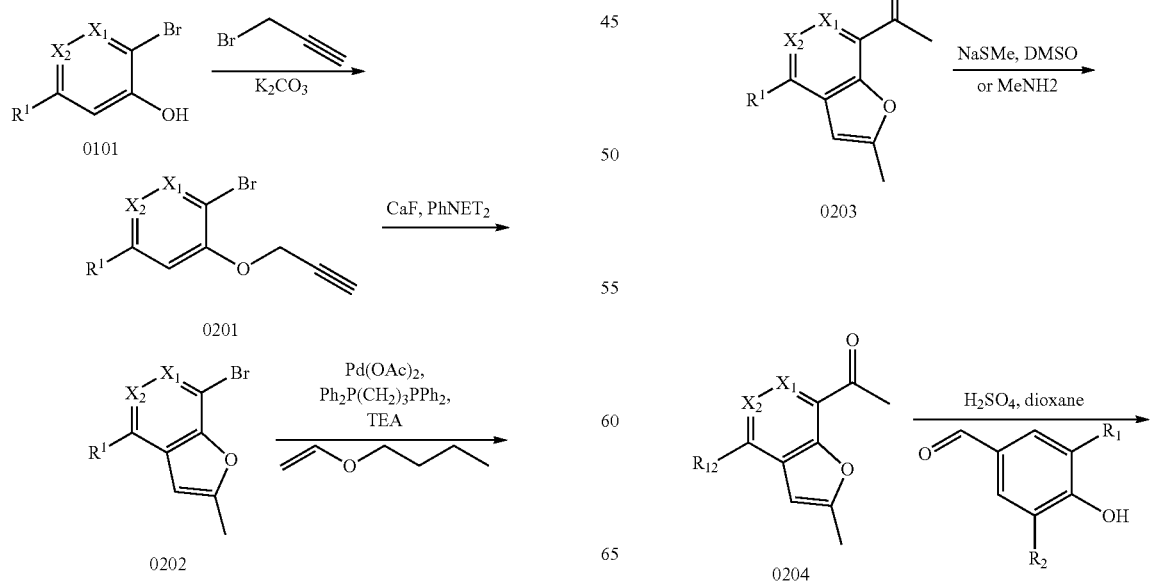
Scheme 2

33
-continued
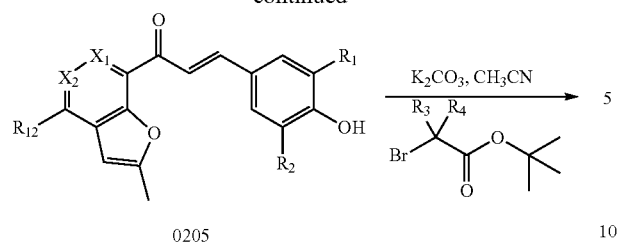
0205
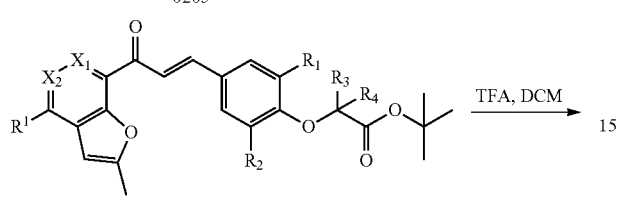
0206
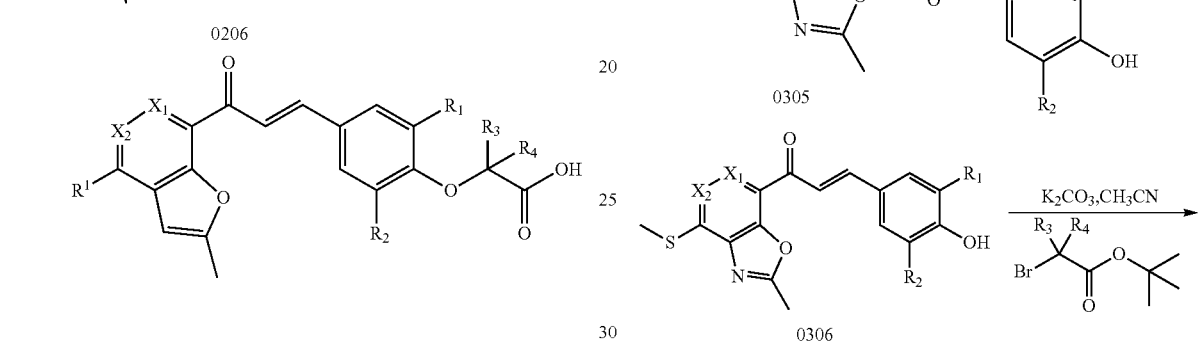
Scheme 3
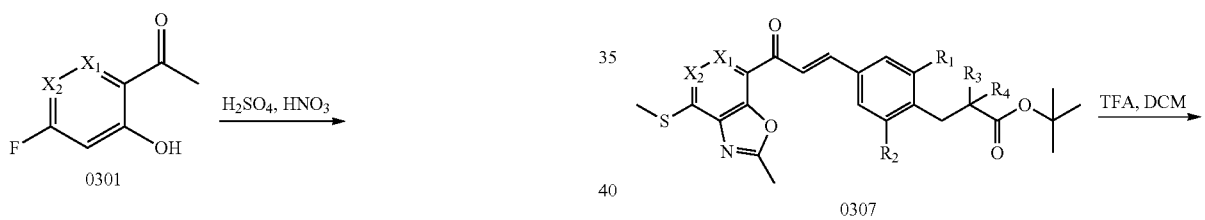
0301
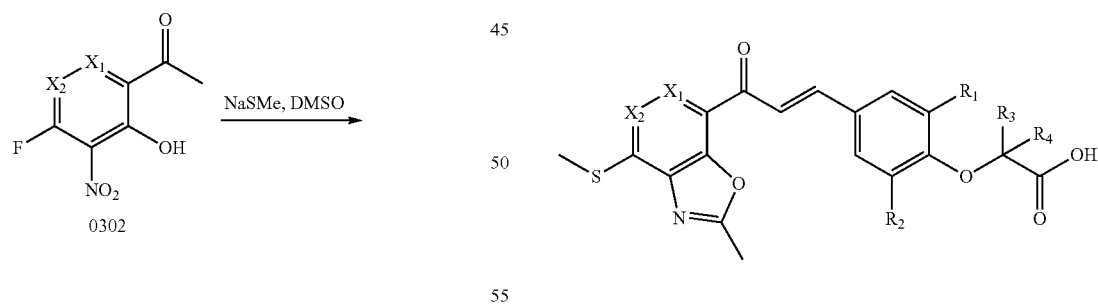
0302
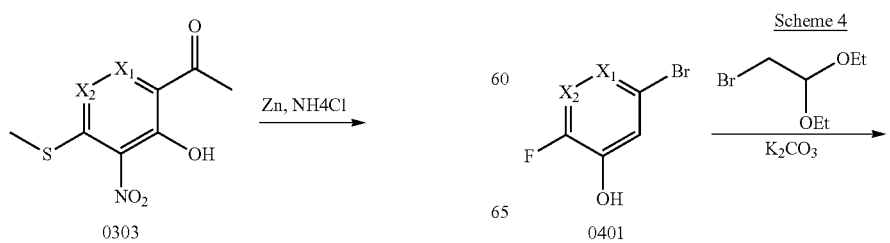
0303
34
-continued
0304
0305
0306
0307
Scheme 4
0401

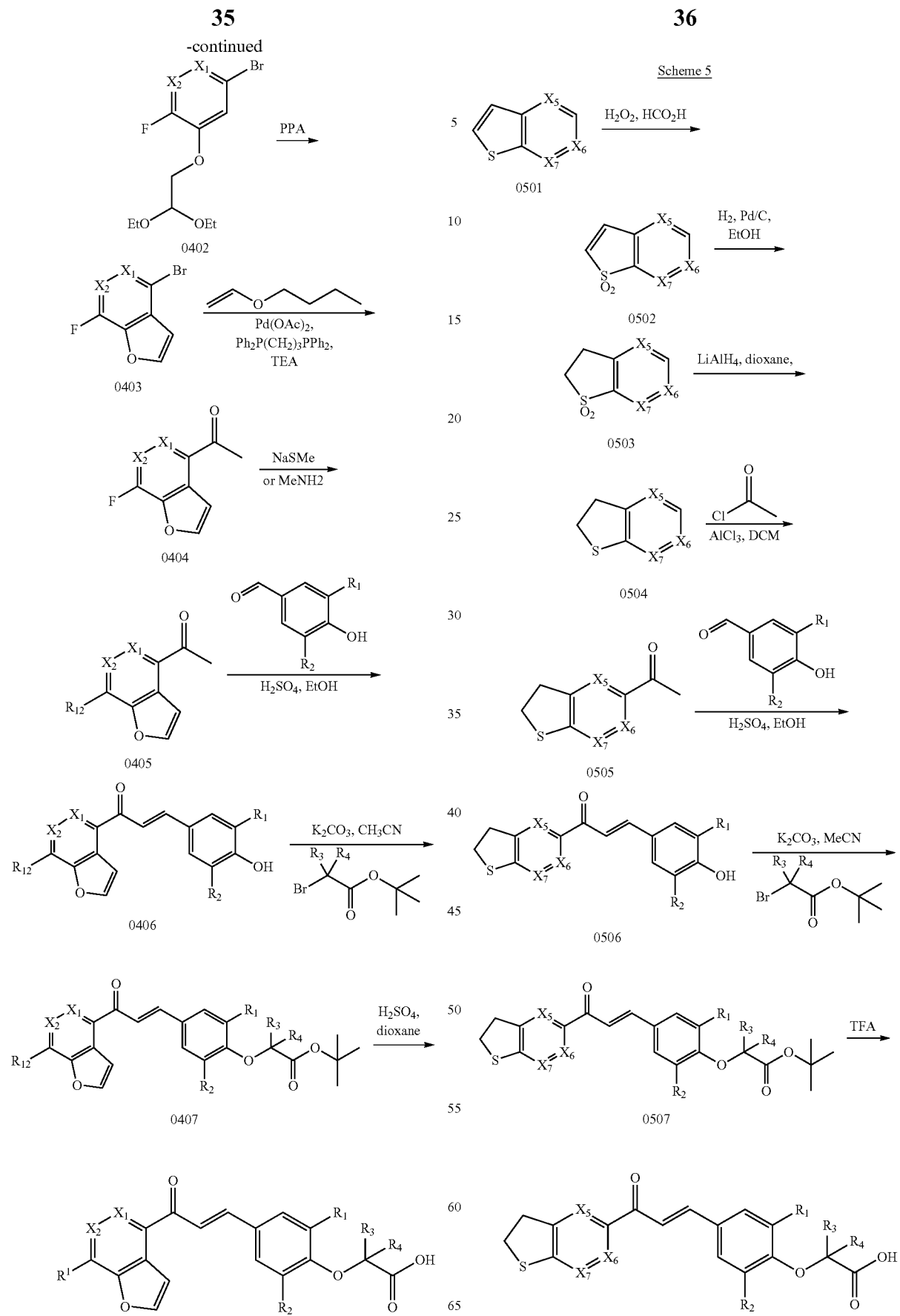

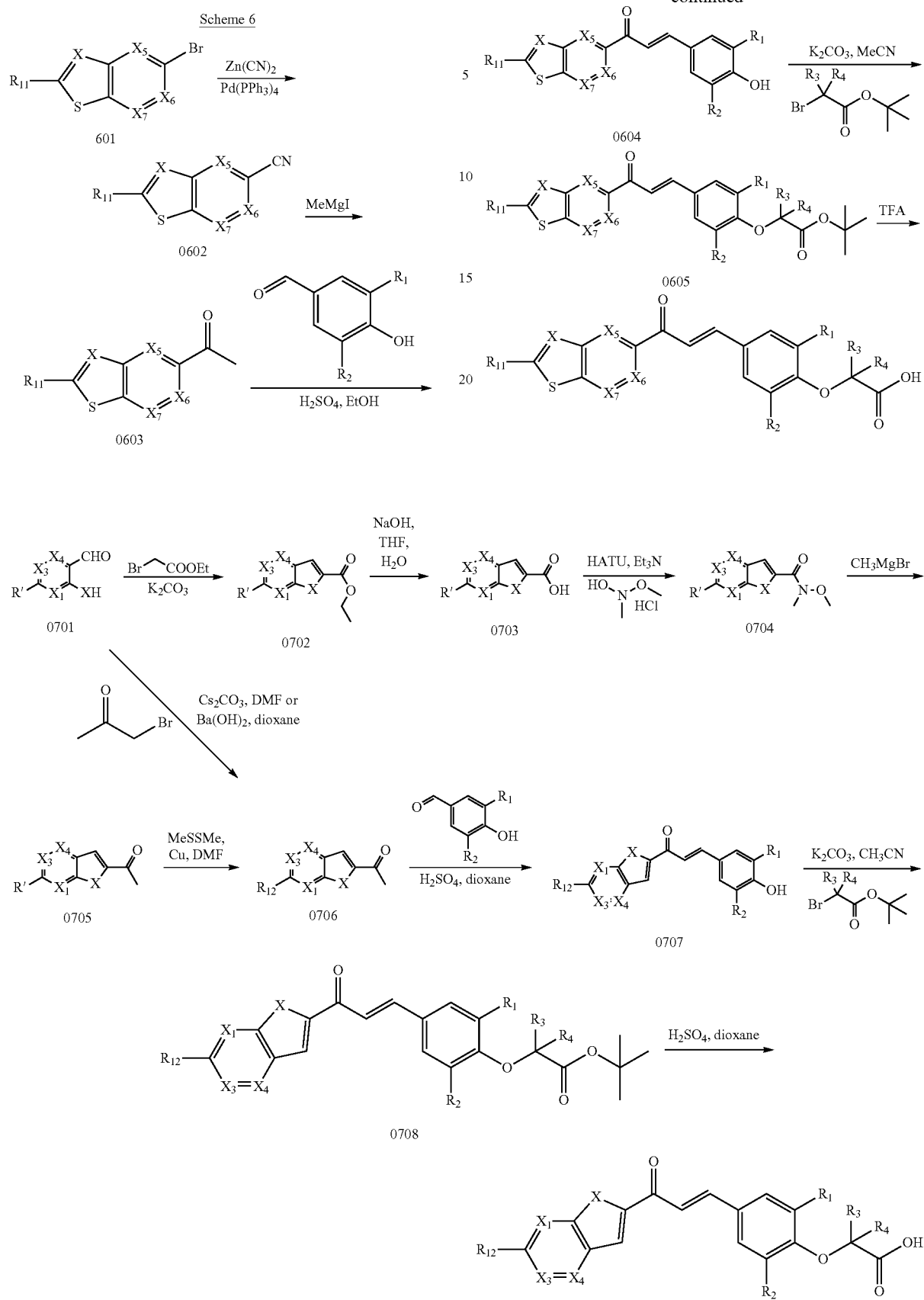

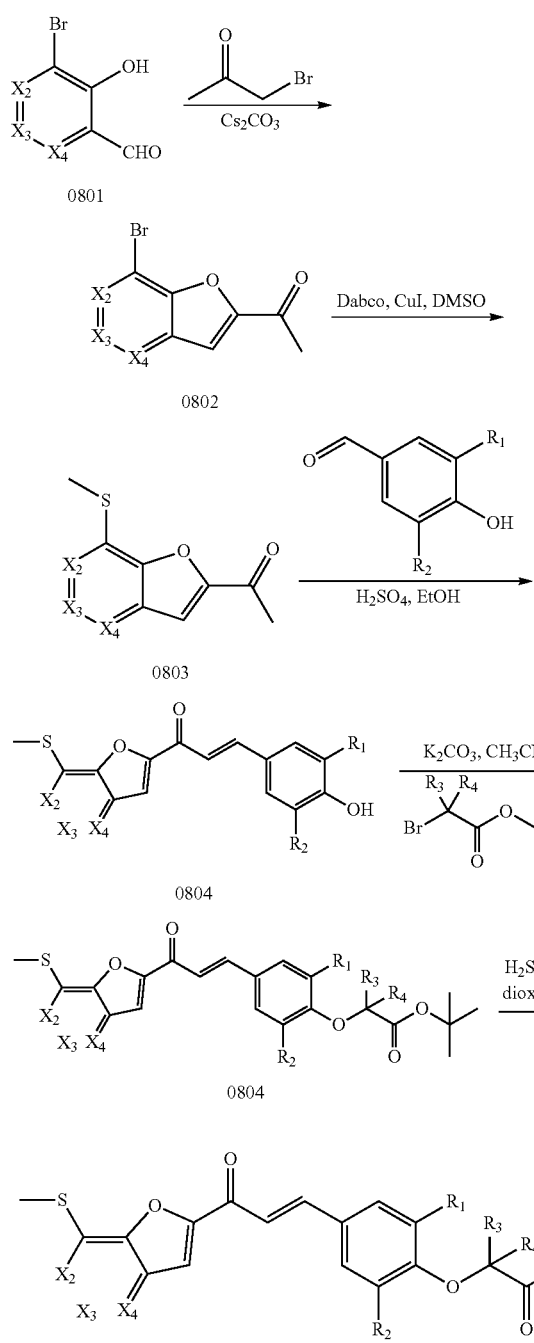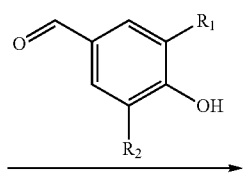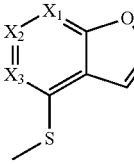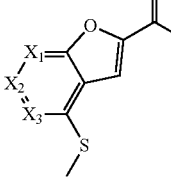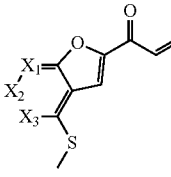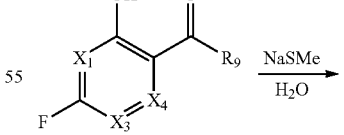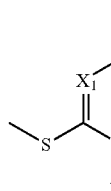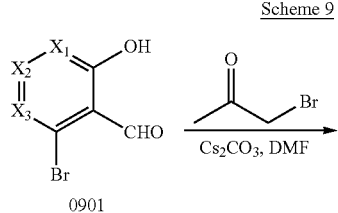

-continued
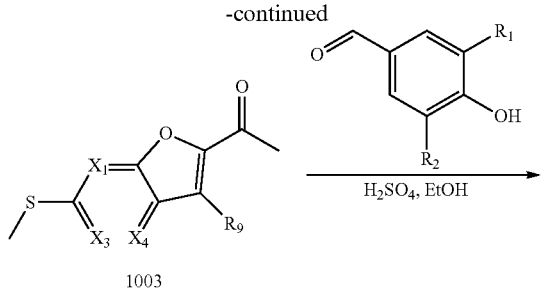
1003
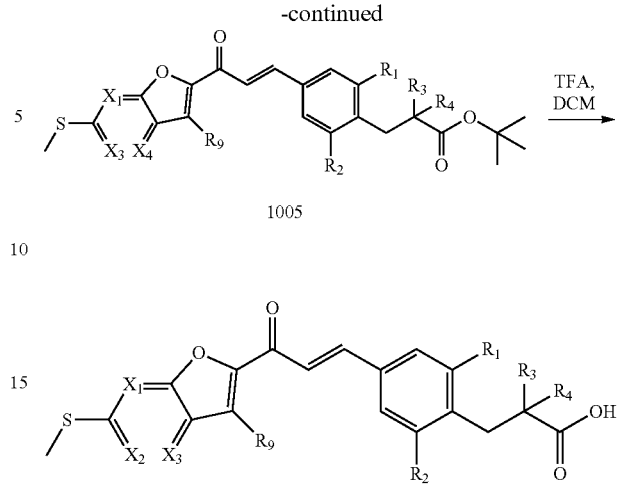
1005
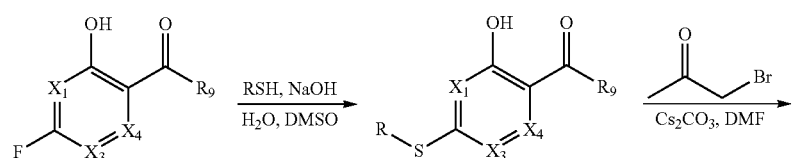
1004
Scheme 11
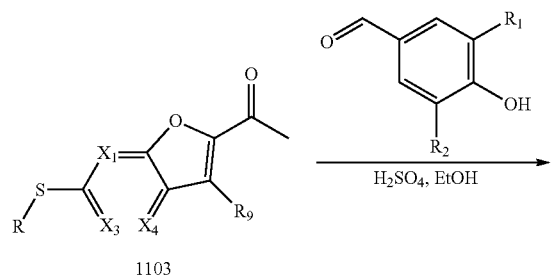
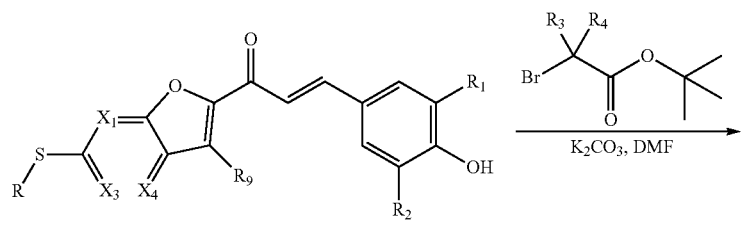
1103
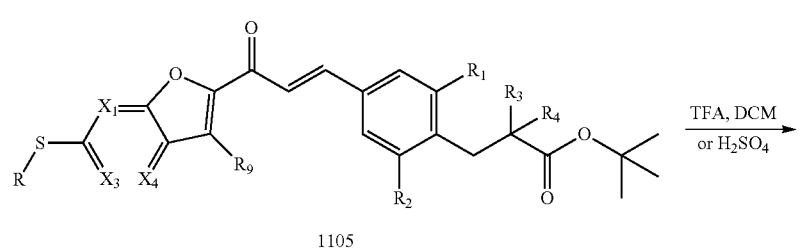
1104
1105

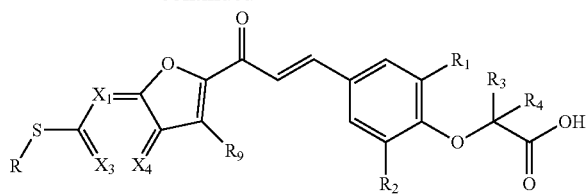
Scheme 12
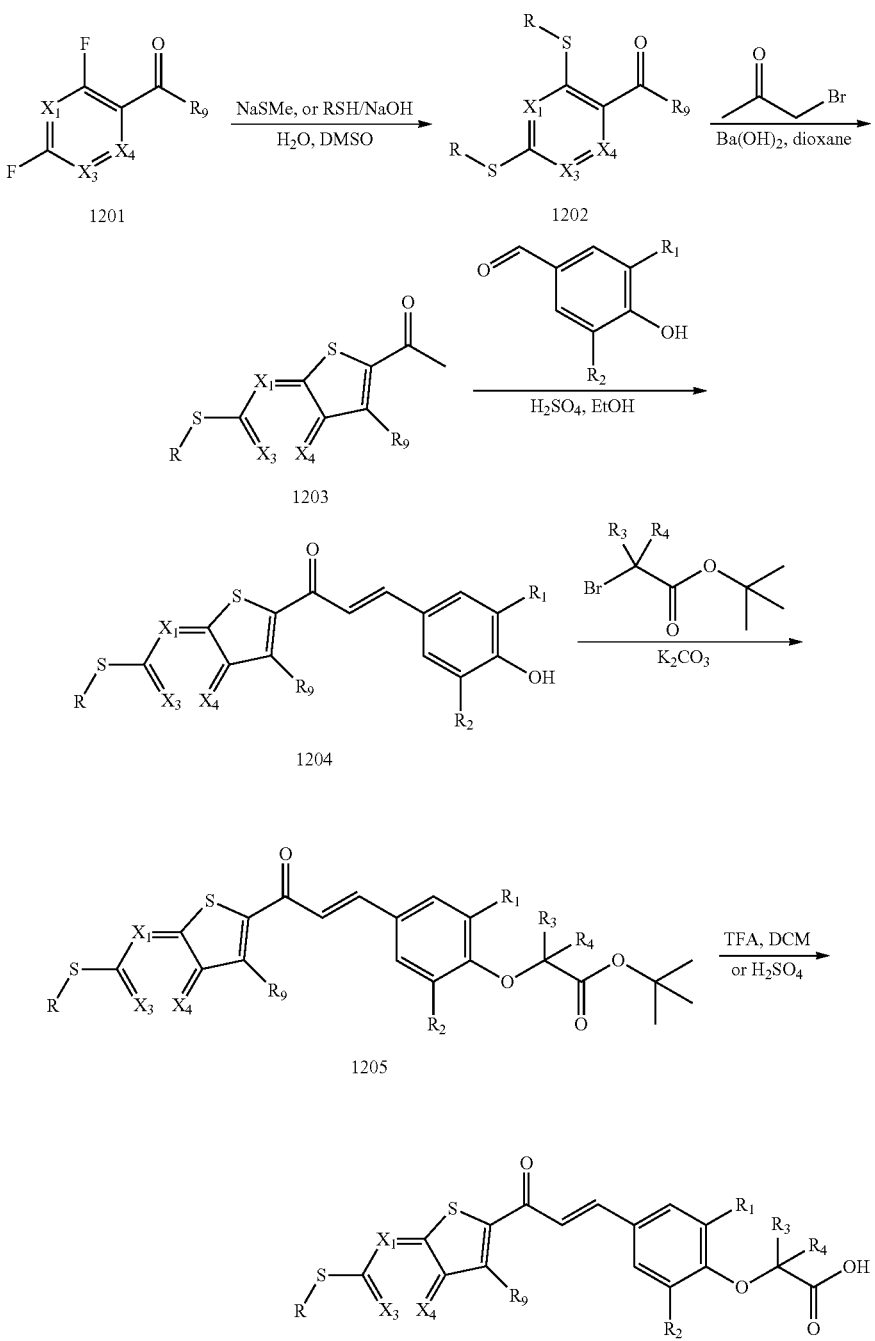

The following am specific examples:

Example 1: Preparation of (E)-2-(4-(3-(4-methoxybenzofuran-7-yl)-3-oxoprop-1-en-1-yl)-2,6-dimethylphenoxy)-2-methylpropanoic acid (Compound 1) (Prepared According to Scheme 1)

Step 1a: Preparation of 1-bromo-2-(2,2-diethoxyethoxy)-4-methoxybenzene (0102-1): 2-bromo-5-methoxyphenol (0101-1) (1.83 g, 9.02 mmol, 1.0 eq.) and 2-bromo-1,1-diethoxyethane (1.42 mL, 9.47 mmol, 1.05 eq.) were dissolved in N,N-dimethylformamide (10 mL) and then potassium carbonate (2.49 g, 18.04 mmol, 2.0 eq.) was added. The air in the reaction system was replaced with nitrogen three times, and then the system was reacted at 95° C. overnight. The reaction mixture was diluted with water (100 mL), and then extracted with EtOAc (30 mL×3). The extract was dried over anhydrous sodium sulfate and concentrated. The residue was purified by silica gel column chromatography (petroleum ether:ethyl acetate=20:1) to obtain a pale yellow oily liquid product 1-bromo-2-(2,2-diethoxyethoxy)-4-methoxybenzene (2.65 g, yield: 92%). LCMS(ESI): m/z 319[M+1]$^+$.

Step 1b: Preparation of 7-bromo-4-methoxybenzofuran (compound 0103-1): 1-Bromo-2-(2,2-diethoxyethoxy)-4-methoxybenzene (102-1) (2.60 g, 8.15 mmol, 1.0 eq.), polyphosphoric acid (8.26 g, 24.45 mmol, 3.0 eq.) and 1,2-dichloroethane (40 mL) were added to the reaction flask, heated to 83° C. and reacted for 3 hours. The reaction solution was cooled to room temperature and then washed with water (30 mL×2). The organic layer was dried over anhydrous sodium sulfate and concentrated. The residue was then purified by column chromatography on silica gel (petroleum ether) to give a white solid product 7-bromo-4-methoxybenzo furan (1.16 g, yield: 63%). LCMS(ESI): m/z 227[M+1]$^+$.

Step 1c: Preparation of 1-(4-methoxybenzofuran-7-yl)ethan-1-one (compound 0104-1): 7-bromo-4-methoxybenzofuran (0103-1) (0.416 g, 1.833 mmol, 1.0 eq.), vinyl n-butyl ether (1.07 mL, 8.247 mmol, 4.5 eq.), palladium acetate (20.6 mg, 0.092 mmol, 0.05 eq.), 1,3-bis(triphenylphosphino)propane (75.5 mg, 0.183 mmol, 0.10 eq.), triethylamine (0.76 mL, 5.499 mmol, 3.0 eq.) and ethylene glycol (6 mL) were added to the reaction flask, then heated to 125° C. under nitrogen and reacted for 6 hours. The reaction mixture was cooled to room temperature and then diluted with water (30 mL) and then extracted with ethyl acetate (30 mL×3). The extract was dried over anhydrous sodium sulfate and concentrated. The obtained oil was dissolved in a solution of diluted hydrochloric acid in 1N (15 mL) and stirred at room temperature for 2 hours. The reaction solution was extracted with ethyl acetate (20 mL×3). The extract was dried over anhydrous s odium sulfate and concentrated. The residue was then purified by column chromatography on silica gel (petroleum ether:ethyl acetate=30:1) to obtain a white solid product 1-(4-methoxybenzofuran-7-yl)ethan-1-one (0.13 g, yield: 37%). LCMS (ESI): m/z 191[M+1]$^+$.

Step 1e: Preparation of (E)-3-(4-hydroxy-3,5-dimethylphenyl)-1-(4-methoxybenzofuran-7-yl)prop-2-en-1-one (compound 0106-1): concentrated sulfuric acid (2 mL) was slowly added dropwise to an ethanol solution (8 ml) of 1-(4-methoxybenzofuran-7-yl)ethan-1-one (0104-1)(130 mg, 0.684 mmol, 1.0 eq.) and 4-hydroxy-3,5-dimethyl benzaldehyde (103 mg, 0.684 mmol, 1.0 eq.), and the mixture was reacted for 3.5 hours at room temperature. The reaction solution was diluted with water (30 mL), and then extracted with ethyl acetate (30 mL×3). The extract was dried over anhydrous sodium sulfate and concentrated to give a yellow solid product (E)-3-(4-hydroxy-3,5-dimethylphenyl)-1-(4-methoxybenzofuran-7-yl)prop-2-en-1-one (0.22 g). LCMS (ESI): m/z 323[M+1]$^+$.

Step 1f: Preparation of tert-butyl (E)-2-(4-(3-(4-methoxybenzofuran-7-yl)-3-oxoprop-1-en-1-yl)-2,6-dimethylphenoxy)-2-methylpropanoate (0107-1): (E)-3-(4-hydroxy-3,5-dimethylphenyl)-1-(4-methoxybenzofuran-7-yl)prop-2-en-1-one (0106-10.22 g, 0.684 mmol, 1.0 eq.) and tert-butyl 2-bromo-2-methylpropanoate (0.75 mL, 4.104 mmol, 6.0 eq.) were dissolved in acetonitrile (10 mL), and then potassium carbonate (0.38 g, 2.74 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=8:1) to obtain a pale yellow solid product tert-butyl (E)-2-(4-(3-(4-methoxybenzofuran-7-yl)-3-oxoprop-1-en-1-yl)-2,6-dimethylphenoxy)-2-methylpropanoate (113 mg, yield: 36%). LCMS(ESI): m/z 465[M+1]$^+$.

Step 1g: Preparation of (E)-2-(4-(3-(4-methoxybenzofuran-7-yl)-3-oxoprop-1-en-1-yl)-2,6-dimethylphenoxy)-2-methylpropanoic acid (compound 1): concentrated sulfuric acid (1 mL) was slowly added dropwise to a solution of tert-butyl (E)-2-(4-(3-(4-methoxybenzofuran-7-yl)-3-oxoprop-1-en-1-yl)-2,6-dimethylphenoxy)-2-meth ylpropanoate (0107-1) 113 mg, 0.244 mmol, 1.0 eq.) in dioxane (8 ml) at room temperature, and the mixture was reacted at room temperature for 2 hours. The reaction solution was diluted with water (30 mL), and then extracted with ethyl acetate (30 mL×3). The extract was dried over anhydrous sodium sulfate and concentrated. The residue was then purified by column chromatography on silica gel (dichloromethane:methanol=20:1) to obtain a yellow solid product (E)-2-(4-(3-(4-methoxybenzofuran-7-yl)-3-oxoprop-1-en-1-yl)-2,6-dimethylphenoxy)-2-methylpropanoic acid (70 mg, yield: 70%). LCMS(ESI): m/z 409[M+1]$^+$; Melting point: 190~193° C.: $^1$HNMR (DMSO-d$_6$, 400 MHz): δ12.95 (s, 1H), 8.11 (d, J=2.0 Hz, 1H), 8.04 (d, J=7.6 Hz, 1H), 7.87 (d, J=15.6 Hz, 1H), 7.65 (d, J=15.6 Hz, 1H), 7.51 (s, 2H), 7.07 (d, J=2.4 Hz, 1H), 6.99 (d, J=8.4 Hz, 1H), 4.02 (s, 3H), 2.23 (s, 6H), 1.40 (s, 6H).

Example 2: Preparation of (E)-2-(2,6-dimethyl-4-(3-(4-(methylamino)benzofuran-7-yl)-3-oxoprop-1-en-1-yl)phenoxy)-2-methylpropanoic acid (Compound 2) (Prepared According to Scheme 1)

Step 2a: Preparation of 1-bromo-2-(2,2-diethoxyethoxy)-4-fluorobenzene (compound 0102-2): 2-bromo-5-fluorophenol (0101-2)(1.73 g, 9.06 mmol, 1.0 eq.) and 2-bromo-1,1-diethoxyethane (5.45 mL, 36.42 mmol, 4.0 eq.) were dissolved in N,N-dimethylformamide (20 mL), and then potassium carbonate (2.50 g, 18.12 mmol, 2.0 eq.) was added. The air in the reaction system was replaced with nitrogen three times, and then the system was reacted at 95° C. for 8 hours. The reaction soliton was diluted with water (100 mL), and then extracted with ethyl acetate (40 mL×3). The extract was dried over anhydrous sodium sulfate and concentrated. The residue was then purified by column chromatography on silica gel (petroleum ether:ethyl acetate=50:1) to obtain a colorless oily liquid product 1-bromo-2-(2,2-diethoxyethoxy)-4-fluorobenzene (2.78 g, yield: 100%). LCMS(ESI): m/z 307[M+1]$^+$.

Step 2b: Preparation of 7-bromo-4-fluorobenzofuran (compound 0103-2): to a reaction flask were added 1-bromo-2-(2,2-diethoxyethoxy)-4-fluorobenzene (0102-2) (2.75 g, 8.95 mmol, 1.0 eq.), polyphosphoric acid (9.08 g, 26.86 mmol, 3.0 eq.) and 1,2-dichloroethane (40 mL), and the mixture was heated to 83° C. and reacted for 3 hours. The reaction solution was cooled to room temperature and then washed with water (30 mL×2). The organic layer was dried over anhydrous sodium sulfate and concentrated. Then the residue was purified by column chromatography on silica gel (petroleum ether) to obtain a pale yellow solid product 7-bromo-4-fluorobenzofuran (0.992 g, yield: 52%). LCMS (ESI): m/z 215[M+1]$^+$.

Step 2c: Preparation of 1-(4-fluorobenzofuran-7-yl)ethan-1-one (compound 0104-2): 7-bromo-4-fluorobenzo furan (0103-2) (0.95 g, 4.42 mmol, 1.0 eq.) was dissolved in anhydrous toluene (15 mL), and the mixture w as cooled to −78° C. in a dry ice acetone bath. Then n-butyl lithium (2.5M, 2.47 mL, 6.19 mmol, 1.4 eq.) was slowly added dropwise. After the addition, the mixture was stirred at −78° C. for 1.5 hours. N-methoxy-N-methylacetamide (1.17 mL, 11.05 mmol, 2.5 eq.) was added dropwise and then the mixture was slowly warmed up to room temperature and stirred for 4 hours. The reaction was quenched by adding a saturated ammonium chloride solution (50 mL). The aqueous layer was extracted with ethyl acetate (30 mL×3). The organic layers were combined, dried over anhydrous sodium sulfate and concentrated. The obtained crude product was purified by column chromatography on silica gel (petroleum ether:ethyl acetate=30:1) to obtain a pale yellow solid product-(4-fluorobenzofuran-7-yl)ethan-1-one (0.28 g, yield: 36%). LCMS(ESI): m/z 179[M+1]$^+$.

Step 2d: Preparation of 1-(4-(methylamino)benzofuran-7-yl)ethan-1-one (compound 0105-2): to a flask we re added 1-(4-fluorobenzofuran-7-yl)ethan-1-one (0104-2) (0.254 g, 1.427 mmol, 1.0 eq.), dimethylamine aqueous solution (25% aqueous solution, 0.71 g, 5.708 mmol, 4.0 eq.) and dimethyl sulfoxide (5 mL), and then the mixture was reacted at 60° C. overnight. The reaction solution was cooled to room temperature, diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=2:1) to obtain a pale yellow solid product 1-(4-(methylamino)benzofuran-7-yl)ethan-1-one (0.251 g, yield: 93%). LCMS(ESI): m/z 190[M+1]$^+$.

Step 2e: Preparation of ethyl (E)-2-(2,6-dimethyl-4-(3-(4-(methylamino)benzofuran-7-yl)-3-oxoprop-1-en-1-yl)phenoxy)-2-methylpropanoate (compound 0108-2): to a reaction flask were added 1-(4-(methylamino)benzofuran-7-yl) ethan-1-one (0105-2) (146 mg, 0.771 mmol, 1.0 eq.), tert-butyl 2-(4-formyl-2,2-dimethylphenoxy)-2-methylpropanoate (225 mg, 0.771 mmol, 1.0 eq.) and ethanol (8 mL), and then concentrated sulfuric acid (2 mL) was added dropwise. The mixture was stirred at 30° C. overnight. The reaction solution was diluted with water (30 mL), and extracted with ethyl acetate (20 mL×3). The extract was dried over anhydrous sodium sulfate and concentrated. The obtained crude product was purified by column chromatography on silica gel (dichloromethane:methanol=60:1) to obtain a yellow solid product ethyl (E)-2-(2,6-dimethyl-4-(3-(4-(methylamino)benzofuran-7-yl)-3-oxoprop-1-en-1-yl)phenoxy)-2-methylpropanoate (93 mg, yield: 28%). LCMS(ESI): m/z 436[M+1]$^+$.

Step 2f: Preparation of (E)-2-(2,6-dimethyl-4-(3-(4-(methylamino) benzofuran-7-yl)-3-oxoprop-1-en-1-yl)phenoxy)-2-methylpropanoic acid (compound 2): to a reaction flask were added ethyl (E)-2-(2,6-dimethyl-4-(3-(4-(methylamino)benzofuran-7-yl)-3-oxopop-1-en-1-yl)phenoxy)-2-methylpropanoate (0108-2) (93 mg, 0.214 mmol, 1.0 eq.), sodium hydroxide (26 mg, 0.641 mmol, 3.0 eq.), ethanol (5 mL) and water (3 mL). The mixture was stirred at 30° C. overnight. The reaction solution was diluted with water (20 mL), adjusted to pH=5 by adding dilute hydrochloric acid, and then extracted with ethyl acetate (20 mL×3). The extract was dried over anhydrous sodium sulfate and concentrated. The obtained crude product was purified by column chromatography on silica gel (dichloromethane:methanol=30:1) to obtain a yellow solid product (E)-2-(2,6-dimethyl-4-(3-(4-(methylamino)benzofuran-7-yl)-3-oxoprop-1-en-1-yl)phenoxy)-2-methylpropanoic acid (50 mg, yield: 57%). LCMS(ESI): m/z 408[M+1]$^+$; Melting point: 196~199° C.; $^1$HNMR (DMSO-d$_6$, 400 MHz): δ12.92 (s, 1H), 7.95-7.88 (m, 3H), 7.59-7.46 (m, 3H), 7.18-7.14 (m, 2H), 6.40 (d, J=8.4H, 1H), 2.92 (d, J=4.8 Hz, 3H), 2.23 (s, 6H), 1.39 (s, 6H).

Example 3: Preparation of (E)-2-(4-(3-(benzofuran-7-yl)-3-oxoprop-1-en-1-yl)-2,6-dimethylphenoxy)-2-methylpropanoic acid (Compound 3) (Prepared According to Scheme 1)

Step 3a: Preparation of 1-bromo-2-(2,2-diethoxyethoxy) benzene (compound 0102-3): 2-bromo-phenol (0101-3×2.0 g, 11.56 mmol, 1.0 eq.) was dissolved in 30 ml of DMF, and then 2-bromo-1,1-diethoxyethane (2.96 g, 15.03 mmol, 1.3 eq.) and potassium carbonate (3.19 g, 23.12 mmol, 2.0 eq.) were added. The air in the round bottom flask was replaced with nitrogen three times, and then the system was reacted at 100° C. for 8 hours. After the reaction was completed, the reaction solution was diluted with ethyl acetate (100 ml), and washed with semi-saturated brine (150 ml×3). The organic phase was dried over anhydrous sodium sulfate and concentrated. The residue was purified by column chromatography on silica gel (petroleum ether:ethyl acetate=20:1) to obtain a pale yellow oily liquid product 1-bromo-2-(2,2-diethoxyethoxy)benzene (3.33 g, yield: 100%).

Step 3b: Preparation of 7-bromobenzofuran (compound 0103-3): 1-bromo-2-(2,2-diethoxyethoxy)benzene (0102-3) (3.33 g, 11.56 mol, 1.0 eq.) was dissolved in DCE (60 ml), and then PPA (11.72 g, 34.68 mmol, 3.0 eq.) was added. The air in the round bottom flask was replaced with nitrogen three times, and then the system was refluxed at 83° C. for 3 hours. After the reaction was completed, dichloromethane (100 ml) was added and then the mixture was washed with water (100 ml×3). The organic phase was dried over anhydrous sodium sulfate and concentrated. Then the residue was purified by column chromatography on silica gel (petroleum ether=100%) to obtain a pale yellow solid product 7-bromobenzofuran (1.336 g, yield: 58%).

Step 3c: Preparation of 1-(benzofuran-7-yl)ethanone (compound 0104-3): 7-bromobenzofuran (0103-3)(1.06 g, 5.36 mmol, 1.0 eq.) was dissolved ethylene glycol (10 ml), and then butyl vinyl ether (0.698 g, 6.97 mmol, 1.3 eq.), palladium acetate (0.12 g, 0.536 mmol, 0.1 eq.), DPPP (0.221 g, 0.536 mmol, 0.1 eq.) and TEA (1.08 g, 10.71 mmol, 2.0 eq.) were added. The reaction solution was reacted in a sealed tube filled with nitrogen at 150° C. for 1 hour. After the reaction was completed, it was diluted with ethyl acetate (50 ml), washed with water (100 ml×3). The organic phase was dried over anhydrous sodium sulfate and concentrated. Then the residue was dissolved in tetrahydrofuran (15 ml) and then 1M HCl (12 ml) was added. The mixture was reacted at room temperature for 3 hours. After the reaction was completed, it was extracted with ethyl acetate (100 ml). The organic phase was dried over anhydrous sodium sulfate and concentrated. The residue was purified by column chromatography on silica gel (petroleum ether:ethyl acetate=10:1) to obtain a pale yellow solid product 1-(benzofuran-7-yl)ethanone (0.79 g, yield: 92%). LCMS(ESI): m/z 161[M+1]$^+$.

Step 3 d: Preparation of (E)-1-(benzofuran-7-yl)-3-(4-hydroxy-3,5-dimethylphenyl)prop-2-en-1-one (compound 0106-3): 1-(benzofuran-7-yl)ethanone (0104-3)(0.79 g, 4.93 mol, 1.0 eq.) was dissolved in 10 ml of dioxane, then 4-hydroxy-3,5-dimethyl benzaldehyde (0.81 g, 5.42 mmol, 1.1 eq.) was added, and then concentrated sulfuric acid (3 ml) was added with stirring. The mixture was reacted at room temperature for 15 h. After the reaction was completed, the reaction solution was diluted with ethyl acetate (100 ml), washed with semi-saturated brine (150 ml-3). The organic phase was dried over anhydrous sodium sulfate and concentrated. The residue was purified by column chromatography on silica gel (petroleum ether:ethyl acetate=5:1) to obtain a pale yellow solid product (E)-1-(benzofuran-7-yl)-3-(4-hydroxy-3,5-dimethylphenyl)prop-2-en-1-one (0.8 g, yield: 56%). LCMS(ESI): m/z 293[M+1]$^+$.

Step 3e: Preparation of (E)-tert-butyl 2-(4-(3-(benzofuran-7-yl)-3-oxoprop-1-en-1-yl)-2,6-dimethylphenoxy)-2-methylpropanoate (compound 0107-3): (E)-1-(benzofuran-7-yl)-3-(4-hydroxy-3,5-dimethylphenyl)prop-2-en-1-one (0106-3)(0.8 g, 2.74 mmol, 1.0 eq.) was dissolved in 20 ml of acetonitrile and then potassium carbonate (1.88 g, 13.7 mmol, 5.0 eq.) and tert-butyl 2-bromo-2-methylpropanoate (3.05 g, 13.7 mmol, 5.0 eq.) were added. The air in the round bottom flask was replaced with nitrogen three times, and then the system was reacted at 82° C. for 20 h. After the reaction was completed, the reaction solution was concentrated. Then the reaction solution was diluted with ethyl acetate (100 ml) and washed with water (150 ml×3). The organic phase was dried over anhydrous sodium sulfate and concentrated. The residue was purified by column chromatography on silica gel (petroleum ether:ethyl acetate=15:1) to obtain a pale yellow solid product (E)-tert-butyl 2-(4-(3-(benzofuran-7-yl)-3-oxoprop-1-en-1-yl)-2,6-dimethylphenoxy)-2-methylpropanoate (0.5 g, yield: 42%). LCMS(ESI): m/z 435[M+1]$^+$.

Step 3f: Preparation of (E)-2-(4-(3-(benzofuran-7-yl)-3-oxoprop-1-en-1-yl)-2,6-dimethylphenoxy)-2-methylpropanoic acid (compound 3): (E)-tert-butyl 2-(4-(3-(benzofuran-7-yl)-3-oxoprop-1-en-1-yl)-2,6-dimethylphenoxy)-2-methylpropanoate (0107-3) (0.5 g, 1.15 mmol, 1.0 eq.) was dissolved in 10 ml of dichloromethane and then trifluoroacetate (4 ml) was added with stirring. The mixture was reacted at room temperature for 15 h. After the reaction was completed, it was diluted with dichloromethane (50 ml), washed with semi-saturated brine (150 ml×3). The organic phase was dried over anhydrous sodium sulfate and concentrated. The residue was washed with a mixed liquid (petroleum ether:ethyl acetate=1:1) to obtain a pale yellow solid product (E)-2-(4-(3-(benzofuran-7-yl)-3-oxoprop-1-en-1-yl)-2,6-dimethylphenoxy)-2-methylpropanoic acid (0.17 g, yield: 40%). LCMS(ESI): m/z 339[M+1]$^+$; melting point: 125~128° C.; $^1$HNMR (DMSO-d$_6$, 30 MHz): δ12.95 (s, 1H), 8.19 (d, J=2.1 Hz, 1H), 7.96 (d, J=7.8 Hz, 1H), 7.92 (d, J=7.8 Hz, 1H), 7.84 (d, J=15.6 Hz, 1H), 7.66 (d, J=15.6 Hz, 1H), 7.42 (d, J=7.8 Hz, 1H), 7.52 (s, 2H), 7.11 (d, J=2.1 Hz, 1H), 2.22 (s, 6H), 1.39 (s, 6H).

Example 4: Preparation of (E)-2-(2,6-dimethyl-4-(3-(4-(methylthio)benzofuran-7-yl)-3-oxoprop-1-en-1-yl)phenoxy)-2-methylpropanoic acid (Compound 5) (Prepared According to Scheme 1)

Step 4a: Preparation of 1-(4-(methylthio)benzofuran-7-yl)ethan-1-one (compound 0105-5): to a reaction flask were added 1-(4-fluorobenzofuran-7-yl)ethan-1-one (0104-2) (0.25 g, 1.404 mmol, 1.0 eq.), sodium methyl mercaptan (40%, 0.49 g, 2.81 mmol, 2.0 eq.) and dimethyl sulfoxide (5 ml). The mixture was stirred at room temperature for 1 hour. The reaction solution was diluted with water (50 mL), and extracted with ethyl acetate (30 mL×3). The extract was dried over anhydrous sodium sulfate and concentrated. The residue was purified by column chromatography on silica gel (petroleum ether:ethyl acetate=15:1) to obtain a pale yellow solid product 1-(4-(methylthio)benzofuran-7-yl)ethan-1-one (0.224 g, yield: 78%). LCMS(ESI): m/z 207 [M+1]$^+$.

Step 4b: Preparation of (E)-3-(4-hydroxy-3,5-dimethylphenyl)-1-(4-(methylthio)benzofuran-7-yl)prop-2-en-1-one (compound 0106-5): concentrated sulfuric acid (2 mL) was slowly added dropwise to an solution of 1-(4-(methylthio)benzofuran-7-yl)ethan-1-one (0105-5214 mg, 1.04 mmol, 1.0 eq.) and 4-hydroxy-3,5-dimethyl benzaldehyde (156 mg, 1.04 mmol, 1.0 eq.) in ethanol (8 ml). The mixture was reacted at room temperature for 3 hours. The reaction solution was diluted with water (30 mL) and then extracted with ethyl acetate (30 mL×3). The extract was dried over anhydrous sodium sulfate and concentrated to give a yellow solid product (E)-3-(4-hydroxy-3,5-dimethylphenyl)-1-(4-(methylthio)benzofuran-7-yl)prop-2-en-1-one (0.35 g). LCMS(ESI): m/z, 339[M+1]$^+$.

Step 4c: Preparation of tert-butyl (E)-2-(2,6-dimethyl-4-(3-(4-(methylthio)benzofuran-7-yl)-3-oxoprop-1-en-1-yl)phenoxy)-2-methylpropanoate (compound 0107-5): (E)-3-(4-hydroxy-3,5-dimethylphenyl)-1-(4-(methylthio) benzofuran-7-yl)prop-2-en-1-one (0106-5)(0.35 g, 1.04 mmol, 1.0 eq.) and tert-butyl 2-bromo-2-methylpropanoate (1.16 mL, 6.21 mmol, 6.0 eq.) were dissolved in acetonitrile (10 mL) and then potassium carbonate (0.57 g, 4.16 mmol, 4.0 eq.) was added. The air in the reaction system was replaced with nitrogen three times, and then the system was reacted at 83° C. for 24 hours. After the reaction was completed, the mixture was concentrated to give a crude product, which was purified by column chromatography on silica gel (petroleum ether:ethyl acetate=10:1) to obtain a yellow solid product tert-butyl (E)-2-(2,6-dimethyl-4-(3-(4-(methylthio)benzofuran-7-yl)-3-oxoprop-1-en-1-yl)phenoxy)-2-methylpropanoate (227 mg, yield: 45%). LCMS (ESI): m/z 481 [M+1]$^+$.

Step 4d: Preparation of (E)-2-(2,6-dimethyl-4-(3-(4-(methylthio)benzofuran-7-yl)-3-oxoprop-1-en-1-yl)phenoxy)-2-methylpropanoic acid (compound 5): concentrated sulfuric acid (1 mL) was slowly added dropwise to a solution of tert-butyl (E)-2-(2,6-dimethyl-4-(3-(4-(methylthio)benzofuran-7-yl)-3-oxoprop-1-en-1-yl)phenoxy)-2-methylpropanoate (0107-5)(227 mg, 0.472 mmol, 1.0 eq.) in dioxane (8 ml) at room temperature. The mixture was reacted at room temperature for 1.5 hours. The reaction solution was diluted with water (30 mL) and then extracted with ethyl acetate (30 mL×3). The extract was dried over anhydrous sodium sulfate and concentrated. The residue was then purified by column chromatography on silica gel (dichloromethane: methanol=20:1) to obtain a yellow solid product (E)-2-(2, 6-dimethyl-4-(3-(4-(methylthio)benzofuran-7-yl)-3-oxoprop-1-en-1-yl)phenoxy)-2-methylpropanoic acid (110 mg, yield: 55%). LCMS(ESI): m/z 425[M+1]$^+$; melting point: 102~105° C.; $^1$HNMR (DMSO-d$_6$, 400 MHz): δ12.94 (s, 1H), 8.22 (d, J=2.4 Hz, 1H), 7.97 (d, J=8.0 Hz, 1H), 7.85 (d, J=16.0 Hz, 1H), 7.66 (d, J=15.6 Hz, 1H), 7.64 (s, 2H), 7.27 (d, J=7.6 Hz, 1H), 7.06 (d, J=2.0 Hz, 1H), 2.67 (s, 3H), 2.23 (s, 6H), 1.40 (s, 6H).

Example 5: Preparation of (E)-2-methyl-2-(4-(3-(4-(methylthio)benzofuran-7-yl)-3-oxoprop-1-en-1-yl) phenoxy)propanoic acid (Compound 12) (Prepared According to Scheme 1)

Step 5a: Preparation of (E)-3-(4-hydroxyphenyl)-1-(4-(methylthio)benzofuran-7-yl)prop-2-en-1-one (compound 0106-12): 1-(4-(methylthio)benzofuran-7-yl)ethanone (0105-5)(0.3 g, 1.45 mmol, 1.0 eq.) was dissolved in 10 ml of dioxane, then 4-hydroxybenzaldehyde (0.213 g, 1.75 mmol, 1.2 eq.) was added, and then concentrated sulfuric acid (3 ml) was added with stirring. The mixture was reacted at room temperature for 15 h. After the reaction was completed, the reaction solution was diluted with ethyl acetate (100 ml) and washed with semi-saturated brine (150 ml×3). The organic phase was dried over anhydrous sodium sulfate and concentrated. The residue was purified by column chromatography on silica gel (petroleum ether:ethyl acetate=5:1) to obtain a pale yellow solid product (E)-3-(4-hydroxyphenyl)-1-(4-(methylthio)benzofuran-7-yl)prop-2-en-1-one (0.28 g, yield: 62%). LCMS(ESI): m/z 311[M+1]$^+$.

Step 5b: Preparation of tert-butyl (E)-2-methyl-2-(4-(3-(4-(methylthio)benzofuran-7-yl)-3-oxoprop-1-en-1-yl) phenoxy)propanoate (compound 0107-12): (E)-3-(4-hydroxyphenyl)-1-(4-(methylthio)benzofuran-7-yl)prop-2-en-1-one (0106-12) (0.28 g, 0.9 mmol, 1.0 eq.) was dissolved in 20 ml of acetonitrile and then potassium carbonate (0.623 g, 4.5 mmol, 5.0 eq.) and tert-butyl 2-bromoisobutyrate (1.007 g, 4.5 mmol, 5.0 eq.) were added. The air in the round bottom flask was replaced with nitrogen three times, and then the system was reacted at 82° C. for 20 h. After the reaction was completed, the reaction solution was concentrated. The reaction solution was diluted by ethyl acetate (100 ml) and washed with water (150 ml×3). The organic phase was dried over anhydrous sodium sulfate and concentrated. The residue was purified by column chromatography on silica gel (petroleum ether:ethyl acetate=15:1) to obtain a yellow solid product tert-butyl (E)-2-methyl-2-(4-(3-(4-(methylthio)benzofuran-7-yl)-3-oxoprop-1-en-1-yl)phenoxy)propanoate (0.2 g, yield: 50%). LCMS(ESI): m/z 453 [M+1]$^+$.

Step 5c: Preparation of (E)-2-methyl-2-(4-(3-(4-(methylthio)benzofuran-7-yl)-3-oxoprop-1-en-1-yl)phenoxy) propanoic acid (compound 12): tert-butyl (E)-2-methyl-2-(4-(3-(4-(methylthio)benzofuran-7-yl)-3-oxoprop-1-en-1-yl) phenoxy)propanoate (0107-12) (0.2 g, 0.44 mmol, 1.0 eq.) was dissolved in 10 ml of dichloromethane and then trifluoroacetate (4 ml) was added with stirring. The mixture was reacted at room temperature for 15 h. After the reaction was completed, the reaction solution was diluted with dichloromethane (50 ml) and washed with semi-saturated brine (150 ml×3). The organic phase was dried over anhydrous sodium sulfate and concentrated. The residue was washed with a mixed liquid (petroleum ether:ethyl acetate=1:1) to obtain a yellow solid product (E)-2-methyl-2-(4-(3-(4-(methylthio)benzofuran-7-yl)-3-oxoprop-1-en-1-yl)phenoxy)propanoic acid (0.041 g, yield: 23%). LCMS(ESI): m/z 397[M+1]$^+$; Melting point: 167~170° C.; $^1$HNMR (DMSO-d$_6$, 400 MHz): δ13.20 (s, 1H), 8.20 (d, J=1.6 Hz, 1H), 7.95 (d, J=8 Hz, 1H), 7.86 (d, J=15.6 Hz, 1H), 7.77 (d, J=8.4 Hz, 2H), 7.73 (d, J=16.4 Hz, 1H), 7.26 (d, J=8 Hz, 1H), 7.06 (d, J=1.6 Hz, 1H), 6.88 (d, J=8.4 Hz, 2H), 2.66 (s, 3H), 1.57 (s, 6H).

Example 6: Preparation of (E)-2-(2,6-dimethyl-4-(3-(4-(methylthio)benzofuran-7-yl)-3-oxoprop-1-en-1-yl)phenoxy)acetic acid (Compound 13) (Prepared According to Scheme 1)

Step 6a: Preparation of (E)-3-(4-hydroxy-3,5-dimethylphenyl)-1-(4-(methylthio)benzofuran-7-yl)prop-2-en-1-one (compound 0106-13): 1-(4-(methylthio)benzofuran-7-yl)ethanone (0105-5)(0.38 g, 1.84 mmol, 1.0 eq.) was dissolved in 10 ml of dioxane, then 4-hydroxy-3,5-dimethyl benzaldehyde (0.332 g, 2.21 mmol, 1.2 eq.) was added and then concentrated sulfuric acid (3 ml) was added with stirring. The mixture was reacted at room temperature for 15 h. After the reaction was completed, the reaction solution was diluted with ethyl acetate (100 ml) and washed with semi-saturated brine (150 ml×3). The organic phase was dried over anhydrous sodium sulfate and concentrated. The residue was purified by column chromatography on silica gel (petroleum ether:ethyl acetate=5:1) to obtain a pale yellow solid product (E)-3-(4-hydroxy-3,5-dimethylphenyl)-1-(4-(methylthio)benzofuran-7-yl)prop-2-en-1-one (0.52 g, yield: 84%). LCMS(ESI): m/z 339[M+1]$^+$.

Step 6b: Preparation of tert-butyl (E)-2-(2,6-dimethyl-4-(3-(4-(methylthio)benzofuran-7-yl)-3-oxoprop-1-en-1-yl) phenoxy)acetate (compound 0107-13): (E)-3-(4-hydroxy-3,5-dimethylphenyl)-1-(4-(methylthio)benzofuran-7-yl)prop-2-en-1-one (0106-13)0.52 g, 1.54 mmol, 1.0 eq.) was dissolved in 20 ml of acetonitrile and then potassium carbonate (1.06 g, 7.68 mmol, 5.0 eq.) and tert-butyl 2-bromo-2-methylpropanoate (1.28 g, 7.68 mmol, 5.0 eq.) were added. The air in the round bottom flask was replaced with nitrogen three times, and then the system was reacted at 82° C. for 20 h. After the reaction was completed, the reaction solution was concentrated. Then the reaction solution was diluted with ethyl acetate (100 ml) and washed with water (150 ml×3). The organic phase was dried over anhydrous sodium sulfate and concentrated. The residue was purified by column chromatography on silica gel (petroleum ether:ethyl acetate=15:1) to obtain a yellow solid product tert-butyl (E)-2-(2,6-dimethyl-4-(3-(4-(methylthio)benzofuran-7-yl)-3-oxoprop-1-en-1-yl)phenoxy)acetate (0.39 g, yield: 60%). LCMS(ESI): m/z 425[M+1]$^+$.

Step 6c: Preparation of ((E)-2-(2,6-dimethyl-4-(3-(4-(methylthio)benzofuran-7-yl)-3-oxoprop-1-en-1-yl)phenoxy)acetic acid (compound 13): tert-butyl (E)-2-(2,6-dimethyl-4-(3-(4-(methylthio)benzofuran-7-yl)-3-oxoprop-1-en-1-yl)phenoxy)acetate (0107-13)0.39 g, 0.918 mmol, 1.0 eq.) was dissolved in 5 ml of tetrahydrofuran and then 4 ml of ethanol, 5 ml of water and sodium hydroxide (0.07 g, 1.837 mmol, 2.0 eq.) were added. The mixture was reacted at room temperature for 15 h. After the reaction was completed, it was adjusted to pH=1 by adding 1M hydrochloric acid (20 ml) and extracted with ethyl acetate (100 ml). The organic phase was dried over anhydrous sodium sulfate and concentrated. The residue was purified by column chromatography on silica gel (dichloromethane:methanol:acetic acid=100:1:0.25) to obtain a yellow solid product (E)-2-(2,6-dimethyl-4-(3-(4-(methylthio)benzofuran-7-yl)-3-oxoprop-1-en-1-yl)phenoxy)acetic acid (0.139 g, yield: 38%). LCMS(ESI): m/z 397[M+1]$^+$; Melting point: 218~221° C.; $^1$HNMR (DMSO-d$_6$, 400 MHz): δ12.9 (s, 1H), 8.22 (d, J=2.4 Hz, 1H), 7.97 (d, J=8 Hz, 1H), 7.86 (d, J=15.6 Hz, 1H), 7.67 (d, J=15.6 Hz, 1H), 7.53 (s, 2H), 7.26 (d, J=8 Hz, 1H), 7.06 (d, J=2 Hz, 1H), 4.44 (s, 2H), 2.67 (s, 3H), 2.29 (s, 6H).

Example 7: Preparation of (E)-2-(2,6-dimethyl-4-(3-(2-methyl-4-(methylthio)benzofuran-7-yl)-3-oxoprop-1-en-1-yl)phenoxy)-2-methylpropanoic acid (Compound 14) (Prepared According to Scheme 2)

Step 7a: Preparation of 1-bromo-4-fluoro-2-(prop-2-yn-1-yloxy)benzene (compound 0201-14): to a solution of 2-bromo-5-fluorophenol (0101-21.91 g, 10 mmol, 1.0 eq.) and potassium carbonate (2.76 g, 20 mmol, 2.0 eq.) in dimethylformamide (20 ml) was added 3-bromoprop-1-yne (1.31 g, 11 mmol, 1.1 eq.) at room temperature. The mixture was reacted at room temperature for 1 hour. The reaction solution was diluted with eth yl acetate (100 ml) and washed with water (50 ml×1) and semi-saturated brine (100 ml×2) separately. The organic phase was dried by rotary evaporation. The residue was purified by column chromatography on silica gel (the eluent: petroleum ether:ethyl acetate=10:1) to obtain a pale yellow liquid product 1-bromo-4-fluoro-2-(prop-2-yn-1-yloxy)benzene (2.29 g, yield: 100%). LCMS (ESI): m/z 230 [M+1]$^+$.

Step 7b: Preparation of 7-bromo-4-fluoro-2-methylbenzofuran (N-081-4) (compound 0202-14): to a sealed tube were added 1-bromo-4-fluoro-2-(prop-2-yn-1-yloxy)benzene (0201-14) (2.29 g, 10 mmol, 1.0 eq.), cesium fluoride (2.28 g, 15 mmol, 1.5 eq.) and diethyl aniline (15 ml). The mixture was heated to relux for 4 hours. The reaction solution was cooled to room temperature, diluted with ethyl ether (100 ml) and filtered. The filtrate was washed with 1M hydrochloric acid (60 ml×3). The organic phase was dried by rotary evaporation. The residue was purified by column chromatography on silica gel (the eluent: 100% petroleum ether) to obtain a white solid product 7-bromo-4-fluoro-2-methylbenzofuran (1.57 g, yield: 69%). LCMS(ESI): m/z 230 [M+1]$^+$.

Step 7c: Preparation of 1-(4-fluoro-2-methylbenzofuran-7-yl)ethan-1-one (compound 0203-14): to a sealed tube were added 7-bromo-4-fluoro-2-methylbenzofuran (0202-14) (1.57 g, 7 mmol, 1.0 eq.), 1-(vinyloxy) butane (0.91 g, 9.1 mmol, 1.3 eq.), palladium acetate (0.157 g, 0.7 mmol, 0.1 eq.), 1,3-bis (diphenylphosphino)propane (0.288 g, 0.7 mmol, 0.1 eq.), triethylamine (1.42 g, 14 mmol, 2.0 eq.) and ethylene glycol (20 ml). The mixture was reacted at 145° C. for 1 hour. The reaction solution was diluted with ethyl acetate (100 ml) and washed with semi-saturated brine (100 ml×3). The organic phase was dried by rotary evaporation. The residue was dissolved in tetrahydrofuran (30 ml), to which 1M hydrochloric acid (15 ml) was added. The mixture was stirred at room temperature for 3 hours, and then extracted with ethyl acetate (100 ml×1). The organic phase was mixed with silica gel and was then dried by rotary evaporation. The residue was purified by column chromatography on silica gel (the eluent: petroleum ether:ethyl acetate=10:1) to obtain a pale yellow solid product 1-(4-fluoro-2-methylbenzofuran-7-yl)ethan-1-one (0.99 g, yield: 74%). LCMS(ESI): m/z 193 [M+1]$^+$.

Step 7d: Preparation of 1-(2-methyl-4-(methylthio)benzofuran-7-yl)ethan-1-one (compound 0204-14): to a solution of 1-(4-fluoro-2-methylbenzofuran-7-yl)ethan-1-one (0203-14)(0.99 g, 5.2 mmol, 1.0 eq.) in dimethyl sulfoxide (30 ml) was added a 20% sodium methyl mercaptan solution (4 ml, 10.4 mmol, 2.0 eq.). The mixture was reacted at room temperature for two hours. The reaction solution was diluted with ethyl acetate (150 ml) and washed with semi-saturated brine (100 ml×3). The organic phase was dried by rotary evaporation to obtain a yellow solid product 1-(2-methyl-4-(methylthio)benzofuran-7-yl)ethan-1-one (1.04 g, yield: 91%). LCMS(ESI): m/z 221 [M+1]$^+$.

Step 7e: Preparation of (E)-3-(4-hydroxy-3,5-dimethylphenyl)-1-(2-methyl-4-(methylthio)benzofuran-7-yl)prop-2-en-1-one (compound 0205-14): to a solution of 1-(2-methyl-4-(methylthio)benzofuran-7-yl)ethan-1-one (0204-14) (44 g, 2.0 mmol, 1.0 eq.) and 4-hydroxy-3,5-dimethyl benzaldehyde (0.33 g, 2.2 mmol, 1.1 eq.) in dioxane (10 ml) was added concentrated sulfuric acid (2 ml) slowly. The reaction was stirred at room temperature for 3 days. The reaction solution was diluted with ethyl acetate (150 ml) and washed with semi-saturated brine (100 ml-3). The organic phase was dried by rotary evaporation. The residue was purified by column chromatography on silica gel (the eluent: 100% dichloromethane) to obtain a yellow solid product (E)-3-(4-hydroxy-3,5-dimethylphenyl)-1-(2-methyl-4-(methylthio)benzofuran-7-yl)prop-2-en-1-one (0.74 g, yield: 100%). LCMS(ESI): m/z 353 [M+1]$^+$.

Step 7f: Preparation of tert-butyl (E)-2-(2,6-dimethyl-4-(3-(2-methyl-4-(methylthio)benzofuran-7-yl)-3-oxoprop-1-en-1-yl)phenoxy)-2-methylpropanoate (compound 0206-14): to a solution of (E)-3-(4-hydroxy-3,5-dimethylphenyl)-1-(2-methyl-4-(methylthio)benzofuran-7-yl)prop-2-en-1-one (0205-14)(0.704 g, 2.0 mmol, 1.0 eq.) in acetonitrile (50 ml) were added potassium carbonate (1.38 g, 10.0 mmol, 5.0 eq.) and tert-butyl 2-bromoisobutyrate (2.23 g, 10.0 mmol, 5.0 eq.). The reaction solution was heated to 82° C. and refluxed overnight under the protection of nitrogen. The reaction solution was dried by rotary evaporation. The residue was diluted with ethyl acetate (150 ml) and washed with water (100 ml-2). The organic phase was dried by rotary evaporation. The residue was purified by column chromatography on silica gel (the eluent: petroleum ether:ethyl acetate=10:1) to obtain a yellow oil product tert-butyl (E)-2-(2,6-dimethyl-4-(3-(2-methyl-4-(methylthio)benzofuran-7-yl)-3-oxoprop-1-en-1-yl)phenoxy)-2-methylpropanoate (0.28 g, yield: 28%). LCMS(ESI): m/z 495 [M+1]$^+$.

Step 7g: Preparation of (E)-2-(2,6-dimethyl-4-(3-(2-methyl-4-(methylthio)benzofuran-7-yl)-3-oxoprop-1-en-1-yl)phenoxy)-2-methylpropanoic acid (compound 14): to a solution of tert-butyl (E)-2-(2,6-dimethyl-4-(3-(2-methyl-4-(methylthio)benzofuran-7-yl)-3-oxoprop-1-en-1-yl)phenoxy)-2-methylpropanoate (0206-14)(0.28 g, 0.57 mmol, 1 eq.) in dichloromethane (10 ml) was added trifluoroacetate (2 ml) slowly. The reaction solution w as reacted at room temperature for two hours. The reaction solution was diluted with dichloromethane (100 ml) and washed with water (100 ml×2). The organic phase was dried over anhydrous sodium sulfate and filtered. The filtrate was dried by rotary evaporation. The residue was recrystallized with methanol (2 ml) to obtain a yellow solid product (E)-2-(2,6-dimethyl-4-(3-(2-methyl-4-(methylthio)benzofuran-7-yl)-3-oxoprop-1-en-1-yl)phenoxy)-2-methylpropanoic acid (140 mg, yield: 56.0%). LCMS(ESI): m/z 439[M+1]$^+$; Melting point: 187~190° C.; $^1$HNMR (DMSO, 300 MHz): δ 12.95 (s, 1H), 6.68-7.89 (m, 7H), 2.64 (s, 3H), 2.54 (s, 3H), 2.23 (s, 6H), 1.39 (s, 6H).

Example 8: Preparation of (E)-2-(2,6-dimethyl-4-(3-(2-methyl-4-(methylthio) benzo[d]oxazol-7-yl)-3-oxoprop-1-en-1-yl)phenoxy)-2-methylpropanoic acid (Compound 20) (Prepared According to Scheme 3)

Step 8a: Preparation of 1-(4-fluoro-2-hydroxy-3-nitrophenyl) ethan-1-one (compound 0302-20): to a solution of 1-(4-fluoro-2-hydroxyphenyl)ethan-1-one (0301-20)(1.0 g, 6.49 mmol, 1.0 eq.) in 82% sulfuric acid (9 ml) was added 70% nitric acid (0.5 ml, 7.14 mmol, 1.1 eq.) at 0° C. The mixture was reacted at 0° C. for half an hour. Then, the reaction solution was poured into ice-water (100 ml), which was extracted with dichloro methane (50 ml×2). The organic phase was dried by rotary evaporation. The residue was purified by column chromatography on silica gel (the eluent: petroleum ether:ethyl acetate=10:1) to obtain a pale yellow solid product 1-(4-fluoro-2-hydroxy-3-nitrophenyl) ethan-1-one (0.36 g, yield: 28%). LCMS(ESI): m/z 200 [M+1]$^+$.

Step 8b: Preparation of 1-(2-hydroxy-4-(methylthio)-3-nitrophenyl)ethan-1-one (compound 0303-20): to a solution of 1-(4-fluoro-2-hydroxy-3-nitrophenyl) ethan-1-one (0302-20) (0.34 g, 1.71 mmol, 1.0 eq.) in dimethyl sulfoxide (8 ml) was added a 20% sodium methyl mercaptan solution (1.19 g, 3.42 mmol, 2.0 eq.). The mixture was reacted at room temperature for half an hour. The reaction solution was diluted with water (100 ml), adjusted to a pH value of 2 with M hydrochloric acid, extracted with ethyl acetate (100 ml×1) and washed with semi-saturated brine (100 ml×2). The organic phase was dried by rotary evaporation. The residue was purified by column chromatography on silica gel (the eluent: petroleum ether:ethyl acetate=2:1) to obtain a yellow solid product 1-(2-hydroxy-4-(methylthio)-3-nitrophenyl) ethan-1-one (0.30 g, yield: 73%). LCMS(ESI): m/z 228 [M+1]$^+$.

Step 8c: Preparation of 1-(3-amino-2-hydroxy-4-(methylthio)phenyl)ethan-1-one (compound 0304-20): to a reaction flask were added 1-(2-hydroxy-4-(methylthio)-3-nitrophenyl)ethan-1-one (0303-20)(0.18 g, 0.8 mmol, 1.0 eq.), zinc powder (0.52 g, 8.0 mmol, 10.0 eq.), ammonium chloride (0.432 g, 8.0 mmol, 10.0 eq.) and methanol (15 ml). The mixture was reacted at room temperature for half an hour. The reaction solution was diluted with ethyl acetate (100 ml) and filtered. The filtrate was dried by rotary evaporation to obtain a crude brown solid product 1-(3-amino-2-hydroxy-4-(methylthio)phenyl)ethan-1-one (0.158 g, yield: 100%). LCMS(ESI): m/z 198 [M+1]$^+$.

Step 8d: Preparation of 1-(2-methyl-4-(methylthio)benzo[d]oxazol-7-yl)ethan-1-one (compound 0305-20): to a solution of 1-(3-amino-2-hydroxy-4-(methylthio)phenyl)ethan-1-one (0304-20) (0.158 g, 0.8 mmol, 1.0 eq.) in toluene (20 ml) was added triethyl orthoacetate (0.5 ml, 2.6 mmol, 3.3 eq.). The mixture was refluxed for 1 hour. To the reaction solution was added 1M hydrochloric acid (20 ml), which was dried by rotary evaporation. The residue was diluted with ethyl acetate (100 ml) and washed with semi-saturated brine (100 ml×1). The organic phase was dried, and filtered. The filtrate was dried by rotary evaporation to obtain a brown solid product 1-(2-methyl-4-(methylthio)benzo[d]oxazol-7-yl)ethan-1-one (0.26 g, yield: 77%). LCMS(ESI): m/z 222 [M+1]$^+$.

Step 8e: Preparation of (E)-3-(4-hydroxy-3,5-dimethylphenyl)-1-(2-methyl-4-(methylthio)benzo[d]oxazol-7-yl)prop-2-en-1-one (compound 0306-20): to a solution of 1-(2-methyl-4-(methylthio)benzo[d]oxazol-7-yl)ethan-1-one (0305-20)(0.26 g, 1.2 mmol, 1.0 eq.) and 4-hydroxy-3,5-dimethyl benzaldehyde (0.195 g, 1.3 mmol, 1.1 eq.) in dioxane (10 ml) were added concentrated sulfuric acid (2 ml) slowly. The reaction was stirred at room temperature for 2 days. The reaction solution was diluted with ethyl acetate (100 ml) and washed with semi-saturated brine (100 ml×3). The organic phase was dried by rotary evaporation. The residue was sonicated with a mixed solvent (petroleum ether:ethyl acetate=3:1, 28 ml) for 5 minutes and filtered. The filtrate was washed with petroleum ether (30 ml) to obtain a yellow solid product (E)-3-(4-hydroxy-3,5-dimethylphenyl)-1-(2-methyl-4-(methylthio)benzo[d]oxazol-7-yl)prop-2-en-1-one (0.27 g, yield: 64%). LCMS(ESI): m/z 354[M+1]$^+$.

Step 8f: Preparation of tert-butyl (E)-2-(2,6-dimethyl-4-(3-(2-methyl-4-(methylthio)benzo[d]oxazol-7-yl)-3-oxoprop-1-en-1-yl)phenoxy)-2-methylpropanoate (compound 0307-20): to a solution of (E)-3-(4-hydroxy-3,5-di methylphenyl)-1-(2-methyl-4-(methylthio)benzo[d]oxazol-7-yl) prop-2-en-1-one (0306-20)(0.27 g, 0.77 mmol, 1.0 eq.) in acetonitrile (20 ml) were added potassium carbonate (0.159 g, 1.15 mmol, 1.5 eq.) and tert-butyl 2-bromoisobutyrate (0.256 g, 1.15 mmol, 1.5 eq.). The reaction solution was heated to 82° C. and refluxed overnight un der the protection of nitrogen. The reaction solution was dried by rotary evaporation. The residue was purified by column chromatography on silica gel (the eluent: petroleum ether:ethyl acetate=3:1) to obtain a yellow oil product tert-butyl (E)-2-(2,6-dimethyl-4-(3-(2-methyl-4-(methylthio)benzo[d]oxazol-7-yl)-3-oxoprop-1-en-1-yl)phenoxy)-2-methylpropanoate (0.076 g, yield: 20%). LCMS(ESI): m/z 496[M+1]$^+$.

Step 8g: Preparation of (E)-2-(2,6-dimethyl-4-(3-(2-methyl-4-(methylthio)benzo[d]oxazol-7-yl)-3-oxoprop-1-en-1-yl)phenoxy)-2-methylpropanoic acid (compound 20): to a solution of tert-butyl (E)-2-(2,6-dimethyl-4-(3-(2-methyl-4-(methylthio)benzo[d]oxazol-7-yl)-3-oxoprop-1-en-1-yl)phenoxy)-2-methylpropanoate (0307-20)(0.076 g, 0.15 mmol, 1.0 eq.) in dichloromethane (10 ml) was added trifluoroacetate (2 ml) slowly. The reaction solution was reacted overnight at room temperature. The reaction solution was diluted with dichloromethane (50 ml) and washed with water (50 ml×2). The organic phase was dried by rotary evaporation. The residue was recrystallized with a solution (petroleum ether:ethyl acetate=2:1) (2 ml) to obtain a yellow solid product (E)-2-(2,6-dimethyl-4-(3-(2-methyl-4-(methylthio)benzo[d]oxazol-7-yl)-3-oxoprop-1-en-1-yl)phenoxy)-2-methylpropanoic acid (42 mg, yield: 64%). LCMS (ESI): m/z 440[M+1]$^+$; Melting point: 186~189° C.; $^1$HNMR (DMSO, 300 MHz): δ12.97 (s, 1H), 7.27-8.03 (m, 6H), 2.71 (s, 3H), 2.66 (s, 3H), 2.23 (s, 6H), 1.39 (s, 6H).

Example 9: Preparation of (E)-2-(2,6-dimethyl-4-(3-(7-(methylthio)benzofuran-4-yl)-3-oxoprop-1-en-1-yl)phenoxy)-2-methylpropanoic acid (Compound 27) (Prepared According to Scheme 4)

Step 9a: Preparation of 4-bromo-2-(2,2-diethoxyethoxy)-1-fluorobenzene (compound 0402-27): 5-bromo-2-fluorobenzene (0401-27)(2.1 g, 10.9 mmol, 1.0 eq.) and 2-bromo-1,1-diethoxyethane (2.15 mL, 14.29 mmol, 1.3 eq.) were dissolved in N,N-dimethylformamide (15 mL) and then potassium carbonate (3.03 g, 21.99 mmol, 2.0 eq.) was added. The air in the reaction system was replaced with nitrogen three times, and then the system was reacted at 95° C. overnight. The reaction solution was diluted with water (100 mL) and then extracted with ethyl acetate (40 mL×3). The extract was dried over anhydrous sodium sulfate and concentrated. The residue was then purified by column chromatography on silica gel (petroleum ether:ethyl acetate=50:1) to obtain a colorless oily liquid product 4-bromo-2-(2,2-diethoxyethoxy)-1-fluorobenzene (3.37 g. yield: 100%). LCMS(ESI): m/z 307[M+1]$^+$.

Step 9b: Preparation of 4-bromo-7-fluorobenzofuran (compound 0403-27): to a reaction flask were added 4-bromo-2-(2,2-diethoxyethoxy)-1-fluorobenzene (0402-27)(3.37 g, 10.97 mmol, 1.0 eq.), polyphosphoric acid (11.12 g, 32.91 mmol, 3.0 eq.) and 1,2-dichloroethane (40 mL). The mixture was heated to 83° C. and reacted for 3 hours. The reaction solution was cooled to room temperature and then washed with water (30 mL×2). The organic layer was dried over anhydrous sodium sulfate and concentrated. Then the residue was purified by column chromatography on silica gel (petroleum ether) to obtain a pale yellow solid product 4-bromo-7-fluorobenzofuran (0.9 g, yield: 38%). LCMS(ESI): m/z 215[M+1]$^+$.

Step 9c: Preparation of 1-(7-fluorobenzofuran-4-yl)ethan-1-one (compound 0404-27): to a reaction flask were added 4-bromo-7-fluorobenzofuran (0403-27)(0.805 g, 3.74 mmol, 1.0 eq.), vinyl n-butyl ether (2.18 mL, 16.85 mmol, 4.5 eq.), palladium acetate (42 mg, 0.187 mmol, 0.05 eq.), 1,3-bis(triphenylphosphino)propane (0.154 g, 0.37 mmol, 0.10 eq.), triethylamine (1.56 mL, 11.22 mmol, 3.0 eq.) and ethylene glycol (8 mL). The mixture was heated to 125° C. and reacted for 6 hours under the protection of nitrogen. The reaction solution was cooled to room temperature, diluted with water (30 mL), and extracted with ethyl acetate (30 mL×3). The extract was dried over anhydrous sodium sulfate and concentrated. The obtained oil was dissolved in 1N diluted hydrochloric acid solution (15 mL) and stirred at room temperature for 2 hours. The reaction solution was extracted with ethyl acetate (20 mL×3). The extract was dried over anhydrous sodium sulfate and concentrated. The residue was then purified by column chromatography on silica gel (petroleum ether:ethyl acetate=30:1) to obtain a white solid 1-(7-fluorobenzofuran-4-yl)ethan-1-one (0.57 g, yield: 86%). LCMS(ESI): m/z 179[M+1]$^+$.

Step 9d: Preparation of 1-(7-(methylthio)benzofuran-4-yl)ethan-1-one (compound 0405-27): to a reaction flask were added 1-(7-fluorobenzofuran-4-yl)ethan-1-one (0404-27)(0.27 g, 1.52 mmol, 1.0 eq.), sodium methyl mercaptan (40%, 0.53 g, 3.04 mmol, 2.0 eq.) and dimethyl sulfoxide (5 ml). The mixture was reacted at room temperature for 1 hour. The reaction solution was diluted with water (50 mL) and extracted with ethyl acetate (30 mL×3). The extract was dried over anhydrous sodium sulfate and concentrated. Then the residue was purified by column chromatography on silica gel (petroleum ether:ethyl acetate=15:1) to obtain a pale yellow solid 1-(7-(methylthio)benzofuran-4-yl)ethan-1-one (0.29 g, yield: 93%). LCMS(ESI): m/z 207 [M+1]$^+$.

Step 9e: Preparation of (E)-3-(4-hydroxy-3,5-dimethylphenyl)-1-(7-(methylthio)benzofuran-4-yl)prop-2-en-1-one (compound 0406-27): to a solution of 1-(7-(methylthio)benzofuran-4-yl)ethan-1-one (0405-27) (290 mg, 1.41 mmol, 1.0 eq.) and 4-hydroxy-3,5-dimethyl benzaldehyde (210 mg, 1.41 mmol, 1.0 eq.) in ethanol (8 ml) was slowly added dropwise concentrated sulfuric acid (2 mL). The mixture was reacted at room temperature for 3.5 hours. The reaction solution was diluted with water (30 mL) and then extracted with ethyl acetate (30 mL×3). The extract was dried over anhydrous sodium sulfate and concentrated to give a yellow solid product (E)-3-(4-hydroxy-3,5-dimethylphenyl)-1-(7-(methylthio)benzofuran-4-yl)prop-2-en-1-one (0.47 g). LCMS(ESI): m/z 339[M+1]$^+$.

Step 9f: Preparation of tert-butyl (E)-2-(2,6-dimethyl-4-(3-(7-(methylthio)benzofuran-4-yl)-3-oxoprop-1-en-1-yl)phenoxy)-2-methylpropanoate (compound 0407-27): (E)-3-(4-hydroxy-3,5-dimethylphenyl)-1-(7-(methylthio)benzofuran-4-yl)prop-2-en-1-one (0406-27)(0.47 g, 1.39 mmol, 1.0 eq.) and tert-butyl 2-bromo-2-methylpropanoate (1.56 mL, 8.34 mmol, 6.0 eq.) were dissolved in acetonitrile (10 mL) and then potassium carbonate (0.77 g, 5.56 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a pale yellow solid product tert-butyl (E)-2-(2,6-dimethyl-4-(3-(7-(m ethylthio)benzofuran-4-yl)-3-oxoprop-1-en-1-yl)phenoxy)-2-methylpropanoate (234 mg, yield: 35%). LCMS(ESI): m/z 481[M+1]$^+$.

Step 9g: Preparation of (E)-2-(2,6-dimethyl-4-(3-(7-(methylthio)benzofuran-4-yl)-3-oxoprop-1-en-1-yl)phenoxy)-2-methylpropanoic acid (compound 27): to a solution of tert-butyl (E)-2-(2,6-dimethyl-4-(3-(7-(methylthio)benzofuran-4-yl)-3-oxoprop-1-en-1-yl)phenoxy)-2-methylpropanoate (0407-27)(234 mg, 0.487 mmol, 1.0 eq.) in dioxane (8 ml) was slowly added dropwise concentrated sulfuric acid (1 mL) at room temperature. The mixture was reacted at room temperature for 1.5 hours. The reaction solution was diluted with water (30 mL) and then extracted with ethyl acetate (30 mL×3). The extract was dried over anhydrous sodium sulfate and concentrated. The residue was then purified by column chromatography on silica gel (dichloromethane:methanol=20:1) to obtain a pale yellow solid product (E)-2-(2,6-dimethyl-4-(3-(7-(methylthio)benzofuran-4-yl)-3-oxoprop-1-en-1-yl)phenoxy)-2-methylpropanoic acid (160 mg, yield: 77%). LCMS(ESI): m/z 425 [M+1]$^+$; Melting point: 162~165° C.; $^1$HNMR (DMSO-d$_6$, 500 MHz): δ12.95 (s, 1H), 8.26-8.21 (m, 2H), 7.89 (d, J=8.4 Hz, 1H), 7.63 (d, J=5.6 Hz, 1H), 7.58-7.54 (m, 3H), 7.32 (d, J=8.0 Hz, 1H), 2.70 (s, 3H), 2.23 (s, 6H), 1.40 (s, 6H).

Example 10: Preparation of (E)-2-(4-(3-(2,3-dihydrobenzo[b]thiophen-5-yl)-3-oxoprop-1-en-1-yl)-2,6-dimethylphenoxy)-2-methylpropanoic acid (Compound 36) (Prepared According to Scheme 5)

Step 10a: Preparation of benzo[b]thiophene-1,1-dioxide (compound 0502-36): to a solution of benzo[b]thiophene (0501-36)(2.0 g, 15 mmol, 1.0 eq.) in dichloromethane (20 ml) were added 30% hydrogen peroxide solution (6 ml) and formic acid (4 ml) separately. The mixture was stirred at room temperature overnight. Then sodium bicarbonate solution (100 ml) was added to the mixture, which was extracted with dichloromethane (100 ml×3). The organic phases were combined, dried over anhydrous sodium sulfate, and filtered. The filtrate was dried by rotary evaporation to obtain a white solid product benzo[b]thiophene-1,1-dioxide (4.0 g, yield: 99%). LCMS(ESI): m/z 167 [M+]$^+$.

Step 10b: Preparation of 2,3-dihydrobenzo[b]thiophene-1,1-dioxide (compound 0503-36): to a solution of benzo[b]thiophene-1,1-dioxide (0502-36) (4.0 g, 22.5 mmol) in methanol (80 ml) and ethyl acetate (80 ml) was added palladium carbon (1.0 g) and then hydrogen was passed in. The mixture was stirred at room temperature overnight. The reaction solution was filtered and the filtrate was dried by rotary evaporation to obtain a crude white solid product 2,3-dihydrobenzo[b]thiophene-1,1-dioxide (3.80 g, yield: 99%). LCMS(ESI): m/z 169 [M+1]$^+$.

Step 10c: Preparation of 2,3-dihydrobenzo[b]thiophene (compound 0504-36): to a solution of lithium tetrahydroaluminum (3.8 g, 100 mmol, 4.5 eq.) in tetrahydrofuran (150 ml) was added dropwise a solution of benzo[b]thiophene-1,1-dioxide (0503-36)(3.8 g, 23 mmol, 1.0 eq.) in tetrahydrofuran (50 ml) at 0° C. The reaction solution was rewarmed to room temperature and reacted overnight. The reaction solution was cooled to 0° C., and after water (3.8 ml), 15% sodium hydroxide solution (12 ml) and water (3.8 ml) were added slowly successively, the mixture was stirred for half an hour. The solution was filtered and the filtrate was dried by rotary evaporation. The residue was purified by column chromatography on silica gel (the eluent: petroleum ether:ethyl acetate=20:1) to obtain a colorless oil product 2,3-dihydrobenzo[b]thiophene (0.91 g, yield: 29%). LCMS (ESI): m/z 137 [M+1]$^+$.

Step 10d: Preparation of 1-(2,3-dihydrobenzo[b]thiophen-5-yl)ethan-1-one (compound 0505-36): to a solution of 2,3-dihydrobenzo[b]thiophene (0504-36)(0.78 g, 6 mmol, 1.0 eq.) and acetyl chloride (0.94 g, 10 mmol, 2.0 eq.) in dichloromethane (40 ml) was added aluminum trichloride (0.96 g, 7.2 mmol, 1.2 eq.) at 0° C. The react ion solution was stirred at 0° C. for half an hour and 1N hydrochloric acid (20 ml) was added, and the mixture was stirred for half an hour. Two phases were separated and the aqueous phase was extracted with dichloromethane (50 ml×2). The organic phases were combined and dried by rotary evaporation. The residue w as purified by column chromatography on silica gel (the eluent: petroleum ether:ethyl acetate=10:1) to obtain a yellow oil product 1-(2,3-dihydrobenzo[b]thiophen-5-yl)ethan-1-one (0.99 g, yield: 79%). LCMS(ESI): m/z 179 [M+]$^+$.

Step 10e: Preparation of (E)-1-(2,3-dihydrobenzo[b]thiophen-5-yl)-3-(4-hydroxy-3,5-dimethylphenyl)prop-2-en-1-one (compound 0506-36): to a solution of 1-(2,3-dihydrobenzo[b]thiophen-5-yl)ethan-1-one (0505-36)(0.81 g, 4.6 mmol, 1.0 eq.) and 4-hydroxy-3,5-dimethyl benzaldehyde (0.69 g, 4.6 mmol, 1.0 eq.) in ethanol (20 ml) was added concentrated sulfuric acid (4 ml) slowly. The reaction was stirred at room temperature overnight. The reaction solution was diluted with ethyl acetate (15 ml) and washed with semi-saturated brine (100 ml×3). The organic phase was dried by rotary evaporation. The residue was purified by column chromatography on silica gel (the eluent: petroleum ether:ethyl acetate=6:1) to obtain a yellow solid product (E)-1-(2,3-dihydrobenzo[b]thiophen-5-yl)-3-(4-hydroxy-3,5-dimethylphenyl)prop-2-en-1-one (0.45 g, yield: 26%). LCMS(ESI): m/z 311 [M+]$^+$.

Step 10f: Preparation of tert-butyl (E)-2-(4-(3-(2,3-dihydrobenzo[b]thiophen-5-yl)-3-oxoprop-1-en-1-yl)-2,6-dimethylphenoxy)-2-methylpropanoate (compound 0507-36): to a solution of (E)-1-(2,3-dihydrobenzo[b]thiophen-5-yl)-3-(4-hydroxy-3,5-dimethylphenyl)prop-2-en-1-one (0506-360.45 g, 1.5 mmol, 1.0 eq.) in acetonitrile (30 ml) were added potassium carbonate (1.04 g, 7.5 mmol, 5.0 eq.) and tert-butyl 2-bromoisobutyrate (1.67 g, 7.5 mmol, 5.0 eq.). The reaction solution was heated to 82° C. and refluxed overnight under the protection of nitrogen. The reaction solution was dried by rotary evaporation. The residue was diluted with ethyl acetate (100 ml) and washed with water (100 ml×2). The organic phase was dried by rotary evaporation. The residue was purified by column chromatography on silica gel (the eluent: petroleum ether:ethyl acetate=20:1) to obtain a yellow oil product tert-butyl (E)-2-(4-(3-(2,3-dihydrobenzo[b]thiophen-5-yl)-3-oxoprop-1-en-1-yl)-2,6-dimethylphenoxy)-2-methylpropanoate (0.18 g, yield: 27%). LCMS(ESI): m/z 453 [M+]$^+$.

Step 10g: Preparation of (E)-2-(4-(3-(2,3-dihydrobenzo[b]thiophen-5-yl)-3-oxoprop-1-en-1-yl)-2,6-dimethyl phenoxy)-2-methylpropanoic acid (compound 36): to a solution of tert-butyl (E)-2-(4-(3-(2,3-dihydrobenzo[b]thiophen-5-yl)-3-oxoprop-1-en-1-yl)-2,6-dimethylphenoxy)-2-methylpropanoate (0507-36)(0.18 g, 0.40 mmol, 1.0 eq.) in dichloromethane (12 ml) was added trifluoroacetate (2 ml) slowly. The reaction solution was stirred overnight at room temperature. The reaction solution was poured into water (100 ml) and extracted with dichloromethane (100 ml×2). The organic phases were combined, dried over anhydrous sodium sulfate, and filtered. The filtrate was dried by rotary evaporation. The residue was purified by column chromatography on silica gel (the eluent: dichloromethane:methanol:formic acid=300:3:0.5) to obtain a yellow solid product (E)-2-(4-(3-(2,3-dihydrobenzo[b]thiophen-5-yl)-3-oxoprop-1-en-1-yl)-2,6-dimethylphenoxy)-2-methylpropanoic acid (150 mg, yield: 95.0%). LCMS(ESI): m/z 397[M+1]$^+$; Melting point: 157~160° C.; $^1$HNMR (DMSO, 50 MHz): δ12.57 (s, 1H), 7.40-8.01 (m, 7H), 3.44-3.46 (t, 2H, J=7.5 Hz), 3.33-3.37 (t, 2H, J=7.5 Hz), 2.22 (s, 6H), 1.39 (s, 6H).

Example 11: Preparation of (E)-2-(4-(3-(benzo[b]thiophen-5-yl)-3-oxoprop-1-en-1-yl)-2,6-dimethylphenoxy)-2-methylpropanoic acid (Compound 38) (Prepared According to Scheme 6)

Step 11a: Preparation of benzo[b]thiophene-5-carbonitrile (compound 0602-38): to a reaction flask were added 5-bromobenzo[b]thiophene (0601-38)(2.13 g, 10 mmol, 1.0 eq.), zinc cyanide (2.34 g, 20 mmol, 2.0 eq.), tetratriphenylphosphine palladium (1.16 g, 1 mmol, 0.1 eq.) and dimethylformamide (16 ml). The reaction was stirred under reflux overnight. The reaction solution was diluted with ethyl acetate (200 ml) and washed with semi-saturated brine (100 ml×3). The organic phase was dried by rotary evaporation. The residue was purified by column chromatography on silica gel (the eluent: petroleum ether:ethyl acetate=10:1) to obtain a white solid product benzo[b]thiophene-5-carbonitrile (1.57 g, yield: 99%). LCMS(ESI): m/z 160 [M+1]$^+$.

Step 11b: Preparation of 1-(benzo[b]thiophen-5-yl)ethan-1-one (compound 0603-38): to a solution of benzo[b]thiophene-5-carbonitrile (0602-38) 1.41 g, 8.9 mmol, 1.0 eq.) in tetrahydrofuran (30 ml) was added 3M methyl magnesium bromide (10.7 mmol, 1.2 eq.) at 0° C. The mixture was rewarmed to room temperature and stirred overnight, and then a saturated ammonium chloride solution (100 ml) was added, which was then extracted with dichloromethane (100 ml×2). The organic phases were combined and dried by rotary evaporation. The residue was dissolved in dioxane (30 ml) and then 10% sulfuric acid (30 ml) was added, which was then refluxed overnight. The reaction solution was cooled to room temperature and extracted with dichloromethane (100 ml×2). The organic phases were combined and dried by rotary evaporation. The residue was purified by column chromatography on silica gel (the eluent: petroleum ether:ethyl acetate=10:1) to obtain a white solid product 1-(benzo[b]thiophen-5-yl)ethan-1-one (0.99 g, yield: 63%). LCMS(ESI): m/z 177[M+1]$^+$.

Step 11c: Preparation of (E)-1-(benzo[b]thiophen-5-yl)-3-(4-hydroxy-3,5-dimethylphenyl)prop-2-en-1-one (compound 0604-38): to a solution of 1-(benzo[b]thiophen-5-yl)ethan-1-one (0603-38)(0.81 g, 4.6 mmol, 1.0 eq.) and 4-hydroxy-3,5-dimethyl benzaldehyde (0.69 g, 4.6 mmol, 1.0 eq.) in dioxane (20 ml) was added concentrated sulfuric acid (4 ml) slowly. The mixture was heated to 50° C. and stirred overnight. The reaction solution was diluted with ethyl acetate (100 ml) and washed with semi-saturated brine (100 ml×3). The organic phase was dried by rotary evaporation. The residue was purified by column chromatography on silica gel (the eluent: petroleum ether:ethyl acetate=5:1) to obtain a yellow solid product (E)-1-(benzo[b]thiophen-5-yl)-3-(4-hydroxy-3,5-dimethylphenyl)prop-2-en-1-one (0.22 g, yield: 16%). LCMS(ESI): m/z 309 [M+1]$^+$.

Step 11d: Preparation of tert-butyl (E)-2-(4-(3-(benzo[b]thiophen-5-yl)-3-oxoprop-1-en-1-yl)-2,6-dimethylphenoxy)-2-methylpropanoate (compound 0605-38): to a solution of (E)-1-(benzo[b]thiophen-5-yl)-3-(4-hydroxy-3,5- dimethylphenyl)prop-2-en-1-one (0604-38)(0.22 g, 0.72 mmol, 1.0 eq.) in acetonitrile (20 ml) were added potassium carbonate (0.497 g, 3.6 mmol, 5.0 eq.) and tert-butyl 2-bromoisobutyrate (0.796 g, 3.6 mmol, 5.0 eq.). The reaction solution was heated to 82° C. and refluxed overnight under the protection of nitrogen. The reaction solution was dried by rotary evaporation. The residue was purified by column chromatography on silica gel (the eluent: petroleum ether: ethyl acetate=10:1) to obtain a yellow oil product tert-butyl (E)-2-(4-(3-(benzo[b]thiophen-5-yl)-3-oxoprop-1-en-1-yl)-2,6-dimethylphenoxy)-2-methylpropanoate (0.11 g, yield: 34%). LCMS(ESI): m/z 451 [M+1]$^+$.

Step 11e: Preparation of (E)-2-(4-(3-(benzo[b]thiophen-5-yl)-3-oxoprop-1-en-1-yl)-2,6-dimethylphenoxy)-2-methylpropanoic acid (compound 38): to a solution of tert-butyl (E)-2-(4-(3-(benzo[b]thiophen-5-yl)-3-oxoprop-1-en-1-yl)-2,6-dimethylphenoxy)-2-methylpropanoate (0605-380.11 g, 0.24 mmol, 1.0 eq.) in dichloromethane (20 ml) was added trifluoroacetate (1 ml) slowly. The reaction solution was stirred at room temperature over night. The reaction solution was poured into water (100 ml) and extracted with dichloromethane (100 ml×2). The organic phases were combined, dried over anhydrous sodium sulfate, and filtered. The filtrate was dried by rotary evaporation. The residue was purified by column chromatography on silica gel (the eluent: dichloromethane:methanol:formic acid=300:3:0.5) to obtain a yellow solid product (E)-2-(4-(3-(benzo[b]thiophen-5-yl)-3-oxoprop-1-en-1-yl)-2,6-dimethylphenoxy)-2-methylpropanoic acid (100 mg, yield: 99.0%). LCMS(ESI): m/z 395 [M+1]$^+$; Melting point: 150~152° C.; $^1$HNMR (DMSO, 500 MHz): 12.92 (s, 1H), 8.78 (d, 1H, J=3 Hz), 8.20 (d, 1H, J=8.7 Hz), 8.10 (dd, 1H, J$_1$=8.7 Hz, J$_2$=1.5 Hz), 7.97 (m, 2H), 7.70 (m, 4H), 2.23 (s, 6H), 1.40 (s, 6H).

Example 12: Preparation of (E)-2-(4-(3-(benzo[d]thiazol-5-yl)-3-oxoprop-1-en-1-yl)-2,6-dimethylphenoxy)-2-methylpropanoic acid (Compound 39) (Prepared According to Scheme 6)

Step 12a: Preparation of (E)-1-(benzo[d]thiazol-5-yl)-3-(4-hydroxy-3,5-dimethylphenyl)prop-2-en-1-one (compound 0604-39): to a solution of 1-(benzo[d]thiazol-5-yl)ethan-1-one (0603-39)(0.23 g, 1.30 mmol, 1.0 eq.) in a mixed solution of ethanol (10 ml) and 1,4-dioxane (2 ml) was added 4-hydroxy-3,5-dimethyl benzaldehyde (0.21 g, 1.43 mmol, 1.1 eq.) and then added dropwise 98% sulfuric acid (3 ml). The reaction solution was reacted at room temperature overnight. Ethanol (8 ml) was added additionally and the mixture was reacted at room temperature for another 5 hours. 4-hydroxy-3,5-dimethyl benzaldehyde (0.10 g, 0.65 mmol, 0.5 eq.) and 98% sulfuric acid (2 ml) were added additionally. The reaction solution was stirred at room temperature overnight. The resulting reaction solution was diluted with ethyl acetate (100 ml) and washed with water (100 ml×2). The organic phase was dried by rotary evaporation. The residue was purified by column chromatography on silica gel (the eluent: petroleum ether:ethyl acetate=4:1→dichloromethane:methanol=40:1) to obtain a yellow solid product (E)-1-(benzo[d]thiazol-5-yl)-3-(4-hydroxy-3,5-dimethylphenyl)prop-2-en-1-one (0.35 g, yield: 80.7%). LCMS(ESI): m/z 310 [M+1]$^+$.

Step 12b: Preparation of tert-butyl (E)-2-(4-(3-(benzo[d]thiazol-5-yl)-3-oxoprop-1-en-1-yl)-2,6-dimethylphenoxy)-2-methylpropanoate (compound 0605-39): to a solution of ((E)-1-(benzo[d]thiazol-5-yl)-3-(4-hydroxy-3,5-dimethylphenyl)prop-2-en-1-one (0604-39)(0.30 g, 0.97 mmol, 1.0 eq.) in N,N-dimethylformamide (15 ml) were added potassium carbonate (0.54 g, 3.38 mmol, 4.0 eq.) and tert-butyl 2-bromoisobutyrate (1.30 g, 5.82 mmol, 6.0 eq.). The reaction solution was heated to 82° C. and refluxed for 0.75 days under the protection of nitro gen. The reaction solution was diluted with ethyl acetate (300 ml) and washed with semi-saturated brine (300 ml×3). The organic phase was dried by rotary evaporation. The residue was purified by column chromatography on silica gel (the eluent: petroleum ether: ethyl acetate=4:1) to obtain a pale yellow solid product tert-butyl (E)-2-(4-(3-(benzo[d]thiazol-5-yl)-3-oxoprop-1-en-1-yl)-2,6-dimethylphenoxy)-2-methylpropanoate (0.24 g, yield: 47.1%). LCMS(ESI): m/z 452 [M+1]$^+$.

Step 12c: Preparation of (E)-2-(4-(3-(benzo[d]thiazol-5-yl)-3-oxoprop-1-en-1-yl)-2,6-dimethylphenoxy)-2-methylpropanoic acid (compound 39): to a solution of tert-butyl (E)-2-(4-(3-(benzo[d]thiazol-5-yl)-3-oxoprop-1-en-1-yl)-2,6-dimethylphenoxy)-2-methylpropanoate (0605-39)(0.24 g, 0.53 mmol, 1.0 eq.) in dichloromethane (12 ml) was added trifluoroacetate (3 ml) slowly. The reaction solution was stirred at room temperature for 3 hours. The reaction solution was poured into water (100 ml), and extracted with dichloromethane (100 ml-2). The organic phases were combined and dried over anhydrous sodium sulfate, and filtered. The filtrate was dried by rotary evaporation. The residue was dried by rotary evaporation with methanol once to obtain a yellow solid product (E)-2-(4-(3-(benzo[d]thiazol-5-yl)-3-oxoprop-1-en-1-yl)-2,6-dimethylphenoxy)-2-methylpropanoic acid (210 mg, yield: 100%). LCMS(ESI): m/z 396 [M+1]$^+$; Melting point: 170~172° C.; $^1$HNMR (DMSO, 500 MHz): δ12.94 (s, 1H), 9.56 (s, 1H), 8.98 (s, 1H), 8.35-8.38 (d, 1H, J=11 Hz), 8.20-8.23 (dd, 1H, J$_1$=10.5 Hz, J$_2$=1.5 Hz), 8.02-8.06 (d, 1H, =19 Hz), 7.69-7.73 (d, 1H, J=19 Hz), 7.65 (s, 2H), 2.24 (s, 6H), 1.40 (s, 6H).

Example 13: Preparation of (E)-2-(4-(3-(6-methoxybenzofuran-2-yl)-3-oxoprop-1-en-1-yl)-2,6-dimethylphenoxy)-2-methylpropanoic acid (Compound 43) (Prepared According to Scheme 7)

Step 13a: Preparation of 1-(6-methoxybenzofuran-2-yl)ethan-1-one (compound 0706-43): 2-hydroxy-4-methoxybenzaldehyde (0701-430.3 g, 1.97 mmol, 1.0 eq.) and bromoacetone (0.17 mL, 1.97 mmol, 1.0 eq.) were dissolved in N,N-dimethylformamide (6 mL) and then cesium carbonate (0.96 g, 2.96 mmol, 1.5 eq.) was added. After the air in the system was replaced by nitrogen three times, the mixture was reacted at 60° C. overnight. The reaction solution was diluted with water (50 mL) and then extracted with ethyl acetate (20 mL×3). The extract was dried over anhydrous sodium sulfate and concentrated. The residue was then purified by column chromatography on silica gel (petroleum ether:ethyl acetate=6:1) to obtain a white solid product 1-(6-methoxybenzofuran-2-yl)ethan-1-one (0.308 g, yield: 82%). LCMS(ESI): m/z 191[M+1]$^+$.

Step 13b: Preparation of (E)-3-(4-hydroxy-3,5-dimethylphenyl)-1-(6-methoxybenzofuran-2-yl)prop-2-en-1-one (compound 0707-43): to a solution of 1-(6-methoxybenzofuran-2-yl)ethan-1-one (0706-43)(200 mg, 1.053 mmol, 1.0 eq.) and 4-hydroxy-3,5-dimethyl benzaldehyde (158 mg, 1.053 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (30 mL×3). The extract was dried over anhydrous sodium sulfate and concentrated to give a yellow solid product (E)-3-(4-hydroxy-3,5-dimethylphenyl)-1-(6-methoxybenzofuran-2-yl)prop-2-en-1-one (339 mg). LCMS (ESI): m/z 323[M+1]$^+$.

Step 13c: Preparation of tert-butyl (E)-2-(4-(3-(6-methoxybenzofuran-2-yl)-3-oxoprop-1-en-1-yl)-2,6-dimethylphenoxy)-2-methylpropanoate (compound 0708-43): (E)-3-(4-hydroxy-3,5-dimethylphenyl)-1-(6-methoxybenzofuran-2-yl)prop-2-en-1-one (0707-43339 mg, 1.053 mmol, 1.0 eq.) and tert-butyl 2-bromo-2-methylpropanoate (1.15 mL, 6.32 mmol, 6.0 eq.) were dissolved in acetonitrile (10 mL) and then potassium carbonate (0.58 g, 4.21 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=8:1) to obtain a yellow solid product tert-butyl (E)-2-(4-(3-(6-methoxybenzofuran-2-yl)-3-oxoprop-1-en-1-yl)-2,6-dimethylphenoxy)-2-methylpropanoate (158 mg, yield: 28%). LCMS(ESI): m/z 465 [M+1]$^+$.

Step 13d: Preparation of (E)-2-(4-(3-(6-methoxybenzofuran-2-yl)-3-oxoprop-1-en-1-yl)-2,6-dimethylphenoxy)-2-methylpropanoic acid (compound 43): to a solution of tert-butyl (E)-2-(4-(3-(6-methoxybenzofuran-2-yl)-3-oxoprop-1-en-1-yl)-2,6-dimethylphenoxy)-2-methylpropanoate (0708-43)(158 mg, 0.341 mmol, 1.0 eq.) in dioxane (8 ml) was added dropwise concentrated sulfuric acid (1 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(4-(3-(6-methoxybenzofuran-2-yl)-3-oxoprop-1-en-1-yl)-2,6-di methylphenoxy)-2-methylpropanoic acid (87 mg, yield: 63%). LCMS(ESI): m/z 409[M+1]$^+$; Melting point: 177~179° C.; $^1$HNMR (DMSO-d$_6$, 400 MHz): δ12.94 (s, 1H), 8.23 (s, 1H), 7.76-7.64 (m, 3H), 7.57 (s, 2H), 7.35 (d, J=1.6 Hz, 1H), 7.04-7.01 (m, 1H), 3.87 (s, 3H), 2.23 (s, 6H), 1.40 (s, 6H).

Example 14: Preparation of (E)-2-(4-(3-(benzofuran-2-yl)-3-oxoprop-1-en-1-yl)-2,6-dimethylphenoxy)-2-methylpropanoic acid (Compound 49) (Prepared According to Scheme 7)

Step 14a: Preparation of 1-(benzofuran-2-yl)ethan-1-one (compound 0706-49): 2-hydroxybenzaldehyde (0701-49) (0.36 g, 2.95 mmol, 1.0 eq.) and bromoacetone (0.24 mL, 2.95 mmol, 1.0 eq.) were dissolved in N,N-dimethylformamide (6 mL) and then cesium carbonate (1.25 g, 3.84 mmol, 1.5 eq.) was added. The air in the reaction system was replaced by nitrogen three times, and after that it was reacted at 60° C. overnight. The reaction solution was diluted with water (50 mL) and then extracted with ethyl acetate (20 mL×3). The extract was dried over anhydrous sodium sulfate and concentrated. The residue was then purified by column chromatography on silica gel (petroleum ether:ethyl acetate=10:1) to obtain a white solid product 1-(benzofuran-2-yl)ethan-1-one (0.356 g, yield: 75%). LCMS(ESI): m/z 161[M+1]$^+$.

Step 14b: Preparation of (E)-1-(benzofuran-2-yl)-3-(4-hydroxy-3,5-dimethylphenyl)prop-2-en-1-one (compound 0707-49): to a solution of 1-(benzofuran-2-yl)ethan-1-one (0706-49)(200 mg, 1.25 mmol, 1.0 eq.) and 4-hydroxy-3,5-dimethyl benzaldehyde (188 mg, 1.25 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (30 mL×3). The extract was dried over anhydrous sodium sulfate and concentrated to give a yellow solid product (E)-1-(benzofuran-2-yl)-3-(4-hydroxy-3,5-dimethylphenyl)prop-2-en-1-one (365 mg). LCMS(ESI): m/z 293[M+1]$^+$.

Step 14c: Preparation of tert-butyl (E)-2-(4-(3-(benzofuran-2-yl)-3-oxoprop-1-en-1-yl)-2,6-dimethylphenoxy)-2-methylpropanoate (compound 0708-49): (E)-1-(benzofuran-2-yl)-3-(4-hydroxy-3,5-dimethylphenyl)prop-2-en-1-one (0707-49)(365 mg, 1.25 mmol, 1.0 eq.) and tert-butyl 2-bromo-2-methylpropanoate (1.37 mL, 7.5 mmol, 6.0 eq.) were dissolved in acetonitrile (10 mL) and then potassium carbonate (0.69 g, 5.0 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a yellow solid product tert-butyl (E)-2-(4-(3-(benzofuran-2-yl)-3-oxoprop-1-en-1-yl)-2,6-dimethyl phenoxy)-2-methylpropanoate (163 mg, yield: 30%). LCMS (ESI): m/z 435[M+1]$^+$.

Step 14d: Preparation of (E)-2-(4-(3-(benzofuran-2-yl)-3-oxoprop-1-en-1-yl)-2,6-dimethylphenoxy)-2-methyl propanoic acid (compound 49): to a solution of tert-butyl (E)-2-(4-(3-(benzofuran-2-yl)-3-oxoprop-1-en-1-yl)-2,6-dimethylphenoxy)-2-methylpropanoate (0708-49)(163 mg, 0.375 mmol, 1.0 eq.) in dioxane (8 ml) was added dropwise concentrated sulfuric acid (1 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(4-(3-(benzofuran-2-yl)-3-oxoprop-1-en-1-yl)-2,6-dimethylphenoxy)-2-methylpropanoic acid (91 mg, yield: 64%). LCMS(ESI): m/z 379[M+1]$^+$, Melting point: 157~160° C.; $^1$HNMR (DMSO-d$_6$, 400 MHz): δ12.95 (s, 1H), 8.29 (s, 1H), 7.88 (d, J=8.0 Hz, 1H), 7.80-7.69 (m, 3H), 7.59-7.56 (m, 3H), 7.42-7.39 (m, 1H), 2.24 (s, 6H), 1.40 (s, 6H).

Example 15: Preparation of (E)-2-(2,6-dimethyl-4-(3-(6-methylbenzofuran-2-yl)-3-oxoprop-1-en-1-yl)phenoxy)-2-methylpropanoic acid (Compound 50) (Prepared According to Scheme 7)

Step 15a: Preparation of 1-(6-methylbenzofuran-2-yl)ethan-1-one (compound 0706-50): 2-hydroxy-4-methyl benzaldehyde (0701-50 0.3 g, 2.20 mmol, 1.0 eq.) and bromoacetone (0.18 mL, 2.20 mmol, 1.0 eq.) were dissolved in N,N-dimethylformamide (6 mL) and then cesium carbonate (1.08 g, 3.31 mmol, 1.5 eq.) was added. The air in the reaction system was replaced with nitrogen three times, and then the system was reacted at 60° C. overnight. The reaction solution was diluted with water (50 mL) and then extracted with ethyl acetate (20 mL×3). The extract was dried over anhydrous sodium sulfate and concentrated. The residue was then purified by column chromatography on silica gel (petroleum ether:ethyl acetate=10:1) to obtain a white solid product 1-(6-methylbenzofuran-2-yl)ethan-1-one (0.305 g, yield: 80%). LCMS(ESI): m/z 175[M+1]$^+$.

Step 15b: Preparation of (E)-3-(4-hydroxy-3,5-dimethylphenyl)-1-(6-methylbenzofuran-2-yl)prop-2-en-1-one (compound 0707-50): to a solution of 1-(6-methylbenzofuran-2-yl)ethan-1-one (0706-50)(200 mg, 1.15 mmol, 1.0 eq.) and 4-hydroxy-3,5-dimethyl benzaldehyde (172 mg, 1.15 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (30 mL×3). The extract was dried over anhydrous sodium sulfate and concentrated to give a yellow solid product (E)-3-(4-hydroxy-3,5-dimethylphenyl)-1-(6-methylbenzofuran-2-yl)prop-2-en-1-one (352 mg). LCMS (ESI): m/z 307 [M+1]$^+$.

Step 15c: Preparation of tert-butyl (E)-2-(2,6-dimethyl-4-(3-(6-methylbenzofuran-2-yl)-3-oxoprop-1-en-1-yl) phenoxy)-2-methylpropanoate (compound 008-50): (E)-3-(4-hydroxy-3,5-dimethylphenyl)-1-(6-methylbenzofuran-2-yl)prop-2-en-1-one (0707-50)(352 mg, 1.15 mmol, 1.0 eq.) and tert-butyl 2-bromo-2-methylpropanoate (1.26 mL, 6.9 mmol, 6.0 eq.) were dissolved in acetonitrile (10 mL) and then potassium carbonate (0.63 g, 4.6 mmol, 4.0 eq.) was added. The air in the reaction system was replaced with nitrogen three times, and then the system was reacted at 83° C. overnight. After the reaction was completed, the mixture was concentrate d to give a crude product, which was purified by column chromatography on silica gel (petroleum ether:ethyl acetate=15:1) to obtain a yellow solid product tert-butyl (E)-2-(2,6-dimethyl-4-(3-(6-methylbenzofuran-2-yl)-3-oxoprop-1-en-1-yl)phenoxy)-2-methylpropanoate (175 mg, yield: 34%). LCMS(ESI): m/z 449[M+1]$^+$.

Step 15d: Preparation of (E)-2-(2,6-dimethyl-4-(3-(6-methylbenzofuran-2-yl)-3-oxoprop-1-en-1-yl)phenoxy)-2-methylpropanoic acid (compound 50): to a solution of tert-butyl (E)-2-(2,6-dimethyl-4-(3-(6-methylbenzofuran-2-yl)-3-oxoprop-1-en-1-yl)phenoxy)-2-methylpropanoate (0708-50175 mg, 0.391 mmol, 1.0 eq.) in dioxane (8 ml) was added dropwise concentrated sulfuric acid (1 mL) slowly at room temperature. The mixture was reacted at room temperature for 1.5 hours. The reaction solution was diluted with water (20 mL) and extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(2,6-dimethyl-4-(3-(6-methylbenzofuran-2-yl)-3-oxoprop-1-en-1-yl)phenoxy)-2-methylpropanoic acid (89 mg, yield: 58%). LCMS(ESI): m/z 393[M+1]$^+$; Melting point: 18~182° C.: $^1$HNMR (DMSO-d$_6$, 400 MHz): δ12.96 (s, 1H), 8.25 (s, 1H), 7.77-7.57 (m, 3H), 7.57 (d, J=6.8 Hz, 3H), 7.24 (d, J=8.0 Hz, 1H), 2.49 (s, 3H), 2.24 (s, 6H), 1.40 (s, 6H).

Example 16: Preparation of (E)-2-(2,6-dimethyl-4-(3-(6-(methylthio)benzofuran-2-yl)-3-oxoprop-1-en-1-yl)phenoxy)-2-methylpropanoic acid (Compound 51) (Prepared According to Scheme 7)

Step 16a: Preparation of ethyl 6-bromobenzofuran-2-carboxylate (compound 0702-51): to a flask were added 4-bromo-2-hydroxybenzaldehyde (0701-51)(2.5 g, 12.44 mmol, 1.0 eq.), potassium carbonate (6.86 g, 49.75 mmol, 4.0 eq.) and bromoethyl acetate (4.13 mL, 37.32 mmol, 3.0 eq.). The mixture was reacted at 130° C. for 4.5 hours. The reaction solution was cooled to room temperature, diluted with water (50 mL) and extracted with ethyl acetate (40 mL×3). The extract was dried over anhydrous sodium sulfate and concentrated. The residue was then purified by column chromatography on silica gel (petroleum ether:ethyl acetate=30:1) to obtain a white solid product ethyl 6-bromobenzofuran-2-carboxylate (1.09 g, yield: 33%). LCMS (ESI): m/z 269[M+1]$^+$.

Step 16b: Preparation of 6-bromobenzofuran-2-carboxylic acid (compound 0703-51): to a reaction flask were added ethyl 6-bromobenzofuran-2-carboxylate (0702-51) (1.09 g, 4.05 mmol, 1.0 eq.), sodium hydroxide (0.65 g, 16.21 mmol, 4.0 eq.), tetrahydrofuran (12 mL) and water (10 mL). The mixture was stirred at 45° C. for 2 hours. The reaction solution was diluted with water (20 mL), adjusted to a pH valve of 5 by adding dropwise 1N diluted hydrochloric acid solution and then extracted with ethyl acetate (20 mL×3). The extract was dried over anhydrous sodium sulfate and concentrated to give a yellow solid product 6-bromobenzofuran-2-carboxylic acid (0.89 g, yield: 91%). LCMS(ESI): m/z 241[M+1]$^+$.

Step 16c: Preparation of 6-bromo-N-methoxy-N-methylbenzofuran-2-carboxamide (compound 0704-51): 6-bromobenzofuran-2-carboxylic acid (0703-51)(0.89 g, 3.69 mmol, 1.0 eq.), N,O-dimethylhydroxylamine hydrochloride (0.47 g, 4.80 mmol, 1.3 eq.), HATU (1.68 g, 4.43 mmol, 1.2 eq.) and triethylamine (1.28 mL, 9.23 mmol, 2.5 eq.) were dissolved in dichloromethane (20 mL) and the mixture was reacted at room temperature for 1 hour. The reaction solution was diluted with water (20 mL) and extracted with dichloromethane (20 mL×3). The extract was dried over anhydrous sodium sulfate and concentrated. The residue was then purified by column chromatography on silica gel (petroleum ether:ethyl acetate=5:1) to obtain a white solid product 6-bromo-N-methoxy-N-methylbenzofuran-2-carboxamide (1.07 g, yield: 100%). LCMS(ESI): m/z 284[M+1]$^+$.

Step 16d: Preparation of 1-(6-bromobenzofuran-2-yl) ethan-1-one (compound 0705-51): 6-bromo-N-methoxy-N-methylbenzofuran-2-carboxamide (0704-51)(1.05 g, 3.70 mmol, 1.0 eq.) was dissolved in dried tetrahydrofuran (15 mL) and then cooled to 0° C. under an ice-water bath. Then methyl magnesium bromide (3Methyl ether solution, 2.46 mL, 7.39 mmol, 2.0 eq.) was added dropwise slowly. The reaction solution was war med to room temperature and reacted for 1 hour. The reaction was quenched by saturated ammonium chlor ide solution (30 mL) and extracted with ethyl acetate (30 mL×3). The extract was dried over anhydrous sodium sulfate, and concentrated to obtain a white solid product 1-(6-bromobenzofuran-2-yl)ethan-1-one (0.81 g, yield: 92%). LCMS(ESI): m/z 239[M+1]$^+$.

Step 16e: Preparation of 1-(6-(methylthio)benzofuran-2-yl)ethan-1-one (compound 0706-51): to a flask were added 1-(6-bromobenzofuran-2-yl)ethan-1-one (0705-51)(0.75 g, 3.14 mmol, 1.0 eq.), dimethyl disulfide (1.11 mL, 12.56 mmol, 4.0 eq.), copper powder (1.69 g, 26.67 mmol, 8.5 eq.) and N,N-dimethylformamide (15 mL)). The mixture was heated to 140° C. and reacted for 24 hours under the protection of nitrogen. The reaction solution was cooled to room temperature, diluted with water (50 mL), and extracted with ethyl acetate (40 mL×3). The extract was dried over anhydrous sodium sulfate and concentrated. The residue was then purified by column chromatography on silica gel (petroleum ether:ethyl acetate=30:1) to obtain a pale yellow solid product 1-(6-(methylthio)benzofuran-2-yl)ethan-1-one (0.142 g, yield: 22%). LCMS(ESI): m/z 207[M+1]$^+$.

Step 16f: Preparation of (E)-3-(4-hydroxy-3,5-dimethylphenyl)-1-(6-(methylthio)benzofuran-2-yl)prop-2-en-1-one (0707-51): to a solution of 1-(6-(methylthio)benzofuran-2-yl)ethan-1-one (0706-51)(50 mg, 0.243 mmol, 1.0 eq.) and 4-hydroxy-3,5-dimethyl benzaldehyde (37 mg, 0.243 mmol, 1.0 eq.) in ethanol (4 ml) was added dropwise concentrated sulfuric acid (1 mL) slowly. The mixture was reacted at room temperature for 3.5 hours. The reaction solution was diluted with water (20 mL) and then extracted with ethyl acetate (30 mL×3). The extract was dried over anhydrous sodium sulfate and concentrated to give a yellow solid product (E)-3-(4-hydroxy-3,5-dimethylphenyl)-1-(6-(methylthio)benzofuran-2-yl)prop-2-en-1-one (82 mg). LCMS(ESI): m/z 339[M+1]$^+$.

Step 16g: Preparation of tert-butyl (E)-2-(2,6-dimethyl-4-(3-(6-(methylthio)benzofuran-2-yl)-3-oxoprop-1-en-1-yl) phenoxy)-2-methylpropanoate (compound 0708-51): (E)-3-(4-hydroxy-3,5-dimethylphenyl)-1-(6-(methylthio) benzofuran-2-yl)prop-2-en-1-one (0707-5182 mg, 0.243 mmol, 1.0 eq.) and tert-butyl 2-bromo-2-methylpropanoate (0.27 mL, 1.458 mmol, 6.0 eq.) were dissolved in acetonitrile (6 mL) and then potassium carbonate (0.134 g, 0.972 mmol, 4.0 eq.) was added. The air in the reaction system was replaced with nitrogen three times, and then the system was reacted at 83° C. for 24 hours. After the reaction was completed, the mixture was concentrated to give a crude product, which was purified by column chromatography on silica gel (petroleum ether:ethyl acetate=0:1) to obtain a yellow solid product tert-butyl (E)-2-(2,6-dimethyl-4-(3-(6-(methylthio)benzofuran-2-yl)-3-oxoprop-1-en-1-yl)phenoxy)-2-methylpropanoate (35 mg, yield: 30%). LCMS (ESI): m/z 481[M+1]$^+$.

Step 16 h: Preparation of (E)-2-(2,6-dimethyl-4-(3-(6-(methylthio)benzofuran-2-yl)-3-oxoprop-1-en-1-yl)phenoxy)-2-methylpropanoic acid (compound 51): to a solution of tert-butyl (E)-2-(2,6-dimethyl-4-(3-(6-(methylthio)benzofuran-2-yl)-3-oxoprop-1-en-1-yl)phenoxy)-2-methylpropanoate (0708-51)(35 mg, 0.073 mmol, 1.0 eq.) in dioxane (5 ml) was added dropwise concentrated sulfuric acid (0.5 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(2,6-dimethyl-4-(3-(6-(methylthio)benzofuran-2-yl)-3-oxoprop-1-en-1-yl)phenoxy)-2-methylpropanoic acid (25 mg, yield: 81%). LCMS(ESI): m/z 425[M+1]$^+$; Melting point: 180~182° C.; $^1$HNMR (DMSO-d$_6$, 400 MHz): δ12.96 (s, 1H), 8.24 (s, 1H), 7.78-7.64 (m, 4H), 7.58 (s, 2H), 7.30-7.27 (m, 1H), 2.59 (s, 3H), 2.23 (s, 6H), 1.40 (s, 6H).

Example 17: Preparation of (E)-2-methyl-2-(4-(3-(6-(methylthio)benzofuran-2-yl)-3-oxoprop-1-en-1-yl) phenoxy)propanoic acid (Compound 56) (Prepared According to Scheme 7)

Step 17a: Preparation of (E)-3-(4-hydroxyphenyl)-1-(6-(methylthio)benzofuran-2-yl)prop-2-en-1-one (compound 0707-56): to a solution of 1-(6-(methylthio)benzofuran-2-yl)ethan-1-one (0706-51) (95 mg, 0.461 mmol, 1.0 eq.) and 4-hydroxybenzaldehyde (56 mg, 0.461 mmol, 1.0 eq.) in ethanol (8 ml) was added dropwise concentrated sulfuric acid (2 mL) slowly. The mixture was reacted at room temperature overnight. The reaction solution was diluted with water (20 mL) and then extracted with ethyl acetate (30 mL×3). The extract was dried over anhydrous sodium sulfate and concentrated to give a yellow solid product (E)-3-(4-hydroxyphenyl)-1-(6-(methylthio)benzofuran-2-yl)prop-2-en-1-one (143 mg). LCMS(ESI): m/z 311[M+1]$^+$.

Step 17b: Preparation of tert-butyl (E)-2-methyl-2-(4-(3-(6-(methylthio)benzofuran-2-yl)-3-oxopop-1-en-1-yl)phenoxy)propanoate (compound 0708-56): (E)-3-(4-hydroxyphenyl)-1-(6-(methylthio)benzofuran-2-yl)prop-2-en-1-one (0707-56)(143 mg, 0.461 mmol, 1.0 eq.) and tert-butyl 2-bromo-2-methylpropanoate (0.42 mL, 2.306 mmol, 5.0 eq.) were dissolved in acetonitrile (8 mL) and then potassium carbonate (0.25 g, 1.844 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a yellow solid product tert-butyl (E)-2-methyl-2-(4-(3-(6-(methylthio)benzofuran-2-yl)-3-oxoprop-1-en-1-yl)phenoxy)propanoate (98 mg, yield: 47%). LCMS(ESI): m/z 453[M+1]$^+$.

Step 17c: Preparation of (E)-2-methyl-2-(4-(3-(6-(methylthio)benzofuran-2-yl)-3-oxoprop-1-en-1-yl)phenoxy) propanoic acid (compound 56): to a solution of tert-butyl (E)-2-methyl-2-(4-(3-(6-(methylthio)benzofuran-2-yl)-3-oxoprop-1-en-1-yl)phenoxy)propanoate (0708-56)(98 mg, 0.217 mmol, 1.0 eq.) in dioxane (8 ml) was added dropwise concentrated sulfuric acid (1 mL) slowly at room temperature. The mixture was reacted at room temperature for 2 hours. The reaction solution was diluted with water (20 mL) and then extracted with ethyl acetate (20 mL×3). The extract was dried over anhydrous sodium sulfate and concentrated. The residue w as then purified by column chromatography on silica gel (dichloromethane:methanol=20:1) to obtain a yellow solid product (E)-2-methyl-2-(4-(3-(6-(methylthio) benzofuran-2-yl)-3-oxoprop-1-en-1-yl)phenoxy)propanoic acid (70 mg, yield: 81%). LCMS(ESI): m/z 397[M+1]$^+$; Melting point: 218~220° C.; $^1$HNMR (DMSO-d$_6$, 400 MHz): δ13.24 (s, 1H), 8.21 (s, 1H), 7.84-7.74 (m, 5H), 7.63 (s, 1H), 7.30-7.27 (m, 1H), 6.88 (d, J=8.4 Hz, 2H), 2.59 (s, 3H), 1.58 (s, 6H).

Example 18: Preparation of (E)-2-(2,6-dimethyl-4-(3-(6-(methylthio)benzofuran-2-yl)-3-oxoprop-1-en-1-yl)phenoxy)acetic acid (Compound 57) (Prepared According to Scheme 7)

Step 18a: Preparation of tert-butyl (E)-2-(2,6-dimethyl-4-(3-(6-(methylthio)benzofuran-2-yl)-3-oxoprop-1-en-1-yl) phenoxy)acetate (compound 0708-57): (E)-3-(4-hydroxy-3,5-dimethylphenyl)-1-(6-(methylthio)benzofuran-2-yl)prop-2-en-1-one (0707-51)(112 mg, 0.331 mmol, 1.0 eq.) and tert-butyl bromoacetate (0.21 mL, 1.325 mmol, 6.0 eq.) were dissolved in acetonitrile (8 mL) and then potassium carbonate (0.183 g, 1.325 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a yellow solid product tert-butyl (E)-2-(2,6-dimethyl-4-(3-(6-(methylthio)benzofuran-2-yl)-3-oxoprop-1-en-1-yl)phenoxy)acetate (60 mg, yield: 40%). LCMS (ESI): m/z 453[M+1]$^+$.

Step 18b: Preparation of (E)-2-(2,6-dimethyl-4-(3-(6-(methylthio)benzofuran-2-yl)-3-oxoprop-1-en-1-yl)phenoxy)acetic acid (compound 57): to a solution of tert-butyl (E)-2-(2,6-dimethyl-4-(3-(6-(methylthio)benzofuran-2-yl)-3-oxoprop-1-en-1-yl)phenoxy)acetate (0708-57)(60 mg, 0.133 mmol, 1.0 eq.) in dioxane (5 ml) was added dropwise concentrated sulfuric acid (0.5 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid (E)-2-(2,6-dimethyl-4-(3-(6-(methylthio)benzofuran-2-yl)-3-oxoprop-1-en-1-yl)phenoxy)acetic acid (30 mg, yield: 57%). LCMS(ESI): m/z 397[M+1]$^+$; melting point: 220~223° C.: $^1$HNMR (DMSO-d$_6$, 400 MHz): δ12.96 (s, 1H), 8.25 (s, 1H), 7.79-7.70 (m, 3H), 7.66-7.59 (m, 3H), 7.30-7.28 (m, 1H), 4.45 (s, 2H), 2.59 (s, 3H), 2.30 (s, 6H).

Example 19: Preparation of (E)-2-(2,6-dimethyl-4-(3-(7-(methylthio)benzofuran-2-yl)-3-oxoprop-1-en-1-yl)phenoxy)-2-methylpropanoic acid (Compound 58) (Prepared According to Scheme 8)

Step 19a: Preparation of 1-(7-bromobenzofuran-2-yl)ethan-1-one (compound 0802-58): 3-bromo-2-hydroxy benzaldehyde (0801-58)(2.39 g, 11.9 mmol, 1.0 eq.) and bromoacetone (1.63 g, 11.9 mmol, 1.0 eq.) were dissolved in N,N-dimethylformamide (20 mL) and then cesium carbonate (5.82 g, 17.85 mmol, 1.2 eq.) was added. The air in the reaction system was replaced with nitrogen three times, and then the system was reacted at 60° C. overnight. The reaction solution was diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=10:1) to obtain a white solid product 1-(7-bromobenzofuran-2-yl)ethan-1-one (1.37 g, yield: 40%). LCMS(ESI): m/z 239[M+]$^+$.

Step 19b: Preparation of 1-(7-(methylthio)benzofuran-2-yl)ethan-1-one (compound 0803-58): to a flask were added 1-(7-bromobenzofuran-2-yl)ethan-1-one (0802-581.27 g, 5.31 mmol, 1.0 eq.), triethylene diamine (1.19 g, 10.62 mmol, 2.0 eq.), cuprous iodide (1.01 g, 5.31 mmol, 1.0 eq.) and dimethyl sulfoxide (20 m L)). The mixture was heated to 170° C. and reacted overnight under the protection of nitrogen. The reaction solution was cooled to room temperature, diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=30:1) to obtain a pale yellow solid product 1-(7-(methylthio)benzofuran-2-yl)ethan-1-one (0.35 g, yield: 30%). LCMS(ESI): m/z 207 [M+1]$^+$.

Step 19c: Preparation of (E)-3-(4-hydroxy-3,5-dimethylphenyl)-1-(7-(methylthio)benzofuran-2-yl)prop-2-en-1-one (compound 0804-58): to a solution of 1-(7-(methylthio)benzofuran-2-yl)ethan-1-one (0803-58) (350 mg, 1.70 mmol, 1.0 eq.) and 4-hydroxy-3,5-dimethyl benzaldehyde (255 mg, 1.70 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (30 mL×3). The extract was dried over anhydrous sodium sulfate and concentrated. The residue was then purified by column chromatography on silica gel (petroleum ether:ethyl acetate=5:1) to obtain a yellow solid product (E)-3-(4-hydroxy-3,5-dimethylphenyl)-1-(7-(methylthio)benzofuran-2-yl)prop-2-en-1-one (380 mg, yield: 66%). LCMS(ESI): m/z 339[M+1]$^+$.

Step 19d: Preparation of tert-butyl (E)-2-(2,6-dimethyl-4-(3-(7-(methylthio)benzofuran-2-yl)-3-oxoprop-1-en-1-yl)phenoxy)-2-methylpropanoate (compound 0805-58): (E)-3-(4-hydroxy-3,5-dimethylphenyl)-1-(7-(methylthio)benzofuran-2-yl)prop-2-en-1-one (0804-58380 mg, 1.124 mmol, 1.0 eq.) and tert-butyl 2-bromo-2-methylpropanoate (1.25 mL, 6.75 mmol, 6.0 eq.) were dissolved in acetonitrile (10 mL) and then potassium carbonate (0.62 g, 4.50 mmol, 4.0 eq.) was added. The air in the reaction system was replaced with nitrogen three times, and then the system was reacted at 83° C. overnight. After the reaction was completed, the mixture w as concentrated to give a crude product, which was purified by column chromatography on silica gel (petroleum ether:ethyl acetate=10:1) to obtain a yellow solid product tert-butyl (E)-2-(2,6-dimethyl-4-(3-(7-(methylthio)benzofuran-2-yl)-3-oxoprop-1-en-1-yl)phenoxy)-2-methylpropanoate (83 mg, yield: 15%). LCMS (ESI): m/z 481[M+1]$^+$.

Step 19e: Preparation of (E)-2-(2,6-dimethyl-4-(3-(7-(methylthio)benzofuran-2-yl)-3-oxopop-1-en-1-yl)phenoxy)-2-methylpropanoic acid (compound 58): to a solution of tert-butyl (E)-2-(2,6-dimethyl-4-(3-(7-(methylthio)benzofuran-2-yl)-3-oxoprop-1-en-1-yl)phenoxy)-2-methylpropanoate (0805-58)(83 mg, 0.173 mmol, 1.0 eq.) in dioxane (5 ml) was added dropwise concentrated sulfuric acid (0.5 mL) slowly at room temperature. The mixture was reacted at room temperature for 2 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(2,6-dimethyl-4-(3-(7-(methylthio)benzofuran-2-yl)-3-oxoprop-1-en-1-yl)phenoxy)-2-methylpropanoic acid (70 mg, yield: 95%). LCMS(ESI): m/z 425[M+1]$^+$; melting point: 151~154° C.: $^1$HNMR (DMSO-d$_6$, 400 MHz): δ12.97 (s, 1H), 8.34 (s, 1H), 7.78-7.68 (m, 3H), 7.60 (s, 2H), 7.46-7.38 (m, 2H), 2.63 (s, 3H), 2.24 (s, 6H), 1.40 (s, 6H).

Example 20: Preparation of (E)-2-(2,6-dimethyl-4-(3-(4-(methylthio)benzofuran-2-yl)-3-oxoprop-1-en-1-yl)phenoxy)-2-methylpropanoic acid (Compound 60) (Prepared According to Scheme 9)

Step 20a: Preparation of 1-(4-bromobenzofuran-2-yl)ethan-1-one (compound 0902-60): 2-bromo-6-hydroxy benzaldehyde (0901-60)(2.39 g, 11.9 mmol, 1.0 eq.) and bromoacetone (1.63 g, 11.9 mmol, 1.0 eq.) were dissolved in N,N-dimethylformamide (20 mL) and then cesium carbonate (5.82 g, 17.85 mmol, 1.2 eq.) was added. The air in the reaction system was replaced with nitrogen three times, and then the system was reacted at 60° C. overnight. The reaction solution was diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=10:1) to obtain a white solid product 1-(4-bromobenzofuran-2-yl)ethan-1-one (1.44 g, yield: 42%). LCMS(ESI): m/z 239[M+1]$^+$.

Step 20b: Preparation of 1-(4-(methylthio)benzofuran-2-yl)ethan-1-one (compound 0903-60): to a flask were added 1-(4-bromobenzofuran-2-yl)ethan-1-one (0902-60)(1.22 g, 5.10 mmol, 1.0 eq.), dimethyl disulfide (2.26 mL, 25.5 mmol, 5.0 eq.), copper powder (2.76 g, 43.38 mmol, 8.5 eq.) and N,N-dimethylformamide (20 mL)). The mixture was heated to 140° C. and reacted overnight under the protection of nitrogen. The reaction solution was cooled to room temperature, diluted with water (50 mL), and then extracted with ethyl acetate (30 mL×3). The extract was dried over anhydrous sodium sulfate and concentrated. The residue was then purified by column chromatography on silica gel (petroleum ether:ethyl acetate=30:1) to obtain a pale yellow solid product 1-(4-(methylthio)benzofuran-2-yl)ethan-1-one (0.148 g, yield: 14%). LCMS(ESI): m/z 207[M+1]⁺.

Step 20c: Preparation of (E)-3-(4-hydroxy-3,5-dimethylphenyl)-1-(4-(methylthio)benzofuran-2-yl)prop-2-en-1-one (compound 0904-60): to a solution of 1-(4-(methylthio)benzofuran-2-yl)ethan-1-one (0903-60) (148 mg, 0.718 mmol, 1.0 eq.) and 4-hydroxy-3,5-dimethyl benzaldehyde (108 mg, 0.718 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and extracted with ethyl acetate (30 mL×3). The extract was dried over anhydrous sodium sulfate and concentrated to give a yellow solid (E)-3-(4-hydroxy-3,5-dimethylphenyl)-1-(4-(methylthio)benzofuran-2-yl)prop-2-en-1-one (217 mg, yield: 89%). LCMS(ESI): m/z 339[M+1]⁺.

Step 20d: Preparation of tert-butyl (E)-2-(2,6-dimethyl-4-(3-(4-(methylthio)benzofuran-2-yl)-3-oxoprop-1-en-1-yl)phenoxy)-2-methylpropanoate (compound 0905-60): (E)-3-(4-hydroxy-3,5-dimethylphenyl)-1-(4-(methylthio)benzofuran-2-yl)prop-2-en-1-one (0904-60) (217 mg, 0.642 mmol, 1.0 eq.) and tert-butyl 2-bromo-2-methylpropanoate (0.71 mL, 3.85 mmol, 6.0 eq.) were dissolved in acetonitrile (10 mL) and then potassium carbonate (0.35 g, 2.568 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a yellow solid product tert-butyl (E)-2-(2,6-dimethyl-4-(3-(4-(methylthio)benzofuran-2-yl)-3-oxoprop-1-en-1-yl)phenoxy)-2-methylpropanoate (98 mg, yield: 32%). LCMS(ESI): m/z 481[M+1]⁺.

Step 20e: Preparation of (E)-2-(2,6-dimethyl-4-(3-(4-(methylthio)benzofuran-2-yl)-3-oxopop-1-en-1-yl)phenoxy)-2-methylpropanoic acid (compound 60): to a solution of tert-butyl (E)-2-(2,6-dimethyl-4-(3-(4-(methylthio) benzofuran-2-yl)-3-oxoprop-1-en-1-yl)phenoxy)-2-methylpropanoate (0905-60)(98 mg, 0.204 mmol, 1.0 eq.) in dioxane (5 ml) was added dropwise concentrated sulfuric acid (0.5 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloromethane:methanol=20:1) to obtain a yellow solid product (E)-2-(2,6-dimethyl-(3-(4-(methylthio)benzofuran-2-yl)-3-oxoprop-1-en-1-yl)phenoxy)-2-methylpropanoic acid (63 mg, yield: 73%). LCMS(ESI): m/z 425[M+1]⁺; melting point: 196~198° C.; ¹HNMR (DMSO-d₆, 400 MHz): δ12.96 (s, 1H), 8.36 (s, 1H), 7.87 (d, J=15.6 Hz, 1H), 7.70 (d, J=15.6 Hz, 1H), 7.62 (s, 2H), 7.56-7.52 (m, 2H), 7.26-7.22 (m, 1H), 2.65 (s, 3H), 2.24 (s, 6H), 1.40 (s, 6H).

Example 21: Preparation of (E)-2-(2,6-dimethyl-4-(3-(3-methyl-6-(methylthio)benzofuran-2-yl)-3-oxoprop-1-en-1-yl)phenoxy)-2-methylpropanoic acid (Compound 62) (Prepared According to Scheme 10)

Step 21a: Preparation of 1-(2-hydroxy-4-(methylthio)phenyl)ethan-1-one (compound 1002-62): to a solution of 1-(4-fluoro-2-hydroxyphenyl)ethan-1-one (1001-622.3 g, 14.92 mmol, 1.0 eq.) in water (3 ml) was added a 20% sodium methyl mercaptan aqueous solution (30 ml). The mixture was refluxed at 100° C. overnight. The reaction solution was diluted with water (150 ml), adjusted to a pH value of 5-6 with diluted hydrochloric acid, extracted with ethyl acetate (80 ml-2) and then washed with semi-saturated brine (50 ml×2). The organic phase was dried by rotary evaporation to obtain a crude pale yellow oil product 1-(2-hydroxy-4-(methylthio)phenyl)ethan-1-one (2.69 g, yield: 98.9%). LCMS(ESI): m/z 183 [M+1]⁺.

Step 21b: Preparation of 1-(3-methy-6-(methylthio)benzofuran-2-yl)ethan-1-one (compound 1003-62): to a reaction flask were added 1-(2-hydroxy-4-(methylthio)phenyl)ethan-1-one (1002-62)(890 mg, 4.88 mmol, 1.0 eq.) and DMF (40 ml), and then cesium carbonate (4.77 g, 14.64 mmol, 3.0 eq.) and bromoacetone (803 mg, 5.86 mmol, 1.2 eq.) were added. The mixture was reacted at 80° C. overnight, and then cooled to room temperature. The reaction solution was poured into water (200 ml) and extracted with ethyl acetate (100 ml×2). The extract was washed with saturated brine three times, dried over anhydrous sodium sulfate and filtered. The filtrate was dried by rotary evaporation. The obtained residue was purified by column chromatography on silica gel (the eluent: petroleum ether:ethyl acetate=10:1) to obtain a white solid product 1-(3-methyl-6-(methylthio)benzofuran-2-yl)ethan-1-one (251 m g, yield: 25.1%). LCMS(ESI): m/z 221 [M+1]⁺.

Step 21c: Preparation of (E)-3-(4-hydroxy-3,5-dimethylphenyl)-1-(3-methyl-6-(methylthio)benzofuran-2-yl)prop-2-en-1-one (compound 1004-62): to a solution of 1-(3-methyl-6-(methylthio)benzofuran-2-yl)ethan-1-one (1003-62)(0.22 g, 1.0 mmol, 1.0 eq.) and 4-hydroxy-3,5-dimethyl benzaldehyde (0.165 g, 1.1 mmol, 1.1 eq.) in anhydrous ethanol (20 ml) was added concentrated sulfuric acid (4 ml) slowly. The reaction was stirred at room temperature for 1 day. The reaction solution was poured into ice-water, extracted with dichloromethane (100 ml×2). The extract was washed with semi-saturated brine (100 ml-3), and dried over anhydrous sodium sulfat e. The organic phase was dried by rotary evaporation to obtain a crude yellow liquid product (E)-3-(4-hydroxy-3,5-dimethylphenyl)-1-(3-methyl-6-(methylthio)benzofuran-2-yl)prop-2-en-1-one (0.334 g, yield: 94.7%). LCMS(ESI): m/z 353[M+1]⁺.

Step 21d: Preparation of tert-butyl (E)-2-(2,6-dimethyl-4-(3-(3-methyl-6-(methylthio)benzofuran-2-yl)-3-oxoprop-1-en-1-yl)phenoxy)-2-methylpropanoate (compound 1005-62): to a solution of ((E)-3-(4-hydroxy-3,5-dimethylphenyl)-1-(3-methyl-6-(methylthio)benzofuran-2-yl)prop-2-en-1-one (1004-62) 0.334 g, 0.95 mmol, 1.0 eq.) in DMF (30 ml) were added potassium carbonate (0.393 g, 2.85 mmol, 3.0 eq.) and then tert-butyl 2-bromoisobutyrate (2.1 g, 9.5 mmol, 10.0 eq.) in three batches. The reaction solution was heated to 100° C. and reacted overnight under the protection of nitrogen. The reaction solution was cooled to room temperature, poured into water and extracted with ethyl acetate (100 ml×2). The organic phases were combined and washed with brine three times, dried over anhydrous sodium sulfate and concentrated under reduced pressure. The residue was purified by column chromatography on silica gel (the eluent: petroleum ether:ethyl acetate=3:1) to obtain a yellow solid product tert-butyl (E)-2-(2,6-dimethyl-4-(3-(3-methyl-6-(methylthio)benzofuran-2-yl)-3-oxoprop-1-en-1-yl)phenoxy)-2-methylpropanoate (0.246 g, yield: 52.3%). LCMS(ESI): m/z 495[M+1]⁺.

Step 21e: Preparation of (E)-2-(2,6-dimethyl-4-(3-(3-methyl-6-(methylthio)benzofuran-2-yl)-3-oxoprop-1-en-1-yl)phenoxy)-2-methylpropanoic acid (compound 62): to a solution of tert-butyl (E)-2-(2,6-dimethyl-4-(3-(3-methyl-6-(methylthio)benzofuran-2-yl)-3-oxoprop-1-en-1-yl)phenoxy)-2-methylpropanoate (1005-62) (0.246 g, 0.497 mmol, 1.0 eq.) in dichloromethane (25 ml) was added trifluoroacetate (2.5 ml) slowly. The reaction solution was reacted at room temperature overnight. The reaction solution was diluted with dichloromethane (75 ml) and washed with water (50 ml×2). The organic phase was dried over anhydrous sodium sulfate and dried by rotary evaporation under reduced pressure. The residue was purified by column chromatography on silica gel (the eluent: dichloromethane:methanol=20:1) to obtain an orange solid product (E)-2-(2,6-dimethyl-4-(3-(3-methyl-6-(methylthio)benzofuran-2-yl)-3-oxoprop-1-en-1-yl)phenoxy)-2-methylpropanoic acid (127 mg, yield: 58.3%). LCMS(ESI): m/z 439[M+1]$^+$: melting point: 193~196° C.; $^1$HNMR (DMSO, 300 MHz): δ12.96 (s, 1H), 7.26-7.75 (m, 7H), 2.60 (s, 3H), 2.58 (s, 3H), 2.23 (s, 6H), 1.39 (s, 6H).

Example 22: Preparation of (E)-2-(2,6-dimethyl-4-(3-(6-(methylthio)benzo[b]thiophen-2-yl)-3-oxoprop-1-en-1-yl)phenoxy)-2-methylpropanoic acid (Compound 81) (Prepared According to Scheme 7)

Step 22a: Preparation of 1-(6-(methylthio)benzo[b]thiophen-2-yl)ethan-1-one (compound 0706-81): to a flask were added 2,4-dimethylthiobenzaldehyde (0701-810.5 g, 2.53 mmol, 1.0 eq.), bromoacetone (0.53 mL, 6.33 mmol, 2.5 eq.), barium hydroxide (0.78 g, 4.55 mmol, 1.8 eq.) and dioxane (10 mL). The mixture was reacted at 92° C. for 20 hours. The reaction solution was cooled to room temperature, diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=10:1) to obtain a pale yellow solid product 1-(6-(methylthio)benzo[b]thiophen-2-yl)ethan-1-one (0.44 g, yield: 78%). LCMS(ESI): m/z 223[M+1]$^+$.

Step 22b: Preparation of (E)-3-(4-hydroxy-3,5-dimethylphenyl)-1-(6-(methylthio)benzo[b]thiophen-2-yl)prop-2-en-1-one (compound 0707-81): to a solution of 1-(6-(methylthio)benzo[b]thiophen-2-yl)ethan-1-one (0706-81) (250 mg, 1.126 mmol, 1.0 eq.) and 4-hydroxy-3,5-dimethyl benzaldehyde (169 mg, 1.126 mmol, 1.0 eq.) in ethanol (8 ml) was added dropwise concentrated sulfuric acid (2 mL) slowly. The mixture was reacted at room temperature for 4 hours. The reaction solution was diluted with water (20 mL) and then extracted with ethyl acetate (30 mL×3). The extract was dried over anhydrous sodium sulfate and concentrated. The residue was then purified by column chromatography on silica gel (petroleum ether:ethyl acetate=5:1) to obtain a yellow solid product (E)-3-(4-hydroxy-3,5-dimethylphenyl)-1-(6-(methylthio)benzo[b]thiophen-2-yl)prop-2-en-1-one (0.291 g, yield: 73%). LCMS(ESI): m/z 355[M+1]$^+$.

Step 22c: Preparation of tert-butyl (E)-2-(2,6-dimethyl-4-(3-(6-(methylthio)benzo[b]thiophen-2-yl)-3-oxoprop-1-en-1-yl)phenoxy)-2-methylpropanoate (compound 0708-81): (E)-3-(4-hydroxy-3,5-dimethylphenyl)-1-(6-(methylthio)benzo[b]thiophen-2-yl)prop-2-en-1-one (0707-81)(291 mg, 0.822 mmol, 1.0 eq.) and tert-butyl 2-bromo-2-methylpropanoate (0.91 mL, 4.93 mmol, 6.0 eq.) were dissolved in acetonitrile (10 mL) and then potassium carbonate (0.45 g, 3.29 mmol, 4.0 eq.) was added. The air in the reaction system was replaced with nitrogen three times, and then the system was reacted at 83° C. overnight. After the reaction was completed, the mixture was concentrated to give a crude product, which was purified by column chromatography on silica gel (petroleum ether:ethyl acetate=10:1) to obtain a pale yellow solid product tert-butyl (E)-2-(2,6-di methyl-4-(3-(6-(methylthio)benzo[b]thiophen-2-yl)-3-oxoprop-1-en-1-yl)phenoxy)-2-methylpropanoate (183 mg, yield: 45%). LCMS(ESI): m/z 497[M+1]$^+$.

Step 22d: Preparation of (E)-2-(2,6-dimethyl-4-(3-(6-(methylthio)benzo[b]thiophen-2-yl)-3-oxoprop-1-en-1-yl)phenoxy)-2-methylpropanoic acid (compound 81): to a solution of tert-butyl (E)-2-(2,6-dimethyl-4-(3-(6-(methylthio)benzo[b]thiophen-2-yl)-3-oxoprop-1-en-1-yl)phenoxy)-2-methylpropanoate (0708-81)(183 mg, 0.369 mmol, 1.0 eq.) in dioxane (5 ml) was added dropwise concentrated sulfuric acid (0.5 mL) slowly at room temperature. The mixture was reacted at room temperature for 1.5 hours. The reaction solution was diluted with water (20 mL) and then extracted with ethyl acetate (20 mL×3). The extract was dried over anhydrous sodium sulfate and concentrated. The residue was then purified by column chromatography on silica gel (dichloro methane:methanol=20:1) to obtain a pale yellow solid product (E)-2-(2,6-dimethyl-4-(3-(6-(methylthio)benzo[b]thiophen-2-yl)-3-oxoprop-1-en-1-yl)phenoxy)-2-methylpropanoic acid (130 mg, yield: 80%). LCMS(ESI): m/z 441[M+1]$^+$; melting point: 203~205° C.; $^1$HNMR (DMSO-d$_6$, 40 MHz): δ12.98 (s, 1H), 8.67 (s, 1H), 7.94-7.87 (m, 3H), 7.64 (d, J=15.6 Hz, 1H), 7.60 (s, 2H), 7.39-7.37 (m, 1H), 2.59 (s, 3H), 2.24 (s, 6H), 1.40 (s, 6H).

Example 23: Preparation of (E)-2-(2,6-dimethyl-4-(3-(6-(methylthio)-1H-indol-2-yl)-3-oxoprop-1-en-1-yl)phenoxy)-2 methylpropanoic acid (Compound 88) (Prepared According to Scheme 7)

Step 23a: Preparation of 1-(6-(methylthio)-1H-indol-2-yl)ethan-1-one (compound 0706-88): 2-trifluoroacetamido-4-(methylthio)benzaldehyde (0701-88)(1.4 g, 5.32 mmol, 1.0 eq.) and bromoacetone (0.89 mL, 10.64 mmol, 2.0 eq.) were dissolved in dimethyl sulfoxide (15 mL) and then potassium carbonate (1.47 g, 10.64 mmol, 2.0 eq.) was added. The air in the reaction system was replaced with nitrogen three times, and then the system was reacted at 60° C. overnight. The reaction solution was diluted with water (50 mL) and then extracted with ethyl acetate (30 mL×3). The extract was dried over anhydrous sodium sulfate and concentrated. The residue was then purified by column chromatography on silica gel (petroleum ether:ethyl acetate=5:1) to obtain a pale yellow solid product 1-(6-(methylthio)-1H-indol-2-yl)ethan-1-one (0.56 g, yield: 51%). LCMS(ESI): m/z 206[M+1]$^+$.

Step 23b: Preparation of tert-butyl (E)-2-(2,6-dimethyl-4-(3-(6-(methylthio)-1H-indol-2-yl)-3-oxoprop-1-en-1-yl)phenoxy)-2-methylpropanoate (0708-88): to a reaction flask was added 1-(6-(methylthio)-1H-indol-2-yl)ethan-1-one (0706-88)(81 mg, 0.394 mmol, 1.0 eq.), tert-butyl 2-(4-formyl-2,2-dimethylphenoxy)-2-methylpropanoate (115 mg, 0.394 mmol, 1.0 eq.), sodium hydroxide (0.205 g, 5.122 mmol, 13.0 eq.), ethanol (10 mL) and water (5 mL). The reaction was stirred at 30° C. overnight. The reaction solution was diluted with water (20 mL), adjusted to a pH value of 5 with N diluted hydrochloric acid solution and then extracted with ethyl acetate (20 mL×3). The extract was dried over anhydrous sodium sulfate and concentrated. The obtained crude product was purified by column chromatography on silica gel (dichloromethane:methanol=100:1) to obtain a yellow solid product tert-butyl (E)-2-(2,6-dimethyl-4-(3-(6-(methylthio)-1H-indol-2-yl)-3-oxoprop-1-en-1-yl)phenoxy)-2-methylpropanoate (0.139 g, yield: 74%). LCMS(ESI): m/z 480[M+1]$^+$.

Step 23c: Preparation of (E)-2-(2,6-dimethyl-4-(3-(6-(methylthio)-1H-indol-2-yl)-3-oxoprop-1-en-1-yl)phenoxy)-2 methylpropanoic acid (compound 88): to a solution of tert-butyl (E)-2-(2,6-dimethyl-4-(3-(6-(methylthio)-1H-indol-2-yl)-3-oxoprop-1-en-1-yl)phenoxy)-2-methylpropanoate (0708-88)(0.139 g, 0.290 mmol, 1.0 eq.) in dioxane (5 ml) was added dropwise concentrated sulfuric acid (0.5 mL) slowly at room temperature. The mixture was reacted at room temperature for 1.5 hours. The reaction solution was diluted with water (30 mL), adjusted to a pH value of 5 by adding dropwise 2N sodium hydroxide solution and then extracted with ethyl acetate (30 mL×3). The extract was dried over anhydrous sodium sulfate and concentrated. The residue was then purified by column chromatography on silica gel (dichloromethane:methanol=15:1) to obtain a yellow solid product (E)-2-(2,6-dimethyl-4-(3-(6-(methylthio)-1H-indol-2-yl)-3-oxoprop-1-en-1-yl)phenoxy)-2 methylpropanoic acid (60 mg, yield: 49%). LCMS(ESI): m/z 424[M+1]$^+$, melting point: 184~186° C.; $^1$HNMR (DMSO-d$_6$, 400 MHz): δ12.95 (s, 1H), 11.80 (s, 1H), 7.80-7.73 (m, 2H), 7.66-7.58 (m, 4H), 7.28 (s, 1H), 7.04-7.02 (m, 1H), 2.53 (s, 3H), 2.23 (s, 6H), 1.40 (s, 6H).

Example 24: Preparation of (E)-2-(4-(3-(4-(ethylthio)benzofuran-7-yl)-3-oxoprop-1-en-1-yl)-2,6-dimethylphenoxy)-2-methylpropanoic acid (Compound 6) (Prepared According to Scheme 1)

Step 24a: Preparation of 1-(4-(ethylthio)benzofuran-7-yl)ethan-1-one (compound 0105-6): sodium hydroxide (101 mg, 2.525 mmol, 2.5 eq.) was dissolved in water (1.5 ml) and then ethyl mercaptan (126 mg, 2.02 mmol, 2.0 eq.) was added. The mixture was stirred for min and then a solution of 1-(4-fluorobenzofuran-7-yl)ethan-1-one (0104-2)(180 mg, 1.01 mmol, 1.0 eq.) in DMSO (10 ml) was added. The reaction solution was reacted at room temperature overnight. After the reaction was completed, the reaction solution was diluted with ethyl acetate (100 ml), and washed with water (150 ml×3). The organic phase was dried over anhydrous sodium sulfate and concentrated. The residue was purified by column chromatography on silica gel (petroleum ether:ethyl acetate=15:1) to obtain a product 1-(4-(ethylthio)benzofuran-7-yl)ethan-1-one (119 mg, yield: 54%).

Step 24b: Preparation of (E)-1-(4-(ethylthio)benzofuran-7-yl)-3-(4-hydroxy-3,5-dimethylphenyl)prop-2-en-1-one (compound 0106-6): 1-(4-(ethylthio)benzofuran-7-yl)ethan-1-one (0105-6)(119 mg, 0.58 mmol, 1.0 eq.) was dissolved in dioxane (6 ml) and 4-hydroxy-3,5-dimethyl benzaldehyde (105 mg, 0.696 mmol, 1.28 eq.) was added, and then concentrated sulfuric acid (1 ml) was added with stirring. The mixture was reacted at room temperature overnight. After the reaction was completed, the reaction solution was diluted with ethyl acetate (100 ml) and washed with semi-saturated brine (150 ml×3). The organic phase was dried over anhydrous sodium sulfate and concentrated. The residue was purified by column chromatography on silica gel (petroleum ether:ethyl acetate=5:1) to obtain a yellow solid product (E)-1-(4-(ethylthio)benzofuran-7-yl)-3-(4-hydroxy-3,5-dimethylphenyl)prop-2-en-1-one (140 mg, yield: 69%).

Step 24c: Preparation of tert-butyl (E)-2-(4-(3-(4-(ethylthio)benzofuran-7-yl)-3-oxoprop-1-en-1-yl)-2,6-dimethylphenoxy)-2-methylpropanoate (compound 0107-6): (E)-1-(4-(ethylthio)benzofuran-7-yl)-3-(4-hydroxy-3,5-dimethylphenyl)prop-2-en-1-one (0106-60.26 g, 0.397 mmol, 1.0 eq.) was dissolved in acetonitrile (30 ml) and then potassium carbonate (548 mg, 3.97 mmol, 10.0 eq.) and tert-butyl 2-bromo-2-methylpropanoate (886 mg, 3.97 mmol, 10.0 eq.) were added. The air in the round bottom flask was replaced with nitrogen three times, and then the system was reacted at 91° C. for 20 hours. After the reaction was completed, the reaction solution was concentrated. Then the reaction solution was diluted with ethyl acetate (100 ml) and washed with water (150 ml×3). The organic phase was dried over anhydrous sodium sulfate and concentrated. The residue was purified by column chromatography on silica gel (petroleum ether:ethyl acetate=15:1) to obtain a yellow solid product tert-butyl (E)-2-(4-(3-(4-(ethylthio)benzofuran-7-yl)-3-oxopop-1-en-1-yl)-2,6-dimethylphenoxy)-2-methylpropanoate (91 mg, yield: 46%). LCMS(ESI): m/z 495[M+1]$^+$.

Step 24d: Preparation of (E)-2-(4-(3-(4-(ethylthio)benzofuran-7-yl)-3-oxoprop-1-en-1-yl)-2,6-dimethylphenoxy)-2-methylpropanoic acid (compound 6): tert-butyl (E)-2-(4-(3-(4-(ethylthio)benzofuran-7-yl)-3-oxoprop-1-en-1-yl)-2,6-dimethylphenoxy)-2-methylpropanoate (0107-6)(78 mg, 0.158 mmol, 1.0 eq.) was dissolved in DCM (8 ml) and then trifluoroacetate (1.5 ml) was added. The mixture was stirred overnight. After the reaction was completed, the reaction solution was washed with water (100 ml-3), and extracted with dichloromethane (100 ml). The organic phase was dried over anhydrous sodium sulfate and concentrated to obtain a yellow solid product (E)-2-(4-(3-(4-(Ethylthio)benzofuran-7-yl)-3-oxoprop-1-en-1-yl)-2,6-dimethylphenoxy)-2-methylpropanoic acid (45 mg, yield: 65%). LCMS(ESI): m/z 439[M+1]$^+$, melting point: 102~105° C.; $^1$HNMR (DMSO-d$_6$, 300 MHz): δ 12.95 (s, 1H), 7.05-8.22 (m, 8H), 3.24 (q, J=6.0 HZ, 2H), 2.23 (s, 6H), 1.40 (s, 6H), 1.36 (t, J=6.0 HZ, 3H).

Example 25: Preparation of (E)-2-(4-(3-(4-(isobutylthio)benzofuran-7-yl)-3-oxoprop-1-en-1-yl)-2,6-dimethylphenoxy)-2-methylpropanoic acid (Compound 9) (Prepared According to Scheme 1)

Step 25a: Preparation of 1-(4-(isobutylthio)benzofuran-7-yl)ethan-1-one (compound 0105-9): sodium hydroxide (99 mg, 2.475 mmol, 2.5 eq.) was dissolved in water (1.5 ml) and then isobutyl mercaptan(179 mg, 1.98 mmol, 2.0 eq.) was added. The mixture was stirred for 10 min and then a solution of 1-(4-fluorobenzofuran-7-yl)ethan-1-one (0104-2)(176 mg, 0.99 mmol, 1.0 eq.) in DMSO (8 ml) was added. The reaction solution was reacted at 60° C. for 1 hour. After the reaction was completed, the reaction solution was diluted with ethyl acetate (100 ml) and washed with water (150 ml×3). The organic phase was dried over anhydrous sodium sulfate and concentrated. The residue was purified by column chromatography on silica gel (petroleum ether: ethyl acetate=20:1) to obtain 1-(4-(isobutylthio)benzofuran-7-yl)ethan-1-one (246 mg).

Step 25b: Preparation of (E)-3-(4-hydroxy-3,5-dimethylphenyl)-1-(4-(isobutylthio)benzofuran-7-yl)prop-2-en-1-one (compound 0106-9): 1-(4-(isobutylthio)benzofuran-7-yl)ethan-1-one (0105-9) (246 mg, 0.99 mmol, 1.0 eq.) was dissolved in dioxane (10 ml), then 4-hydroxy-3,5-dimethyl benzaldehyde (193 mg, 1.287 mmol, 1.3 eq.) was added and then concentrated sulfuric acid (1 ml) was added with stirring. The mixture was reacted at room temperature overnight. After the reaction was completed, the reaction solution was diluted with ethyl acetate (100 ml) and washed with semi-saturated brine (150 ml×3). The organic phase was dried over anhydrous sodium sulfate and concentrated. The residue was purified by column chromatography on silica gel (petroleum ether:ethyl acetate=5:1) to obtain a yellow solid product (E)-3-(4-hydroxy-3,5-dimethylphenyl)-1)-1-(4-(isobutylthio)benzofuran-7-yl)prop-2-en-1-one (255 mg, yield: 68%).

Step 25c: Preparation of tert-butyl (E)-2-(4-(3-(4-(isobutylthio)benzofuran-7-yl)-3-oxoprop-1-en-1-yl)-2,6-dimethylphenoxy)-2-methylpropanoate (compound 0107-9): (E)-3-(4-hydroxy-3,5-dimethylphenyl)-1-(4-(isobutylthio)benzofuran-7-yl)prop-2-en-1-one (0106-9255 mg, 0.67 mmol, 1.0 eq.) was dissolved in acetonitrile (20 ml) and then potassium carbonate (925 mg, 6.70 mmol, 10.0 eq.) and ter-butyl 2-bromo-2-methylpropanoate (1.49 g, 6.70 mmol, 10.0 eq.) were added. The air in the round bottom flask was replaced with nitrogen three times, and then the system was reacted at 91° C. for 20 hours. After the reaction was completed, the reaction solution was concentrated. Then the reaction solution was diluted with ethyl acetate (100 ml) and washed with water (150 ml×3). The organic phase was dried over anhydrous sodium sulfate and concentrated. The residue was purified by column chromatography on silica gel (petroleum ether:ethyl acetate=20:1) to obtain a yellow solid product tert-butyl (E)-2-(4-(3-(4-(isobutylthio)benzofuran-7-yl)-3-oxoprop-1-en-1-yl)-2,6-dimethylphenoxy)-2-methylpropanoate (234 mg, yield: 67%). LCMS(ESI): m/z 523[M+1]$^+$.

Step 25d: Preparation of (E)-2-(4-(3-(4-(isobutylthio)benzofuran-7-yl)-3-oxoprop-1-en-1-yl)-2,6-dimethylphenoxy)-2-methylpropanoic acid (compound 9): tert-butyl (E)-2-(4-(3-(4-(isobutylthio)benzofuran-7-yl)-3-oxoprop-1-en-1-yl)-2,6-dimethylphenoxy)-2-methylpropanoate (0107-9)(234 mg, 0.448 mmol, 1.0 eq.) was dissolved in DCM (10 ml) and trifluoroacetate (1 ml) was added. The mixture was stirred overnight. After the reaction was completed, it was washed with water (100 ml×3) and extracted with dichloromethane (100 ml). The organic phase was dried over anhydrous sodium sulfate and concentrated. The residue was purified by preparative liquid phase to obtain a yellow solid product (E)-2-(4-(3-(4-(isobutylthio)benzofuran-7-yl)-3-oxoprop-1-en-1-yl)-2,6-dimethylphenoxy)-2-methylpropanoic acid (136 mg, yield: 65%). LCMS(ESI): m/z 467[M+1]$^+$, melting point: 110~113° C.: $^1$HNMR (DMSO-d$_6$, 300 MHz): 312.88 (s, 1H), 7.09-8.24 (m, 8H), 3.12 (d, J=6.9 HZ, 2H), 2.25 (s, 6H), 1.95 (m, 1H), 1.41 (s, 6H), 1.08 (d, J=6.6 HZ, 6H).

Example 26: Preparation of (E)-2-(4-(3-(6-ethoxylbenzofuran-2-yl)-3-oxoprop-1-en-1-yl)-2,6-dimethylphenoxy)-2-methylpropanoic acid (Compound 44) (Prepared According to Scheme 7)

Step 26a: Preparation of 1-(6-ethoxylbenzofuran-2-yl)ethan-1-one (compound 0706-44): 4-ethoxy-2-hydroxybenzaldehyde (0701-44) 428 mg, 2.58 mol, 1.0 eq.) was dissolved in DMF (20 ml) and bromoacetone (389 mg, 2.838 mmol, 3.0 eq.) was added. The mixture was reacted at 85° C. for 5 hours. After that the mixture was diluted with ethyl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=15:1) to obtain a yellow solid product 1-(6-ethoxylbenzofuran-2-yl)ethan-1-one (317 mg, yield: 60%). LCMS(ESI): m/z 205[M+1]$^+$.

Step 26b: Preparation of (E)-1-(6-ethoxybenzofuran-2-yl)-3-(4-hydroxy-3,5-dimethylphenyl)prop-2-en-1-one (compound 0707-44): 1-(6-ethoxybenzofuran-2-yl)ethan-1-one (0706-44317 mg, 1.55 mol, 1.0 eq.) was dissolved in dioxane (10 ml), then 4-hydroxy-3,5-dimethyl benzaldehyde (0.279 g, 1.86 mmol, 1.2 eq.) was added, and then concentrated sulfuric acid (1 ml) was added at room temperature with stirring. The mixture was reacted for 15 hours. After the reaction was completed, the reaction solution was diluted with ethyl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=5:1) to obtain a yellow solid product (E)-1-(6-ethoxybenzofuran-2-yl)-3-(4-hydroxy-3,5-dimethylphenyl)prop-2-en-1-one (0.473 g, yield: 91%). LCMS (ESI): m/z 337[M+1]$^+$.

Step 26c: Preparation of tert-butyl (E)-2-(4-(3-(6-ethoxybenzofuran-2-yl)-3-oxoprop-1-en-1-yl)-2,6-dimethyl phenoxy)-2-methylpropanoate (compound 0708-44): (E)-1-(6-ethoxybenzofuran-2-yl)-3-(4-hydroxy-3,5-dimethylphenyl)prop-2-en-1-one (0707-44)(0.473 g, 1.41 mmol, 1.0 eq.) was dissolved in acetonitrile (30 ml) and potassium carbonate (1.946 g, 14.1 mmol, 10.0 eq.) and tert-butyl 2-bromoisobutyrate (3.146 g, 14.1 mmol, 10.0 eq.) were added. The air in the round bottom flask was replaced with nitrogen three times, and then the system was reacted at 91° C. for 20 hours. After the reaction was completed, the reaction solution was concentrated. Then the reaction solution was diluted with ethyl acetate (50 ml) and washed with water (50 ml×3). The organic phase was dried over anhydrous sodium sulfate and concentrated. The residue was purified by column chromatography on silica gel (petroleum ether:ethyl acetate=15:1) to obtain a yellow solid product tert-butyl (E)-2-(4-(3-(6-ethoxybenzofuran-2-yl)-3-oxoprop-1-en-1-yl)-2,6-dimethylphenoxy)-2-methylpropanoate (0.495 g, yield: 74%). LCMS(ESI): m/z 479[M+1]$^+$.

Step 26d: Preparation of (E)-2-(4-(3-(6-ethoxylbenzofuran-2-yl)-3-oxoprop-1-en-1-yl)-2,6-dimethylphenoxy)-2-methylpropanoic acid (compound 44): tert-butyl (E)-2-(4-(3-(6-ethoxybenzofuran-2-yl)-3-oxoprop-1-en-1-yl)-2,6-dimethylphenoxy)-2-methylpropanoate (0708-44)(200 mg, 0.418 mmol, 1.0 eq.) was dissolved in dichloromethane (10 ml) and trifluoroacetate (1 ml) was added with stirring. The mixture was reacted at room temperature for 15 hours. After the reaction was completed, the reaction solution was diluted with dichloromethane (50 ml) and washed with water (50 ml×3). The organic phase was dried over anhydrous sodium sulfate and concentrated. The residue was washed with 3 ml of methanol to obtain a yellow solid product (E)-2-(4-(3-(6-ethoxybenzofuran-2-yl)-3-oxoprop-1-en-1-yl)-2,6-dimethylphenoxy)-2-methylpropanoic acid (137 mg, yield: 78%). LCMS(ESI): m/z 423[M+1]$^+$, melting point: 146~148° C.; $^1$HNMR (DMSO-d$_6$, 300 MHz): δ12.95 (s, 1H), 6.98-8.21 (m, 8H), 4.17 (q, J=6.9 HZ, 2H), 2.23 (s, 6H), 1.39 (m, 9H).

Example 27: Preparation of (E)-2-(4-(3-(3-ethyl-6-(methylthio)benzofuran-2-yl)-3-oxoprop-1-en-1-yl)-2,6-dimethylphenoxy)-2-methylpropanoic acid (Compound 63) (Prepared According to Scheme 10)

Step 27a: Preparation of 1-(3-ethyl-6-(methylthio)benzofuran-2-yl)ethan-1-one (compound 1003-63): 1-(2-hydroxy-4-(methylthio)phenyl)propan-1-one (1002-63)(0.77 g, 3.92 mol, 1.0 eq.) was dissolved in DMF (10 ml) and bromoacetone (0.81 g, 5.88 mmol, 1.5 eq.) and cesium carbonate (2.77 g, 7.84 mmol, 2.0 eq.) were added. The mixture was reacted at 80° C. for 3 hours. After the reaction was completed, it was diluted with eth yl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=15:1) to obtain a yellow oil product 1-(3-ethyl-6-(methylthio)benzofuran-2-yl) ethan-1-one (0.72 g, yield: 78%). LCMS(ESI): m/z 235[M+1]$^+$.

Step 27b: Preparation of (E)-1-(3-ethyl-6-(methylthio)benzofuran-2-yl)-3-(4-hydroxy-3,5-dimethylphenyl)prop-2-en-1-one (compound 1004-63): 1-(3-ethyl-6-(methylthio)benzofuran-2-yl)ethan-1-one (1003-63) (0.7 g, 2.98 mol, 1.0 eq.) was dissolved in anhydrous ethanol (10 ml), then 4-hydroxy-3,5-dimethyl benzaldehyde (0.447 g, 2.98 mmol, 1.0 eq.) was added and then concentrated sulfuric acid (2 ml) was added at room temperature with stirring. The mixture was reacted for 15 hours. After the reaction was completed, it was diluted with ethyl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=5:1) to obtain a yellow solid product (E)-1-(3-ethyl-6-(methylthio)benzofuran-2-yl)-3-(4-hydroxy-3,5-dimethylphenyl)prop-2-en-1-one (0.95 g, yield: 87%). LCMS(ESI): m/z 367[M+1]$^+$.

Step 27c: Preparation of tert-butyl (E)-2-(4-(3-(3-ethyl-6-(methylthio)benzofuran-2-yl)-3-oxoprop-1-en-1-yl)-2,6-dimethylphenoxy)-2-methylpropanoate (compound 1005-63): (E)-1-(3-ethyl-6-(methylthio)benzofuran-2-yl)-3-(4-hydroxy-3,5-dimethylphenyl)prop-2-en-1-one (1004-63) (0.27 g, 0.74 mmol, 1.0 eq.) was dissolved in 20 ml of acetonitrile and potassium carbonate (1.0 g, 7.4 mmol, 10.0 eq.) and tert-butyl 2-bromoisobutyrate (1.65 g, 7.4 mmol, 10.0 eq.) were added. The air in the round bottom flask was replaced with nitrogen three times, and then the system was reacted at 83° C. for 20 hours. After the reaction was completed, the reaction solution was concentrated. Then the reaction solution was diluted with ethyl acetate (5 ml) and washed with water (50 ml×3). The organic phase was dried over anhydrous sodium sulfate and concentrated. The residue was purified by column chromatography on silica gel (petroleum ether:ethyl acetate=15:1) to obtain a yellow oil product tert-butyl (E)-2-(4-(3-(3-ethyl-6-(methylthio)benzofuran-2-yl)-3-oxoprop-1-en-1-yl)-2,6-dimethylphenoxy)-2-methylpropanoate (0.184 g, yield: 49%). LCMS(ESI): m/z 509[M+1]$^+$.

Step 27d: Preparation of (E)-2-(4-(3-(3-ethyl-6-(methylthio)benzofuran-2-yl)-3-oxoprop-1-en-1-yl)-2,6-dimethylphenoxy)-2-methylpropanoic acid (compound 63): tert-butyl (E)-2-(4-(3-(3-ethyl-6-(methylthio)benzofuran-2-yl)-3-oxoprop-1-en-1-yl)-2,6-dimethylphenoxy)-2-methylpropanoate (1005-63) (0.184 g, 0.36 mmol, 1.0 eq.) was dissolved in 10 ml of dichloromethane and trifluoroacetate (1 ml) was added with stirring. The mixture was reacted at room temperature for 15 hours. After the reaction was completed, the reaction solution was diluted with dichloromethane (50 ml) and washed with water (50 ml×3). The organic phase was dried over anhydrous sodium sulfate and concentrated. The residue was washed with a 3 ml of mixed solution (petroleum ether:ethyl acetate=1:1) to obtain a yellow solid product (E)-2-(4-(3-(3-ethyl-6-(methylthio)benzofuran-2-yl)-3-oxoprop-1-en-1-yl)-2,6-dimethylphenoxy)-2-methylpropanoic acid (35 mg, yield: 21%). LCMS (ESI): m/z 453 [M+1]$^+$; melting point: 174~176° C.; $^1$HNMR (DMSO-d$_6$, 300 MHz): δ13.000 (s, 1H), 7.780 (d, J=8.4 Hz, 1H), 7.691 (d, J=15.6 Hz, 1H), 7.624 (d, J=16 Hz, 1H), 7.593 (s, 1H), 7.501 (s, 2H), 7.274 (d, J=8.8H z, 1H), 3.125 (q, J=7.6 HZ, 2H), 2.589 (s, 3H), 2.237 (s, 6H), 1.397 (s, 6H), 1.245 (t, J=7.6 HZ, 3H).

Example 28: Preparation of (E)-2-(4-(3-(3-isopropyl-6-(methylthio)benzofuran-2-yl)-3-oxoprop-1-en-1-yl)-2,6-dimethylphenoxy)-2-methylpropanoic acid (Compound 64) (Prepared According to Scheme 10)

Step 28a: Preparation of 1-(3-isopropyl-6-(methylthio)benzofuran-2-yl)ethan-1-one (compound 1003-64): 1-(2-hydroxyl-4-(methylthio)phenyl)-2-methylpropan-1-one (1002-64)(0.71 g, 3.38 mol, 1.0 eq.) was dissolved in DMF (10 ml) and bromoacetone (0.69 g, 5.07 mmol, 1.5 eq.) and cesium carbonate (2.39 g, 6.76 mmol, 2.0 eq.) were added. The mixture was reacted at 80° C. for 3 hours. After the reaction was completed, it was diluted with ethyl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=15:1) to obtain a yellow oil product 1-(3-isopropyl-6-(methylthio)benzofuran-2-yl)ethan-1-one (0.74 g, yield: 88%). LCMS (ESI): m/z 249[M+1]$^+$.

Step 28b: Preparation of (E)-3-(4-hydroxy-3,5-dimethylphenyl)-1-(3-isopropyl-6-(methylthio)benzofuran-2-yl)prop-2-en-1-one (compound 1004-64): 1-(3-isopropyl-6-(methylthio)benzofuran-2-yl)ethan-1-one (1003-64)(0.71 g, 2.86 mol, 1.0 eq.) was dissolved in anhydrous ethanol (20 ml), then 4-hydroxy-3,5-dimethyl benzaldehyde (0.472 g, 3.146 mmol, 1.1 eq.) was added and then concentrated sulfuric acid (3 ml) was added at room temperature with stirring. The mixture was reacted for 15 hours. After the reaction was completed, it was diluted with ethyl acetate (50 ml) and washed with semi-saturated brine (50 ml×3). The organic phase was dried over anhydrous sodium sulfate and concentrated. The residue was purified by column chromatography on silica gel (petroleum ether:ethyl acetate=5:1) to obtain a yellow solid product (E)-3-(4-hydroxy-3,5-dimethylphenyl)-1-(3-isopropyl-6-(methylthio)benzofuran-2-yl)prop-2-en-1-one (0.95 g, yield: 87%). LCMS(ESI): m/z 381[M+1]$^+$.

Step 28c: Preparation of tert-butyl (E)-2-(4-(3-(3-isopropyl-6-(methylthio)benzofuran-2-yl)-3-oxoprop-1-en-1-yl)-2,6-dimethylphenoxy)-2-methylpropanoate (compound 1005-64): (E)-3-(4-hydroxy-3,5-dimethylphenyl)-1-(3-isopropyl-6-(methylthio)benzofuran-2-yl)prop-2-en-1-one (1004-64)(0.3 g, 0.79 mmol, 1.0 eq.) was dissolved in 20 ml of acetonitrile and then potassium carbonate (1.1 g, 7.9 mmol, 10.0 eq.) and tert-butyl 2-bromoisobutyrate (1.76 g, 7.9 mmol, 10.0 eq.) were added. The air in the round bottom flask was replaced with nitrogen three times, and then the system was reacted at 83° C. for 20 hours. After the reaction was completed, the reaction solution was concentrated. Then the reaction solution was diluted with ethyl acetate (50 ml) and washed with water (50 ml×3). The organic phase was dried over anhydrous sodium sulfate and concentrated. The residue was purified by column chromatography on silica gel (petroleum ether:ethyl acetate=15:1) to obtain a yellow oil product tert-butyl (E)-2-(4-(3-(3-isopopyl-6-(methylthio)benzofuran-2-yl)-3-oxoprop-1-en-1-yl)-2,6-dimethylphenoxy)-2-methylpropanoate (44 mg, yield: 10%). LCMS (ESI): m/z 523[M+1]$^+$.

Step 28d: Preparation of (E)-2-(4-(3-(3-isopropyl-6-(methylthio)benzofuran-2-yl)-3-oxoprop-1-en-1-yl)-2,6-dimethylphenoxy)-2-methylpropanoic acid (compound 64): tert-butyl (E)-2-(4-(3-(3-isopropyl-6-(methylthio)benzofuran-2-yl)-3-oxoprop-1-en-1-yl)-2,6-dimethylphenoxy)-2-methylpropanoate (1005-64)(44 mg, 0.08 mmol, 1.0 eq.) was dissolved in 10 ml of dichloromethane and trifluoroacetate (1 ml) was added with stirring. The mixture was reacted at room temperature for 15 hours. After the reaction was completed, the reaction solution w as diluted with dichloromethane (50 ml) and washed with water (50 ml×3). The organic phase was dried over anhydrous sodium sulfate and concentrated. The residue was washed with a 3 ml mixed solution (petroleum ether:ethyl acetate=1:1) to obtain a yellow solid product (E)-2-(4-(3-(3-isopropyl-6-(methylthio)benzofuran-2-yl)-3-oxoprop-1-en-1-yl)-2,6-dimethylphenoxy)-2-methylpropanoic acid (30 mg, yield: 39%). LCMS(ESI): m/z 467[M+1]$^+$; melting point: 183~186° C.: $^1$HNMR (DMSO-d$_6$, 300 MHz): δ13.00 (s, 1H), 7.90 (d, J=8.4 Hz, 1H), 7.68 (d, J=15.6 Hz, 1H), 7.63 (d, J=16 Hz, 1H), 7.60 (s, 1H), 7.49 (s, 2H), 7.24 (d, J=8.4 Hz, 1H), 4.18 (m, J=10.8 HZ, 1H), 2.58 (s, 3H), 2.23 (s, 6H), 1.40 (d, J=10.8 HZ, 6H), 1.39 (s, 6H).

Example 29: Preparation of (E)-2-(2,6-dimethyl-4-(3-(6-(methylthio)-3-(trifluoromethyl)benzofuran-2-yl)-3-oxoprop-1-en-1-yl)phenoxy)-2-methylpropanoic acid (Compound 73) (Prepared According to Scheme 10)

Step 29a: Preparation of 1-(6-(methylthio)-3-(trifluoromethyl)benzofuran-2-yl)ethan-1-one (1003-73): to a round bottom flask were added 2,2,2-trifluoro-1-(2-hydroxy-4-(methylthio)phenyl)ethan-1-one (1002-73)(0.94 g, 4.0 mmol, 1.0 eq.), bromoacetone (0.55 g, 4.0 mmol, 1.0 eq.), potassium carbonate (1.66 g, 12.0 mmol, 3.0 eq.) and N,N-dimethylformamide (20 ml). The mixture was heated to 100° C. and reacted for 1 hour. The re action solution was diluted with ethyl acetate (15 ml) and washed with semi-saturated brine (100 ml×4). The organic phase was dried by rotary evaporation. The residue was purified by column chromatography on silica gel (the eluent: petroleum ether: ethyl acetate=10:1) to obtain a yellow solid product 1-(6-(methylthio)-3-(trifluoromethyl)benzofuran-2-yl)ethan-1-one (0.61 g, yield: 50%). LCMS(ESI): 275 [M+1]$^+$.

Step 29b: Preparation of (E)-3-(4-hydroxy-3,5-dimethylphenyl)-1-(6-(methylthio)-3-(trifluoromethyl)benzofuran-2-yl)prop-2-en-1-one (1004-73). To a solution of concentrated sulfuric acid (2 ml) in ethanol (10 ml) were added 1-(6-(methylthio)-3-(trifluoromethyl)benzofuran-2-yl) ethan-1-one (1003-73 (0.274 g, 1.0 mmol, 1.0 eq.) and 4-hydroxy-3,5-dimethyl benzaldehyde (0.151 g, 1.0 mmol, 1.0 eq.) slowly. The mixture was stirred at room temperature overnight. The reaction solution was filtered. The solid was washed with ethyl acetate (2 ml×2) and water (20 ml×2) and dried in vacuo to obtain a yellow solid product (E)-3-(4-hydroxy-3,5-dimethylphenyl)-1-(6-(methylthio)-3-(trifluoromethyl)benzofuran-2-yl)prop-2-en-1-one (0.35 g, yield: 86%). LCMS(ESI): 407[M+1]$^+$.

Step 29c: Preparation of tert-butyl (E)-2-(2,6-dimethyl-4-(3-(6-(methylthio)-3-(trifluoromethyl)benzofuran-2-yl)-3-oxoprop-1-en-1-yl)phenoxy)-2-methylpropanoate (1005-73). To a round bottom flask were added (E)-3-(4-hydroxy-3,5-dimethylphenyl)-1-(6-(methylthio)-3-(trifluoromethyl) benzofuran-2-yl)prop-2-en-1-one (104-73)(0.35 g, 0.86 mmol, 1.0 eq.), tert-butyl 2-bromoisobutyrate (1.92 g, 8.6 mmol, 10.0 eq.), potassium carbonate (1.2 g, 8.6 mmol, 10.0 eq.) and acetonitrile (30 ml). The reaction solution was refluxed overnight under the protection of nitrogen. The reaction solution was dried by rotary evaporation. The residue was purified by column chromatography on silica gel (the eluent: petroleum ether:ethyl acetate=10:1) to obtain a yellow paste product tert-butyl (E)-2-(2,6-dimethyl-4-(3-(6-(methylthio)-3-(trifluoromethyl)benzofuran-2-yl)-3-oxoprop-1-en-1-yl)phenoxy)-2-methylpropanoate (0.31 g, yield: 66%). LCMS(ESI): 549 [M+1]$^+$.

Step 29d: Preparation of (E)-2-(2,6-dimethyl-4-(3-(6-(methylthio)-3-(trifluoromethyl)benzofuran-2-yl)-3-oxoprop-1-en-1-yl)phenoxy)-2-methylpropanoic acid (compound 73). To a solution of tert-butyl (E)-2-(2,6-dimethyl-4-(3-(6-(methylthio)-3-(trifluoromethyl)benzofuran-2-yl)-3-oxoprop-1-en-1-yl)phenoxy)-2-methylpropanoate (1005-73) (0.31 g, 0.57 mmol, 1.0 eq.) in dichloromethane (15 ml) was added trifluoroacetate (3 ml) slowly. The reaction solution was stirred at room temperature for 1 hour. The reaction solution was diluted with ethyl acetate (100 ml) and washed with water (100 ml×1). The organic phase was dried by rotary evaporation. The residue was recrystallized with methanol (4 ml) to obtain a yellow solid product (E)-2-(2,6-dimethyl-4-(3-(6-(methylthio)-3-(trifluoromethyl)benzofuran-2-yl)-3-oxoprop-1-en-1-yl)phenoxy)-2-methylpropanoic acid (224 mg, yield: 80%). LCMS(ESI): 493[M+1]$^+$: melting point: 201~203° C.: $^1$HNMR (DMSO, 500 MHz): δ12.90 (s, 1H), 7.40-7.79 (m, 7H), 2.61 (s, 3H), 2.23 (s, 6H), 1.40 (s, 6H).

Example 30: Preparation of (E)-2-(4-(3-(6-(ethylthio)-3-methylbenzofuran-2-yl)-3-oxoprop-1-en-1-yl)-2,6-dimethylphenoxy)-2-methylpropanoic acid (Compound 74) (Prepared According to Scheme 11)

Step 30a: Preparation of 1-(4-(ethylthio)-2-hydroxyphenyl)ethan-1-one (1102-74): to a solution of sodium hydroxide (135 mg, 3.38 mmol, 1.3 eq.) in water (1 ml) was added ethyl mercaptan (0.24 mL, 3.38 mmol, 1.3 eq.). The mixture was stirred at room temperature for 30 min. A solution of 4-fluoro-2-hydroxyacetophenone (0.4 g, 2.60 mmol, 1.0 eq.) in dimethyl sulfoxide (5 ml) was added and then the mixture was heated to 120° C. and reacted for 7 hours. The reaction solution was cooled to room temperature, diluted with water (30 mL), and extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=60:1) to obtain a pale yellow oil liquid 1-(4-(ethylthio)-2-hydroxyphenyl)ethan-1-one (228 mg, yield: 45%). LCMS (ESI): m/z 197[M+1]$^+$.

Step 30b: Preparation of 1-(6-(ethylthio)-3-methylbenzofuran-2-yl)ethan-1-one (1103-74)): 1-(4-(ethylthio)-2-hydroxyphenyl)ethan-1-one (1102-74) (0.228 g, 1.163 mmol, 1.0 eq.) and bromoacetone (0.098 mL, 1.163 mmol, 1.0 eq.) were dissolved in N,N-dimethylformamide (5 mL) and then cesium carbonate (0.455 g, 1.396 mmol, 1.2 eq.) was added. The air in the reaction system was replaced with nitrogen three times, and then reacted at 80° C. for 3 hours. The reaction solution was diluted with water (30 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=10:1) to obtain a pale yellow oil liquid 1-(6-ethylthio)-3-methylbenzofuran-2-yl)ethan-1-one (171 mg, yield: 63%). LCMS(ESI): m/z 235[M+1]$^+$.

Step 30c: Preparation of (E)-1-(6-(ethylthio)-3-methylbenzofuran-2-yl)-3-(4-hydroxy-3,5-dimethylphenyl)prop-2- en-1-one (1104-74): to a solution of 1-(6-(ethylthio)-3-methylbenzofuran-2-yl)ethan-1-one (1103-74) (171 mg, 0.731 mmol, 1.0 eq.) and 4-hydroxy-3,5-dimethyl benzaldehyde (110 mg, 0.731 mmol, 1.0 eq.) in ethanol (8 ml) was added dropwise concentrated sulfuric acid (2 mL) slowly. The mixture was reacted at room temperature for 3 hours. The reaction solution was diluted with water (30 mL) and then extracted with eth yl acetate (30 mL×3). The extract was washed with saturated brine (20 mL×1), dried over anhydrous sodium sulfate and concentrated to obtain a yellow solid (E)-1-(6-(ethylthio)-3-methylbenzofuran-2-yl)-3-(4-hydroxy-3,5-dimethylphenyl)prop-2-en-1-one (267 mg, crude). LCMS(ESI): m/z 367[M+1]$^+$.

Step 30d: Preparation of tert-butyl (E)-2-(4-(3-(6-(ethylthio)-3-methylbenzofuran-2-yl)-3-oxoprop-1-en-1-yl)-2,6-dimethylphenoxy)-2-methylpropanoate (1105-74): (E)-1-(6-(ethylthio)-3-methylbenzofuran-2-yl)-3-(4-hydroxy-3,5-dimethylphenyl)prop-2-en-1-one (1104-74) (268 mg, 0.731 mmol, 1.0 eq.) and tert-butyl 2-bromo-2-methyl propanoate (0.8 mL, 4.386 mmol, 6.0 eq.) were dissolved in acetonitrile (8 mL) and then potassium carbonate (0.404 g, 2.924 mmol, 4.0 eq.) was added. The air in the reaction system was replaced with nitrogen three times, and then reacted at 85° C. overnight. After the reaction was completed, the mixture was concentrated to give a crude product, which was purified by column chromatography on silica gel (petroleum ether:ethyl acetate=20:1) to obtain a yellow oil liquid tert-butyl (E)-2-(4-(3-(6-(ethylthio)-3-methylbenzofuran-2-yl)-3-oxoprop-1-en-1-yl)-2,6-dimethylphenoxy)-2-methylpropanoate (107 mg, yield: 29/). LCMS(ESI): m/z 509 [M+1]$^+$.

Step 30e: Preparation of (E)-2-(4-(3-(6-(ethylthio)-3-methylbenzofuran-2-yl)-3-oxoprop-1-en-1-yl)-2,6-dimethylphenoxy)-2-methylpropanoic acid (compound 74): to a solution of tert-buty (E)-2-(4-(3-(6-(ethylthio)-3-methylbenzofuran-2-yl)-3-oxoprop-1-en-1-yl)-2,6-dimethylphenoxy)-2-methylpropanoate (1105-74) (107 mg, 0.211 mmol, 1.0 eq.) in dioxane (8 ml) was added dropwise concentrated sulfuric acid (1 mL) slowly at room temperature. The mixed solution was stirred at room temperature for 2 hours. The reaction solution was diluted with water (30 mL) and then extracted with ethyl acetate (30 mL×3). The extract was washed with saturated brine (30 mL×1), dried over anhydrous sodium sulfate and concentrated to obtain crude product, which was purified by column chromatography on silica gel (dichloromethane:methanol=20:1) to obtain a yellow solid (E)-2-(4-(3-(6-(ethylthio)-3-methylbenzofuran-2-yl)-3-oxopop-1-en-1-yl)-2,6-dimethylphenoxy)-2-methylpropanoic acid (74 mg, yield: 78%). LCMS(ESI): m/z 453[M+1]$^+$, melting point: 201~204° C.; $^1$HNMR (DMSO-d$_6$, 500 MHz): δ12.94 (s, 1H), 7.78-7.73 (m, 2H), 7.67-7.60 (m, 2H), 7.52 (s, 2H), 7.32-7.29 (m, 1H), 3.18-3.08 (m, 2H), 2.62 (s, 3H), 2.24 (s, 6H), 1.40 (s, 6H), 1.32-1.27 (m, 3H).

Example 31: Preparation of (E)-2-(2,6-dimethyl-4-(3-(3-methyl-6-(propylthio)benzofuran-2-yl)-3-oxoprop-1-en-1-yl)phenoxy)-2-methylpropanoic acid (Compound 75) (Prepared According to Scheme 11)

Step 31a: Preparation of 1-(2-hydroxy-4-(propylthio)phenyl)ethan-1-one (1102-75): to a solution of sodium hydroxide (156 mg, 3.9 mmol, 1.5 eq.) in water (1 ml) was added propanethiol (0.35 mL, 3.9 mmol, 1.5 eq.). The mixture was stirred at room temperature for 30 min. Then a solution of 4-fluoro-2-hydroxyacetophenone (0.4 g, 2.60 mmol, 1.0 eq.) in dimethyl sulfoxide (5 ml) was added. The mixture was heated to 120° C. and reacted for 5 hours. The reaction solution was cooled to room temperature, diluted with water (30 mL) and then extracted with ethyl acetate (30 mL×3). The extract was washed with saturated brine (30 mL×1) and dried over anhydrous sodium sulfate. The obtained crude product after concentration was purified by column chromatography on silica gel (petroleum ether:ethyl acetate=60:1) to obtain a pale yellow oil liquid 1-(2-hydroxy-4-(propylthio)phenyl)ethan-1-one (283 mg, yield: 52%). LCMS (ESI): m/z 211[M+1]$^+$.

Step 31b: Preparation of 1-(3-methyl-6-(propylthio)benzofuran-2-yl)ethan-1-one (1103-75): 1-(2-hydroxy-4-(propylthio)phenyl)ethan-1-one (1102-75) (0.283 g, 1.35 mmol, 1.0 eq.) and bromoacetone (0.113 mL, 1.35 mmol, 1.0 eq.) were dissolved in N,N-dimethylformamide (5 mL) and then cesium carbonate (0.528 g, 1.62 mmol, 1.2 eq.) was added. The air in the reaction system was replaced with nitrogen three times, and then reacted at 80° C. for 3 hours. The reaction solution was diluted with water (30 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=10:1) to obtain a pale yellow oil liquid 1-(3-methyl-6-(propylthio)benzofuran-2-yl)ethan-1-one (194 mg, yield: 58%). LCMS(ESI): m/z 249[M+1]$^+$.

Step 31c: Preparation of (E)-3-(4-hydroxy-3,5-dimethylphenyl)-1-(3-methyl-6-(propylthio)benzofuran-2-yl)prop-2-en-1-one (1104-75): to a solution of 1-(3-methyl-6-(propylthio)benzofuran-2-yl)ethan-1-one (194 mg, 0.782 mmol, 1.0 eq.) and 4-hydroxy-3,5-dimethyl benzaldehyde (117 mg, 0.782 mmol, 1.0 eq.) in ethanol (8 ml) was added dropwise concentrated sulfuric acid (2 mL) slowly. The mixture was reacted at room temperature for 4 hours. The reaction solution was diluted with water (30 mL) and then extracted with ethyl acetate (30 mL×3). The extract was washed with saturated brine (20 mL×1), dried over anhydrous sodium sulfate and concentrated to obtain a yellow solid (E)-3-(4-hydroxy-3,5-dimethylphenyl)-1-(3-methyl-6-(propylthio) benzofuran-2-yl)prop-2-en-1-one ((297 mg, crude). LCMS (ESI): m/z 381[M+1]$^+$.

Step 3d: Preparation of tert-butyl (E)-2-(2,6-dimethyl-4-(3-(3-methyl-6-(propylthio)benzofuran-2-yl)-3-oxoprop-1-en-1-yl)phenoxy)-2-methylpropanoate (1105-75): (E)-3-(4-hydroxy-3,5-dimethylphenyl)-1-(3-methyl-6-(propylthio) benzofuran-2-yl)prop-2-en-1-one (104-75) (297 mg, 0.782 mmol, 1.0 eq.) and tert-butyl 2-bromo-2-methylpropanoate (0.86 mL, 4.69 mmol, 6.0 eq.) were dissolved in acetonitrile and then potassium carbonate (0.432 g, 3.128 mmol, 4.0 eq.) was added. The air in the reaction system was replaced with nitrogen three times and the mixture was reacted at 85° C. overnight. After the reaction was completed, the mixture was concentrated to give a crude product, which was purified by column chromatography on silica gel (petroleum ether:ethyl acetate=20:1) to obtain a yellow oil liquid tert-butyl (E)-2-(2,6-dimethyl-4-(3-(3-methyl-6-(propylthio) benzofuran-2-yl)-3-oxoprop-1-en-1-yl)phenoxy)-2-methylpropanoate (158 mg, yield: 39%). LCMS(ESI): m/z 523[M+1]$^+$.

Step 31e: Preparation of (E)-2-(2,6-dimethyl-4-(3-(3-methyl-6-(propylthio)benzofuran-2-yl)-3-oxoprop-1-en-1-yl)phenoxy)-2-methylpropanoic acid (compound 75): to a solution of tert-butyl (E)-2-(2,6-dimethyl-4-(3-(3-methyl-6-(propylthio)benzofuran-2-yl)-3-oxoprop-1-en-1-yl)phenoxy)-2-methylpropanoate (1105-75) (158 mg, 0.303 mmol, 1.0 eq.) in dioxane (8 ml) was added dropwise concentrated sulfuric acid (1 mL) slowly at room temperature. The mixed solution was stirred at room temperature for 3 hours. The reaction solution was diluted with water (30 mL) and then extracted with ethyl acetate (30 mL×3). The extract was washed with saturated brine (30 mL×1), dried over anhydrous sodium sulfate and concentrated to obtain a crude product which was washed with dichloromethane/petroleum ether (1:2) and dried to obtain a yellow solid (E)-2-(2,6-dimethyl-4-(3-(3-methyl-6-(propylthio)benzofuran-2-yl)-3-oxoprop-1-en-1-yl)phenoxy)-2-methylpropanoic acid (110 mg, yield: 78%). LCMS(ESI): m/z 467[M+1]$^+$, melting point: 159~162° C.; $^1$HNMR (DMSO-d$_6$, 500 MHz): δ12.95 (s, 1H), 7.77-7.72 (m, 2H), 7.67-7.65 (m, 2H), 7.60 (s, 2H), 7.33-7.29 (m, 1H), 3.10-3.06 (m, 2H), 2.61 (s, 3H), 2.24 (s, 6H), 1.69-1.62 (m, 2H), 1.40 (s, 6H), 1.04-0.99 (m, 3H).

Example 32: Preparation of (E)-2-(4-(3-(6-(isobutylthio)-3-methylbenzofuran-2-yl)-3-oxoprop-1-en-1-yl)-2,6-dimethylphenoxy)-2-methylpropanoic acid (Compound 76) (Prepared According to Scheme 11)

Step 32a: Preparation of 1-(2-hydroxy-4-(isobutylthio)phenyl)ethan-1-one (1102-76): to a solution of sodium hydroxide (195 mg, 4.87 mmol, 1.5 eq.) in water (1.5 ml) was added isobutyl mercaptan(0.525 mL, 4.87 mmol, 1.5 eq.). The mixture was stirred at room temperature for 30 min. A solution of 4-fluoro-2-hydroxyacetophenone (0.5 g, 3.25 mmol, 1.0 eq.) in dimethyl sulfoxide (5 ml) was added and the mixture was heated to 120° C. and reacted for 6 hours. The reaction solution was cooled to room temperature, diluted with water (30 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=60:1) to obtain a colorless oil liquid 1-(2-hydroxy-4-(isobutylthio)phenyl)ethan-1-one (263 mg, yield: 36%). LCMS(ESI): m/z 225[M+1]$^+$.

Step 32b: Preparation of 1-(6-(isobutylthio)-3-methylbenzofuran-2-yl)ethan-1-one (1103-76): 1-(2-hydroxy-4-(isobutylthio)phenyl)ethan-1-one (1102-76) (0.263 g, 1.174 mmol, 1.0 eq.) and bromoacetone (0.099 mL, 1.174 mmol, 1.0 eq.) were dissolved in N,N-dimethylformamide (5 mL) and then cesium carbonate (0.459 g, 1.409 mmol, 1.2 eq.) was added. The air in the reaction system was replaced with nitrogen three times, and then the mixture was reacted at 80° C. for 5 hours. The reaction solution was diluted with water (30 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=20:1) to obtain a pale yellow oil liquid 1-(6-(isobutylthio)-3-methylbenzofuran-2-yl)ethan-1-one (140 mg, yield: 46%). LCMS(ESI): m/z 263[M+1]$^+$.

Step 32c: Preparation of (E)-3-(4-hydroxy-3,5-dimethylphenyl)-1-(6-(isobutylthio)-3-methylbenzofuran-2-yl)prop-2-en-1-one (1104-76): to a solution of 1-(6-(isobutylthio)-3-methylbenzofuran-2-yl)ethan-1-one (1103-76) (140 mg, 0.534 mmol, 1.0 eq.) and 4-hydroxy-3,5-dimethyl benzaldehyde (80 mg, 0.534 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (20 mL×3). The extract was washed with saturated brine (20 mL×1), dried over anhydrous sodium sulfate and concentrated to obtain a yellow solid (E)-3-(4-hydroxy-3,5-dimethylphenyl)-1-(6-(isobutylthio)-3-methylbenzofuran-2-yl)prop-2-en-1-one (210 mg, crude). LCMS(ESI): m/z 395[M+1]$^+$.

Step 32d: Preparation of tert-butyl (E)-2-(4-(3-(6-(isobutylthio)-3-methylbenzofuran-2-yl)-3-oxoprop-1-en-1-yl)-2,6-dimethylphenoxy)-2-methylpropanoate (1105-76): (E)-3-(4-hydroxy-3,5-dimethylphenyl)-1-(6-(isobutylthio)-3-methylbenzofuran-2-yl)prop-2-en-1-one (1104-76) (210 mg, 0.534 mmol, 1.0 eq.) and tert-butyl 2-bromo-2-methylpropanoate (0.59 mL, 3.204 mmol, 6.0 eq.) were dissolved in acetonitrile (8 mL) and then potassium carbonate (0.295 g, 2.136 mmol, 4.0 eq.) was added. The air in the reaction system was replaced with nitrogen three times, and then the mixture was reacted at 85° C. overnight. After the reaction was completed, the mixture was concentrated to give a crude product, which was purified by column chromatography on silica gel (petroleum ether:ethyl acetate=20:1) to obtain a yellow oil liquid tert-butyl (E)-2-(4-(3-(6-(isobutylthio)-3-methylbenzofuran-2-yl)-3-oxoprop-1-en-1-yl)-2,6-dimethylphenoxy)-2-methylpropanoate (110 mg, yield: 38%). LCMS(ESI): m/z 537[M+1]$^+$.

Step 32e: Preparation of (E)-2-(4-(3-(6-(isobutylthio)-3-methylbenzofuran-2-yl)-3-oxoprop-1-en-1-yl)-2,6-dimethylphenoxy)-2-methylpropanoic acid (compound 76): to a solution of tert-butyl (E)-2-(4-(3-(6-(isobutylthio)-3-methylbenzofuran-2-yl)-3-oxoprop-1-en-1-yl)-2,6-dimethylphenoxy)-2-methylpropanoate (1105-76) (110 mg, 0.205 mmol, 1.0 eq.) in dichloromethane (7 ml) was added dropwise trifluoroacetate (0.7 mL) slowly at room temperature. The mixed solution was stirred at room temperature for 4 hours. The reaction solution was diluted with water (30 mL) and then extracted with ethyl acetate (30 mL×3). The extract was washed with saturated brine (20 mL×1), dried over anhydrous sodium sulfate and concentrated to obtain a crude product which was purified by column chromatography on silica gel (dichloromethane:methanol=20:1) to obtain a yellow solid (E)-2-(4-(3-(6-(isobutylthio)-3-methylbenzofuran-2-yl)-3-oxoprop-1-en-1-yl)-2,6-dimethylphenoxy)-2-methylpropanoic acid (78 mg, yield: 80%). LCMS(ESI): m/z 481[M+1]$^+$, melting point: 151~154° C.; $^1$HNMR (DMSO-d$_6$, 500 MHz): δ12.94 (s, 1H), 7.77-7.72 (m, 2H), 7.67-7.65 (m, 2H), 7.51 (s, 2H), 7.34-7.30 (m, 1H), 2.99 (d, J=11.5 Hz, 2H), 2.61 (s, 3H), 2.24 (s, 6H), 1.99-1.90 (m, 1H), 1.40 (s, 6H), 1.03 (d, J=11.0 Hz, 6H).

Example 33: Preparation of (E)-2-(4-(3-(6-(isopropylthio)-3-methylbenzofuran-2-yl)-3-oxoprop-1-en-1-yl)-2,6-dimethylphenoxy)-2-methylpropanoic acid (Compound 77) (Prepared According to Scheme 11)

Step 33a: Preparation of 1-(2-hydroxy-4-(isopropylthio)phenyl)ethan-1-one (1102-77): to a solution of sodium hydroxide (156 mg, 3.9 mmol, 1.5 eq.) in water (1 ml) was added isopropanethiol (0.36 mL, 3.9 mmol, 1.5 eq.). The mixture was stirred at room temperature for 30 min. A solution of 4-fluoro-2-hydroxyacetophenone (0.4 g, 2.60 mmol, 1.0 eq.) in dimethyl sulfoxide (5 ml) was added and the mixture was heated to 120° C. and reacted for 5 hours. The reaction solution was cooled to room temperature, diluted with water (30 mL) and then extracted with ethyl acetate (30 mL×3). The extract was washed with saturated brine (30 mL×1) and dried over anhydrous sodium sulfate. The obtained crude product after concentration was purified by column chromatography on silica gel (petroleum ether: ethyl acetate=60:1) to obtain a pale yellow oil liquid 1-(2- hydroxy-4-(isopropylthio)phenyl)ethan-1-one (95 mg, yield: 17%). LCMS(ESI): m/z 211[M+1]⁺.

Step 33b: Preparation of 1-(3-methyl-6-(isopropylthio) benzofuran-2-yl)ethan-1-one (1103-77): 1-(2-hydroxy-4-(isopropylthio)phenyl)ethan-1-one (95 mg, 0.452 mmol, 1.0 eq.) and bromoacetone (62 mg, 0.452 mmol, 1.0 eq.) were dissolved in N,N-dimethylformamide (5 mL) and cesium carbonate (0.177 g, 0.542 mmol, 1.2 eq.) was added. The air in the reaction system was replaced with nitrogen three times, and then the mixture was reacted at 80° C. for 5 hours. The reaction solution was diluted with water (30 mL) and then extracted with ethyl acetate (30 mL×3). The extract was washed with saturated brine (20 mL×1) and dried over an hydrous sodium sulfate. The obtained crude product after concentration was purified by column chromatography on silica gel (petroleum ether:ethyl acetate=20:1) to obtain a pale yellow oil liquid 1-(3-methyl-6-(isopropylthio)benzofuran-2-yl)ethan-1-one (80 mg, yield: 71%). LCMS(ESI): m/z 249[M+1]⁺.

Step 33c: Preparation of (E)-3-(4-hydroxy-3,5-dimethylphenyl)-1-(3-methyl-6-(isopropylthio)benzofuran-2-yl) prop-2-en-1-one (1104-77): to a solution of 1-(3-methyl-6-(isopropylthio)benzofuran-2-yl)ethan-1-one (1103-77) (80 mg, 0.323 mmol, 1.0 eq.) and 4-hydroxy-3,5-dimethyl benzaldehyde (48.4 mg, 0.323 mmol, 1.0 eq.) in ethanol (8 ml) was added dropwise concentrated sulfuric acid (2 mL) slowly. The mixture was reacted at room temperature for 4 hours. The reaction solution was diluted with water (30 mL) and then extracted with ethyl acetate (30 mL×3). The extract was washed with saturated brine (20 mL×1), dried over anhydrous sodium sulfate and concentrated to obtain a yellow solid (E)-3-(4-hydroxy-3,5-dimethylphenyl)-1-(3-methyl-6-(iso propylthio)benzofuran-2-yl)prop-2-en-1-one (123 mg, crude). LCMS(ESI): m/z 381[M+1]⁺.

Step 33d: Preparation of tert-butyl (E)-2-(2,6-dimethyl-4-(3-(3-methyl-6-(isopropylthio)benzofuran-2-yl)-3-oxo-prop-1-en-1-yl)phenoxy)-2-methylpropanoate (1105-77): (E)-3-(4-hydroxy-3,5-dimethylphenyl)-1-(3-methyl-6-(iso-propylthio)benzofuran-2-yl)prop-2-en-1-one (1104-77) (122.7 mg, 0.323 mmol, 1.0 eq.) and tert-butyl 2-bromo-2-methylpropanoate (0.36 mL, 1.938 mmol, 6.0 eq.) were dissolved in acetonitrile (8 mL) and then potassium carbonate (0.178 g, 1.292 mmol, 4.0 eq.) was added. The air in the reaction system was replaced with nitrogen three times, and then the mixture was reacted at 85° C. overnight. After the reaction was completed, the mixture was concentrated to give a crude product which was purified by column chromatography on silica gel (petroleum ether:ethyl acetate=20:1) to obtain a yellow solid tert-butyl (E)-2-(2,6-dimethyl-4-(3-(3-methyl-6-(isopropylthio)benzofuran-2-yl)-3-oxoprop-1-en-1-yl)phenoxy)-2-methylpropanoate (75 mg, yield: 44%). LCMS(ESI): m/z 523[M+1]⁺.

Step 33e: Preparation of (E)-2-(4-(3-(6-(isopropylthio)-3-methylbenzofuran-2-yl)-3-oxoprop-1-en-1-yl)-2,6-dimethylphenoxy)-2-methylpropanoic acid (compound 77): to a solution of tert-butyl (E)-2-(2,6-dimethyl-4-(3-(3-methyl-6-(isopropylthio)benzofuran-2-yl)-3-oxoprop-1-en-1-yl)phenoxy)-2-methylpropanoate (1105-77) (75 m g, 0.144 mmol, 1.0 eq.) in dioxane (8 ml) was added dropwise concentrated sulfuric acid (1 mL) slowly at room temperature. The mixed solution was stirred at room temperature for 2 hours. The reaction solution was diluted with water (30 mL) and then extracted with ethyl acetate (30 mL×3). The extract was washed with saturated brine (20 mL×1), dried over anhydrous sodium sulfate and concentrated to give a crude product which was purified by column chromatography on silica gel (dichloromethane:methanol=20:1) to obtain a yellow solid (E)-2-(2,6-dimethyl-4-(3-(3-methyl-6-(isopropylthio)benzofuran-2-yl)-3-oxoprop-1-en-1-yl)phenoxy)-2-methylpropanoic acid (46 mg, yield: 69%). LCMS(ESI): m/z 467[M+1]⁺, melting point: 182~185° C.; ¹HNMR (DMSO-d₆, 500 MHz): δ12.95 (s, 1H), 7.80-7.72 (m, 2H), 7.68-7.60 (m, 2H), 7.52 (s, 2H), 7.37-7.33 (m, 1H), 3.73-3.64 (m, 1H), 2.62 (s, 3H), 2.24 (s, 6H), 1.40 (s, 6H), 1.30 (d, J=11.0 Hz, 6H).

Example 34: Preparation of (E)-2-(2,6-dimethyl-4-(3-(3-methyl-6-(methylthio)benzo[b]thiophen-2-yl)-3-oxoprop-1-en-1-yl)phenoxy)-2-methylpropanoic acid (Compound 82) (Prepared According to Scheme 12)

Step 34a: Preparation of 1-(2,4-bis(methylthio)phenyl)ethan-1-one (1202-82): to a solution of 2,4-difluoroacetophenone (0.6 g, 3.84 mmol, 1.0 eq.) in dimethyl sulfoxide (6 ml) was added sodium methyl mercaptan (a 20% aqueous solution, 3.37 g, 9.61 mmol, 2.5 eq.). The mixture was stirred at room temperature for 2 hours. The reaction solution was diluted with water (30 mL) and then extracted with ethyl acetate (30 mL×3). The extract was washed with saturated brine (20 mL×1), dried over anhydrous sodium sulfate and concentrated to obtain a pale yellow solid 1-(2,4-bis(methylthio)phenyl)ethan-1-one (0.782 g, yield: 96%). LCMS(ESI): m/z 213[M+1]⁺.

Step 34b: Preparation of 1-(3-methyl-6-(methylthio) benzo[b]thiophen-2-yl)ethan-1-one (1203-82): 1-(2,4-bis (methylthio)phenyl)ethan-1-one (1202-82) (0.73 g, 3.44 mmol, 1.0 eq.) and bromoacetone (0.72 mL, 8.61 mmol, 2.5 eq.) were dissolved in dioxane (10 mL) and then barium hydroxide (1.06 g, 6.19 mmol, 1.8 eq.) was added. The air in the reaction system was replaced with nitrogen three times, and then the system was reacted at 105° C. for 24 hours. The reaction solution was cooled to room temperature, diluted with water (40 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=30:1) to obtain a pale yellow solid 1-(3-methyl-6-(methylthio)benzo[b]thiophen-2-yl)ethan-1-one (0.128 g, yield: 16%). LCMS(ESI): m/z 237[M+1]⁺.

Step 34c: Preparation of (E)-3-(4-hydroxy-3,5-dimethylphenyl)-1-(3-methyl-6-(methylthio)benzo[b]thiophen-2-yl)prop-2-en-1-one (1204-82): to a solution of 1-(3-methyl-6-(methylthio)benzo[b]thiophen-2-yl)ethan-1-one (1203-82) (128 mg, 0.542 mmol, 1.0 eq.) and 4-hydroxy-3,5-dimethyl benzaldehyde (81 mg, 0.542 mmol, 1.0 eq.) in ethanol (8 ml) was added dropwise concentrated sulfuric acid (2 mL) slowly. The mixture was reacted at room temperature for 4 hours. The reaction solution was diluted with water (30 mL) and then extracted with ethyl acetate (30 mL×3). The extract was washed with saturated brine (20 mL×1), dried over anhydrous sodium sulfate and concentrated to obtain a yellow solid (E)-3-(4-hydroxy-3,5-dimethylphenyl)-1-(3-methyl-6-(methylthio)benzo[b]thiophen-2-yl)prop-2-en-1-one (199 mg, crude). LCMS(ESI): m/z 369[M+1]⁺.

Step 34d: Preparation of tert-butyl (E)-2-(2,6-dimethyl-4-(3-(3-methyl-6-(methylthio)benzo[b]thiophen-2-yl)-3-oxoprop-1-en-1-yl)phenoxy)-2-methylpropanoate (1205-82): (E)-3-(4-hydroxy-3,5-dimethylphenyl)-1-(3-methyl-6-(methylthio)benzo[b]thiophen-2-yl)prop-2-en-1-one (1204-82) (199 mg, 0.542 mmol, 1.0 eq.) and tert-butyl 2-bromo-2-methylpropanoate (0.6 mL, 3.252 mmol, 6.0 eq.) were dissolved in acetonitrile (8 mL) and then potassium carbonate (0.299 g, 2.168 mmol, 4.0 eq.) was added. The air in the reaction system was replaced with nitrogen three times, and then the system was reacted at 85° C. overnight. After the reaction was completed, the mixture was concentrated to give a crude product which was purified by column chromatography on silica gel (petroleum ether:ethyl acetate=15:1) to obtain a yellow solid tert-butyl (E)-2-(2,6-dimethyl-4-(3-(3-methyl-6-(methylthio)benzo[b]thiophen-2-yl)-3-oxoprop-1-en-1-yl)phenoxy)-2-methylpropanoate (52 mg, yield: 19%). LCMS(ESI): m/z 511[M+1]$^+$.

Step 34e: Preparation of (E)-2-(2,6-dimethyl-4-(3-(3-methyl-6-(methylthio)benzo[b]thiophen-2-yl)-3-oxoprop-1-en-1-yl)phenoxy)-2-methylpropanoic acid (compound 82): to a solution of tert-butyl (E)-2-(2,6-dimethyl-4-(3-(3-methyl-6-(methylthio)benzo[b]thiophen-2-yl)-3-oxoprop-1-en-1-yl)phenoxy)-2-methylpropanoate (1205-82) (52 mg, 0.102 mmol, 1.0 eq.) in dioxane (8 ml) was added dropwise concentrated sulfuric acid (1 mL) slowly at room temperature. The mixed liquid was stirred at room temperature for 2 hours. The reaction solution was diluted with water (30 mL) and then extracted with ethyl acetate (20 mL×3). The extract was washed with saturated brine (20 mL×1), dried over anhydrous sodium sulfate and concentrated to a crude product which was purified by column chromatography on silica gel (dichloromethane:methanol=20:1) to obtain a yellow solid (E)-2-(2,6-dimethyl-4-(3-(3-methyl-6-(methylthio)benzo[b]thiophen-2-yl)-3-oxoprop-1-en-1-yl)phenoxy)-2-methylpropanoic acid (34 mg, yield: 74%). LCMS (ESI): m/z 455[M+1]$^+$, Melting point: 162~165° C.: $^1$HNMR (DMSO-di, 500 MHz): δ12.94 (s, 1H), 7.95-7.91 (m, 2H), 7.65-7.60 (m, 1H), 7.54-7.49 (m, 2H), 7.46-7.38 (m, 2H), 2.76 (s, 3H), 2.59 (s, 3H), 2.23 (s, 6H), 1.40 (s, 6H).

Example 35: Preparation of (E)-2-(4-(3-(6-(ethylthio)-3-methylbenzo[b]thiophen-2-yl)-3-oxoprop-1-en-1-yl)-2,6-dimethylphenoxy)-2-methylpropanoic acid (Compound 94) (Prepared According to Scheme 12)

Step 35a: Preparation of 1-(2,4-bis(ethylthio)phenyl)ethan-1-one (1202-94): to a solution of sodium hydroxide (448 mg, 11.21 mmol, 2.5 eq.) in water (4 ml) was added ethyl mercaptan (0.81 mL, 11.21 mmol, 2.5 eq.). The mixture was stirred at rom temperature for 30 mins. A solution of 2,4-difluoroacetophenone (0.7 g, 4.48 mmol, 1.0 eq.) in dimethyl sulfoxide (10 ml) was added and then the mixture was reacted at room temperature overnight. The reaction solution was diluted with water (40 mL) and then extracted with ethyl acetate (30 mL×3). The extract was washed with saturated brine (30 mL×1), dried over anhydrous sodium sulfate and concentrated to obtain a pale yellow solid 1-(2,4-bis(ethylthio)phenyl)ethan-1-one (1.06 g, yield: 99%). LCMS(ESI): m/z 241[M+1]$^+$.

Step 35b: Preparation of 1-(6-(ethylthio)-3-methylbenzo[b]thiophen-2-yl)ethan-1-one (1203-94): 1-(2,4-bis(ethylthio)phenyl)ethan-1-one (1202-94) (1.06 g, 4.42 mmol, 1.0 eq.) and bromoacetone (0.93 mL, 11.05 mmol, 2.5 eq.) were dissolved in dioxane (15 mL) and then barium hydroxide (1.36 g, 7.95 mmol, 1.8 eq.) was added. The air in the reaction system was replaced with nitrogen three times, and then the system was reacted at 105° C. overnight. The reaction solution was cooled to room temperature, diluted with water (50 mL) and then extracted with ethyl acetate (30 mL×3). The extract was washed with saturated brine (30 mL×1) and dried over anhydrous sodium sulfate. The obtained crude product after concentration was purified by column chromatography on silica gel (petroleum ether:ethyl acetate=30:1) to obtain a pale yellow solid 1-(6-(ethylthio)-3-methylbenzo[b]thiophen-2-yl)ethan-1-one (0.438 g, yield: 40%). LCMS(ESI): m/z 251[M+1]$^+$.

Step 35c: Preparation of (E)-1-(6-(ethylthio)-3-methylbenzo[b]thiophen-2-yl)-3-(4-hydroxy-3,5-dimethylphenyl)prop-2-en-1-one (1204-94): to a solution of 1-(6-(ethylthio)-3-methylbenzo[b]thiophen-2-yl)ethan-1-one (1203-94) (233 mg, 0.932 mmol, 1.0 eq.) and 4-hydroxy-3,5-dimethyl benzaldehyde (140 mg, 0.932 mmol, 1.0 eq.) in ethanol (8 ml) was added dropwise concentrated sulfuric acid (2 mL) slowly. The mixture was reacted at room temperature for 5 hours. The reaction solution was diluted with water (30 mL) and then extracted with ethyl acetate (30 mL×3). The extract was washed with saturated brine (20 mL×1), dried over anhydrous sodium sulfate and concentrated to obtain a yellow solid (E)-1-(6-(ethylthio)-3-methylbenzo[b]thiophen-2-yl)-3-(4-hydroxy-3,5-dimethylphenyl)prop-2-en-1-one (356 mg, crude). LCMS(ESI): m/z 383[M+1]$^+$.

Step 35d: Preparation of tert-butyl (E)-2-(4-(3-(6-(ethylthio)-3-methylbenzo[b]thiophen-2-yl)-3-oxoprop-1-en-1-yl)6-dimethylphenoxy)-2-methylpropanoate (1205-94): (E)-1-(6-(ethylthio)-3-methylbenzo[b]thiophen-2-yl)-3-(4-hydroxy-3,5-dimethylphenyl)prop-2-en-1-one (1204-94) (356 mg, 0.932 mmol, 1.0 eq.) and tert-butyl 2-bromo-2-methylpropanoate (1.0 mL, 5.59 mmol, 6.0 eq.) were dissolved in acetonitrile (10 mL) and then potassium carbonate (0.51 g, 3.728 mmol, 4.0 eq.) was added. The air in the reaction system was replaced with nitrogen three times, and then the system was reacted at 85° C. overnight. After the reaction was completed, the mixture was concentrated to give a crude product which was purified by column chromatography on silica gel (petroleum ether:ethyl acetate=15:1) to obtain a yellow solid tert-butyl (E)-2-(4-(3-(6-(ethylthio)-3-methylbenzo[b]thiophen-2-yl)-3-oxoprop-1-en-1-yl)6-dimethylphenoxy)-2-methylpropanoate (183 mg, yield: 38%). LCMS(ESI): m/z 525[M+1]$^+$.

Step 35e: Preparation of (E)-2-(4-(3-(6-(ethylthio)-3-methylbenzo[b]thiophen-2-yl)-3-oxoprop-1-en-1-yl)-2,6-dimethylphenoxy)-2-methylpropanoic acid (compound 94): to a solution of tert-butyl (E)-2-(4-(3-(6-(ethylthio)-3-methylbenzo[b]thiophen-2-yl)-3-oxoprop-1-en-1-yl)6-dimethylphenoxy)-2-methylpropanoate (1205-94) (183 mg, 0.349 mmol, 1.0 eq.) in dichloromethane (10 ml) was added dropwise trifluoroacetate (1 mL) slowly at room temperature. The mixed solution was stirred at room temperature for 5 hours. The reaction solution was diluted with water (30 mL) and then extracted with ethyl acetate (30 mL×3). The extract was washed with saturated brine (20 mL×1), dried over anhydrous sodium sulfate and concentrated to give a crude product which was purified by column chromatography on silica gel (dichloromethane:methanol=15:1) to obtain a yellow solid (E)-2-(4-(3-(6-(ethylthio)-3-methylbenzo[b]thiophen-2-yl)-3-oxoprop-1-en-1-yl)-2,6-dimethylphenoxy)-2-methylpropanoic acid (145 mg, yield: 89%). LCMS(ESI): m/z 469[M+1]$^+$, melting point: 175~177° C.; $^1$HNMR (DMSO-d$_6$, 500 MHz): δ12.92 (s, 1H), 7.99-7.93 (m, 2H), 7.60 (s, 1H), 7.52 (s, 2H), 7.46-7.41 (m, 2H), 3.16-3.08 (m, 2H), 2.76 (s, 3H), 2.23 (s, 6H), 1.40 (s, 6H), 1.32-1.27 (m, 3H).

Example 36: Preparation of (E)-2-(2,6-dimethoxy-4-(3-(6-(methylthio)benzofuran-2-yl)-3-oxoprop-1-en-1-yl)phenoxy)-2-methylpropanoic acid (Compound 99) (Prepared According to Scheme 7)

Step 36a: Preparation of (E)-3-(4-hydroxy-3,5-dimethoxyphenyl)-1-(6-(methylthio)benzofuran-2-yl)prop-2-en- 1-one (0707-99). To a round bottom flask were added 1-(6-(methylthio)benzofuran-2-yl)ethan-1-one (0706-51) (0.206 g, 1.0 mmol, 1.0 eq.), 4-hydroxy-3,5-dimethoxybenzaldehyde (0.182 g, 1.0 mmol, 1.10 eq.), a solution of dioxane (10 ml) and methanesulfonic acid (2 ml). The mixture was heated to 60° C. and reacted for 4 hours. The reaction solution was diluted with ethyl acetate (100 ml) and washed with water (100 ml-1). The organic phase was dried by rotary evaporation. The residue was purified by column chromatography on silica gel (the eluent: petroleum ether:ethyl acetate=2:1) to obtain a yellow liquid (E)-3-(4-hydroxy-3,5-dimethoxyphenyl)-1-(6-(methylthio)benzofuran-2-yl)prop-2-en-1-one (0.26 g, yield: 70%). LCMS(ESI): 371 [M+1]$^+$.

Step 36b: Preparation of tert-butyl (E)-2-(2,6-dimethoxy-4-(3-(6-(methylthio)benzofuran-2-yl)-3-oxoprop-1-en-1-yl)phenoxy)-2methylpropanoate (0708-99). To a round bottom flask were added (E)-3-(4-hydroxy-3,5-dimethoxyphenyl)-1-(6-(methylthio)benzofuran-2-yl)prop-2-en-1-one (0707-99) (0.26 g, 0.7 mmol, 1.0 eq.), tert-butyl 2-bromoisobutyrate (1.56 g, 7.0 mmol, 10.0 eq.), potassium carbonate (0.97 g, 7.0 mmol, 10.0 eq.) and dimethyl sulfoxide (10 ml). The reaction solution was heated to 100° C. and reacted for 5 hours. The reaction solution was diluted with ethyl acetate (100 ml) and washed with semi-saturated brine (100 ml×4). The organic phase was dried by rotary evaporation. The residue was purified by column chromatography on silica gel (the eluent: petroleum ether:ethyl acetate=5:1) to obtain a yellow paste tert-butyl (E)-2-(2,6-dimethoxy-4-(3-(6-(methylthio)benzofuran-2-yl)-3-oxoprop-1-en-1-yl)phenoxy)-2methylpropanoate (0.09 g, yield: 25%). LCMS(ESI): 513 [M+1]$^+$.

Step 36c: Preparation of (E)-2-(2,6-dimethoxy-4-(3-(6-(methylthio)benzofuran-2-yl)-3-oxoprop-1-en-1-yl)phenoxy)-2-methylpropanoic acid (compound 99). To a solution of tert-butyl (E)-2-(2,6-dimethoxy-4-(3-(6-(methylthio)benzofuran-2-yl)-3-oxoprop-1-en-1-yl)phenoxy)-2methylpropanoate (0708-99) (0.09 g, 0.18 mmol, 1.0 eq.) in dichloromethane (10 ml) was added trifluoroacetate (2 ml) slowly. The reaction solution was stirred at room temperature for 3 hours. The reaction solution was poured into water (100 ml) and extracted with dichloromethane (100 ml×1). The organic phase was dried over anhydrous sodium sulfate and filtered. The filtrate was dried by rotary evaporation. The residue was recrystallized with a solution (petroleum ether: ethyl acetate=2:1) (5 ml) to obtain a yellow solid (E)-2-(2, 6-dimethoxy-4-(3-(6-(methylthio)benzofuran-2-yl)-3-oxoprop-1-en-1-yl)phenoxy)-2-methylpropanoic acid (31 mg, yield: 38%). LCMS(ESI): 457[M+1]$^+$. Melting point: 167~170° C.: $^1$HNMR (DMSO, 500 MHz): 12.97 (s, 1H), 7.21-8.26 (m, 8H), 3.81 (s, 6H), 2.58 (s, 3H), 1.34 (s, 6H).

Example 37: Preparation of (E)-2-(2,6-dichloro-4-(3-(6-(methylthio)benzofuran-2-yl)-3-oxoprop-1-en-1-yl)phenoxy)-2-methylpropanoic acid (Compound 100) (Prepared According to Scheme 7)

Step 37a: Preparation of (E)-3-(3,5-dichloro-4-hydroxyphenyl)-1-(6-(methylthio)benzofuran-2-yl)prop-2-en-1-one (0707-100). To a round bottom flask were added 1-(6-(methylthio)benzofuran-2-yl)ethan-1-one (0706-51) (0.90 g, 4.4 mmol, 1.0 eq.), 4-hydroxy-3,5-dichlorobenzaldehyde (1.18 g, 6.2 mmol, 1.4 eq.), ethanol (15 ml) and sulfuric acid (3 ml). The mixture was heated to 85° C. and reacted for 3 hours. The reaction solution was filtrated and washed with ethanol (2 ml×2). The solid was dissolved in ethyl acetate (150 ml) and washed with brine (100 ml×2). The organic phase was dried over anhydrous sodium sulfate and filtered. The filtrate was dried by rotary evaporation. The residue was dried in vacuo to obtain a brown solid (E)-3-(3,5-dichloro-4-hydroxyphenyl)-1-(6-(methylthio)benzofuran-2-yl)prop-2-en-1-one (1.02 g, yield: 61%). LCMS(ESI): 380 [M+1]$^+$.

Step 37b: Preparation of tert-butyl (E)-2-(2,6-dichloro-4-(3-(6-(methylthio)benzofuran-2-yl)-3-oxoprop-1-en-1-yl)phenoxy)-2-methylpropanoate (0708-100). To a round bottom flask were added (E)-3-(3,5-dichloro-4-hydroxyphenyl)-1-(6-(methylthio)benzofuran-2-yl)prop-2-en-1-one (0707-100) (1.02 g, 2.7 mmol, 1.0 eq.), tert-butyl 2-bromoisobutyrate (6.02 g, 27.0 mmol, 10.0 eq.), sodium bicarbonate (2.72 g, 32.4 mmol, 12.0 eq.) and dimethyl sulfoxide (20 ml). The reaction solution was heated to 100° C. and reacted for 3 hours. The reaction solution was diluted with ethyl acetate (150 ml) and washed with semi-saturated brine (100 ml×4). The organic phase was dried by rotary evaporation. The residue was purified by column chromatography on silica gel (the eluent: petroleum ether:ethyl acetate=8:1) to obtain a yellow paste tert-butyl (E)-2-(2,6-dichloro-4-(3-(6-(methylthio)benzofuran-2-yl)-3-oxoprop-1-en-1-yl)phenoxy)-2methylpropanoate (0.49 g, yield: 35%). LCMS(ESI): 522 [M+1]$^+$.

Step 37c: Preparation of (E)-2-(2,6-dichloro-4-(3-(6-(methylthio)benzofuran-2-yl)-3-oxoprop-1-en-1-yl)phenoxy)-2-methylpropanoic acid (100). To a solution of tert-butyl (E)-2-(2,6-dichloro-4-(3-(6-(methylthio)benzofuran-2-yl)-3-oxoprop-1-en-1-yl)phenoxy)-2methylpropanoate (0708-100) (0.49 g, 0.94 mmol, 1.0 eq.) in dichloromethane (10 ml) was added trifluoroacetate (2 ml) slowly. The mixture was stirred at room temperature over night. The reaction solution was diluted with ethyl acetate (100 ml) and washed with semi-saturated brine (100 ml×1). The organic phase was dried over anhydrous sodium sulfate and filtered. The filtrate was dried by rotary evaporation. The residue was recrystallized with ethyl acetate (3 ml) to obtain a yellow solid (E)-2-(2,6-dichloro-4-(3-(6-(methylthio)benzofuran-2-yl)-3-oxoprop-1-en-1-yl)phenoxy)-2-methylpropanoic acid (220 mg, yield: 50%). LCMS(ESI): 466[M+1]$^+$, melting point: 202~205° C.: $^1$HNMR (DMSO, 500 MHz): δ13.00 (s, 1H), 7.27-8.35 (m, 8H), 2.58 (s, 3H), 1.50 (s, 6H).

Example 38: Preparation of (E)-2-(2,6-diisopropyl-4-(3-(6-(methylthio)benzofuran-2-yl)-3-oxoprop-1-en-1-yl)phenoxy)-2-methylpropanoic acid (Compound 101) (Prepared According to Scheme 7)

Step 38a: Preparation of (E)-3-(4-hydroxy-3,5-diisopropylphenyl)-1-(6-(methylthio)benzofuran-2-yl)prop-2-en-1-one (0707-101). To a round bottom flask were added 1-(6-(methylthio)benzofuran-2-yl)ethan-1-one (0706-51) (0.206 g, 1.0 mmol, 1.0 eq.), 4-hydroxy-3,5-diisopropylbenzaldehyde (0.206 g, 1.0 mmol, 1.10 eq.), a solution of dioxane (10 ml) and methanesulfonic acid (2 ml). The mixture was heated to 55° C. and reacted for 4 hours. The reaction solution was diluted with ethyl acetate (100 ml) and washed with water (100 ml×1) and brine (100 ml×1) separately. The organic phase was dried by rotary evaporation. The residue was purified by column chromatography on silica gel (the eluent: petroleum ether:ethyl acetate=5:1) to obtain a yellow solid (E)-3-(4-hydroxy-3,5-diisopropylphenyl)-1-(6-(methylthio)benzofuran-2-yl)prop-2-en-1-one (0.20 g, yield: 50%). LCMS(ESI): 395 [M+1]$^+$.

Step 38b: Preparation of tert-butyl (E)-2-(2,6-diisopropyl-4-(3-(6-(methylthio)benzofuran-2-yl)-3-oxoprop-1-en-1-yl)phenoxy)-2methylpropanoate (0708-101). To a round bottom flask were added (E)-3-(4-hydroxy-3,5- diisopropylphenyl)-1-(6-(methylthio)benzofuran-2-yl)prop-2-en-1-one (0707-101) (0.20 g, 0.5 mmol, 1.0 eq.), tert-butyl 2-bromoisobutyrate (1.12 g, 5.0 mmol, 10.0 eq.), potassium carbonate (0.69 g, 5.0 mmol, 10.0 eq.) and acetonitrile (20 ml). The reaction solution was refluxed overnight under the protection of nitrogen. The reaction solution was dried by rotary evaporation. The residue was purified by column chromatography on silica gel (the eluent: petroleum ether: ethyl acetate=10:1) to obtain a yellow oil tert-butyl (E)-2-(2,6-diisopropyl-4-(3-(6-(methylthio)benzofuran-2-yl)-3-oxoprop-1-en-1-yl)phenoxy)-2methylpropanoate (0.11 g, yield: 41%). LCMS(ESI): 537 [M+1]$^+$.

Step 38c: Preparation of (E)-2-(2,6-diisopropyl-4-(3-(6-(methylthio)benzofuran-2-yl)-3-oxoprop-1-en-1-yl)phenoxy)-2-methylpropanoic acid (compound 101). To a solution of tert-butyl (E)-2-(2,6-diisopropyl-4-(3-(6-(methylthio)benzofuran-2-yl)-3-oxoprop-1-en-1-yl)phenoxy)-2methylpropanoate (0708-101) (0.11 g, 0.20 mmol, 1.0 eq.) in dichloromethane (10 ml) was added trifluoroacetate (2 ml) slowly. The reaction solution was stirred at room temperature for 2 hours. The reaction solution was poured into water (100 ml) and extracted with dichloromethane (100 ml×1). The organic phase was dried over anhydrous sodium sulfate and filtered. The filtrate was dried by rotary evaporation. The residue was recrystallized with methanol (3 ml) to obtain a yellow solid (E)-2-(2,6-diisopropyl-4-(3-(6-(methylthio)benzofuran-2-yl)-3-oxoprop-1-en-1-yl)phenoxy)-2-methylpropanoic acid (60 mg, yield: 62%). LCMS(ESI): 481[M+1]$^+$; melting point: 199~202° C.; $^1$HNMR (DMSO, 500 MHz): δ 12.97 (s, 1H), 7.26-8.42 (m, 8H), 3.25 (m, 2H), 2.61 (s, 3H), 1.38 (s, 6H), 1.21 (d, J=8.5 Hz, 12H).

Example 39: Preparation of (E)-2-(2,6-dimethoxy-4-(3-(3-methyl-6-(methylthio)benzofuran-2-yl)-3-oxoprop-1-en-1-yl)phenoxy)-2-methylpropanoic acid (Compound 102) (Prepared According to Scheme 10)

Step 39a: Preparation of (E)-3-(4-hydroxy-3,5-dimethoxyphenyl)-1-(3-methyl-6-(methylthio)benzofuran-2-yl)prop-2-en-1-one (1004-102): to a solution of 1-(3-methyl-6-(methylthio)benzofuran-2-yl)ethan-1-one (1003-62) (150 mg, 0.682 mmol, 1.0 eq.) and 4-hydroxy-3,5-dimethoxybenzaldehyde (124 mg, 0.682 mmol, 1.0 eq.) in ethanol (8 ml) was added dropwise concentrated sulfuric acid (2 mL) slowly. The mixture was reacted at room temperature for 6 hours. The reaction solution was diluted with water (30 mL) and extracted with ethyl acetate (30 mL×3). The extract was washed with saturated brine (30 mL×1), dried over anhydrous sodium sulfate and concentrated to give a yellow solid (E)-3-(4-hydroxy-3,5-dimethoxyphenyl)-1-(3-methyl-6-(methylthio)benzofuran-2-yl)prop-2-en-1-one (260 mg, crude). LCMS(ESI): m/z 385[M+1]$^+$.

Step 39b: Preparation of tert-butyl (E)-2-(2,6-dimethoxy-4-(3-(3-methyl-6-(methylthio)benzofuran-2-yl)-3-oxoprop-1-en-1-yl)phenoxy)-2-methylpropanoate (1005-102): (E)-3-(4-hydroxy-3,5-dimethoxyphenyl)-1-(3-methyl-6-(methylthio)benzofuran-2-yl)prop-2-en-1-one (1004-102) (260 mg, 0.678 mmol, 1.0 eq.) and tert-butyl 2-bromo-2-methylpropanoate (0.73 mL, 4.06 mmol, 6.0 eq.) were dissolved in dimethyl sulfoxide (10 mL) and then potassium carbonate (0.37 g, 2.712 mmol, 4.0 eq.) was added. After the air in the system was replaced by nitrogen three times, the mixture was reacted at 100° C. for 6 hours. The reaction solution was diluted with water (30 mL) and extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=8:1) to obtain a yellow solid tert-butyl (E)-2-(2,6-dimethoxy-4-(3-(3-methyl-6-(methylthio)benzofuran-2-yl)-3-oxoprop-1-en-1-yl)phenoxy)-2-methylpropanoate (180 mg, yield: 50%). LCMS(ESI): m/z 527[M+1]$^+$.

Step 39c: Preparation of (E)-2-(2,6-dimethoxy-4-(3-(3-methyl-6-(methylthio)benzofuran-2-yl)-3-oxoprop-1-en-1-yl)phenoxy)-2-methylpropanoic acid (compound 102): to a solution of tert-butyl (E)-2-(2,6-dimethoxy-4-(3-(3-methyl-6-(methylthio)benzofuran-2-yl)-3-oxoprop-1-en-1-yl)phenoxy)-2-methylpropanoate (1005-102) (180 mg, 0.342 mmol, 1.0 eq.) in dichloromethane (15 ml) was added dropwise trifluoroacetate (1.5 mL) slowly at room temperature. The mixed solution was stirred at room temperature for 5 hours. The reaction solution was diluted with water (30 mL) and extracted with ethyl acetate (30 mL×3). The extract was washed with saturated brine (20 mL×1) and dried over anhydrous sodium sulfate. The obtained crude product after concentration was washed with methanol (5 mL) and filtered. The solid collected was dried in vacuo to obtain a yellow solid (E)-2-(2,6-dimethoxy-4-(3-(3-methyl-6-(methylthio)benzofuran-2-yl)-3-oxoprop-1-en-1-yl)phenoxy)-2-methylpropanoic acid (50 mg, yield: 31%). LCMS(ESI): m/z 471[M+1]$^+$, melting point: 105~108° C.; $^1$HNMR (DMSO-d$_6$, 500 MHz): δ12.36 (s, 1H), 7.77-7.68 (m, 3H), 7.57 (s, 1H), 7.28 (d, J=8.5 Hz, 1H), 7.16 (s, 2H), 3.81 (s, 6H), 2.62 (s, 3H), 2.59 (s, 3H), 1.34 (s, 6H).

Example 40: Preparation of (E)-2-(2,6-dichloro-4-(3-(3-methyl-6-(methylthio)benzofuran-2-yl)-3-oxoprop-1-en-1-yl)phenoxy)-2-methylpropanoic acid (Compound 103)(Prepared According to Scheme 10)

Step 40a: Preparation of (E)-3-(3,5-dichloro-4-hydroxyphenyl)-1-(3-methyl-6-(methylthio)benzofuran-2-yl)prop-2-en-1-one (1004-103): to a solution of 1-(3-methyl-6-(methylthio)benzofuran-2-yl)ethan-1-one (1003-62) (150 mg, 0.682 mmol, 1.0 eq.) and 3,5-dichloro-4-hydroxy-benzaldehyde (130 mg, 0.682 mmol, 1.0 eq.) in ethanol (8 ml) was added dropwise concentrated sulfuric acid (2 mL) slowly. The mixture was reacted at room temperature overnight. The reaction solution was diluted with water (30 mL) and then extracted with ethyl acetate (30 mL×3). The extract was washed with saturated brine (20 mL×1), dried over anhydrous sodium sulfate and concentrated to give a yellow solid (E)-3-(3,5-dichloro-4-hydroxyphenyl)-1-(3-methyl-6-(methylthio)benzofuran-2-yl)prop-2-en-1-one (268 mg, crude). LCMS(ESI): m/z 393[M+1]$^+$.

Step 40b: Preparation of tert-butyl (E)-2-(2,6-dichloro-4-(3-(3-methyl-6-(methylthio)benzofuran-2-yl)-3-oxoprop-1-en-1-yl)phenoxy)-2-methylpropanoate (1005-103): (E)-3-(3,5-dichloro-4-hydroxyphenyl)-1-(3-methyl-6-(methylthio)benzofuran-2-yl)prop-2-en-1-one (1004-103) (268 mg, 0.682 mmol, 1.0 eq.) and tert-butyl 2-bromo-2-methylpropanoate (0.74 mL, 4.09 mmol, 6.0 eq.) were dissolved in dimethyl sulfoxide (10 mL) and then potassium carbonate (0.377 g, 2.73 mmol, 4.0 eq.) was added. The air in the reaction system was replaced with nitrogen three times, and then the system was reacted at 100° C. overnight. The reaction solution was diluted with water (40 mL) and then extracted with ethyl acetate (30 mL×3). The extract was washed with saturated brine (20 mL×1) and dried over anhydrous sodium sulfate. The obtained crude product after concentration was purified by column chromatography on silica gel (petroleum ether:ethyl acetate=20:1) to obtain a yellow oil liquid tert-butyl (E)-2-(2,6-dichloro-4-(3-(3-methyl-6-(methylthio)benzofuran-2-yl)-3-oxoprop-1-en-1-yl)phenoxy)-2-methylpropanoate (96 mg, yield: 26%). LCMS(ESI): m/z 535[M+1]$^+$.

Step 40c: Preparation of (E)-2-(2,6-dichloro-4-(3-(3-methyl-6-(methylthio)benzofuran-2-yl)-3-oxoprop-1-en-1-yl)phenoxy)-2-methylpropanoic acid (compound 103): to a solution of tert-butyl (E)-2-(2,6-dichloro-4-(3-(3-methyl-6-(methylthio)benzofuran-2-yl)-3-oxoprop-1-en-1-yl)phenoxy)-2-methylpropanoate (1005-103) (96 mg, 0.179 mmol, 1.0 eq.) in dichloromethane (10 ml) was added dropwise trifluoroacetate (1.0 mL) slowly at room temperature. The mixed solution was stirred at room temperature for 5 hours. The reaction solution was diluted with water (40 mL) and then extracted with ethyl acetate (30 mL×3). The extract was washed with saturated brine (30 mL×1), dried over anhydrous sodium sulfate and concentrated to give a crude product which was purified by column chromatography on silica gel (dichloromethane:methanol=20:1) to obtain a yellow solid (E)-2-(2,6-dichloro-4-(3-(3-methyl-6-(methylthio)benzofuran-2-yl)-3-oxoprop-1-en-1-yl)phenoxy)-2-methylpropanoic acid (60 mg, yield: 70%). LCMS(ESI): m/z 479[M+1]$^+$, Melting point: 206~208° C.; $^1$HNMR (DMSO-d$_6$, 500 MHz): δ12.99 (s, 1H), 8.03 (s, 2H), 7.80-7.68 (m, 3H), 7.57 (s, 1H), 7.28 (d, J=8.5 Hz, 1H), 2.61 (s, 3H), 2.58 (s, 3H), 1.51 (s, 6H).

Example 41: Preparation of (E)-2-(2,6-diisopropyl-4-(3-(3-methyl-6-(methylthio)benzofuran-2-yl)-3-oxoprop-1-en-1-yl)phenoxy)-2-methylpropanoic acid (Compound 104) (Prepared According to Scheme 10)

Step 41a: Preparation of (E)-3-(4-hydroxy-3,5-diisopropylphenyl)-1-(3-methyl-6-(methylthio)benzofuran-2-yl) prop-2-en-1-one (1004-104): to a solution of 1-(3-methyl-6-(methylthio)benzofuran-2-yl)ethan-1-one (1003-62) (120 mg, 0.545 mmol, 1.0 eq.) and 4-hydroxy-3,5-diisopropylbenzaldehyde (112.4 mg, 0.545 mmol, 1.0 eq.) in ethanol (8 ml) was added dropwise concentrated sulfuric acid (2 mL) slowly. The mixture was reacted at room temperature for 6 hours. The reaction solution was diluted with water (30 mL) and then extracted with ethyl acetate (30 mL×3). The extract was washed with saturated brine (20 mL×1), dried over anhydrous sodium sulfate and concentrated to give a yellow solid (E)-3-(4-hydroxy-3,5-diisopropylphenyl)-1-(3-methyl-6-(methylthio)benzofuran-2-yl)prop-2-en-1-one (222 mg, crude). LCMS(ESI): m/z 409[M+1]$^+$.

Step 41b: Preparation of tert-butyl (E)-2-(2,6-diisopropyl-4-(3-(3-methyl-6-(methylthio)benzofuran-2-yl)-3-oxoprop-1-en-1-yl)phenoxy)-2-methylpropanoate (1005-104): (E)-3-(4-hydroxy-3,5-diisopropylphenyl)-1-(3-methyl-6-(methylthio)benzofuran-2-yl)prop-2-en-1-one (1004-104) (222 mg, 0.545 mmol, 1.0 eq.) and tert-butyl 2-bromo-2-methylpropanoate (0.98 mL, 5.45 mmol, 10.0 eq.) were dissolved in acetonitrile (10 mL) and then potassium carbonate (0.301 g, 2.18 mmol, 4.0 eq.) was added. The air in the reaction system was replaced with nitrogen three times, and then the system was reacted at 85° C. overnight. After the reaction was completed, the mixture was concentrated to give a crude product which was purified by column chromatography on silica gel (petroleum ether:ethyl acetate=20:1) to obtain a yellow oil liquid tert-butyl (E)-2-(2,6-diisopropyl-4-(3-(3-methyl-6-(methylthio)benzofuran-2-yl)-3-oxoprop-1-en-1-yl)phenoxy)-2-methylpropanoate (50 mg, yield: 17/). LCMS(ESI): m/z 551[M+1]$^+$.

Step 41c: Preparation of (E)-2-(2,6-diisopropyl-4-(3-(3-methyl-6-(methylthio)benzofuran-2-yl)-3-oxoprop-1-en-1-yl)phenoxy)-2-methylpropanoic acid (compound 104): to a solution of tert-butyl (E)-2-(2,6-diisopropyl-4-(3-(3-methyl-6-(methylthio)benzofuran-2-yl)-3-oxoprop-1-en-1-yl)phenoxy)-2-methylpropanoate (1005-104) (50 m g, 0.091 mmol, 1.0 eq.) in dichloromethane (5 ml) was added dropwise trifluoroacetate (0.5 mL) slowly at room temperature. The mixed solution was stirred at room temperature for 6 hours. The reaction solution was diluted with water (30 mL) and then extracted with ethyl acetate (30 mL×3). The extract was washed with saturated brine (20 mL×1), dried over anhydrous sodium sulfate and concentrated to a crude product which was purified by column chromatography on silica gel (dichloromethane:methanol=30:1) to obtain a yellow solid (E)-2-(2,6-diisopropyl-4-(3-(3-methyl-6-(methylthio) benzofuran-2-yl)-3-oxoprop-1-en-1-yl)phenoxy)-2-meth ylpropanoic acid (37 mg, yield: 82%). LCMS(ESI): m/z 495[M+1]$^+$, melting point: 186~189° C.; $^1$HNMR (DMSO-d$_6$, 500 MHz): δ13.00 (s, 1H), 7.81-7.75 (m, 2H), 7.69 (s, 1H), 7.65-7.58 (m, 3H), 7.28 (d, J=10.5 Hz, 1H), 3.33-3.25 (m, 2H), 2.62 (s, 3H), 2.60 (s, 3H), 1.38 (s, 6H), 1.20 (d, J=8.5 Hz, 12H).

Example 42: Biological Activity Test

I. Determination of Biological Activity of PPAR Agonists
1. Experimental Method
This example measures the biological activity of a PPAR agonist using the Hela cell/luciferase reporter gene method.

The target plasmids PCMV PPARα (Ampicillin+), PCMV PPARγ (Ampicillin+), PCMV PPARδ (Ampicillin+), and pPPRE3-TK-Luciferase (Ampicillin+) were introduced into DH5a competent cells by heat shock treatment, respectively. After being incubated for 1 hour at 37° C. with shaking (180 rpm), the cells were inoculated on LB agar solid medium containing antibiotic Ampicillin, and invertedly cultured at 37° C. for 12-16 hours. Then the monoclonal colony cultured on the medium was taken and inoculated into LB liquid medium for expanded culture. The desired plasmid was extracted from the resulting bacterial solution with a Plasmid Midi Kit (Qiagen; #12143). The plasmid obtained by centrifugation was suspended in TE buffer, and the plasmid concentration was measured and the mixture was stored at −20° C. Hela cells in the exponential phase were seeded in 6-well plates (8-10$^5$ cells/well), and after 6-8 hours of culture, the cells were transfected using Lipofectamine® 3000 Transfection Reagent (Invitrogen; #L3000015). A plasmid containing a PPAR binding site (peroxisome proliferator response element, PPRE) and a firefly luciferase gene (pPPRE3-TK-Luciferase) and PPAR expression vector were co-transfected into a Hela cell with a total amount of plasmid DNA of 2.5 ug (the mass ratio of each PPAR expression vector is pPPRE:PPARα=6:1, pPPRE:PPARδ=8:1, and pPPRE:PPARγ=2:1) to construct a drug screening cell model for PPAR agonists. PPAR was binded to the ligand and then binded to the peroxisome proliferator response element (PPRE), thereby initiating downstream firefly luciferase expression and its expression intensity was directly proportional to the degree of PPAR activation. The cells after 24 hours transfection were prepared into a cell suspension with a cell concentration of 3×10/ml by a complete culture solution, and seeded into a 96-well plate with 100 ul per well. After overnight culture, the medium was changed to a medium containing 1% FBS.

10 mM candidate compound stock (1000×) were 4-fold diluted in DMSO for 8 points, then supplemented with medium containing 1% FBS to a final concentration of 50 uM (5×) by addition of 25 μl of 5× compound diluent to each well in different concentration gradients and incubated under 37° C., 5% $CO_2$ incubator for 24 hrs. The 96-well plate was taken out and 30 μl of Bright-Glo™ Luciferase Assay System (Promega #E2620) was added to each well. The Luciferase luminescence intensity was measured by a SynergyH1 full-function microplate detector. The obtained data was used to calculate EC50 using GraphPad Prism 5.0 software to determine the biological activity of the compound.

2. Experimental Results

The agonistic activity of the compounds synthesized in Examples 1-41 on PPAR is represented by $EC_{50}$ (see Table 1). $EC_{50}$ refers to the drug concentration at which the compound has a 50% increase in the agonistic activity of the measured PPAR. The compound numbers in Table 1 correspond to the compound numbers in Examples 1-41.

TABLE 1

The agonistic activities of the compounds on three subtypes of PPAR ($EC_{50}$, nM)

| Compound No. | PPARα | PPARδ | PPARγ |
|---|---|---|---|
| 1 | 419.9 | | 172.0 |
| 2 | 947.6 | | |
| 3 | 452.7 | | 576.9 |
| 5 | 24.4 | 36.0 | 26.2 |
| 6 | 9.6 | 118.5 | 62.6 |
| 9 | 46.8 | | |
| 12 | 99.8 | | 279.2 |
| 13 | 475.7 | | 3409.0 |
| 14 | 156.0 | | 122.3 |
| 20 | 165.2 | | |
| 27 | 59.1 | 603.7 | 124.3 |
| 36 | 75.1 | 120.1 | 31.6 |
| 38 | >10000 | 837.9 | |
| 39 | 365.9 | | |
| 43 | 39.8 | 334.8 | 116.4 |
| 44 | 7.67 | | |
| 49 | 873.9 | | |
| 50 | 122.8 | | 167.3 |
| 51 | 4.0 | 64.9 | 35.3 |
| 56 | 83.9 | | 1101.0 |
| 57 | 1180.0 | | |
| 58 | 352.1 | | |
| 60 | 46.7 | 613.9 | 92.3 |
| 62 | 16.6 | 210.3 | 132.4 |
| 63 | 19.2 | 204.8 | 95.5 |
| 64 | 105.2 | | |
| 73 | 3.8 | | |
| 74 | 13.9 | 144.5 | 29.3 |
| 75 | 121.0 | | |
| 76 | 58.9 | | |
| 77 | 121.0 | | |
| 81 | 24.9 | 3636.0 | 94.1 |
| 82 | 70.2 | | |
| 88 | 2445.0 | | |
| 94 | 41.9 | | |
| 99 | 52.1 | | |
| 100 | 2.0 | 87.1 | 475.1 |
| 101 | 476.6 | | |
| 102 | 191.0 | | |
| 103 | 8.7 | 164.0 | 788.1 |
| 104 | 381.6 | | |
| Elafibranor (GFT-505) | 29.2 | 262.2 | 86.6 |

We have found that Elafibranor is also an agonist of PPARγ in addition to PPARα and PPARγ agonists. The compound of the present disclosure is similar to Elafibranor and is an agonist of three subtypes of nuclear hormone receptors, PPARα, PPARδ and PPARγ. Different compounds have different $EC_{50}$ values for the three subtypes. Compared with Elafibranor, compound 51 has a 7-fold and 2-fold increased activity for activation of PPARα and PPARδ, respectively, but has little effect on PPARγ compound 62 has 1-fold increased activity for activation of PPARα, but has a weak activation of PPARγ. At the same time, we also found that compound 100 and compound 103 had extremely high activity for activation of PPARα, their $EC_{50}$ values are 14.6 and 3.4 times of that of Elafibranor respectively. However, compared with Elafibranor, the activities of both of them for activation of PPARγ are significantly reduced. Since different PPAR subtypes play different roles in various diseases, the selective characteristics of different compounds of the present disclosure for PPAR subtypes have potential significance for the treatment of different diseases.

Several Glitazars-like PPAR and PPARγ double agonists for the treatment of diabetes (such as Aeglitazar, muraglitazar, and tesaglitazar) discontinued development due to cardiotoxicity or renal toxicity in clinical trials (Robert S et al. Am Heart J164: 672-680, 2012, Conlon D. Br J Diabetes Vasc Dis 6: 135-137, 2006). The causes of toxicity of PPARγ and PPARγ dual agonist are not fully understood currently. Aeglitazar has a higher activity for activating PPARγ, the $EC_{50}$ for activation of PPARα and PPARγ are 38 nM and 19 nM respectively. The $EC_{50}$ ratio of PPARγ/PPAR is 0.5 (Bénardeau A et al. Bioorg Med Chem Lett. 19: 2468-2473, 2009). Elafibranor has a higher selective activity for PPARα than that of Glitazars. Under the experimental conditions of the present disclosure, Elafibranor activated PPARγ/PPARα in a ratio of 2.97 and the ratios of PPARγ/PPARα activated by the compounds 51, 62, 100 and 103 of the present disclosure were significantly increased on the basis of Elafibranor, which were 8.83, 7.98, 237.55, and 90.59, respectively. It is suggested that the safety of the compounds of the present disclosure may be higher.

II. Pharmacokinetic (PK) Experiments

1. Experimental Method

Male SD rats, weighing 250-300 grams, were fasted overnight before testing. The test compound was dissolved in 30% sulfobutyl-R-cyclodextrin (SBE-β-CD) and administered intragastrically at a dose of 20 mg/kg. Blood was collected 15 minutes, 30 minutes, and 1, 2, 3, 4, 68 and 24 hours after the administration. About 0.3 ml of blood was collected at each time point, placed in a centrifuge tube containing K2-EDTA (dipotassium ethylenediamine tetraacetate) and centrifuged (2,000 g, 10 minutes, 4° C.) to take the plasma, which was stored in an ultra-low temperature refrigerator at −80° C. A 50 μL plasma sample was mixed with 5 μl of internal standard (IS) and extracted with ethyl acetate. The residue was redissolved in acetonitrile after drying under vacuum. The sample was filtered and injected into an LC-MS/MS for analysis.

2. Experimental Results Compared with the control Elafibranor (GFT-505), after oral administration in rats, the compounds 5, 36, 43, 51, 62, 63, 81, 100, and 103 provided by the present disclosure (the numbers are consistent with those in Examples 1-41) have good absorption, highly effective blood exposure, and significantly prolonged half-life (the results are shown in Table 2 and FIG. 1). The Cmax of compounds 5, 36, 62 and 43 are 1.6-2.5 times that of the reference compound Elafibranor their $AUC_{0-24\ h}$ are 1.2-2.5 times that of Elafibranor. The Cmax of compounds 100 and 103 are 4.4-6.8 times that of the reference compound Elafibranor; their $AUC_{0-24\ h}$ are 10.2-37.3 times that of Elafibranor. Cmax refers to the maximum blood concentration, T/2 is the half-life, $AUC_{0-24}$ refers to the area under the 0-24 hour time-concentration curve, and $AUC_{0-inf}$ refers to the area under the 0-Inf time-concentration curve.

TABLE 2

Pharmacokinetics after intragastric administration (20 mg/kg) in rats

| Compound | $T_{max}$ | $C_{max}$ | Terminal $T_{1/2}$ | $AUC_{last}$ | $AUC_{inf}$ |
|---|---|---|---|---|---|
| Elafibranor (GFT-505) | 0.33 | 1138 | 0.82 | 1351 | 1352 |
| 5 | 0.25 | 2853 | 12.31 | 3113 | 3240 |
| 36 | 0.38 | 2745 | 6.42 | 3343 | 3385 |
| 43 | 0.25 | 2777 | 6.84 | 1551 | 1579 |
| 51 | 0.25 | 484 | 12.31 | 412 | 479 |
| 62 | 0.25 | 1833 | 8.87 | 3039 | 3152 |
| 63 | 0.25 | 812 | 4.30 | 1695 | 1722 |
| 81 | 0.25 | 302 | 3.35 | 806 | 811 |
| 100 | 0.25 | 7733 | 4.41 | 13813 | 14023 |
| 103 | 4.08 | 5033 | 3.28 | 50434 | 50864 |

The various technical features of the embodiments described above can be arbitrarily combined. In order to simplify the description, all possible combinations of the technical features in the above embodiments have not been described. However, as long as there is no contradiction in the combination of these technical features, it should be considered as the scope described in this specification.

The above-mentioned embodiments only express several implementation manners of the present disclosure, and the description thereof is more specific and detailed, but it cannot be understood as a limitation on the scope of the disclosure patent. It should be noted that, for those of ordinary skill in the art, without departing from the concept of the present disclosure, several modifications and improvements can be made, which all belong to the protection scope of the present disclosure. Therefore, the protection scope of the present disclosure shall be subject to the appended claims.

What is claimed:

1. A 1,3-disubstituted ketene compound having a structure represented by formula (I) or a pharmaceutically acceptable salt thereof or a stereoisomer thereof or a prodrug molecule thereof:

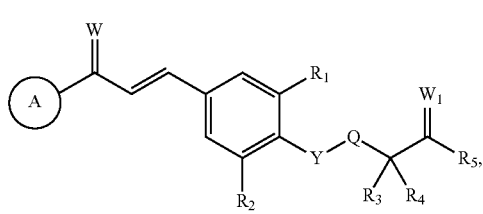

(I)

wherein $R_1$ and $R_2$ are each independently selected from the group consisting of H, halogen, C1-C6 alkyl, C2-C6 alkenyl, C2-C6 alkynyl, C3-C8 cycloalkyl, C3-C8 cycloalkylmethyl, C1-C6 alkoxy, and hydroxyl;

$R_3$ and $R_4$ are each independently selected from the group consisting of H, halogen, C1-C6 alkyl, C2-C6 alkenyl, C2-C6 alkynyl, C3-C8 cycloalkyl, C3-C8 cycloalkylmethyl, C1-C6 alkoxy, and hydroxyl, and $R_3$ and $R_4$ are not H at the same time; or $R_3$ and $R_4$ are bonded to form a 3-8 membered carbocyclic ring or a 3-8 membered heterocyclic ring;

$R_5$ is selected from the group consisting of $OR_6$ and $NR_7R_8$;

Q is a single bond or $CR_7R_8$;

$R_6$, $R_7$, and $R_8$ are each independently selected from the group consisting of H, C1-C6 alkyl, C3-C8 cycloalkyl, and C3-C8 cycloalkylmethyl;

W, $W_1$, and Y are each independently selected from the group consisting of O and S;

ring A is selected from the group consisting of the following structures,

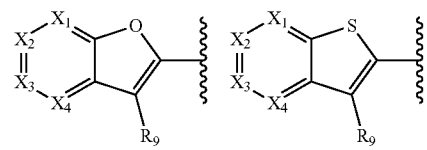

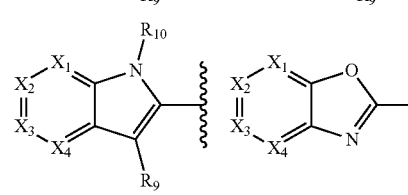

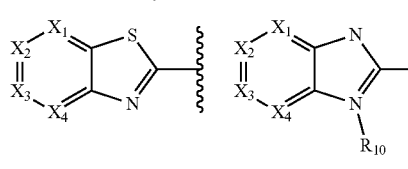

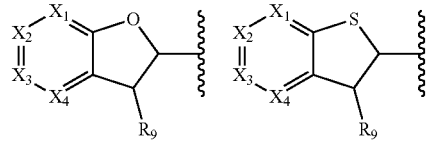

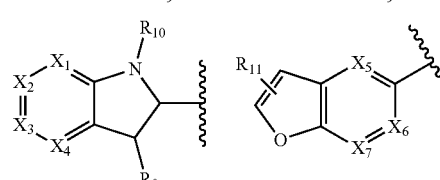

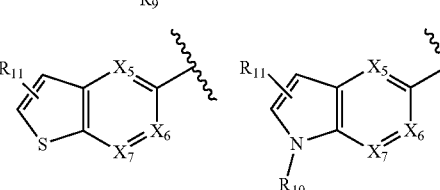

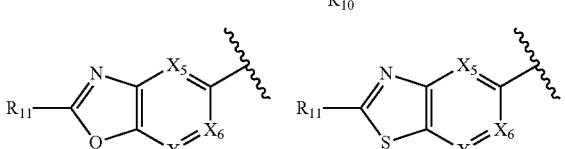

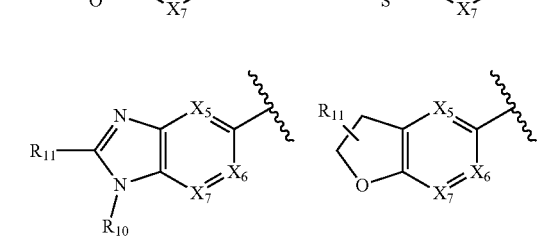

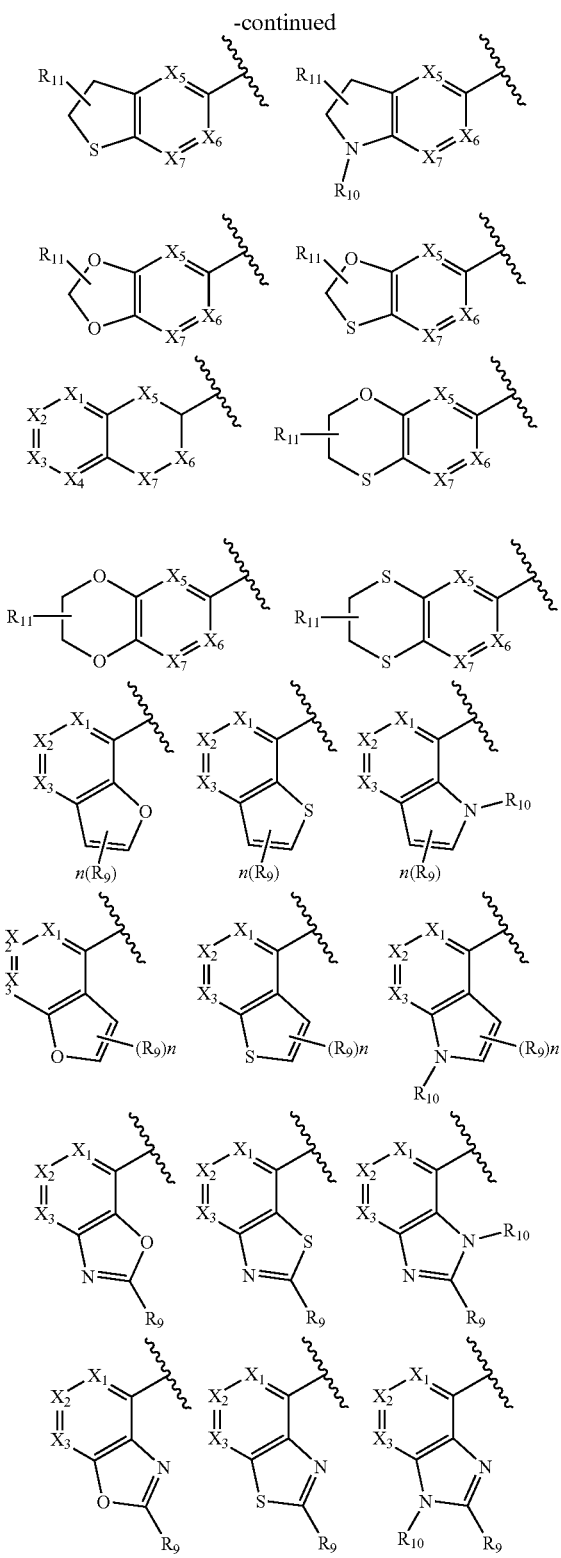

where $X_1$, $X_2$, $X_3$, $X_4$, $X_5$, $X_6$, and $X_7$ are each independently selected from the group consisting of $CR_9$, $CR_{12}$, and N, and at least one of $X_1$, $X_2$, $X_3$, and $X_4$ is $CR_{12}$;

$R_9$ is selected from the group consisting of H, halogen, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, aryl, heteroaryl, nitro, cyano, —OR, —N(R)$_2$, —SR, —C(O)OR, —C(O)N(R)$_2$, —C(O)R, —S(O)R, —S(O)$_2$R, —S(O)2N(R)2, and —N(R)C(O)R;

$R_{10}$ is selected from the group consisting of H, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, and C1-C4 alkylamino-substituted C1-C6 alkyl;

$R_{11}$ is selected from the group consisting of H, —SR, —OR, —N(R)$_2$, C1-C6 alkyl, C3-C8 cycloalkyl, and C3-C8 cycloalkylmethyl;

$R_{12}$ is selected from the group consisting of H, —SR, —OR, —N(R)$_2$, C1-C6 alkyl, C3-C8 cycloalkyl, and C3-C8 cycloalkylmethyl;

n is 0, 1, or 2; and each of R is selected from the group consisting of H, C1-C6 alkyl, C2-C6 alkenyl, C2-C6 alkynyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, and C1-C4 alkylamino-substituted C1-C6 alkyl.

2. The 1,3-disubstituted ketene compound of claim 1 or a pharmaceutically acceptable salt thereof or a stereoisomer thereof or a prodrug molecule thereof, wherein the compound has a structure represented by formula (II):

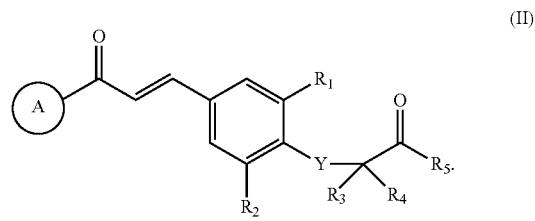

(II)

3. The 1,3-disubstituted ketene compound of claim 1 or a pharmaceutically acceptable salt thereof or a stereoisomer thereof or a prodrug molecule thereof, wherein ring A is selected from the group consisting of the following structures,

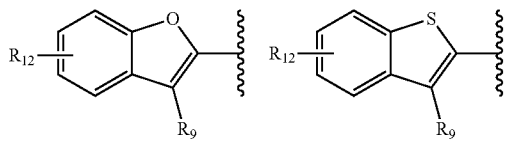

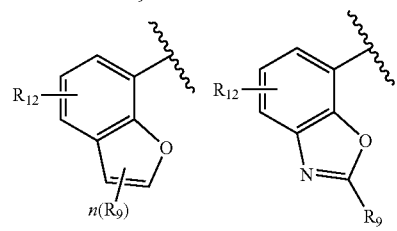

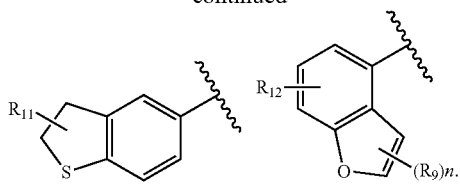

4. The 1,3-disubstituted ketene compound of claim 3 or a pharmaceutically acceptable salt thereof or a stereoisomer thereof or a prodrug molecule thereof,
wherein ring A is selected from the group consisting of the following structures,

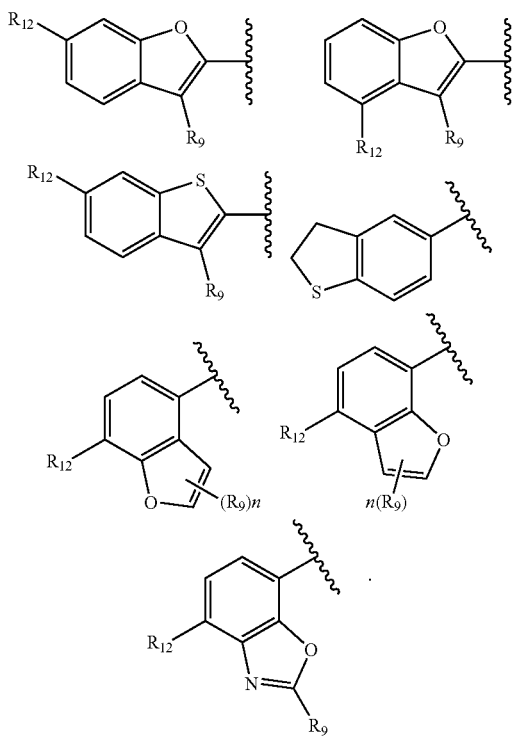

5. The 1,3-disubstituted ketene compound of claim 1 or a pharmaceutically acceptable salt thereof or a stereoisomer thereof or a prodrug molecule thereof,
wherein $R_9$ is selected from the group consisting of H, methyl, ethyl, isopropyl, and trifluoromethyl.

6. The 1,3-disubstituted ketene compound of claim 1 or a pharmaceutically acceptable salt thereof or a stereoisomer thereof or a prodrug molecule thereof,
wherein $R_{12}$ is selected from the group consisting of H, —SR, —OR, —N(R)$_2$, and C1-C6 alkyl, where R is selected from the group consisting of H and C1-C6 alkyl.

7. The 1,3-disubstituted ketene compound of claim 6 or a pharmaceutically acceptable salt thereof or a stereoisomer thereof or a prodrug molecule thereof,
wherein $R_{12}$ is selected from the group consisting of SR and OR, where R is C1-C6 alkyl.

8. The 1,3-disubstituted ketene compound of claim 1 or a pharmaceutically acceptable salt thereof or a stereoisomer thereof or a prodrug molecule thereof,
wherein $R_1$ and $R_2$ are both methyl or chlorine.

9. The 1,3-disubstituted ketene compound of claim 1 or a pharmaceutically acceptable salt thereof or a stereoisomer thereof or a prodrug molecule thereof,
wherein $R_3$ and $R_4$ are each independently selected from the group consisting of H, C1-C6 alkyl, C1-C6 alkoxy, and halogen; or $R_3$ and $R_4$ are bonded to form a 3-8 membered carbocyclic ring.

10. The 1,3-disubstituted ketene compound of claim 9 or a pharmaceutically acceptable salt thereof or a stereoisomer thereof or a prodrug molecule thereof,
wherein $R_3$ and $R_4$ are C1-C6 alkyl.

11. The 1,3-disubstituted ketene compound of claim 1 or a pharmaceutically acceptable salt thereof or a stereoisomer thereof or a prodrug molecule thereof,
wherein $R_5$ is $OR_6$, where $R_6$ is selected from the group consisting of H and C1-C6 alkyl.

12. The 1,3-disubstituted ketene compound of claim 11 or a pharmaceutically acceptable salt thereof or a stereoisomer thereof or a prodrug molecule thereof,
wherein $R_5$ is $OR_6$, where $R_6$ is H.

13. The 1,3-disubstituted ketene compound of claim 1 or a pharmaceutically acceptable salt thereof or a stereoisomer thereof or a prodrug molecule thereof,
wherein Y is O.

14. The 1,3-disubstituted ketene compound of claim 1 or a pharmaceutically acceptable salt thereof or a stereoisomer thereof or a prodrug molecule thereof,
wherein $R_1$ and $R_2$ are each independently selected from the group consisting of H, C1-C6 alkyl, C1-C6 alkoxy, and halogen;
$R_3$ and $R_4$ are each independently selected from the group consisting of H, C1-C6 alkyl, C1-C6 alkoxy, and halogen; or $R_3$ and $R_4$ are bonded to form a 3-8 membered carbocyclic ring;
$R_5$ is $OR_6$, where $R_6$ is selected from the group consisting of H and C1-C6 alkyl;
Y is selected from the group consisting of O and S;
ring A is selected from the group consisting of the following structures,

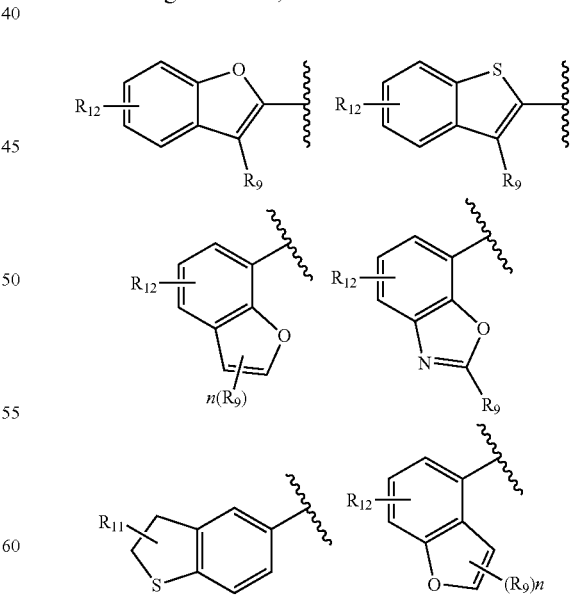

where $R_9$ is selected from the group consisting of H, halogen, C1-C6 alkyl, C3-C8 cycloalkyl, C3-C8 cycloalkylmethyl, halogen-substituted C1-C6 alkyl, hydroxy-substituted C1-C6 alkyl, alkoxy-substituted C1-C6 alkyl, amino-substituted C1-C6 alkyl, C1-C4 alkylamino-substituted C1-C6 alkyl, nitro, cyano, —OR, —N(R)$_2$, —SR, —C(O)OR, —C(O)N(R)2, —C(O)R, —S(O)R, —S(O)$_2$R, —S(O)$_2$N(R)$_2$, and —N(R)C(O)R;

R$_{11}$ is selected from the group consisting of H, —SR, —OR, —N(R)$_2$, and C1-C6 alkyl;

R$_{12}$ is selected from the group consisting of H, —SR, —OR, —N(R)$_2$, and C1-C6 alkyl;

n is 0, 1, or 2; and each of R is selected from the group consisting of H, C1-C6 alkyl, C3-C8 cycloalkyl, C3-C8 cycloalkylmethyl, and halogen-substituted C1-C6 alkyl.

15. The 1,3-disubstituted ketene compound of claim 14 or a pharmaceutically acceptable salt thereof or a stereoisomer thereof or a prodrug molecule thereof, wherein R$_1$ and R$_2$ are each independently selected from the group consisting of C1-C3 alkyl, halogen, and C1-C3 alkoxy;

R$_3$ and R$_4$ are each independently C1-C6 alkyl;

R$_5$ is OR$_6$, where R$_6$ is H;

Y is O;

ring A is selected from the group consisting of the following structures,

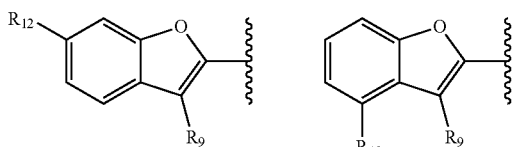
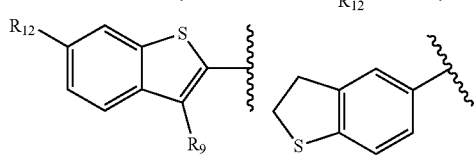
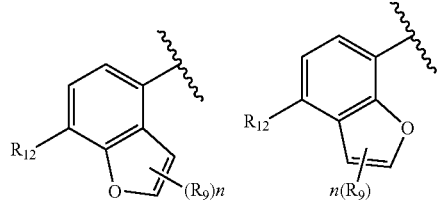
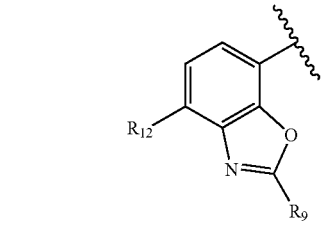

where R$_9$ is selected from the group consisting of H, halogen, C1-C6 alkyl, halogen-substituted C1-C6 alkyl, hydroxy-substituted C1-C6 alkyl, alkoxy-substituted C1-C6 alkyl, —OR, —N(R)$_2$, —SR, —C(O)OR, —C(O)N(R)$_2$, —C(O)R, —S(O)R, —S(O)$_2$R, —S(O)$_2$N(R)$_2$, and —N(R)C(O)R;

R$_{12}$ is selected from the group consisting of H, —SR, —OR, and C1-C6 alkyl;

n is 0 or 1; and each of R is independently selected from the group consisting of H, C1-C6 alkyl, C3-C8 cycloalkyl, C3-C8 cycloalkylmethyl, and halogen-substituted C1-C6 alkyl.

16. The 1,3-disubstituted ketene compound of claim 1 or a pharmaceutically acceptable salt thereof or a stereoisomer thereof or a prodrug molecule thereof, wherein the 1,3-disubstituted ketene compound is selected from the group consisting of the following structures, Compound 1

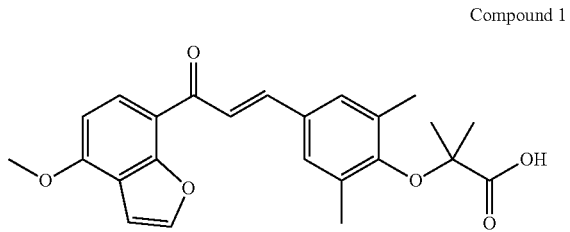

Compound 2

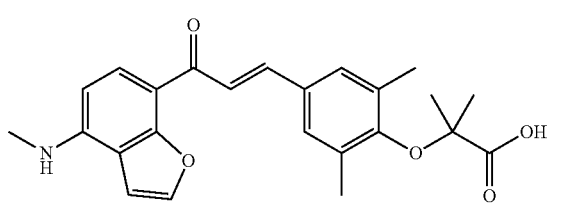

Compound 3

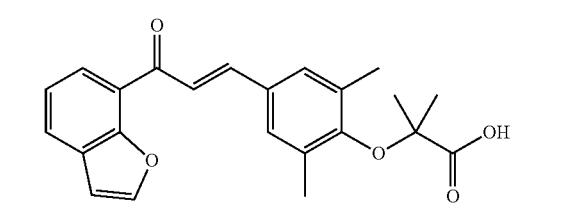

Compound 4

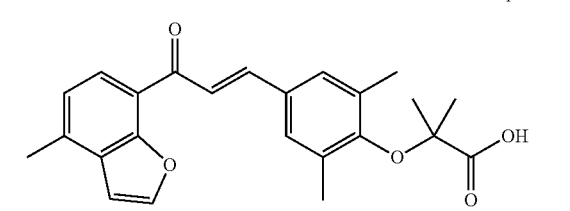

Compound 5

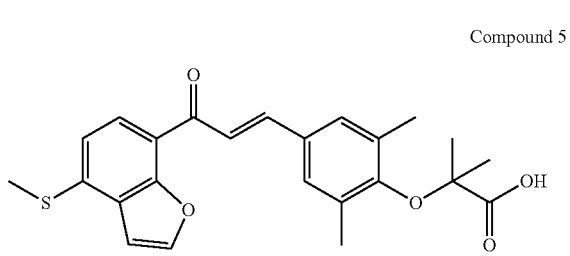

Compound 6

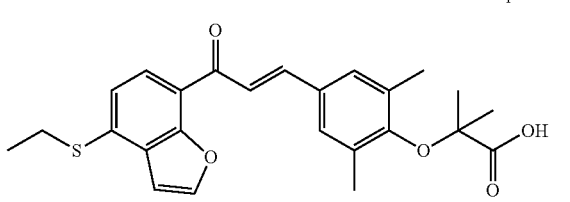

Compound 7
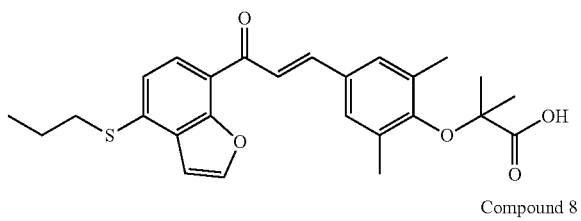
Compound 8
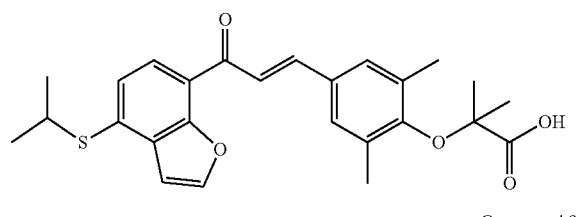
Compound 9
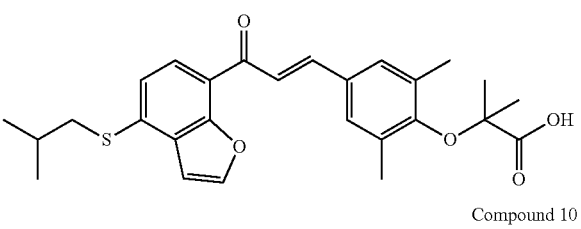
Compound 10
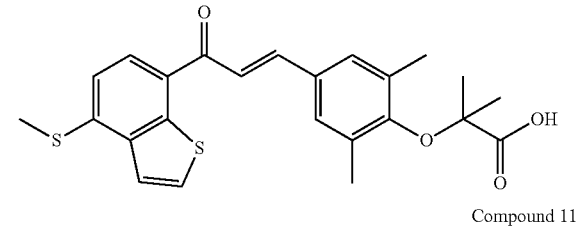
Compound 11
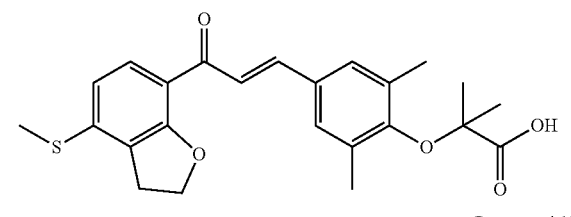
Compound 12
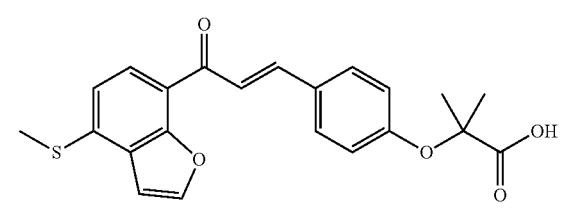
Compound 14
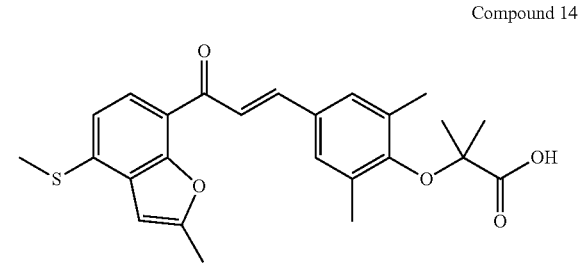
Compound 15
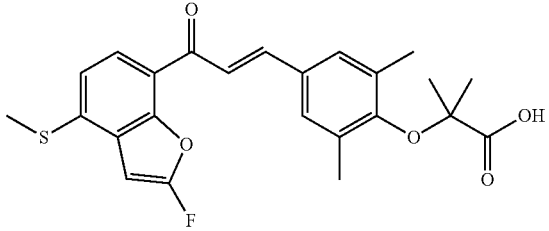
Compound 15
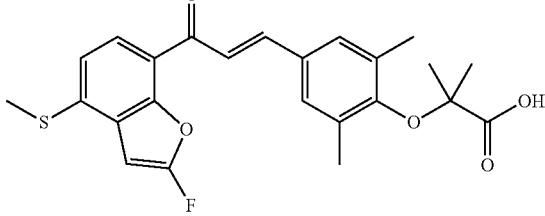
Compound 16
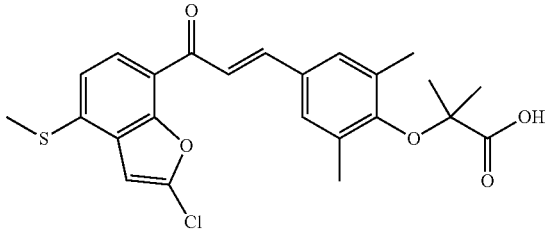
Compound 17
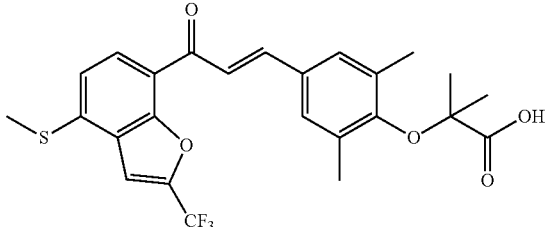
Compound 18
Compound 19
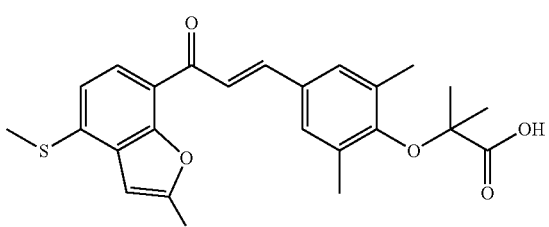

Compound 20
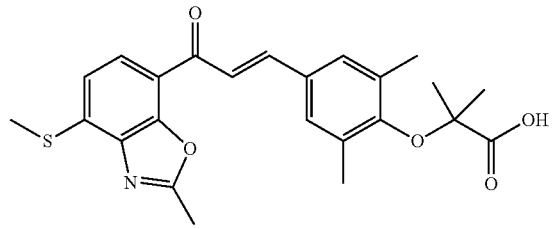
Compound 21
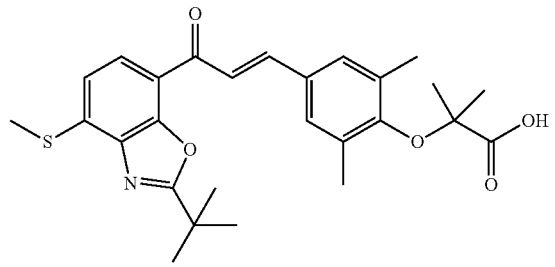
Compound 22
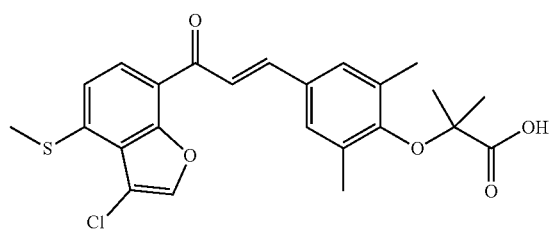
Compound 23
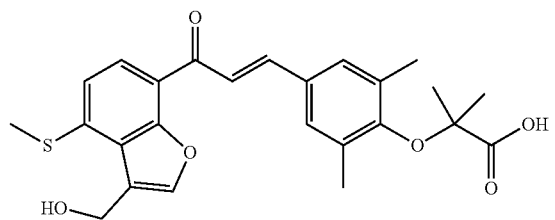
Compound 24
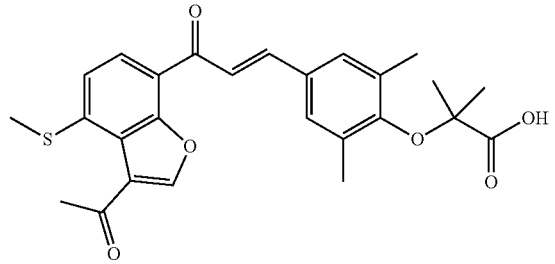
Compound 25
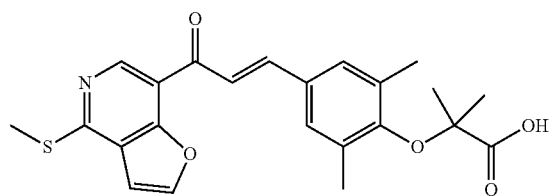
Compound 26
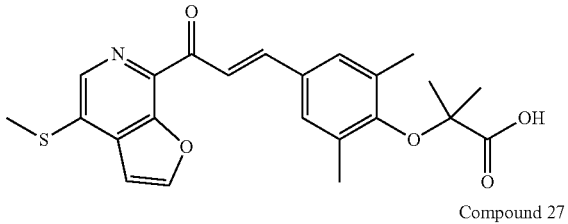
Compound 27
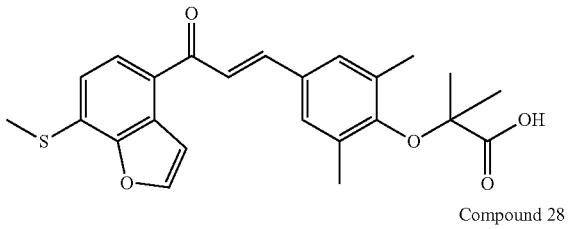
Compound 28
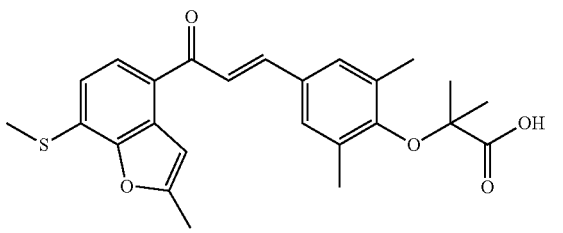
Compound 29
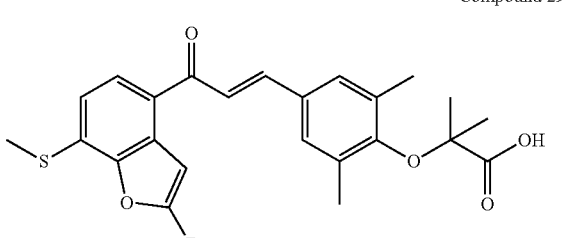
Compound 30
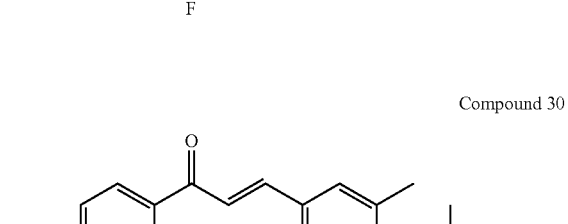
Compound 31
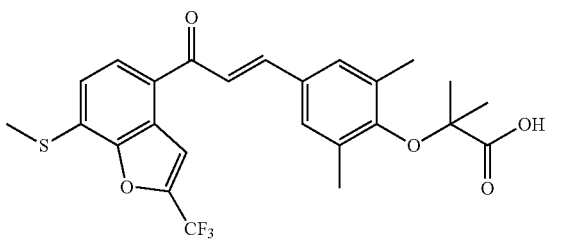

Compound 32
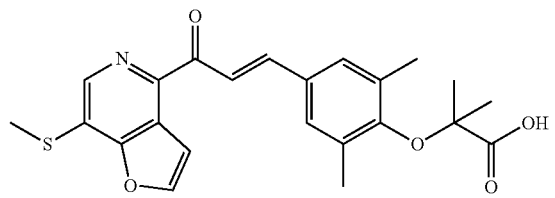
Compound 33
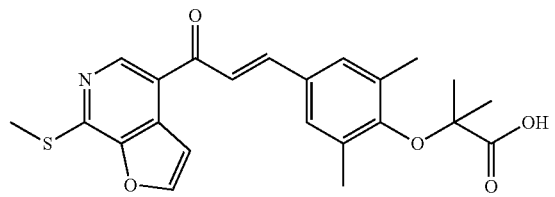
Compound 34
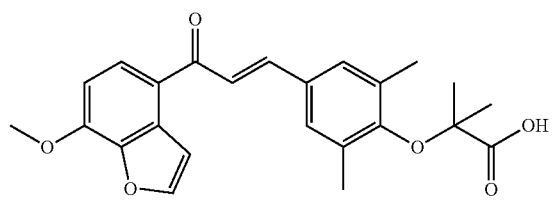
Compound 35
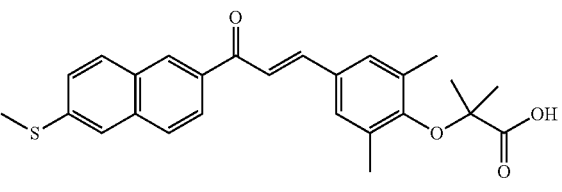
Compound 36
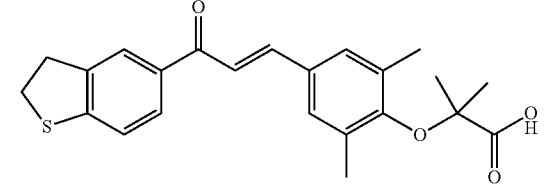
Compound 37
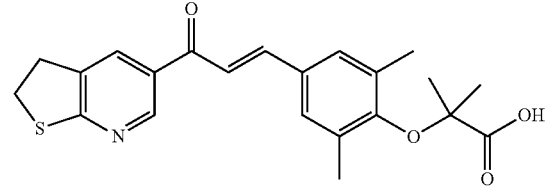
Compound 38
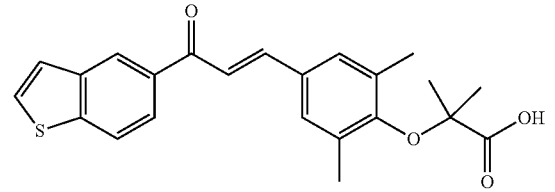
Compound 39
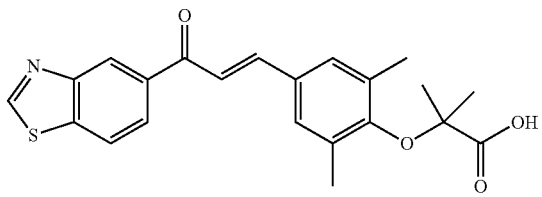
Compound 40
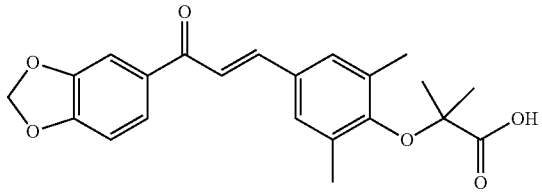
Compound 41
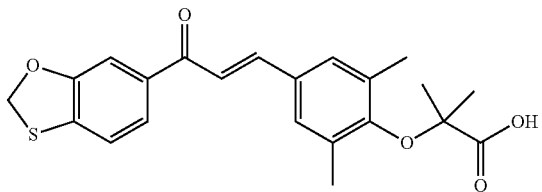
Compound 42
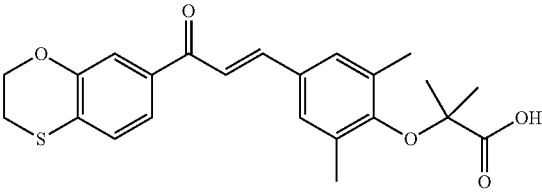
Compound 43
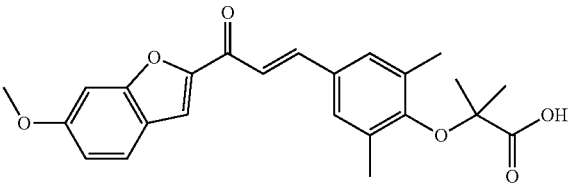
Compound 44
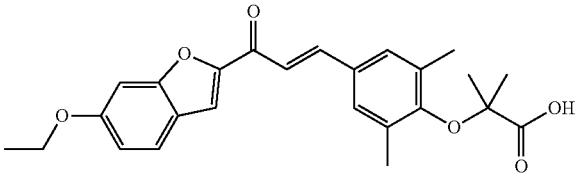
Compound 45
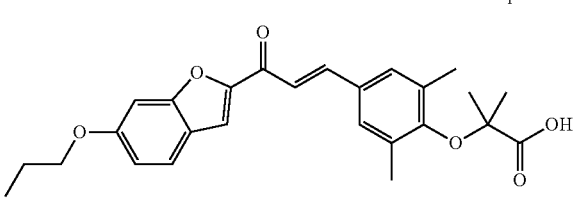

Compound 46
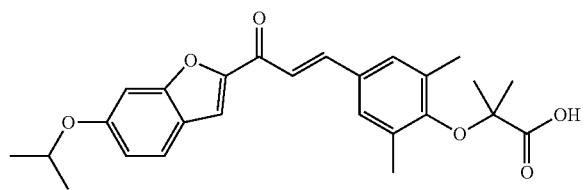
Compound 47
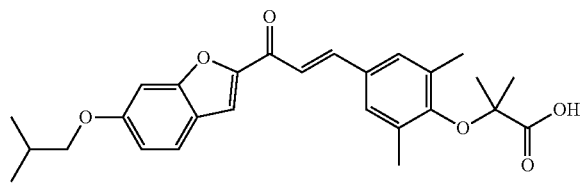
Compound 48
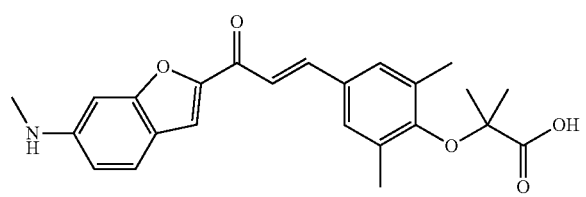
Compound 49
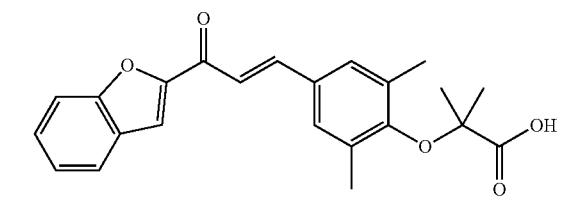
Compound 50
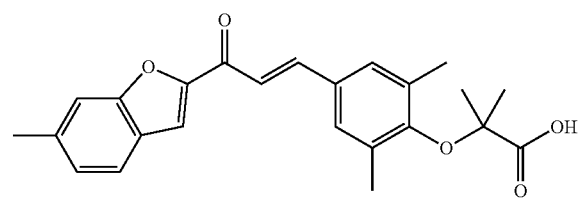
Compound 51
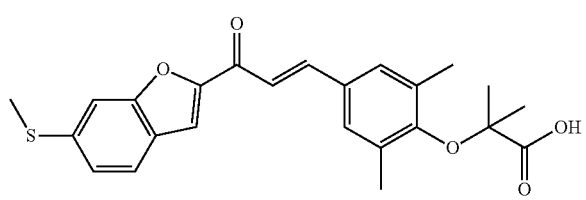
Compound 52
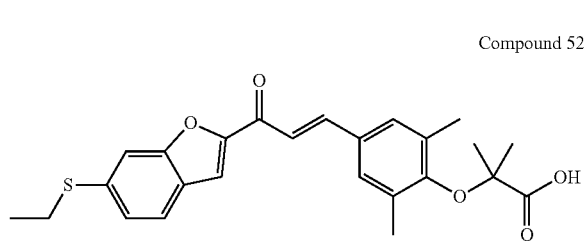
Compound 53
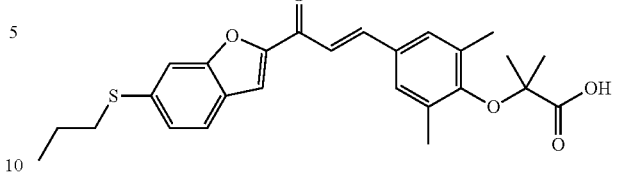
Compound 54
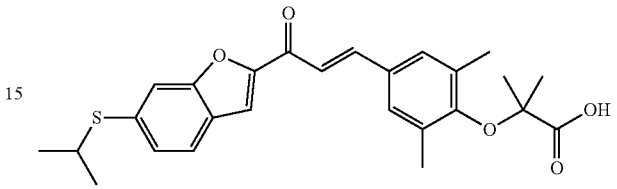
Compound 55
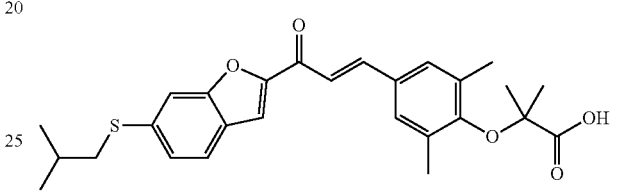
Compound 56
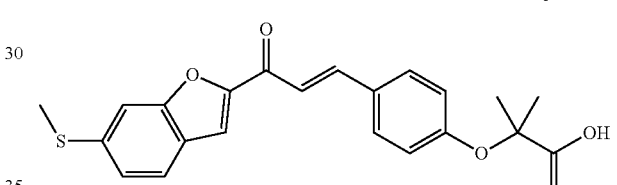
Compound 58
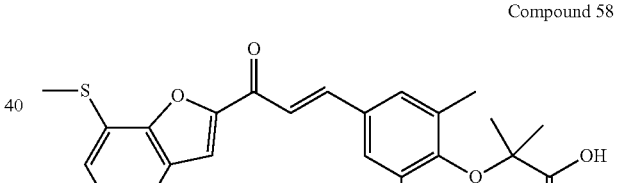
Compound 59
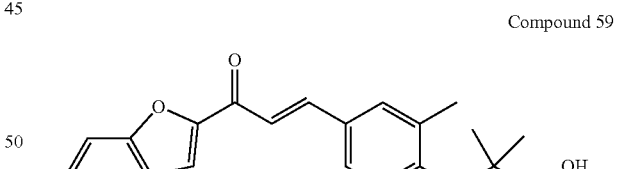
Compound 60
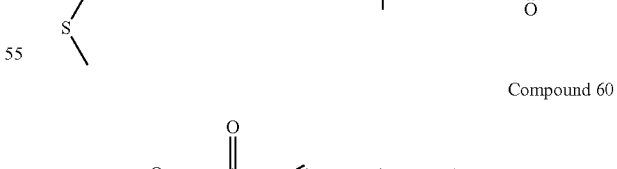
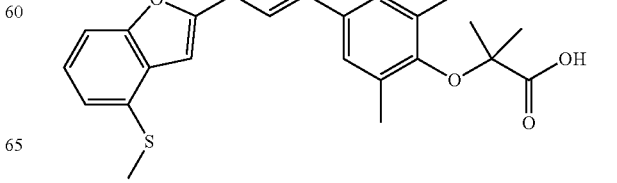

Compound 61
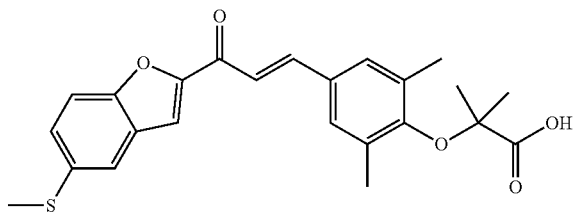
Compound 62
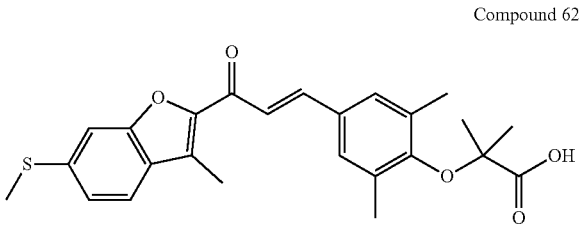
Compound 63
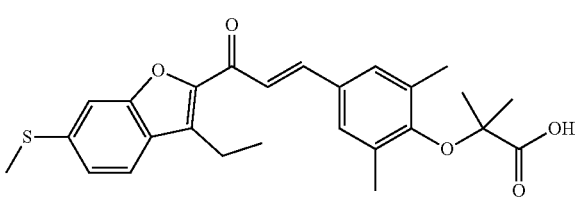
Compound 64
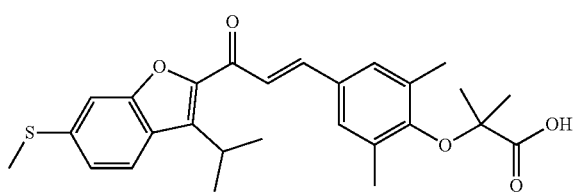
Compound 65
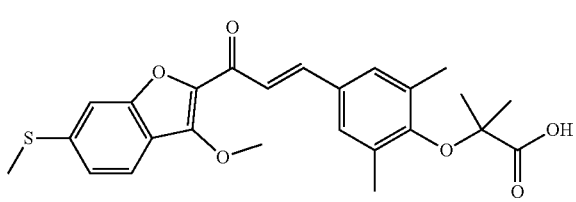
Compound 66
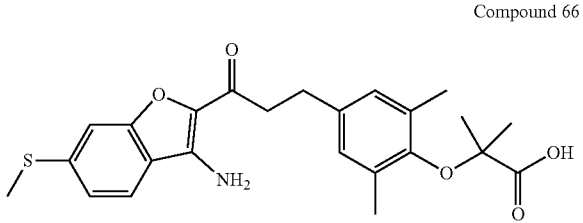
Compound 67
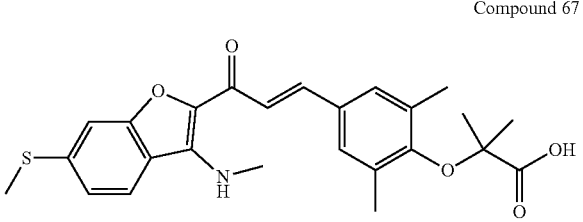
Compound 68
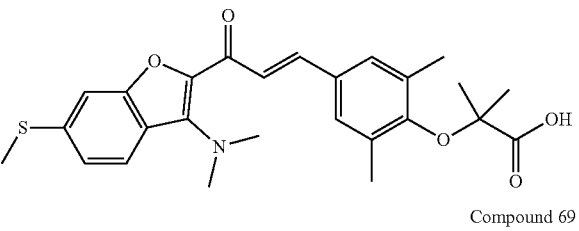
Compound 69
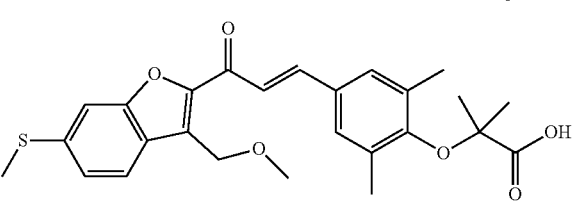
Compound 70
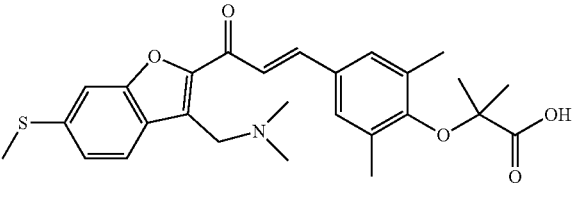
Compound 71
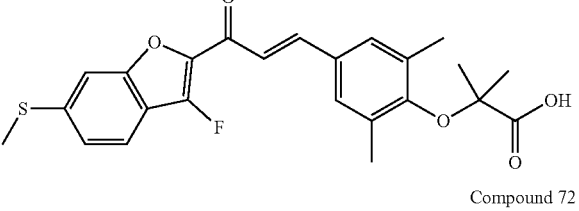
Compound 72
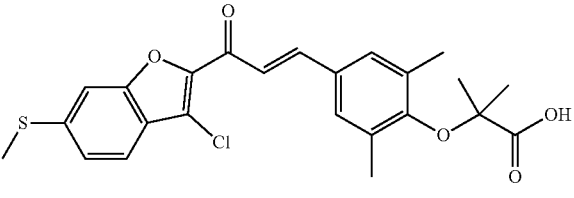
Compound 73
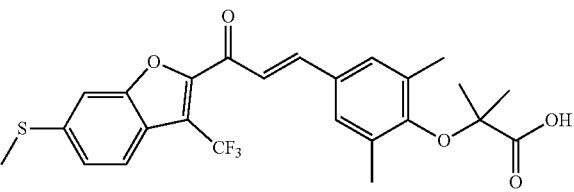
Compound 74
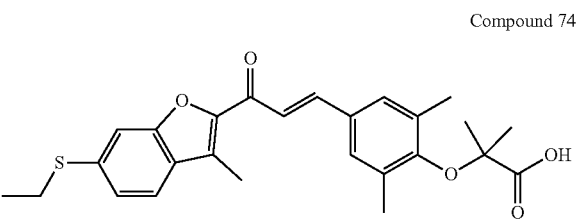

Compound 75
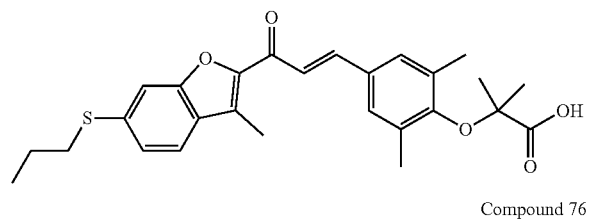
Compound 82
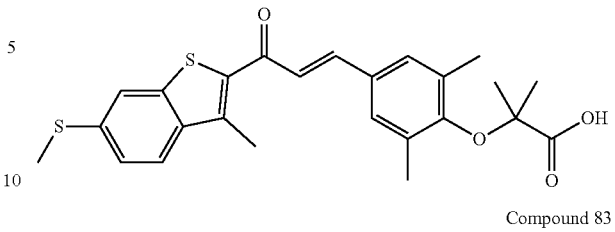
Compound 76
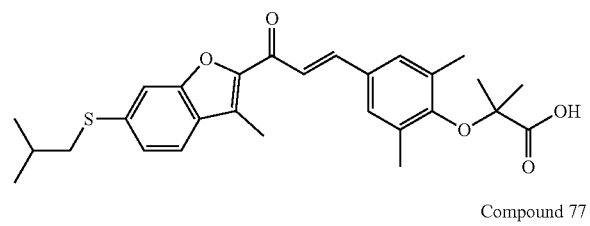
Compound 83
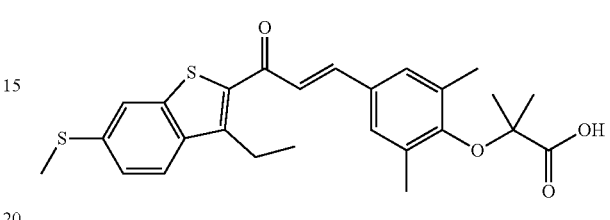
Compound 77
Compound 84
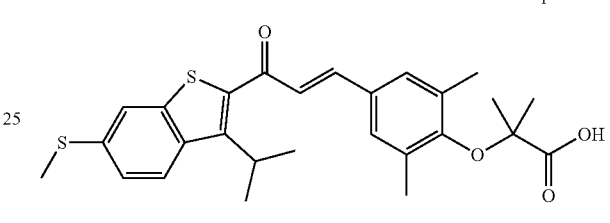
Compound 78
Compound 85
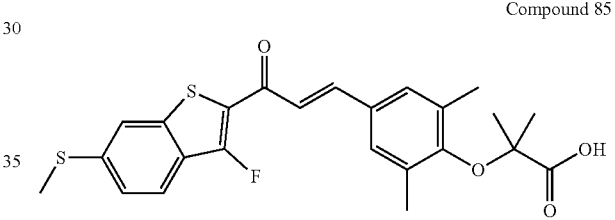
Compound 79
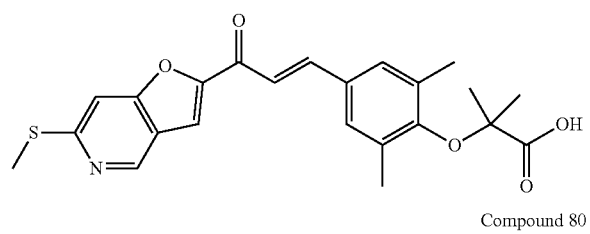
Compound 86
Compound 80
Compound 87
Compound 81
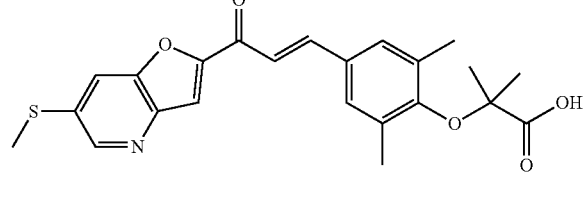
Compound 88
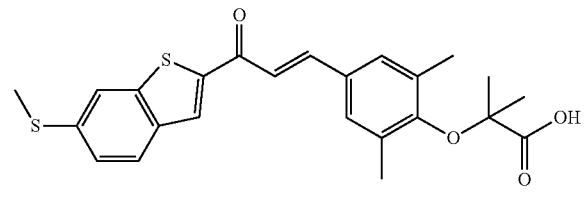
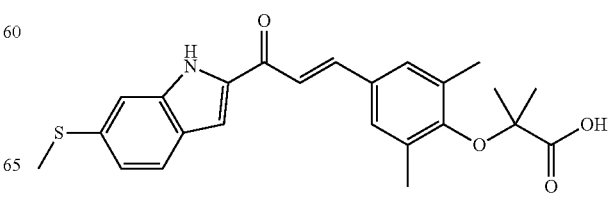

Compound 89
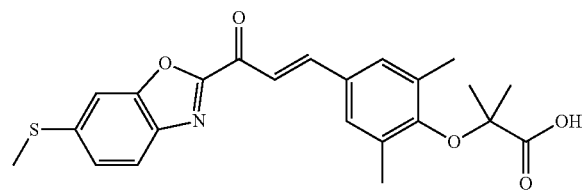
Compound 90
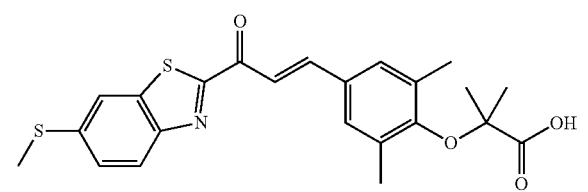
Compound 91
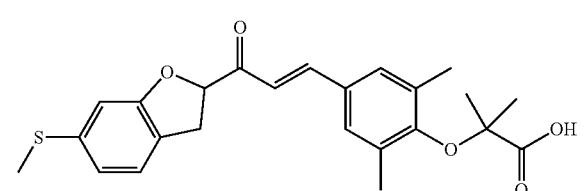
Compound 92
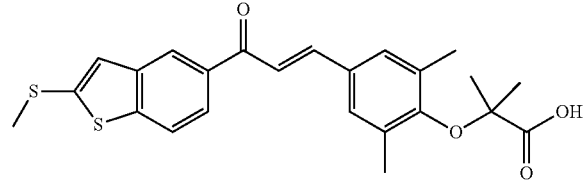
Compound 93
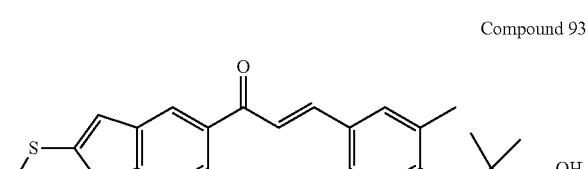
Compound 94
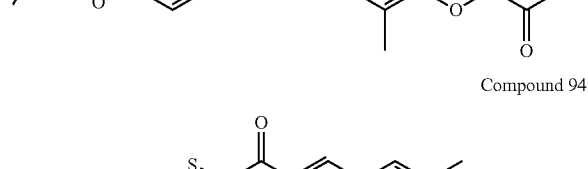
Compound 95
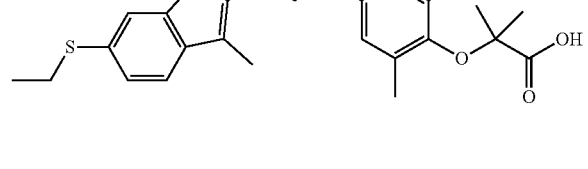
Compound 96
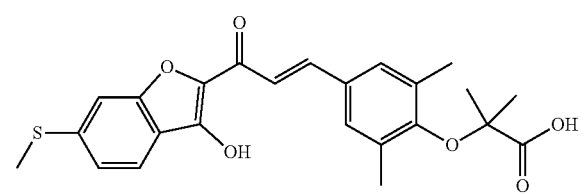
Compound 96
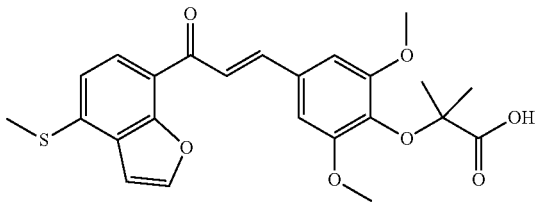
Compound 97
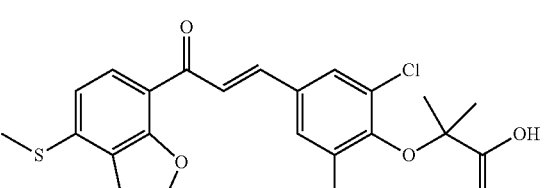
Compound 98
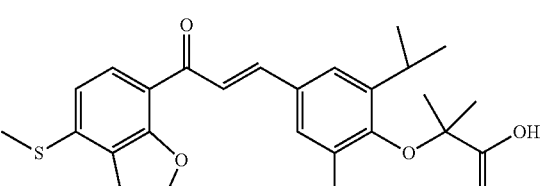
Compound 99
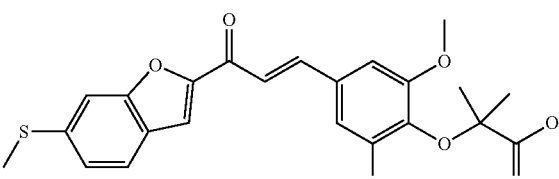
Compound 100
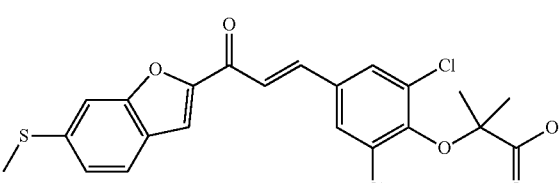
Compound 101
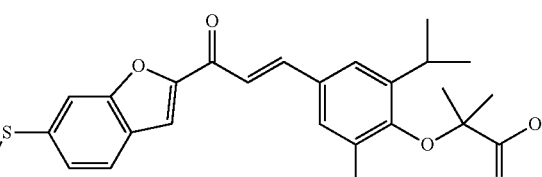
Compound 102

Compound 103
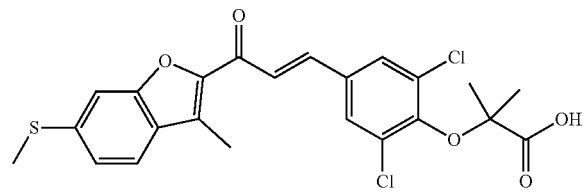
Compound 104
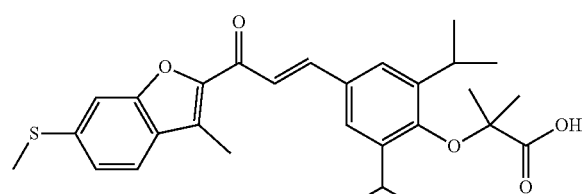
Compound 105
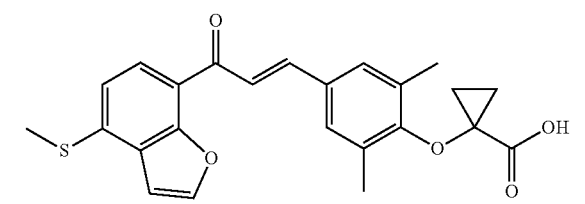
Compound 106
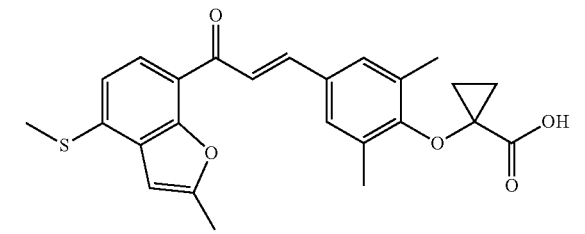
Compound 107
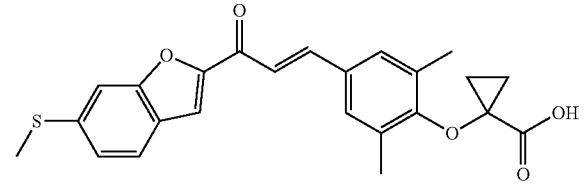
Compound 108
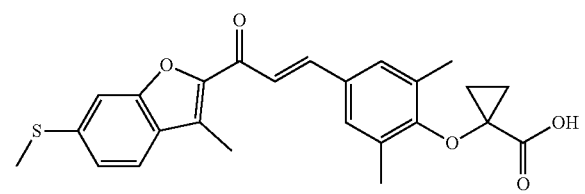
Compound 109
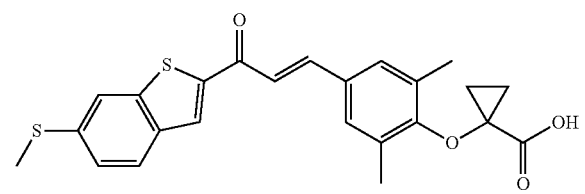
Compound 110
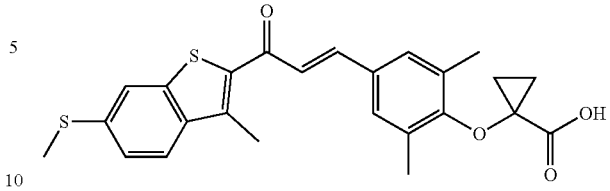
Compound 111
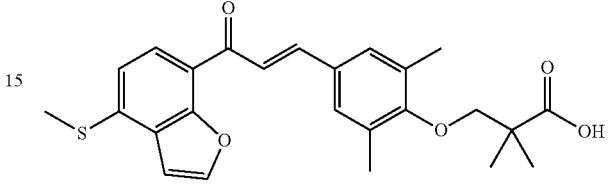
Compound 112
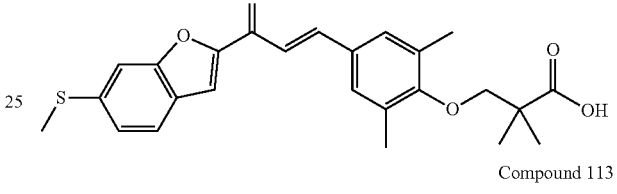
Compound 113
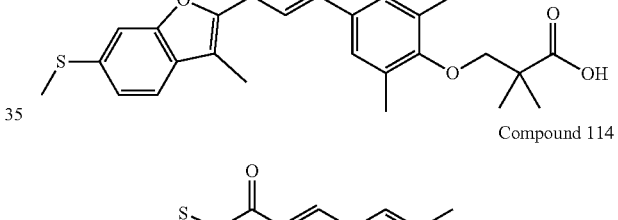
Compound 114
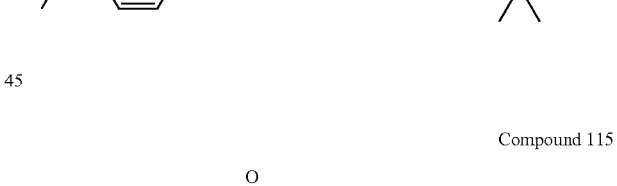
Compound 115
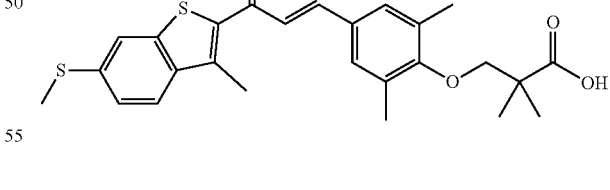
Compound 116
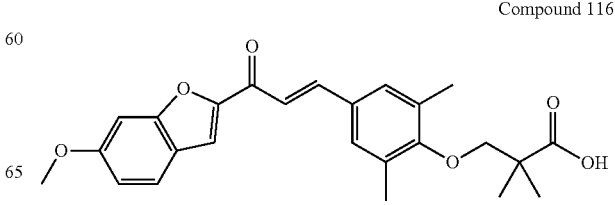

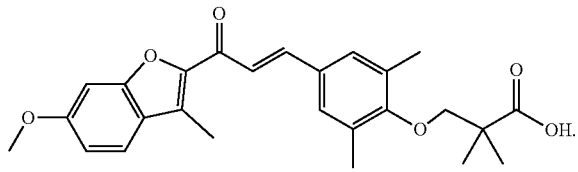

Compound 117

17. A method of preventing or treating a disease associated with abnormal regulation of PPAR, comprising administering the 1,3-disubstituted ketene compound of claim 1 or a pharmaceutically acceptable salt thereof or a stereoisomer thereof or a prodrug molecule thereof to a subject in need thereof, wherein the disease associated with abnormal regulation of PPAR is selected from the group consisting of a disease associated with abnormal metabolism of lipid and glucose, a disease associated with inflammation and abnormal fibrosis, a cardiovascular disease, a kidney disease, and a degenerative brain disease.

18. The method of claim 17, wherein the disease associated with abnormal metabolism of lipid and glucose is diabetes or obesity, the disease associated with inflammation and abnormal fibrosis is nonalcoholic fatty liver disease, nonalcoholic hepatitis, or cholestatic liver disease, the cardiovascular disease is atherosclerosis or heart failure, the kidney disease is renal failure or chronic kidney disease, and the degenerative brain disease is Alzheimer's disease.

19. A pharmaceutical composition for preventing or treating a disease associated with abnormal regulation of PPAR, comprising the 1,3-disubstituted ketene compound of claim 1 or a pharmaceutically acceptable salt thereof or a stereoisomer thereof or a prodrug molecule thereof.

* * * * *